US006895077B2

(12) United States Patent
Karellas et al.

(10) Patent No.: US 6,895,077 B2
(45) Date of Patent: May 17, 2005

(54) SYSTEM AND METHOD FOR X-RAY FLUOROSCOPIC IMAGING

(75) Inventors: Andrew Karellas, Auburn, MA (US); Srinivasan Vedantham, Worcester, MA (US); Sankararaman Suryanarayanan, Worchester, MA (US)

(73) Assignee: University of Massachusetts Medical Center, Worcester, MA (US)

( * ) Notice: Subject to any disclaimer, the term of this patent is extended or adjusted under 35 U.S.C. 154(b) by 34 days.

(21) Appl. No.: 09/990,880

(22) Filed: Nov. 21, 2001

(65) Prior Publication Data

US 2003/0169847 A1 Sep. 11, 2003

(51) Int. Cl.[7] ............................................... H05G 1/64
(52) U.S. Cl. ................... 378/98.3; 378/98.8; 378/98.12; 250/370.09; 250/370.11
(58) Field of Search .............................. 378/44, 62, 98, 378/98.3, 98.8, 98.12; 382/130, 131, 132; 250/370.08, 370.09, 370.11

(56) References Cited

U.S. PATENT DOCUMENTS

| | | | |
|---|---|---|---|
| 2,198,479 A | 4/1940 | Langmuir | 250/214 VT |
| 4,298,800 A | 11/1981 | Goldman | 378/19 |
| 4,709,382 A | 11/1987 | Sones | 378/62 |
| 4,792,900 A | 12/1988 | Sones et al. | 600/407 |
| 5,027,380 A | 6/1991 | Nishiki | 378/4 |
| 5,150,394 A * | 9/1992 | Karellas | 378/62 |
| 5,166,524 A | 11/1992 | Lee et al. | 250/580 |
| 5,168,160 A | 12/1992 | Jeromin et al. | 250/580 |
| 5,293,574 A | 3/1994 | Roehm et al. | 378/98.2 |
| 5,300,784 A | 4/1994 | Fender et al. | 250/484.2 |
| 5,309,496 A | 5/1994 | Winsor | 378/98.2 |
| 5,313,066 A | 5/1994 | Lee et al. | 250/370.09 |
| 5,319,206 A | 6/1994 | Lee et al. | 250/370.09 |
| 5,331,179 A | 7/1994 | Lee et al. | 250/591 |

(Continued)

FOREIGN PATENT DOCUMENTS

| | | |
|---|---|---|
| EP | 0866501 A1 | 9/1998 |
| JP | 8107521 | 4/1996 |
| JP | 11259647 | 9/1999 |
| NL | 9102063 | 12/1991 |
| WO | WO 97/42877 | 11/1997 |

OTHER PUBLICATIONS

Herron, John M., et. al. "X–Ray Imaging With Two–Dimensional Charge–Coupled Device (CCD) Arrays." *Medical Imaging and Instrumentation*, vol. 486, pp. 141–145, 1984.

(Continued)

*Primary Examiner*—Edward J. Glick
*Assistant Examiner*—Courtney Thomas
(74) *Attorney, Agent, or Firm*—Bowditch & Dewey, LLP

(57) ABSTRACT

A system for x-ray fluoroscopic imaging of bodily tissue in which a scintillation screen and a charge coupled device (CCD) is used to accurately image selected tissue. An x-ray source generates x-rays which pass through a region of a subject's body, forming an x-ray image which reaches the scintillation screen. The scintillation screen re-radiates a spatial intensity pattern corresponding to the image, the pattern being detected by the CCD sensor. In a preferred embodiment the imager uses four 8×8-cm three-side buttable CCDs coupled to a CsI:T1 scintillator by straight (non-tapering) fiberoptics and tiled to achieve a field of view (FOV) of 16×16-cm at the image plane. Larger FOVs can be achieved by tiling more CCDs in a similar manner. The imaging system can be operated in a plurality of pixel pitch modes such as 78, 156 or 234-$\mu$m pixel pitch modes. The CCD sensor may also provide multi-resolution imaging. The image is digitized by the sensor and processed by a controller before being stored as an electronic image. Other preferred embodiments may include each image being directed on flat panel imagers made from but not limited to, amorphous silicon and/or amorphous selenium to generate individual electronic representations of the separate images used for diagnostic or therapeutic applications.

45 Claims, 82 Drawing Sheets

U.S. PATENT DOCUMENTS

| | | | |
|---|---|---|---|
| 5,381,000 A | 1/1995 | McKee, Jr. | 250/214 VT |
| 5,381,014 A | 1/1995 | Jeromin et al. | 250/370.09 |
| 5,388,138 A | 2/1995 | Fujiwara | 378/108 |
| 5,463,668 A | 10/1995 | Kagaya | 378/98.2 |
| 5,465,284 A * | 11/1995 | Karellas | 378/62 |
| 5,498,880 A | 3/1996 | Lee et al. | 250/580 |
| 5,563,421 A | 10/1996 | Lee et al. | 250/580 |
| 5,572,034 A * | 11/1996 | Karellas | 250/368 |
| 5,652,430 A | 7/1997 | Lee | 250/370.09 |
| 5,657,400 A | 8/1997 | Granfors et al. | 382/254 |
| 5,661,309 A | 8/1997 | Jeromin et al. | 250/580 |
| 5,751,783 A | 5/1998 | Granfors et al. | 378/108 |
| 5,804,832 A | 9/1998 | Crowell et al. | 250/580 |
| 5,809,105 A | 9/1998 | Roehm et al. | 378/98.12 |
| 5,827,757 A | 10/1998 | Robinson, Jr. et al. | 438/73 |
| 5,844,243 A | 12/1998 | Lee et al. | 250/370.09 |
| 5,864,146 A | 1/1999 | Karellas | 250/581 |
| 5,920,070 A | 7/1999 | Petrick et al. | 250/370.09 |
| 5,970,115 A | 10/1999 | Colbeth et al. | 378/62 |
| 6,031,892 A * | 2/2000 | Karellas | 378/98.3 |
| 6,222,906 B1 * | 4/2001 | Sakaguchi et al. | 378/98.8 |
| 6,285,739 B1 | 9/2001 | Rudin et al. | 378/98.8 |
| 6,353,654 B1 | 3/2002 | Granfors et al. | 378/98.8 |
| 6,393,097 B1 | 5/2002 | Aufrichtig et al. | 378/98.11 |
| 6,498,831 B2 | 12/2002 | Granfors et al. | 378/98.8 |
| 6,521,886 B2 | 2/2003 | Aufrichtig et al. | 250/252.1 |
| 6,623,161 B2 | 9/2003 | Aufrichtig et al. | 378/207 |
| 2003/0058998 A1 | 3/2003 | Aufrichtig et al. | 378/207 |

OTHER PUBLICATIONS

H. Blume, et. al. "Image Intensifier and X–ray Exposure Control Systems," Categorical course in Physics, 87–103, Radiological Society of North America (RSNA), (1995), pp. 87–103.

G. Spekowius, "Simulation of the Imaging Performance of X–ray Image Intensifier/TV Camera Chains," Proc. SPIE 2432, 12–23, Medical Imaging 1995: Physics of Medical Imaging, R.L. Van Metter and J. Beutel; Editors (1995).

Coltman, S. "Fluoroscopic Image Brightening by Electronic Means," Radiology 51, 359–367 (1948).

Burke, et. al. "An Abuttable CCD Imager for Visible and X–Ray Focal Plane Arrays," *IEEE Electron Devices*, vol. 38, No. 5 pp. 1069–1076, May 1991.

W.J. Van der Putten and S. Bouley, "Performance Evaluation of Image Intensifier–TV Fluroscopy Systems," Proc. SPIE vol. 2432, pp. 376–383, Medical Imaging 1995: Physics of Medical Imaging, R.L. Van Metter and J. Beutel; Editors (1995).

Vedantham, S., et. al. "Feasibility of Cardiac Flouroscopy with Large–area Charge–Coupled Devices," *Medical Physics*, vol. 28 No. 8, Aug. 2001.

* cited by examiner 6.865 FPS 13.73 FPS 18.307 FPS 27.46 FPS 6.865 FPS 13.73 FPS 18.307 FPS 27.46 FPS

SYSTEM AND METHOD FOR X-RAY FLUOROSCOPIC IMAGING

GOVERNMENT SUPPORT

The invention was supported, in whole or in part, by a Grant No. R01 HL65551 from the National Institutes For Health. The Government has certain rights in the invention.

BACKGROUND OF THE INVENTION

The term fluoroscopy refers to the use of x-ray imaging techniques for real-time visualization of internal anatomy and function for diagnostic and therapeutic purposes. Physiologic functions such as peristalsis and flow, and real-time image feedback for placement of devices, such as catheters or intravascular stents are typical examples of fluoroscopic imaging. However, fluoroscopy at 30 video frames/second alone is of limited use without the capability of switching to a high detail mode. This mode may be activated by a command to produce a spot image 'snapshot' and in many applications acquisition of rapid sequences of spot images or high detail images at a higher radiation dose are essential. In this mode, the system operates in a rapid sequence radiographic mode, where the exposure per frame at the entrance of the fluoroscopic imaging system is increased from the typical 1 to 3-$\mu$R per video frame (fluoroscopic mode) to about 300-$\mu$R per frame (radiographic mode). In fluoroscopy, the ability to change the spatial resolution during the examination enables physicians to focus on a smaller area and visualize with greater detail. Although the traditional role of fluoroscopy provides enough justification of the importance of maintaining and improving image quality at a reduced radiation dose, in the past few years the role of fluoroscopy has greatly expanded to cover many more diagnostic and therapeutic applications. More interventional fluoroscopic procedures are performed today in younger patients as an alternative to surgery.

In spite of recent developments in non-invasive procedures such as, magnetic resonance imaging, ultrasound and computed tomography, x-ray fluoroscopy remains the "gold-standard" for procedures such as diagnostic percutaneous coronary angiography, angioplasty, stent placement, pacemaker placement, electrophysiology, and peripheral vascular procedures. The success of these procedures is making a major impact not only in the survival rate of patients from cardiovascular disease, but also on the overall quality of life. As these procedures become more effective, younger patients are increasingly becoming candidates for such procedures. It is now common for young patients to undergo cardiac radiofrequency ablation procedures. There are also clinical situations such as the evaluation of coronary artery patency following thrombolysis or in the operating room to assess graft patency where compact bedside angiographic equipment can be extremely useful.

Video pick-up tube-based image intensifiers for fluoroscopy was invented in about 1940 and has been in use since 1948 when Coltman built the first practical image intensifier. Now, image intensifiers are a standard and essential component of fluoroscopic systems. Although several aspects of this technology have evolved over the years, the basic approach of detection remains the same. Image intensifier technology with video tube-based cameras and more recently charge-coupled devices (CCDs) have made a major impact in the field of x-ray fluoroscopy. In spite of the technical improvements, this technology suffers from several inherent limitations. Veiling glare and contrast loss is one of the more typical problems inherent in the electro-optic design of the image intensifier. After conversion of the light from the scintillator to the photocathode, electrons are accelerated in a field potential of about 30 kV. During this stage, a fraction of the electrons undergo scatter within the tube. At the output stage, after conversion from electrons to photons, the light scatters within the optical elements of the output. S-type distortion is also a well-known phenomenon, which makes imaging of a straight object to appear as having an S-shape due to the influence of the earth's magnetic field on the trajectories of electrons within the image-intensifier tube. Shielding of image intensifiers with "mu-metal" is essential but in many cases a significant amount of S-type distortion is still present. This distortion is not only bothersome during treatment procedures requiring high spatial accuracy, but also changes spatially as the intensifier is moved, making it difficult to correct mathematically. Other types of distortion such as pincushion and barrel type distortions are caused by the inherent limitations of the electron focusing optics. Pincushion and barrel distortions are tolerable in many instances but they present a hindrance in the proper visualization of anatomy. Similar effects but for different physical reasons also arise from lens-based optical coupling. The glass input window typically has been the input window of image intensifiers (typically 1 to 3-mm thick), which absorbs useful x-rays and produces forward scatter, but has now been replaced with a thickness of 0.7 to 1.2-mm, of aluminum (Al). While this represents a significant improvement, the input window itself absorbs about 20 to 30% of the useful x-ray beam depending on the photon energy. The high vacuum of the intensifier requires a relatively thick metal window for maintaining mechanical integrity of the tube. In addition to this aluminum layer of the input window, x-rays must pass through another 0.5-mm thick aluminum layer, the scintillator substrate, before they reach the scintillator. In addition, the gain of image intensifiers is known to degrade with time due in part to outgassing of components in the vacuum chamber and degradation of the photocathode. The image quality is noticeably lower after three years of operation and their useful lifetime, if good image quality is to be maintained, is about 3 to 5 years. Also, the relatively large size of image intensifiers may be problematic in biplanar installations. Even in simple fluoroscopic installations the camera tower frequently interferes with the overhead radiographic x-ray tube and other structures.

Image intensifier and electronic readout technology has evolved significantly over the years and the image quality of modern image intensifier with CCD readout is far superior to the earlier approaches. However, radiation exposure to patients during diagnostic and interventional cardiac procedures has increased as a result of the increased complexity of the angiographic procedures performed in current clinical practice. The rapid proliferation of these procedures has resulted in a small but alarming number of non-stochastic radiation effects on patients. These include epilation, erythema and tissue necrosis in a number of cases. Cardiac angiography produces one of the highest radiation exposures of any commonly used diagnostic x-ray procedure. Recently, chronic dermatitis has been reported after repeated therapeutic interventional procedures using prolonged fluoroscopic imaging. All these factors indicate not only the need for safe and good fluoroscopic habits but also the need for developing an alternate technology, which is capable of improving image quality at an even reduced radiation dose. Early attempts have focused on flat panel intensifiers, typically using microchannel plates or solid state detectors. In the past few years, several research groups have been working on developing new technologies and improving existing technology for fluoroscopic applications. While there may be applications where one type of technology is preferable than the other, at this time there still remains a need to provide a higher level of image quality at a minimum radiation dose.

SUMMARY OF THE INVENTION

In accordance with the present invention, an x-ray fluoroscopic apparatus is provided for examining tissues and deep structure of a subject's body. In particular internal organs such as the heart, kidneys, brain and vasculature, and functions such as peristalsis and flow can be examined for diagnostic and therapeutic applications. Cardiovascular fluoroscopic images of small vessels, in the order of approximately 1–2 mm in diameter are provided by preferred embodiments of the present invention. Surgical devices such as guidewires having diameters in the order of approximately 250 microns and bigger can be imaged during surgical procedures using preferred embodiments of the present invention. An x-ray source, such as an x-ray tube or a solid state x-ray source, directs a beam of x-ray radiation toward the subject's body. The radiation is applied to the entire region of the body being examined and a pixellated detector system is used to form images thereof. In a preferred embodiment, a scintillation screen receives the x-ray radiation passing through the body of the subject, and emits radiation in the visible spectrum with a spatial intensity pattern proportional to the spatial intensity pattern of the received x-ray radiation.

An imaging detector, such as, for example, a charge coupled device (CCD) or CMOS imaging sensor then receives radiation from the scintillation screen. This digital imaging sensor generates a discrete electronic representation of the spatial intensity pattern of the radiation emitted from the scintillation screen. The CCD can have interpixel channels and the CCD provides the ability to detect, store and display multiple frames of data to achieve real-time visualization. The detector includes a single or multiple interpixel channel CCDs. Each sensor includes a plurality of detector elements or pixels. Further, each CCD may be an interline transfer device having interpixel channels such that sensitive pixels are located near shielded CCD transport registers. These registers may be horizontally and vertically disposed. An optical element between the screen and the image sensor, such as a non-reducing fiber optic plate couples the scintillation screen radiation onto the image sensor and protects the image from direct x-ray interactions. A controller, either integral with the sensor or located in a separate processing unit then processes the electronic representation generated by the image sensor, and outputs corresponding image data.

In a preferred embodiment the scintillation screen can also be directly attached to an imaging detector. The imaging detector may be a flat panel imager including an indirect detection material such as, but not limited to, amorphous silicon. Thus, in an alternative preferred embodiment, a detector made of amorphous silicon is used to receive and detect the radiation from the scintillation screen to generate the electronic representation of the spatial intensity pattern of the x-ray pattern. The amorphous silicon detector can replace the CCD detector or it can be used to receive the x-rays directly without a scintillator if amorphous selenium or other direct detection material such as cadmium zinc telluride, lead iodide or mercuric iodide is employed. The flat panel imager made of amorphous silicon or selenium may include multiple spatial resolution modes. A central portion may include a higher resolution region made of smaller pixels relative to the peripheral region which is a lower resolution region made of larger pixels. The pixel size may vary and transition in size in different regions of the imaging detector. Further, preferred embodiments may include a plurality of scintillators attached to an imaging detector. These embodiments provide different wavelengths or different absorption or decay characteristics.

In accordance to preferred embodiments of a multi-resolution imaging detector formed from, but not limited to, amorphous silicon and/or amorphous selenium, the pixel sizes vary according to desired applications. In a preferred embodiment the imaging detector includes small pixel regions having a pixel size between the range of 50–200 microns, a mid-size pixel region having pixels ranging between 100–300 microns and a large size pixel region having pixels ranging between 200–400 microns. In particular for a cardiovascular application in the small pixel regions the pixel size varies between 100–250 microns and the pixel size in the large pixel region or low resolution area varies between 200–400 microns.

In a preferred embodiment of the present invention a method for x-ray fluoroscopic imaging includes a step of pre-exposing the subject tissue to identify the regions of interest. The step of pre-exposing uses a low resolution mode or region of a multi-resolution imaging detector in accordance with preferred embodiments of the present invention. The method for x-ray fluoroscopic imaging further includes a step of examining in detail the selected regions of interest. This step uses a high resolution mode or region of a multi-resolution imaging detector. More than one higher resolution mode can be used to provide further examination details regarding the tissue as provided by a plurality of pixel sizes in a multi-resolution imaging detector.

An image store used with the CCD controller allows manipulation of the CCD sensor output signals by a data processor. The system can also be adapted to operate at higher frame rates enabling the counting of x-ray events. This provides energy measurements of x-ray transmissions that are useful in certain applications. Preferred embodiments of the system may operate at variable speeds such as, without limitation, 3, 7.5, 15, 30, 60 and 90 frames per second.

An additional preferred embodiment is directed to systems and methods of x-ray fluoroscopic imaging where a charge coupled device (CCD) is optically coupled to a scintillator and measures or counts the spatial intensity distribution of a radionuclide that has been introduced into bodily tissue, either in vivo or in vitro. CCD's of sufficient thickness can be used to measure gamma ray events without the use of a scintillator in certain applications. However, the use of a scintillator in conjunction with the CCD is required at high gamma-ray energies. The CCD has sufficient resolution and sensitivity to measure such distributions accurately.

In preferred embodiments, the spatial resolution of the detectors may range between 0.2 line pair per mm or cycle/mm to 15 cycles per mm to accurately image the anatomical features or medical devices used in conjunction with the organs or anatomical features.

The CCD acquires "frames" of information by counting the number of gamma-ray events over a selected period of time. Each frame, or a sequence of frames that have been added or summed to provide an image, can be filtered using methods such as, pulse height analysis techniques to substantially reduce or eliminate scattered radiation. The system's discrimination measuring capabilities render it suitable for diverse applications such as, diagnostically significant information and/or therapeutic applications.

In accordance with another aspect of the present invention, a system for x-ray fluoroscopic imaging uses at least one 5×5 cm sensor to image a pediatric heart. In an alternate embodiment, at least four 8×8-cm three-side buttable or interfacing sensors may be tiled to achieve a field of view (FOV) of 16×16-cm. Larger FOVs can be achieved in other preferred embodiments by tiling more sensors in a similar architecture. A particular embodiment of the present system uses a cesium iodide (CsI:T1) scintillator coupled to the sensors by straight (non-tapering) fiberoptics and can be operated in 78, 156 or 234-µm pixel pitch modes.

In a preferred embodiment, the design parameter of pre-sampling modulation transfer function (MTF) is calculated which provides a measure of the signal transfer and spatial resolution characteristics of the system. Further, the detection quantum efficiency is also determined in accordance with preferred embodiments of the present invention which provides a measure of the percentage of incident x-rays effectively used to create the fluoroscopic image. Other measures calculated include scintillation yield of the scintillator, optical coupling efficiency and optimization of thickness of fiberoptic plate, linearity, sensitivity, dynamic range and spatial resolution characteristics of the preferred embodiments of the system. In addition, design aspects, such as, noise characteristics of the CCD, techniques for tiling the CCDs in a seamless fashion, and extending the field of view are also used.

In accordance with a preferred embodiment of the present invention, the plurality of the detector elements (pixels) can be grouped or binned selectively to provide variable resolution of the spatial intensity pattern either within a single interpixel channel CCD or spanning multiple interpixel channel CCD's. In a particular embodiment of the multiple interchannel CCD, any one or more of these CCDs can be operated in any desired resolution by the process of binning.

Preferred embodiments of the present invention may be used for automated estimation of diagnostic characteristics such as ejection fraction, degree of stenosis and the deployment and/or positioning of catheters, guidewires or stents. Further, preferred embodiments of the present invention may be used for rotational angiography and three-dimensional imaging.

The foregoing and other features and advantages of the system and method for x-ray fluoroscopic imaging will be apparent from the following more particular description of preferred embodiments of the system and method as illustrated in the accompanying drawings in which like reference characters refer to the same parts throughout the different views.

Figure 31:
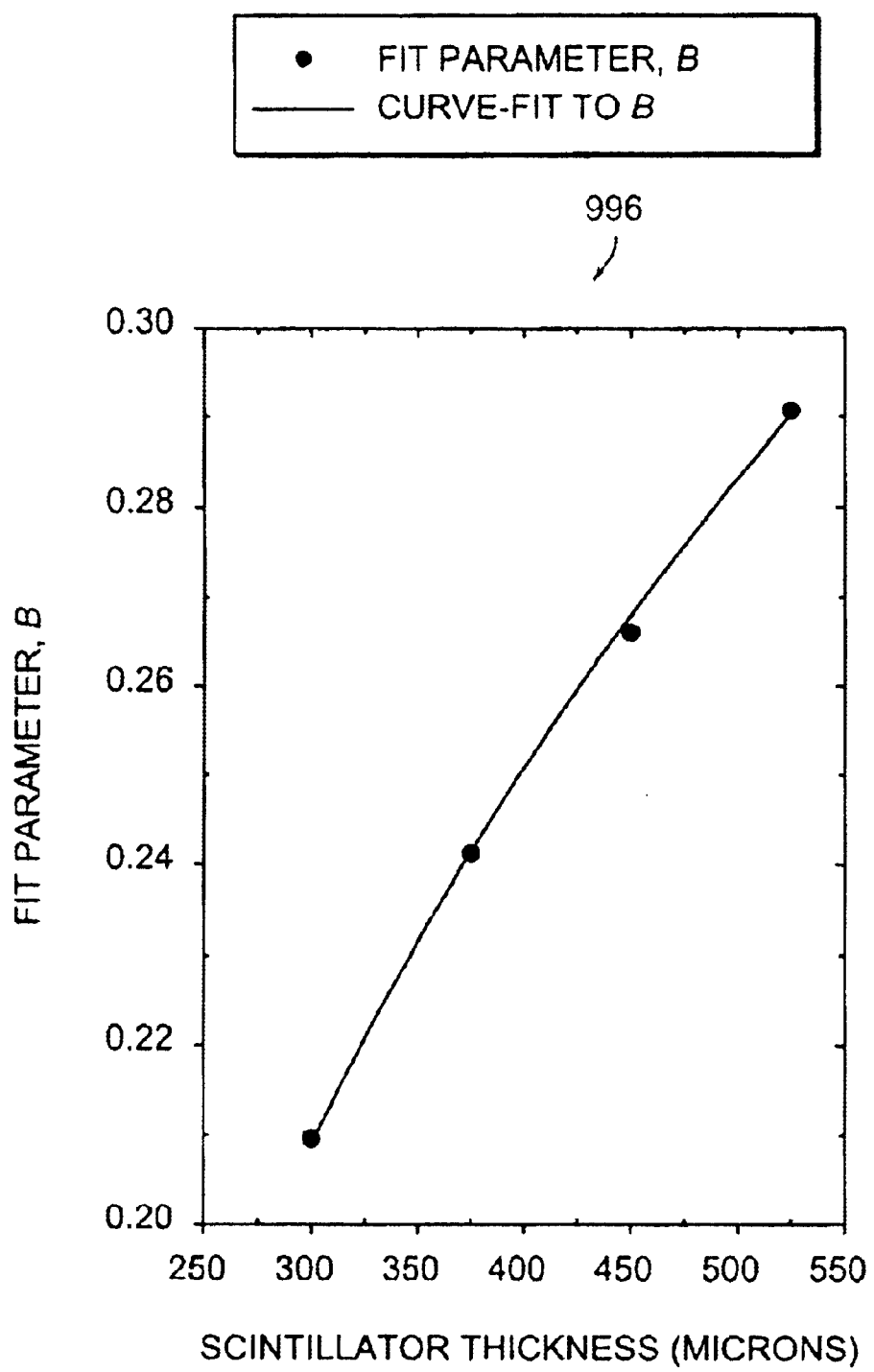
Figure 32B:
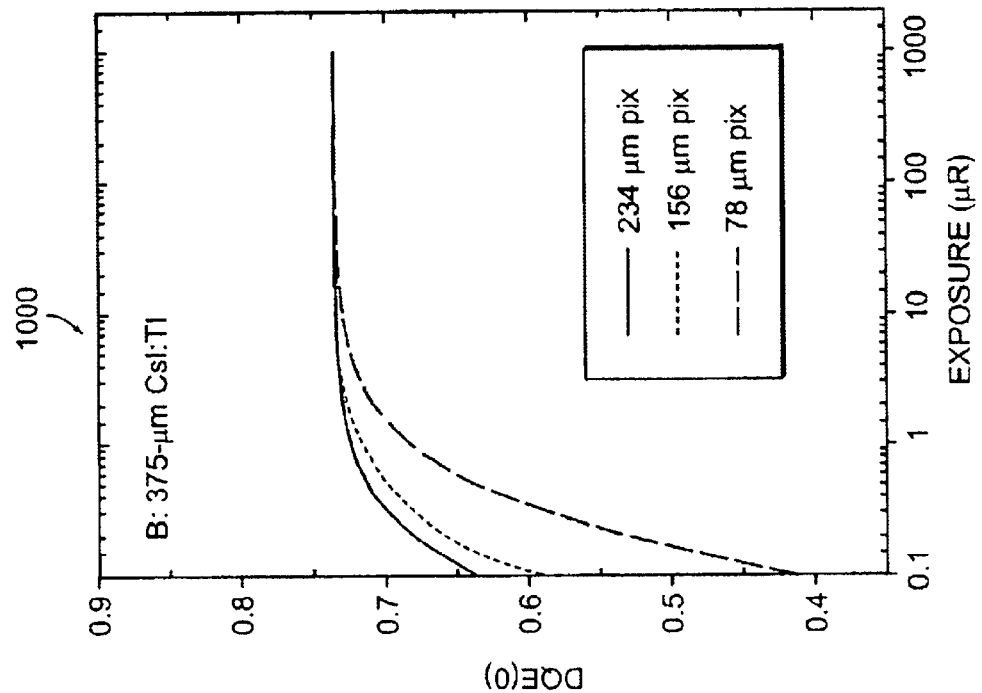
Figure 32A:
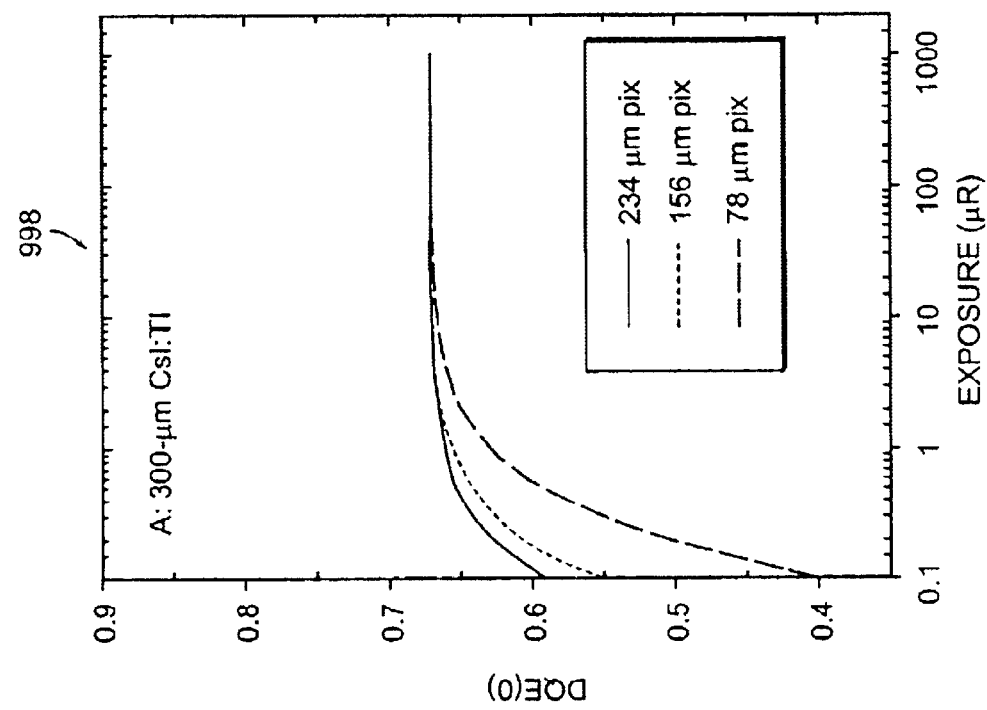
Figure 32D:
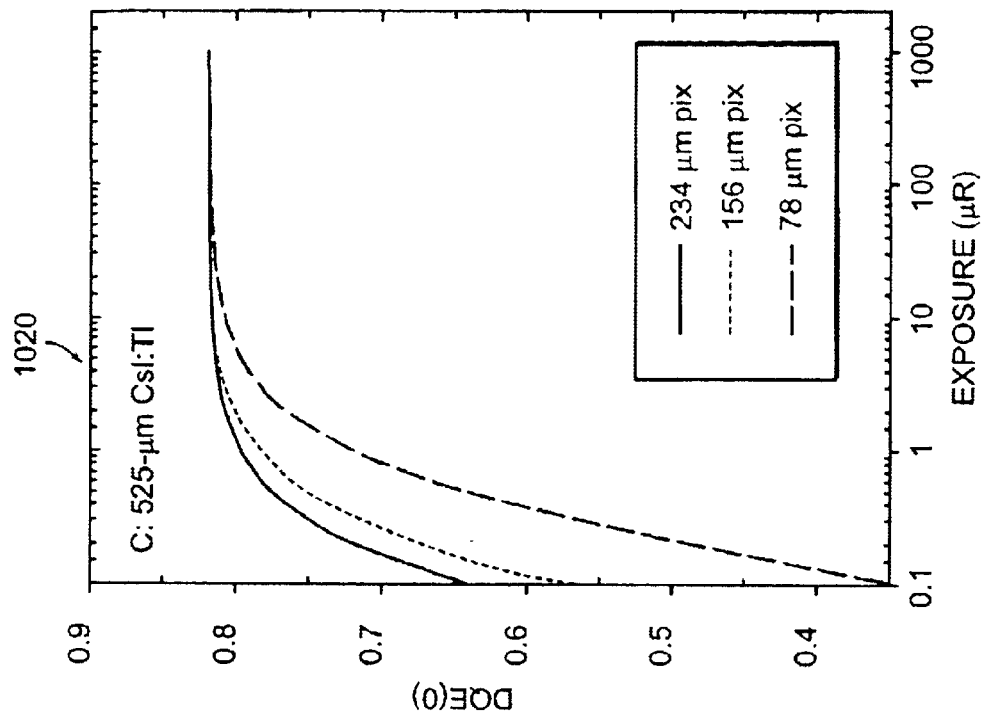
Figure 32C:
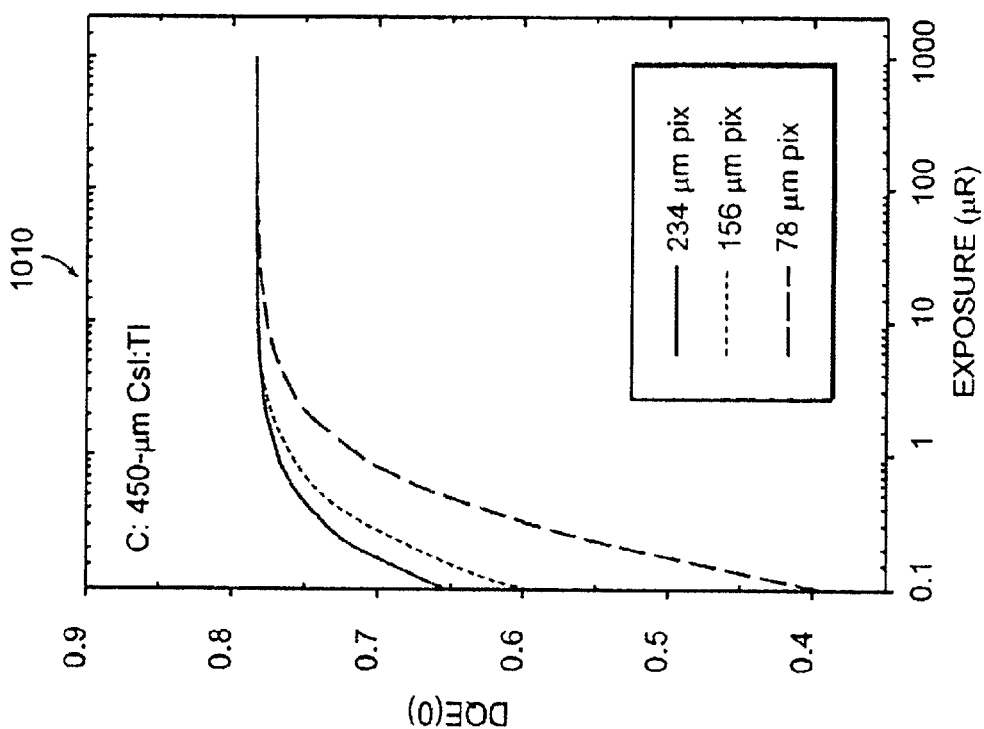
Figure 33:
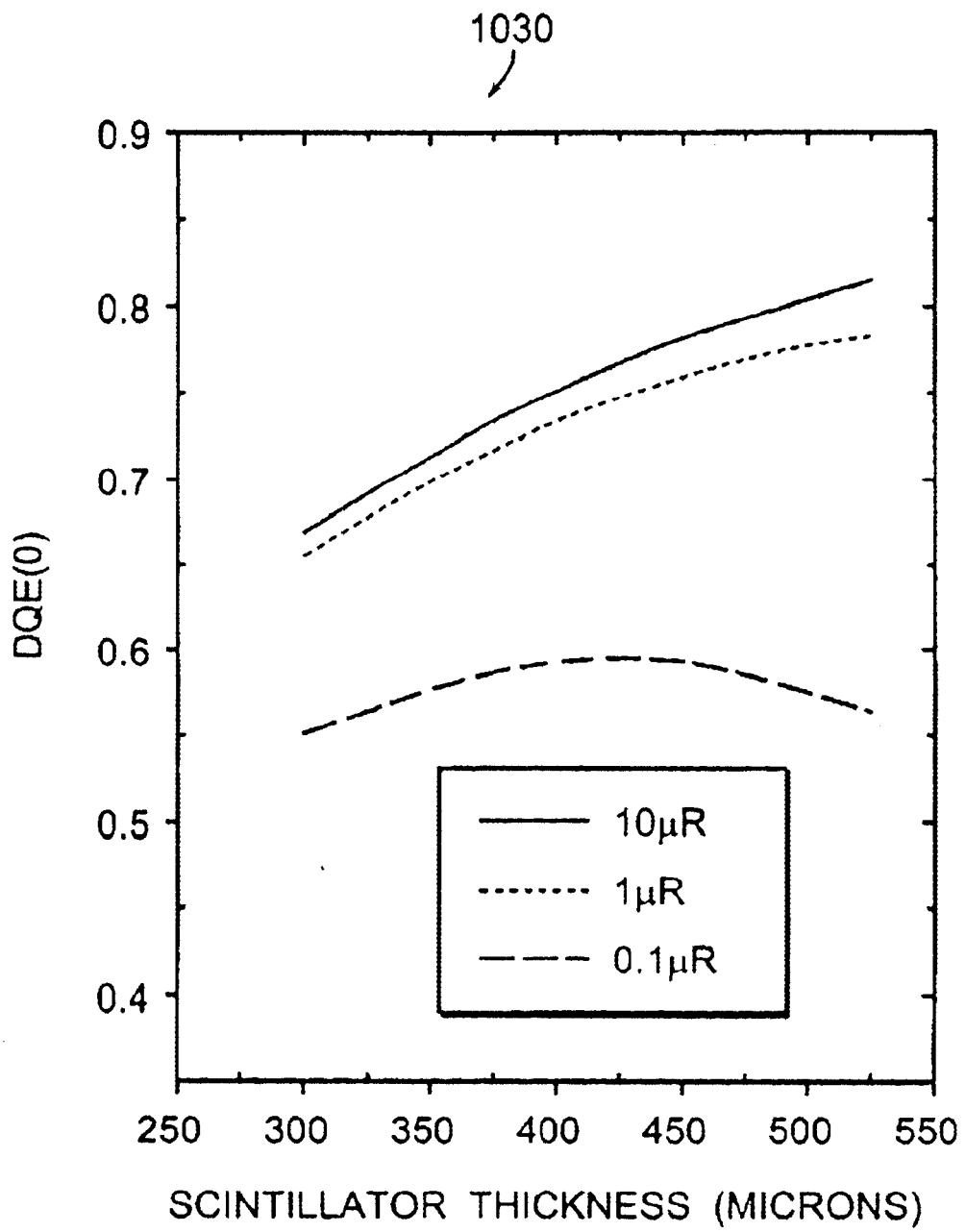
Figure 34A:
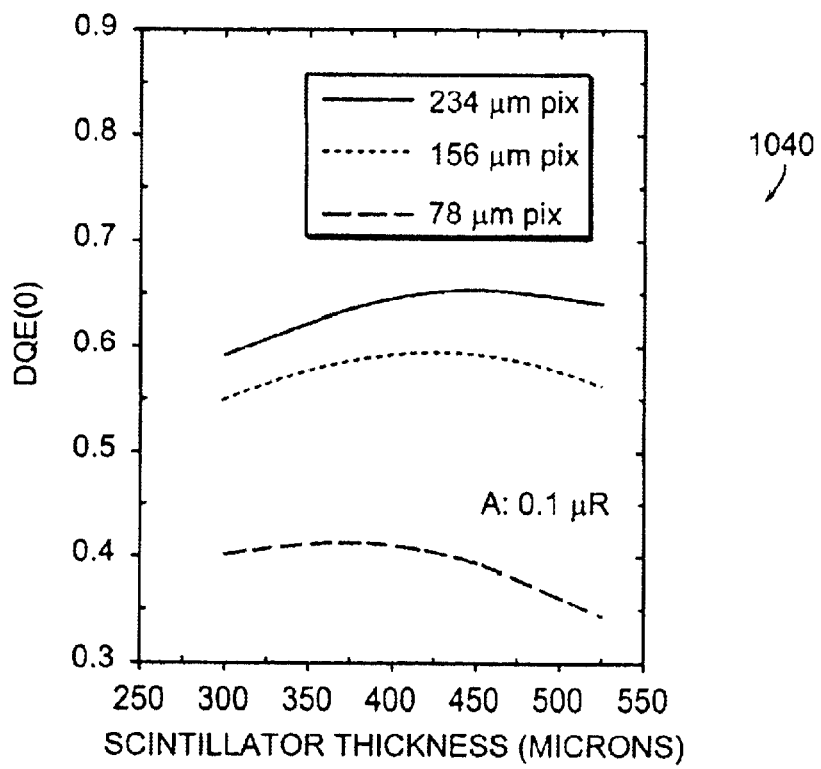
Figure 34B:
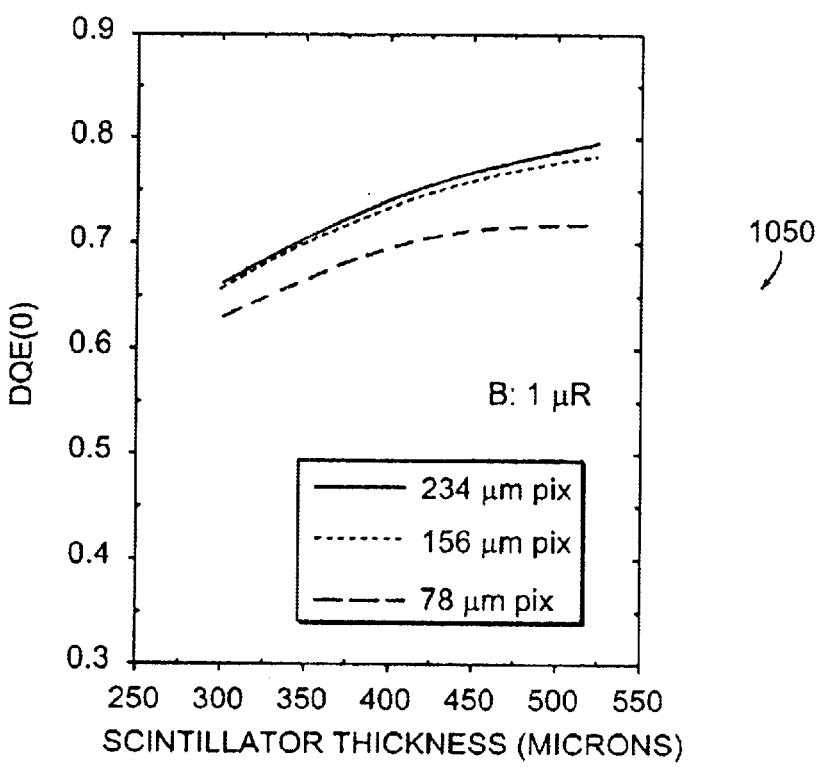
Figure 35A:
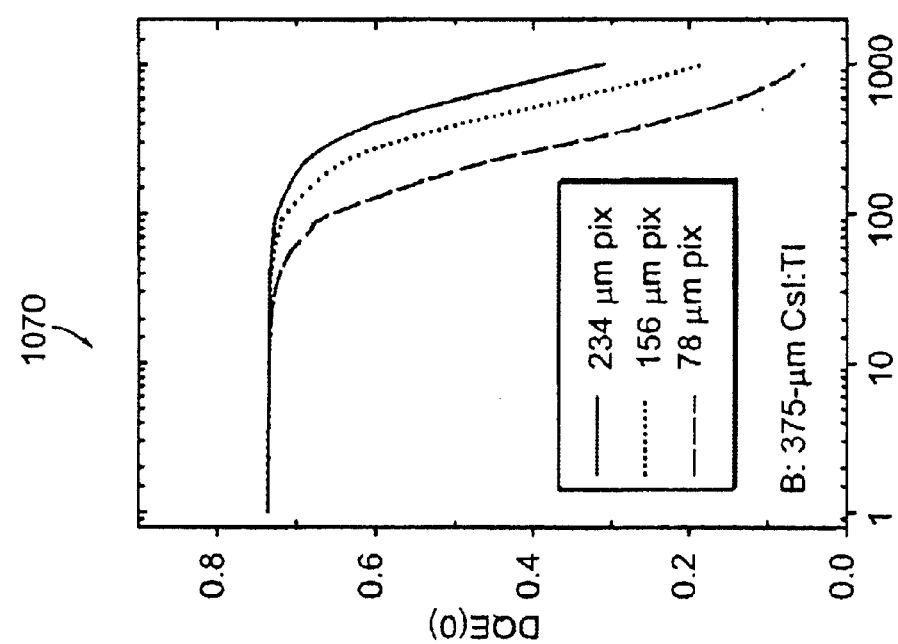
Figure 35B:
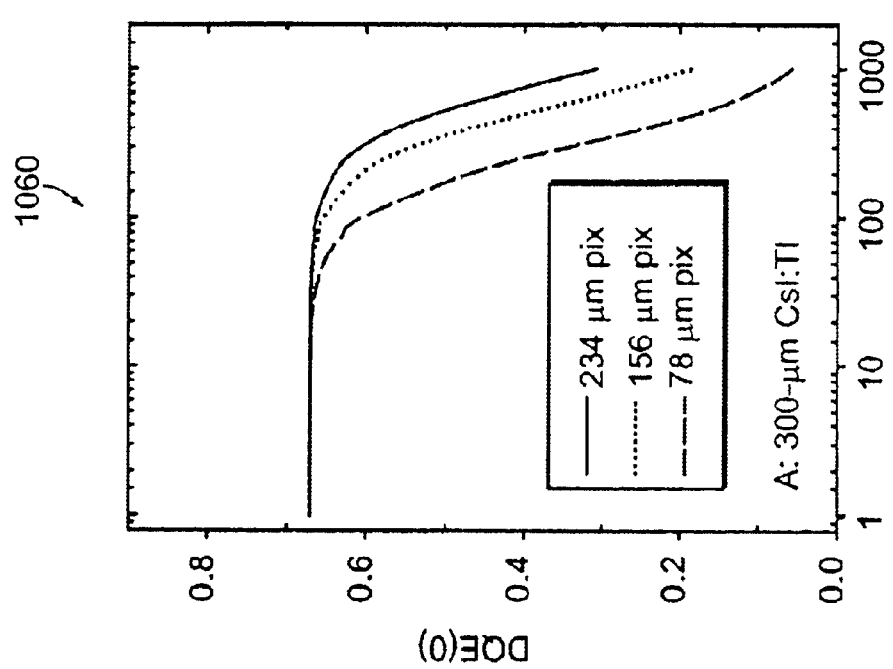
Figure 35D:
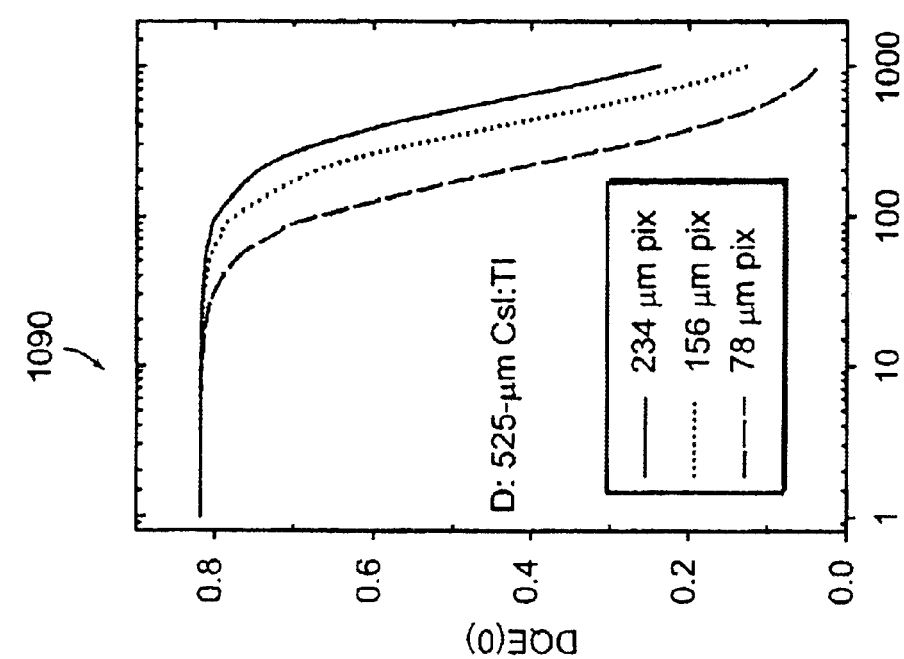
Figure 35C:
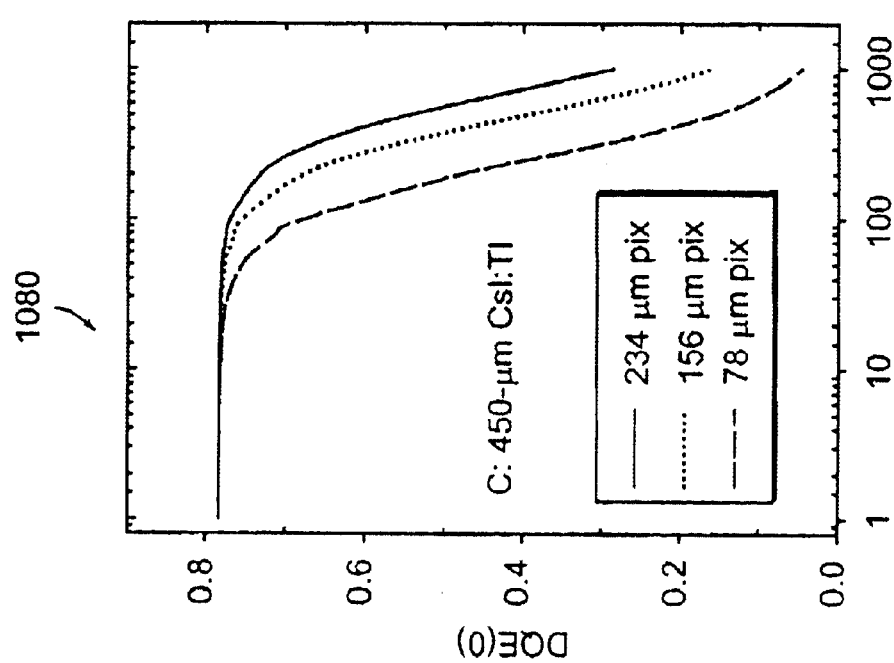
Figure 36A:
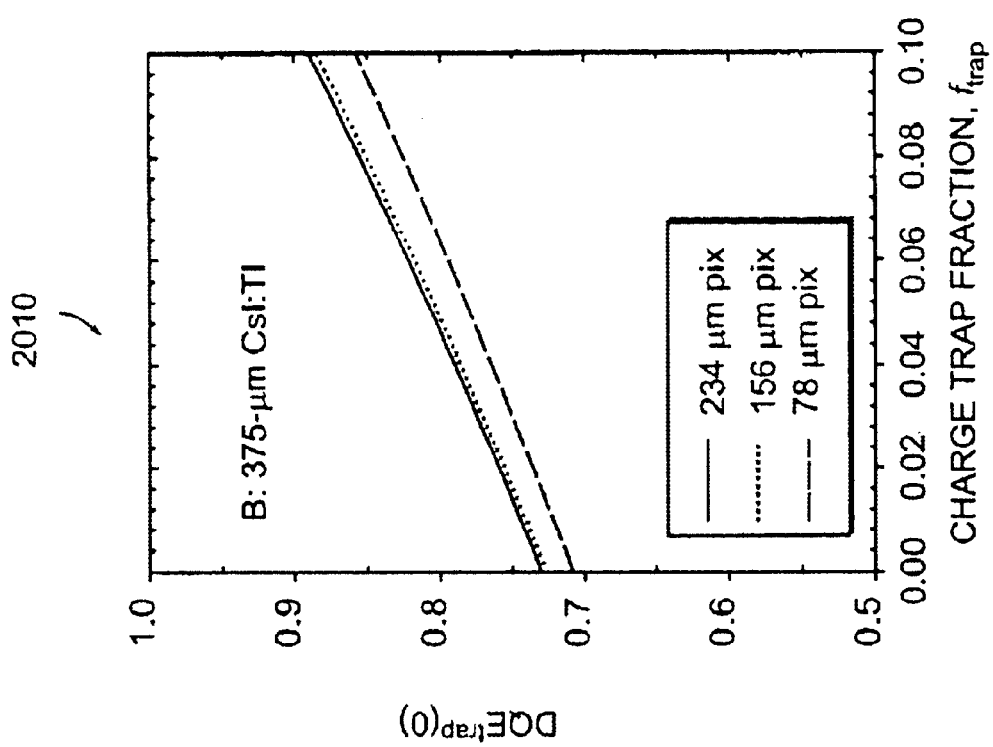
Figure 36B:
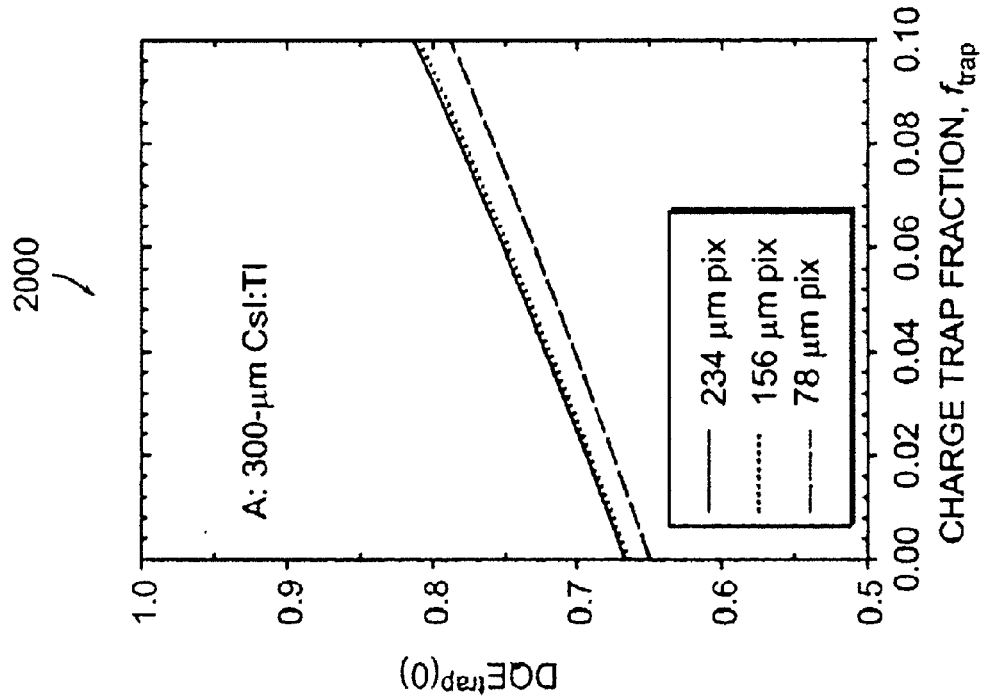
Figure 36D:
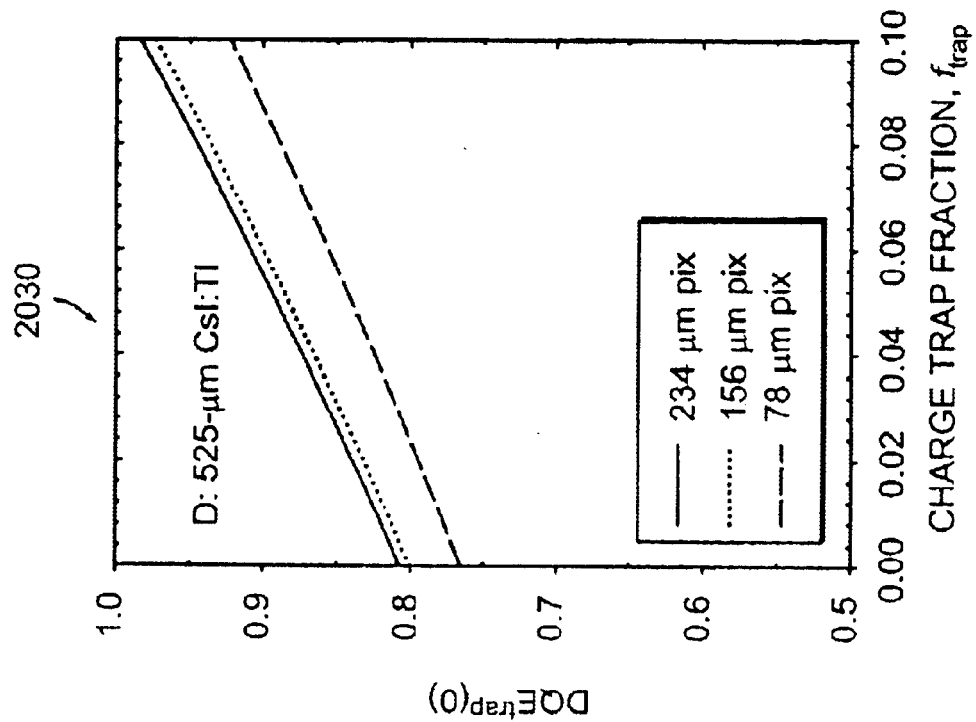
Figure 36C:
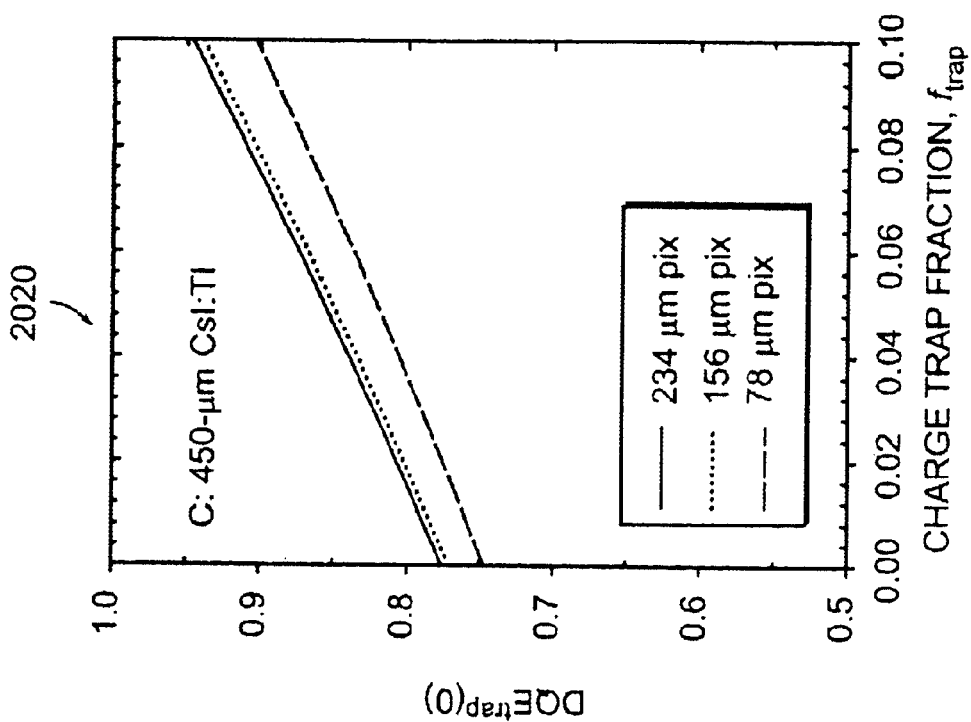
Figure 37A:
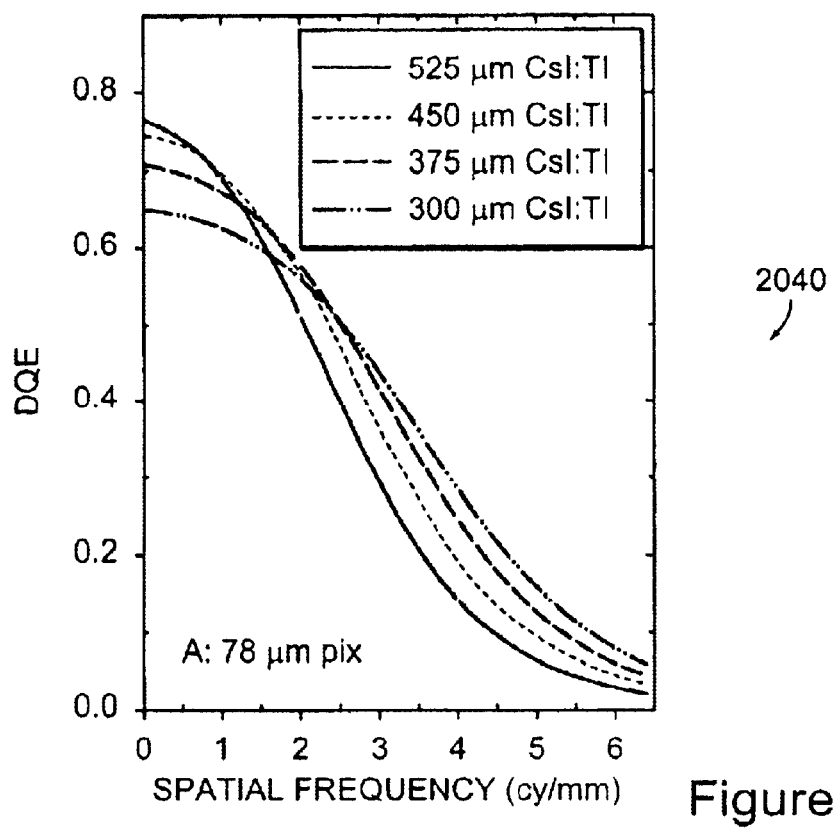
Figure 37B:
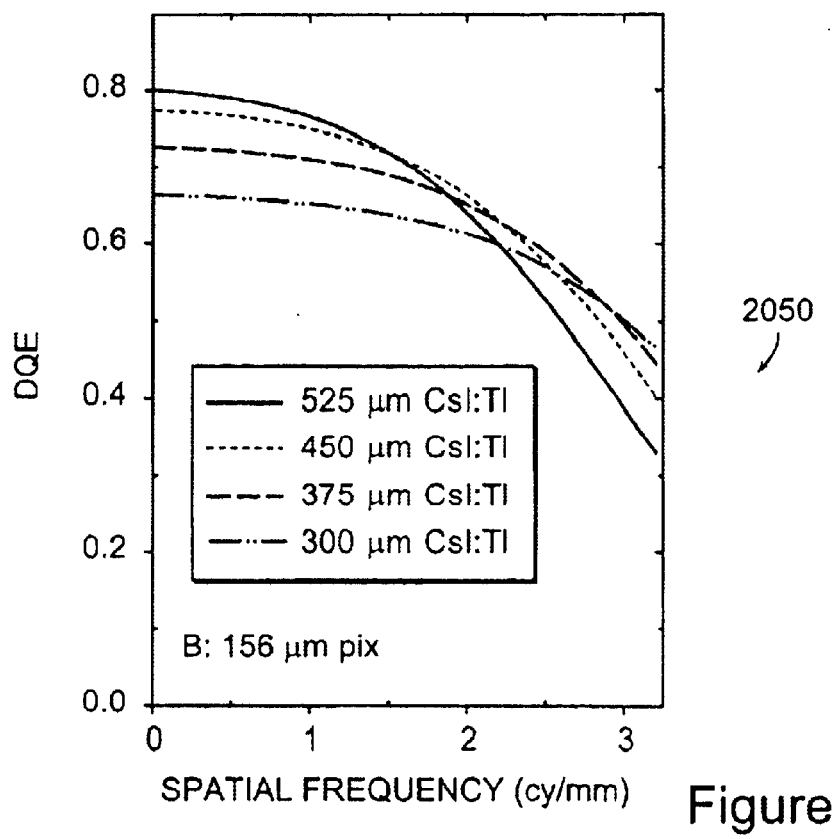
Figure 38A:
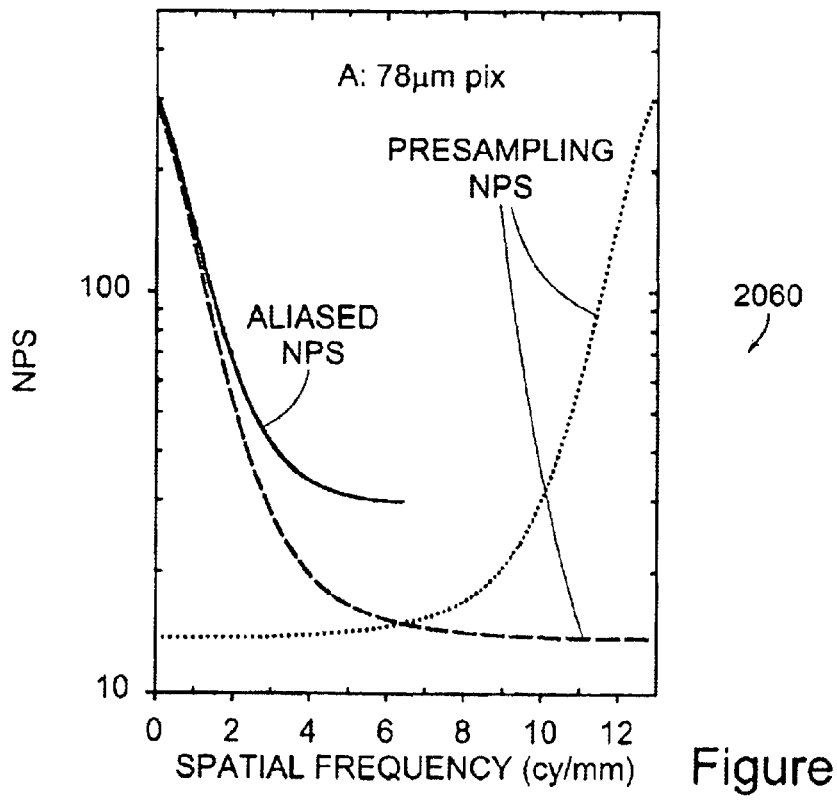
Figure 38B:
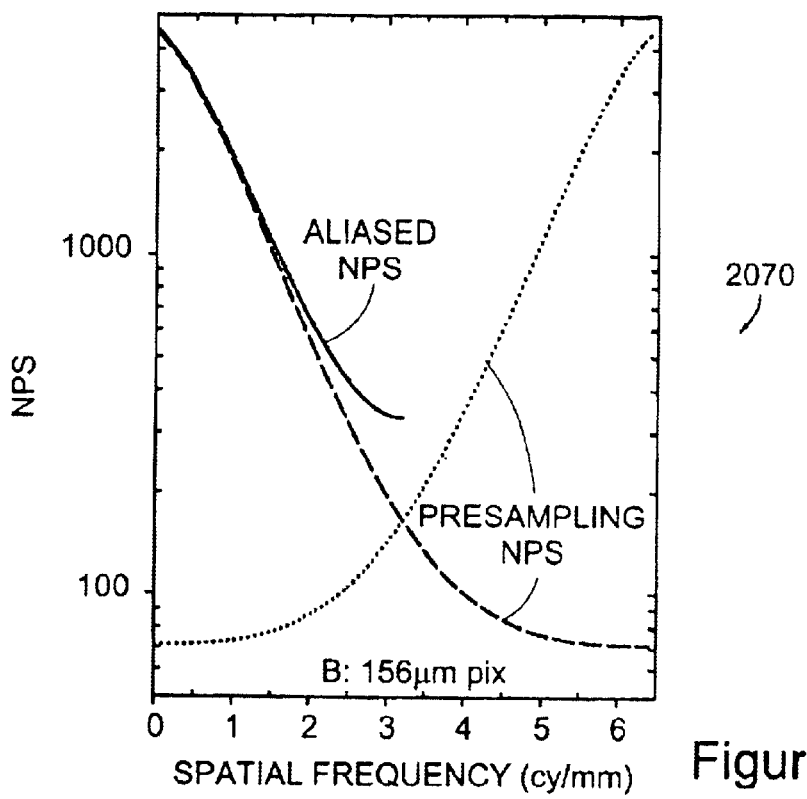
Figure 39:
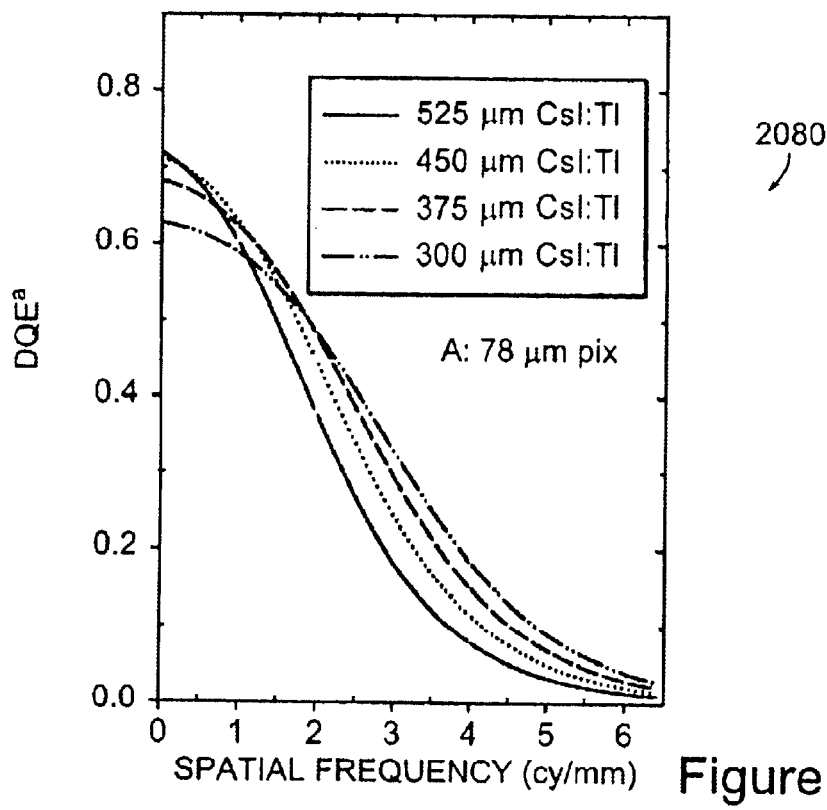
Figure 40:
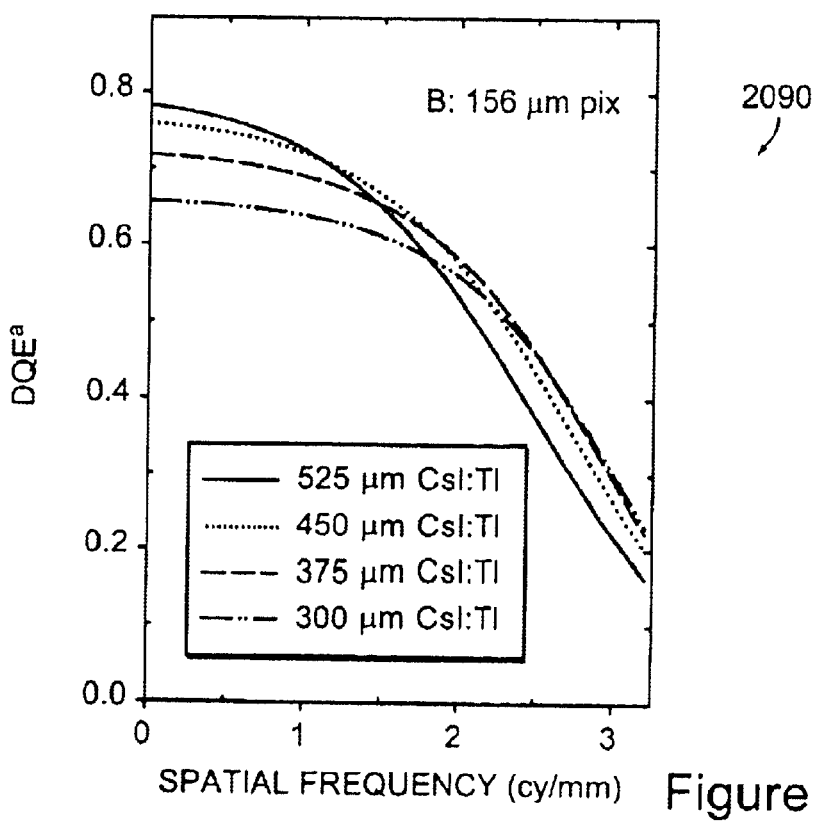
Figure 41A:
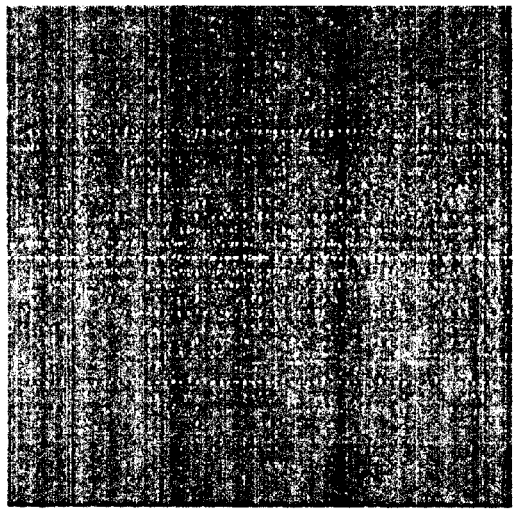
Figure 41B:
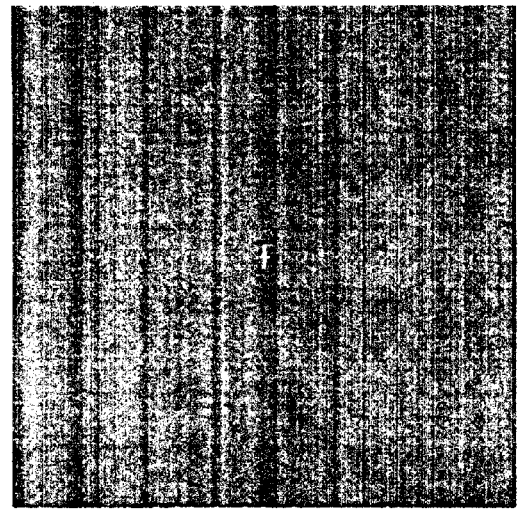
Figure 41C:
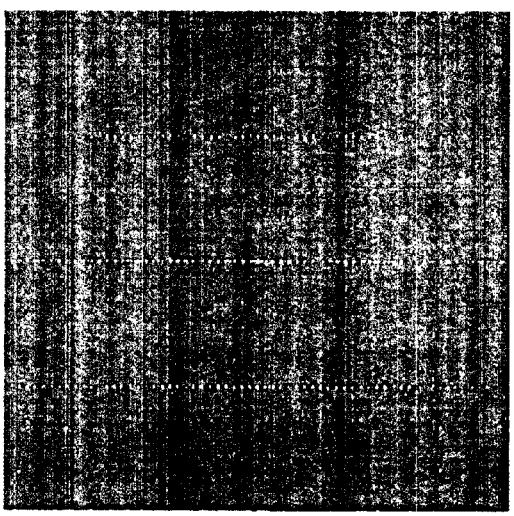
Figure 41D:
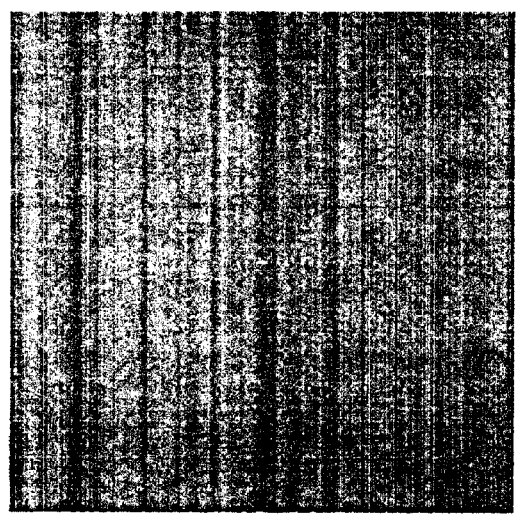
Figure 42A:
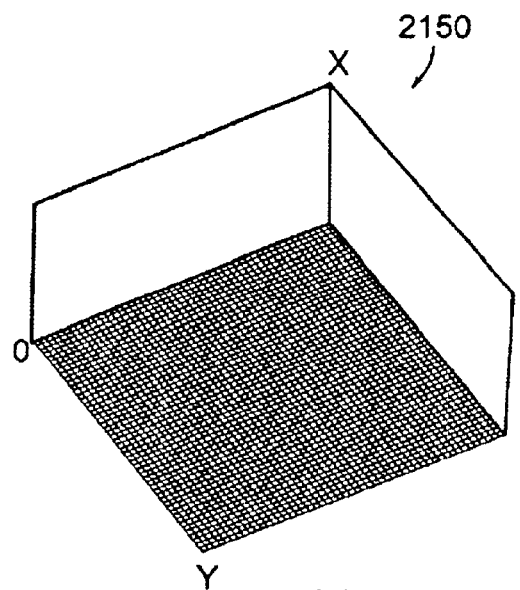
Figure 42B:
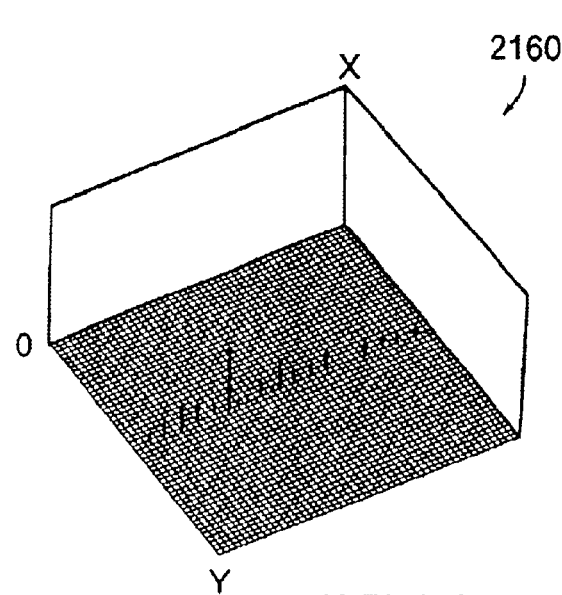
Figure 42C:
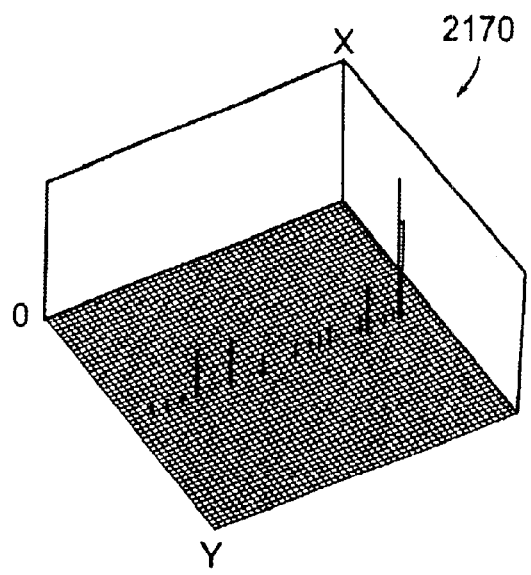
Figure 42D:
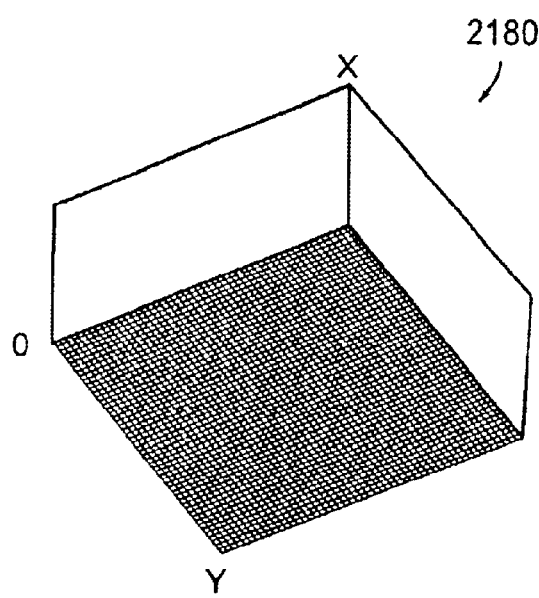
Figure 43:
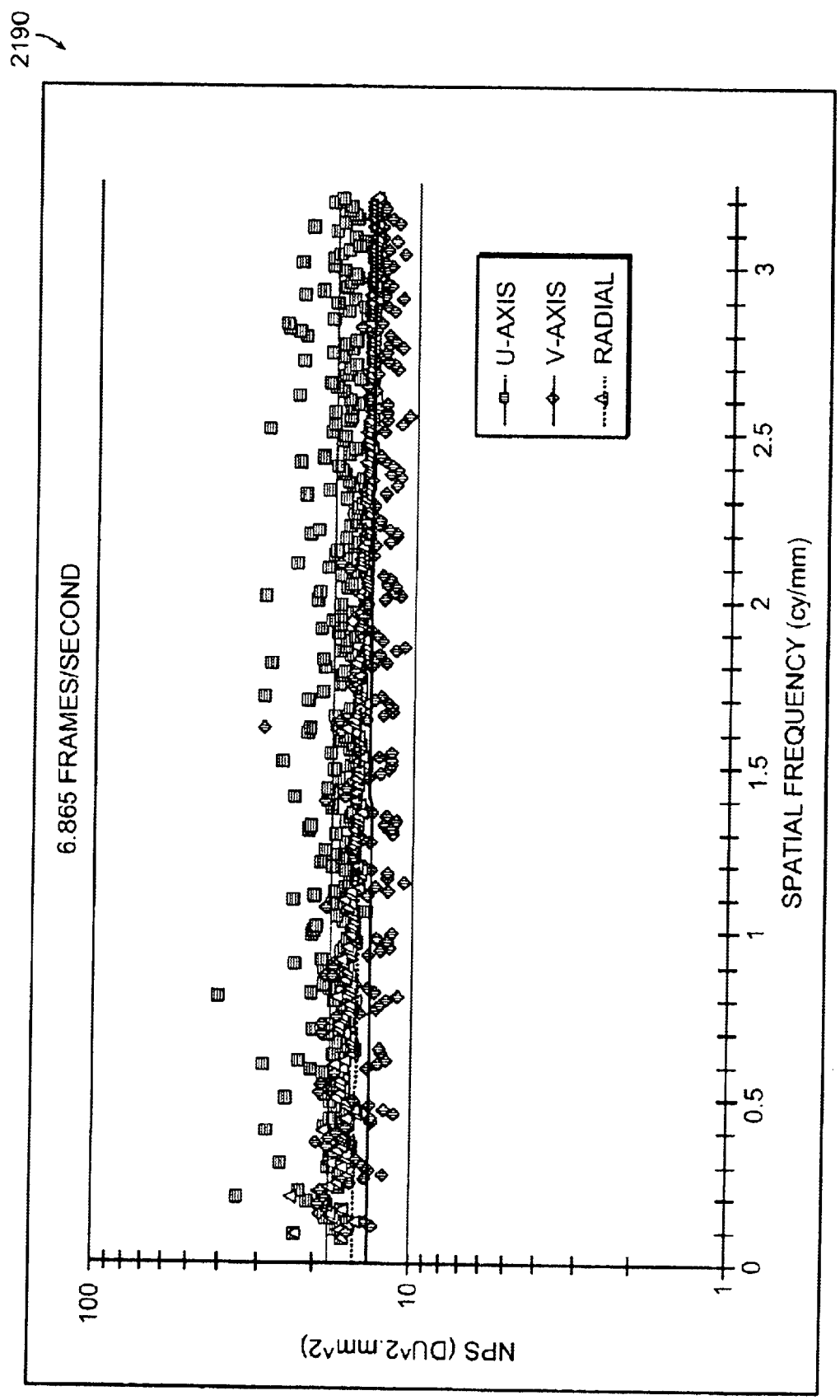
Figure 44:
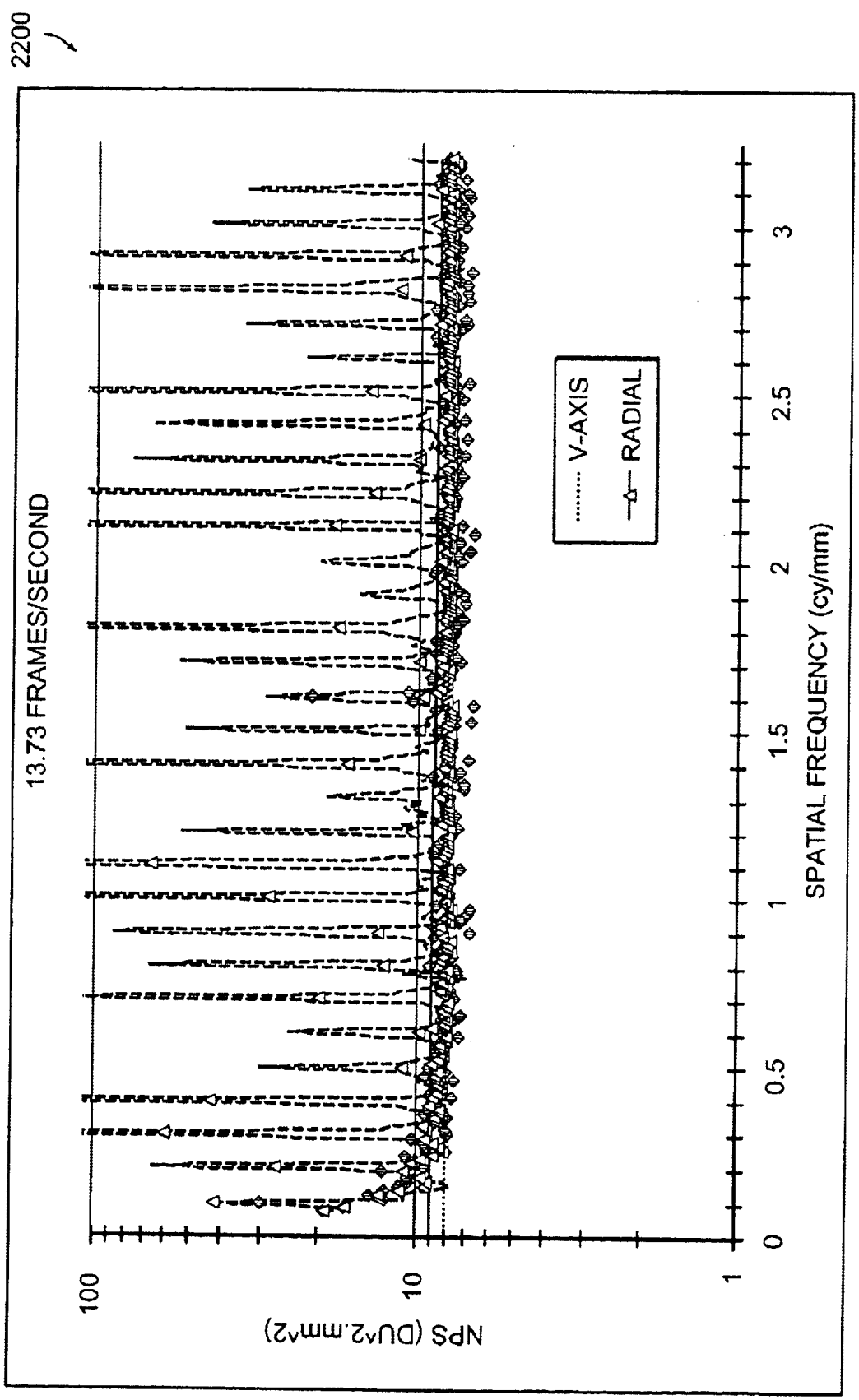
Figure 45:
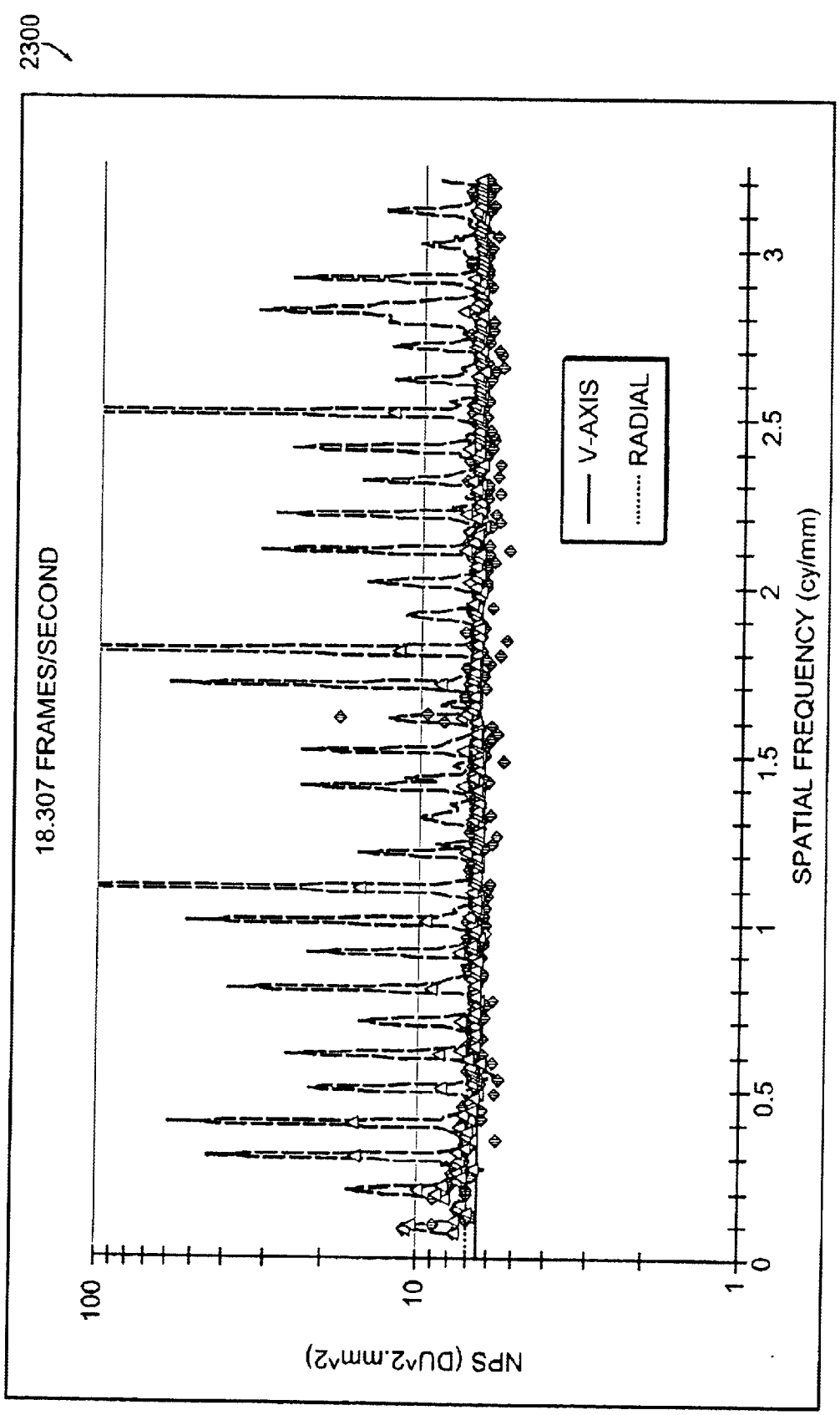
Figure 46:
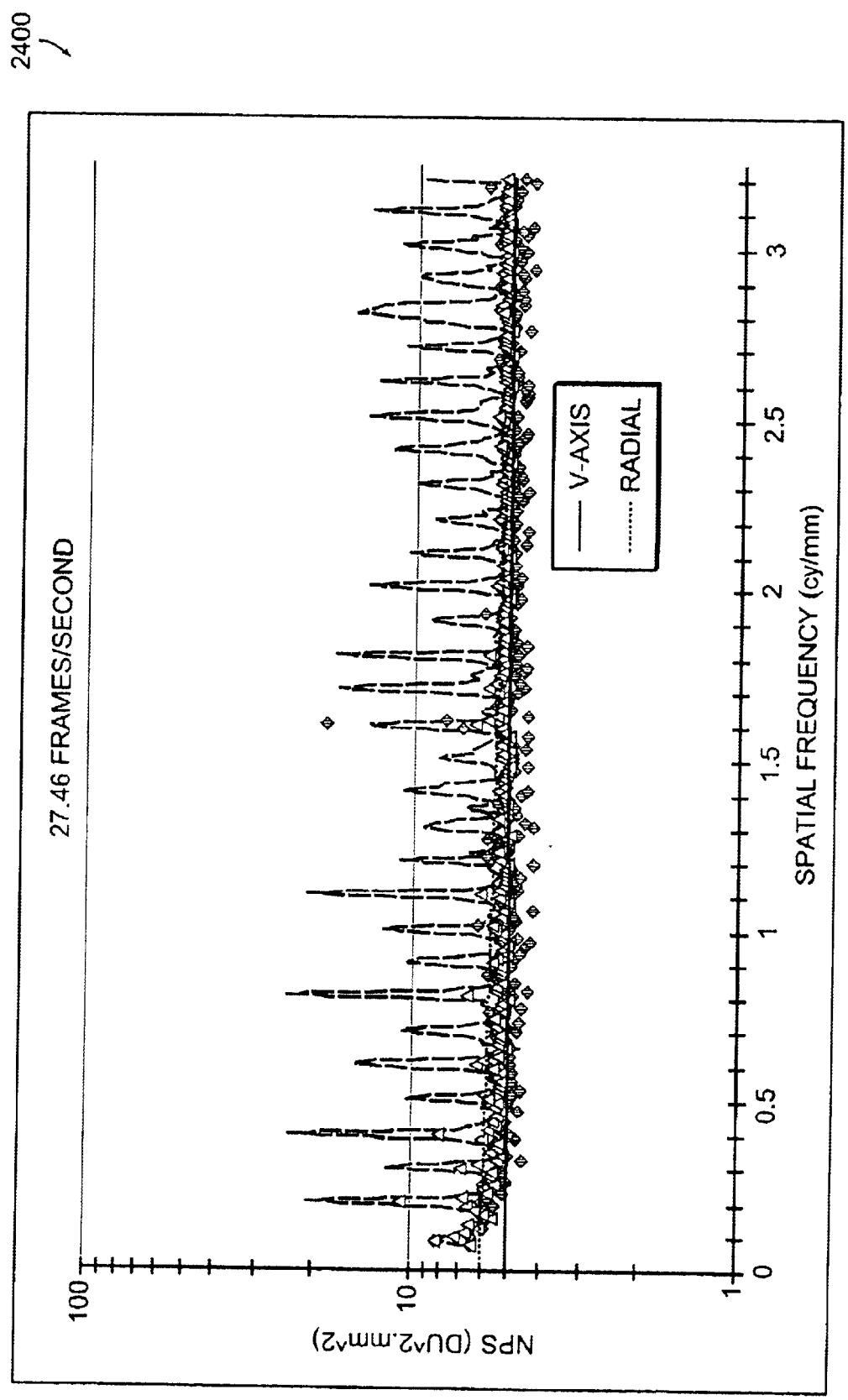
Figure 47:
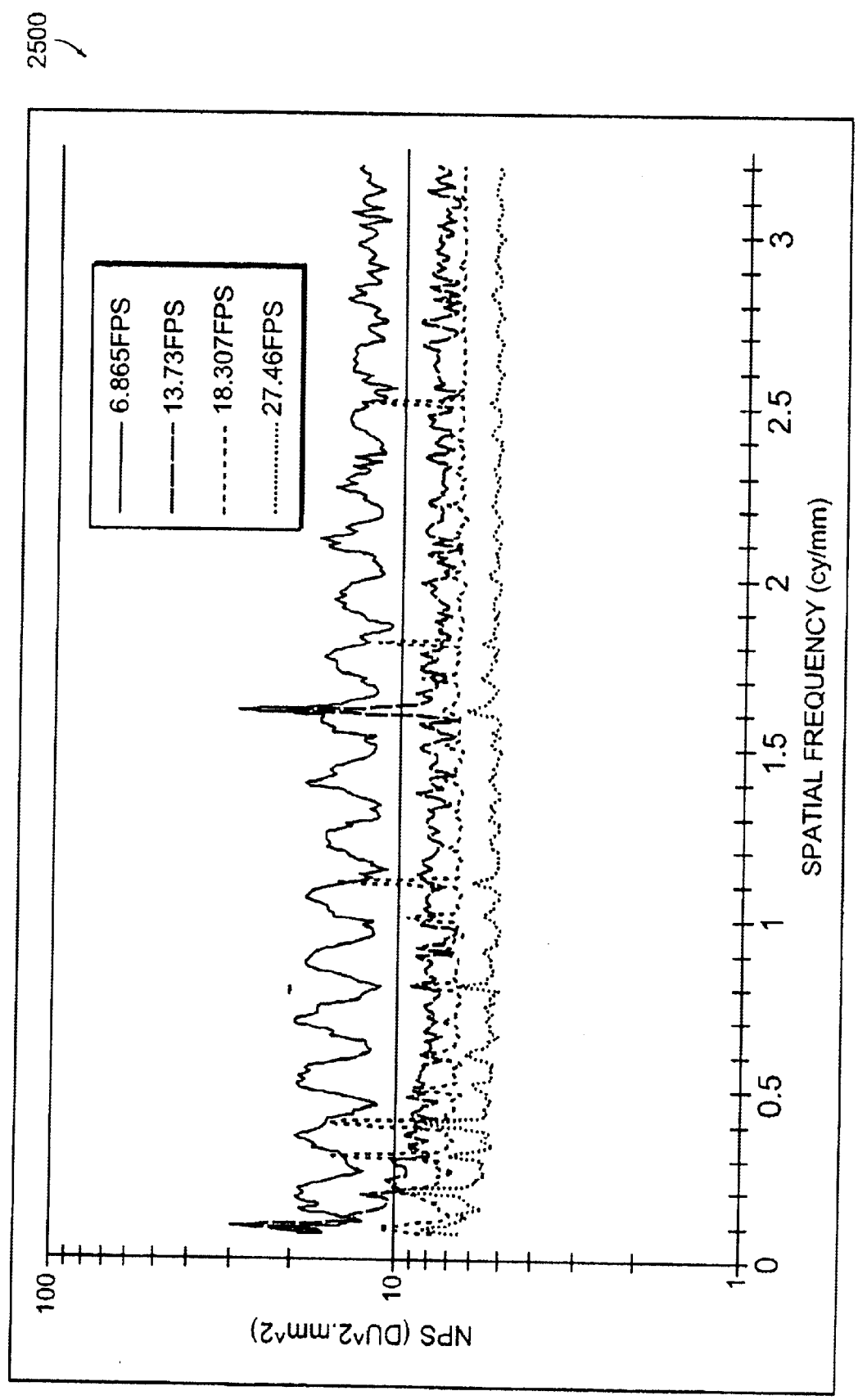
Figure 48:
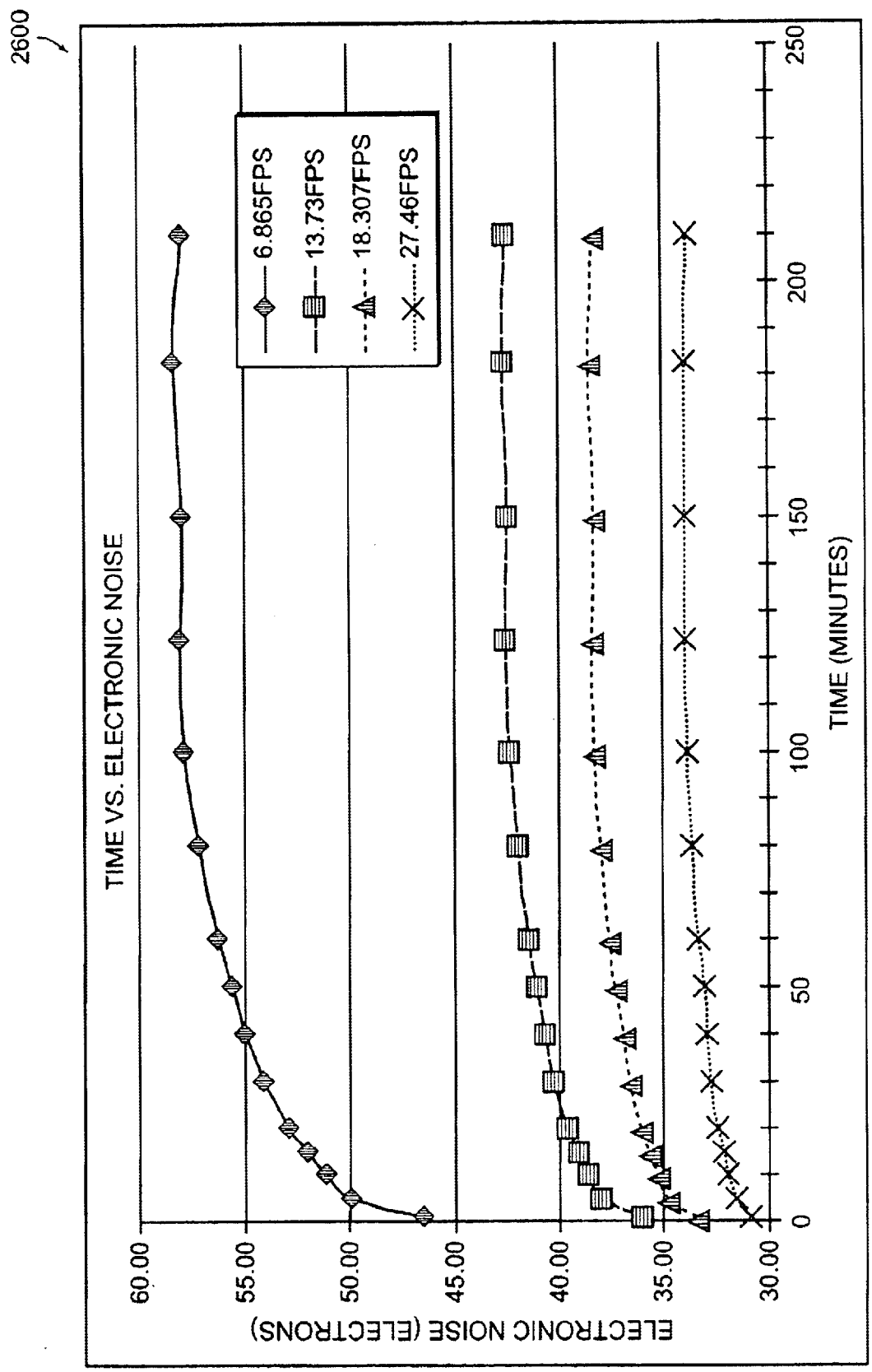
Figure 49:
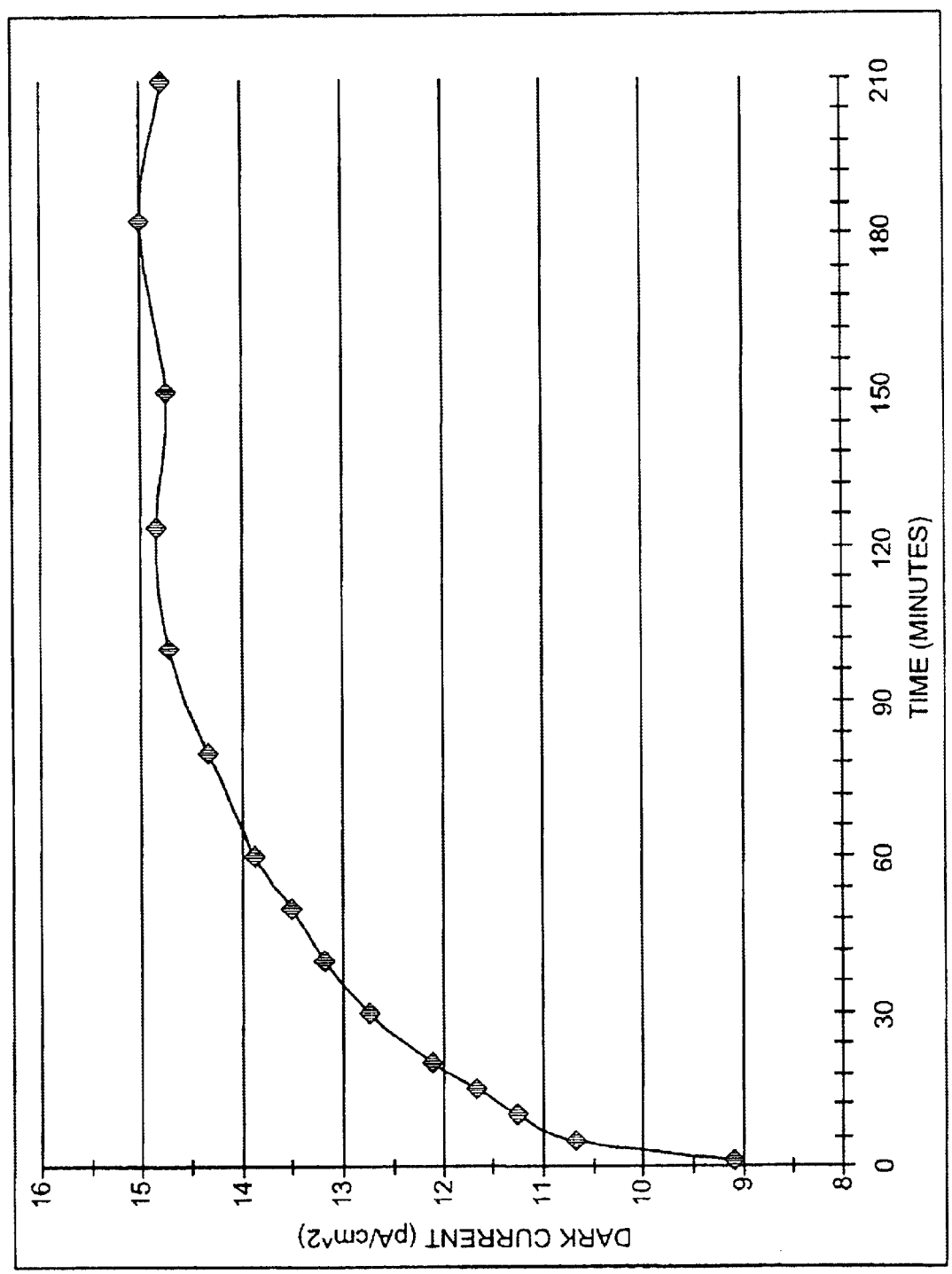
Figure 50:
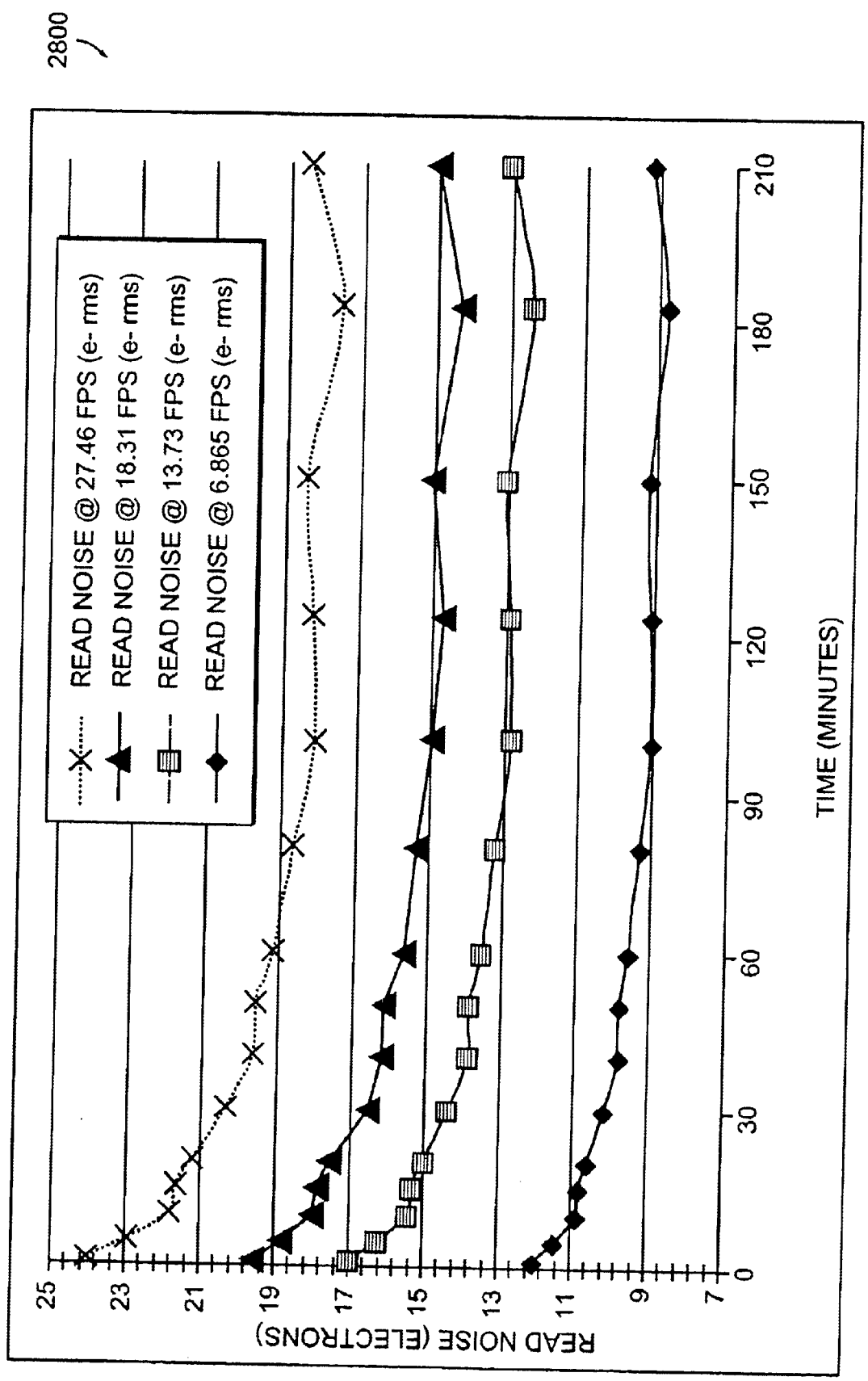
Figure 51:
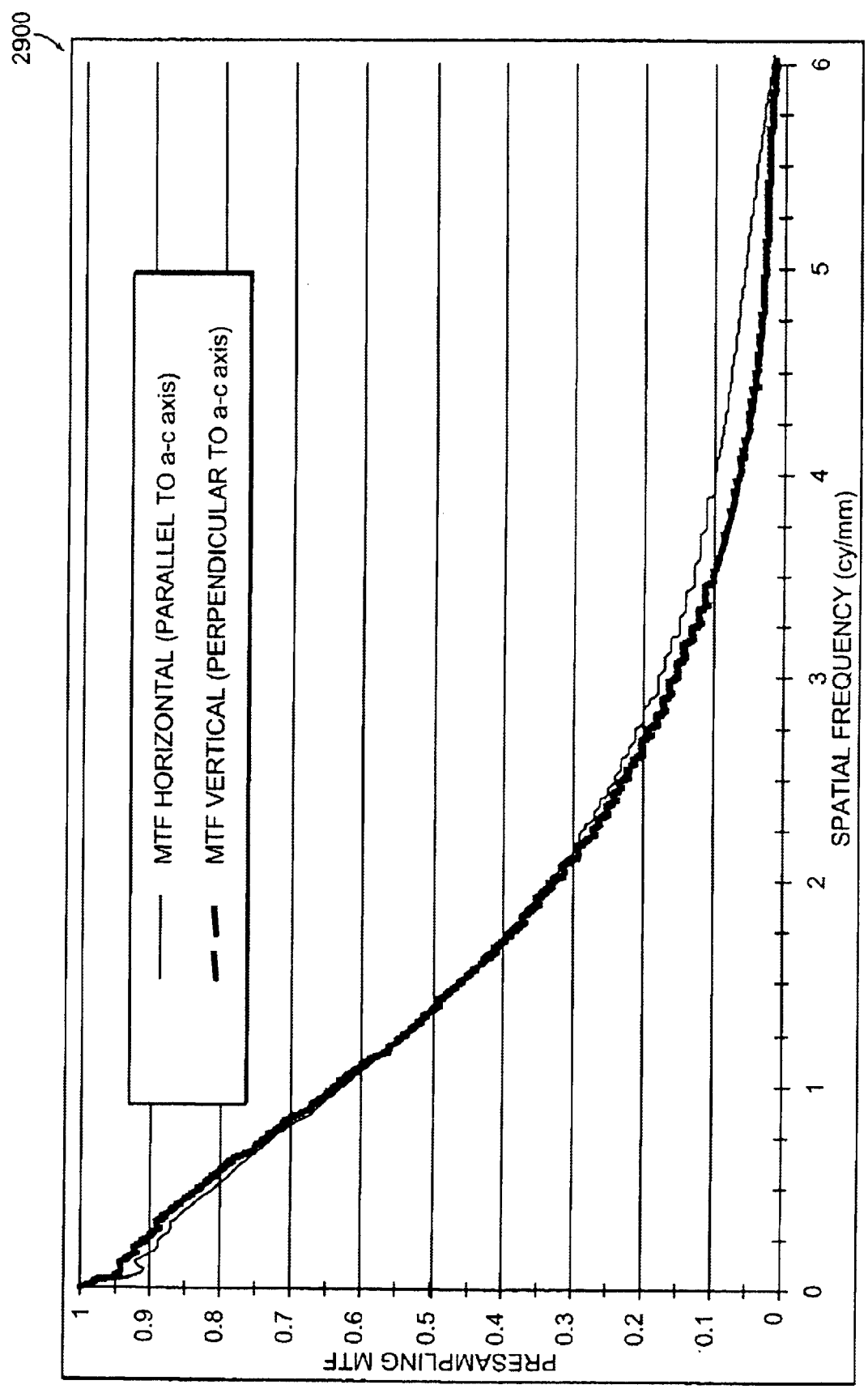
Figure 52:
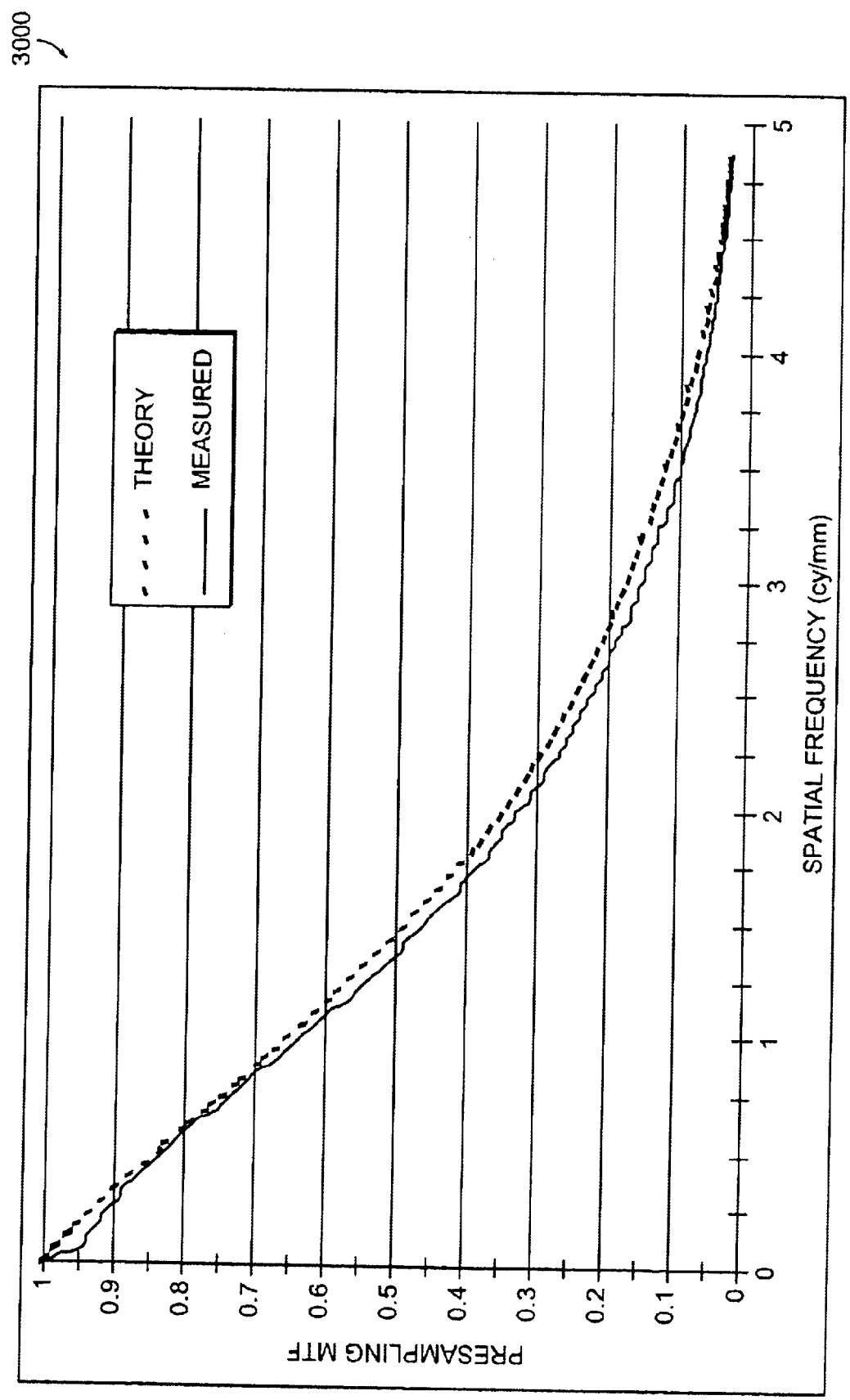
Figure 53:
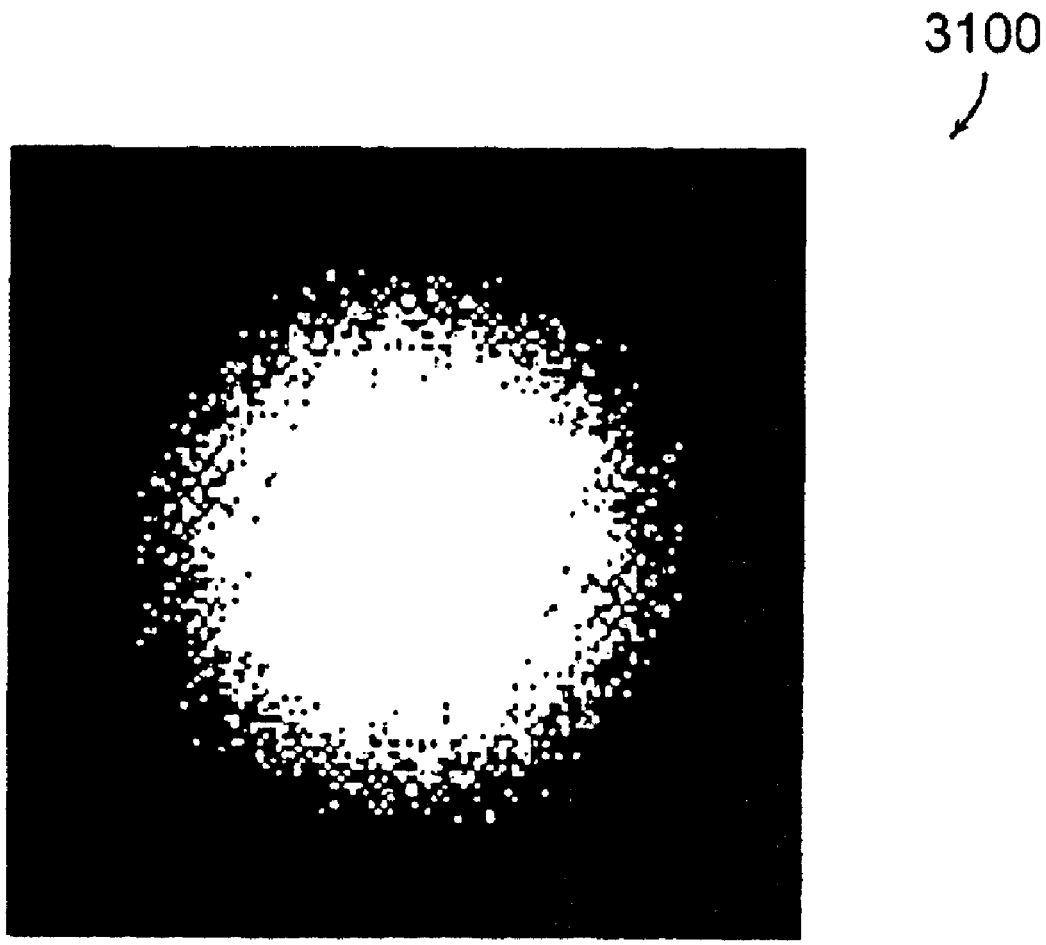
Figure 54:
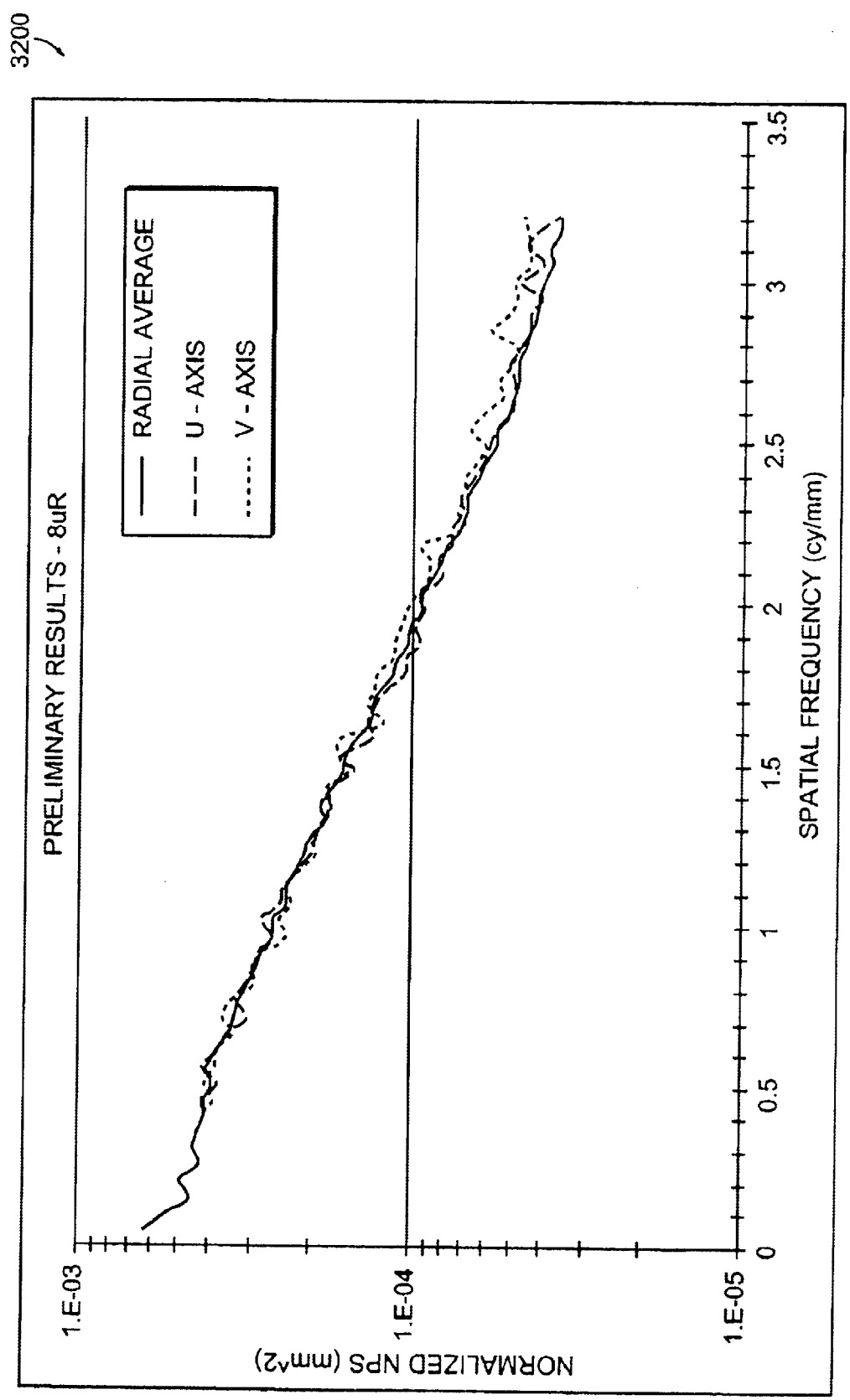
Figure 55:
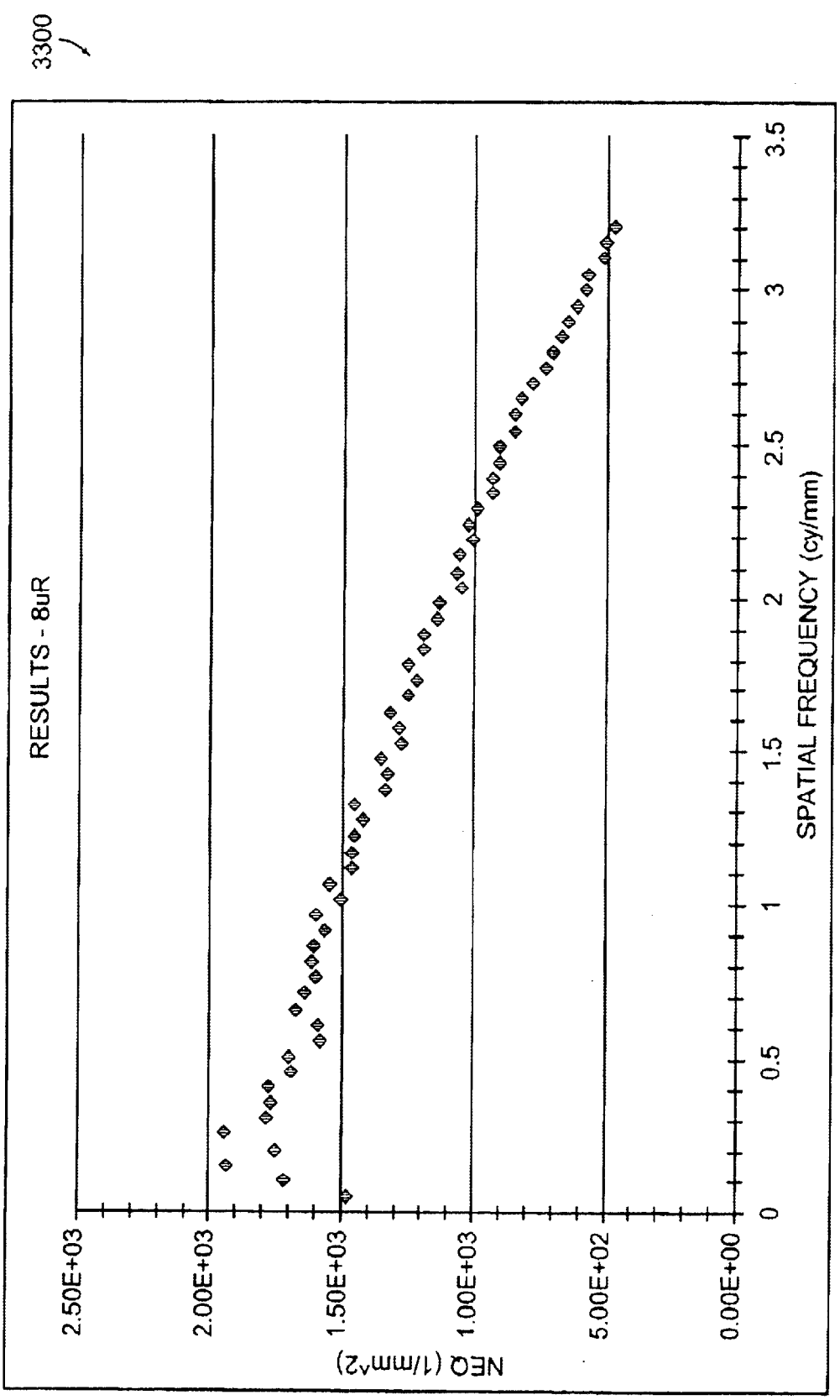
Figure 56:
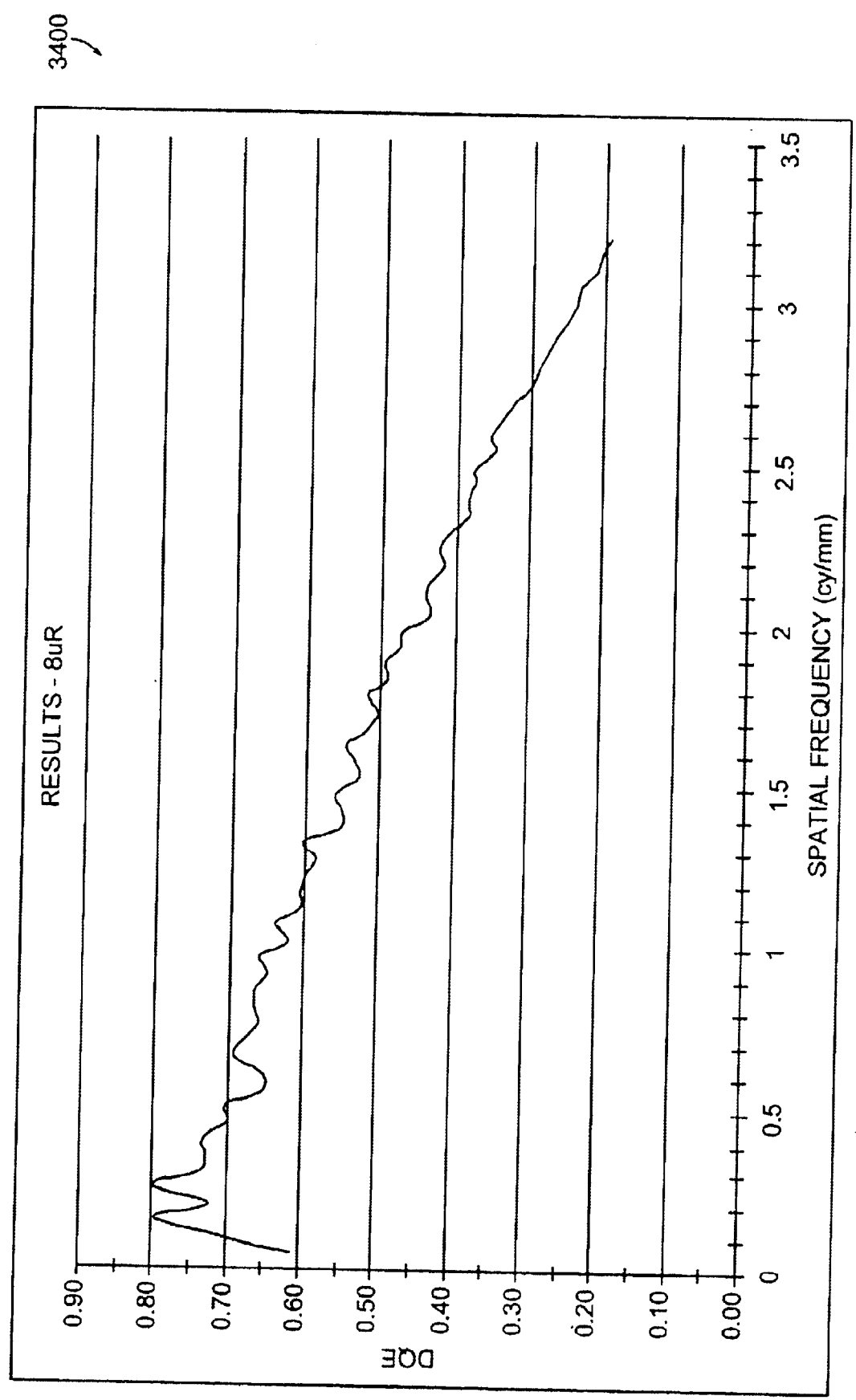
Figure 57:
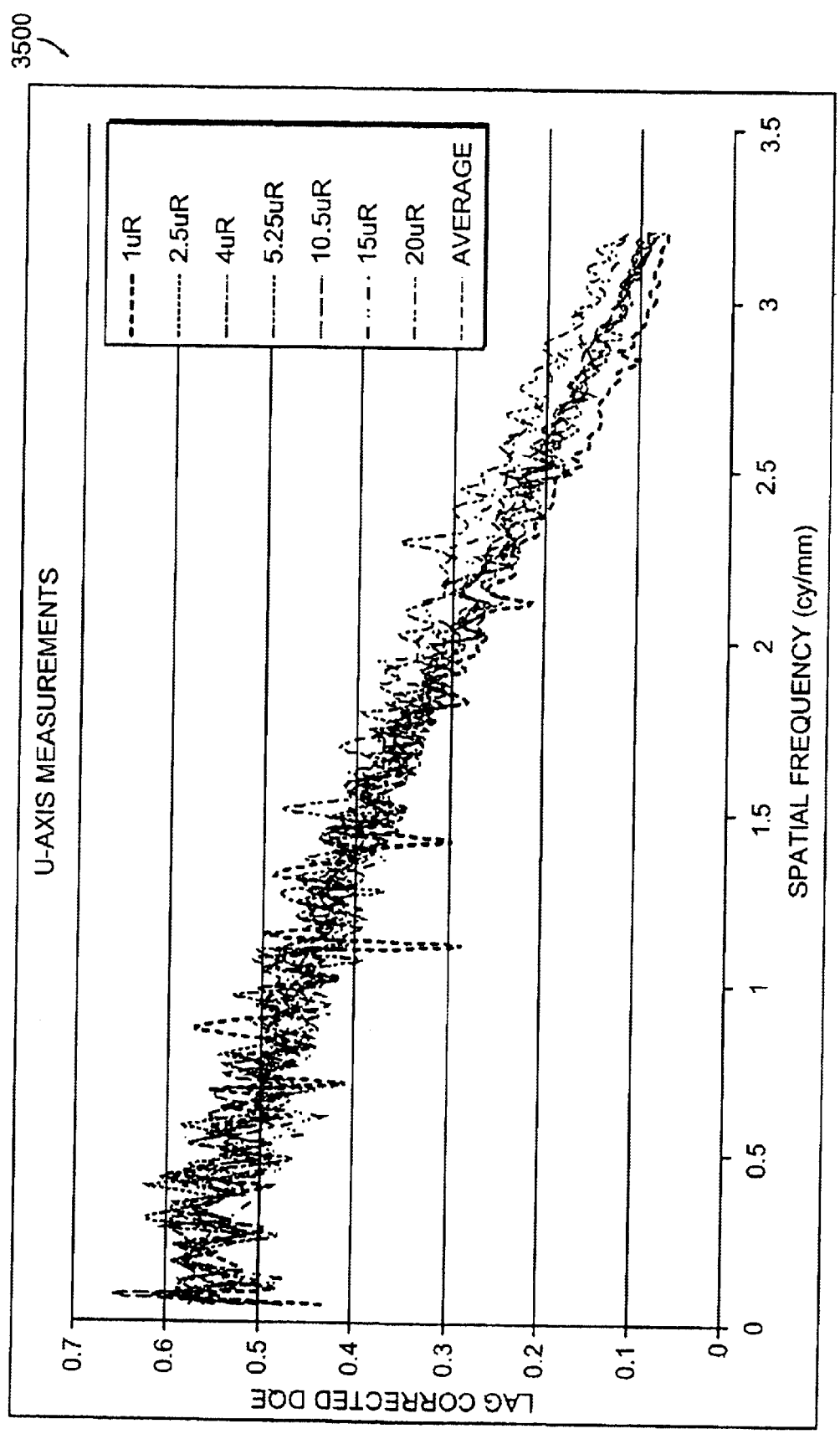
Figure 58:
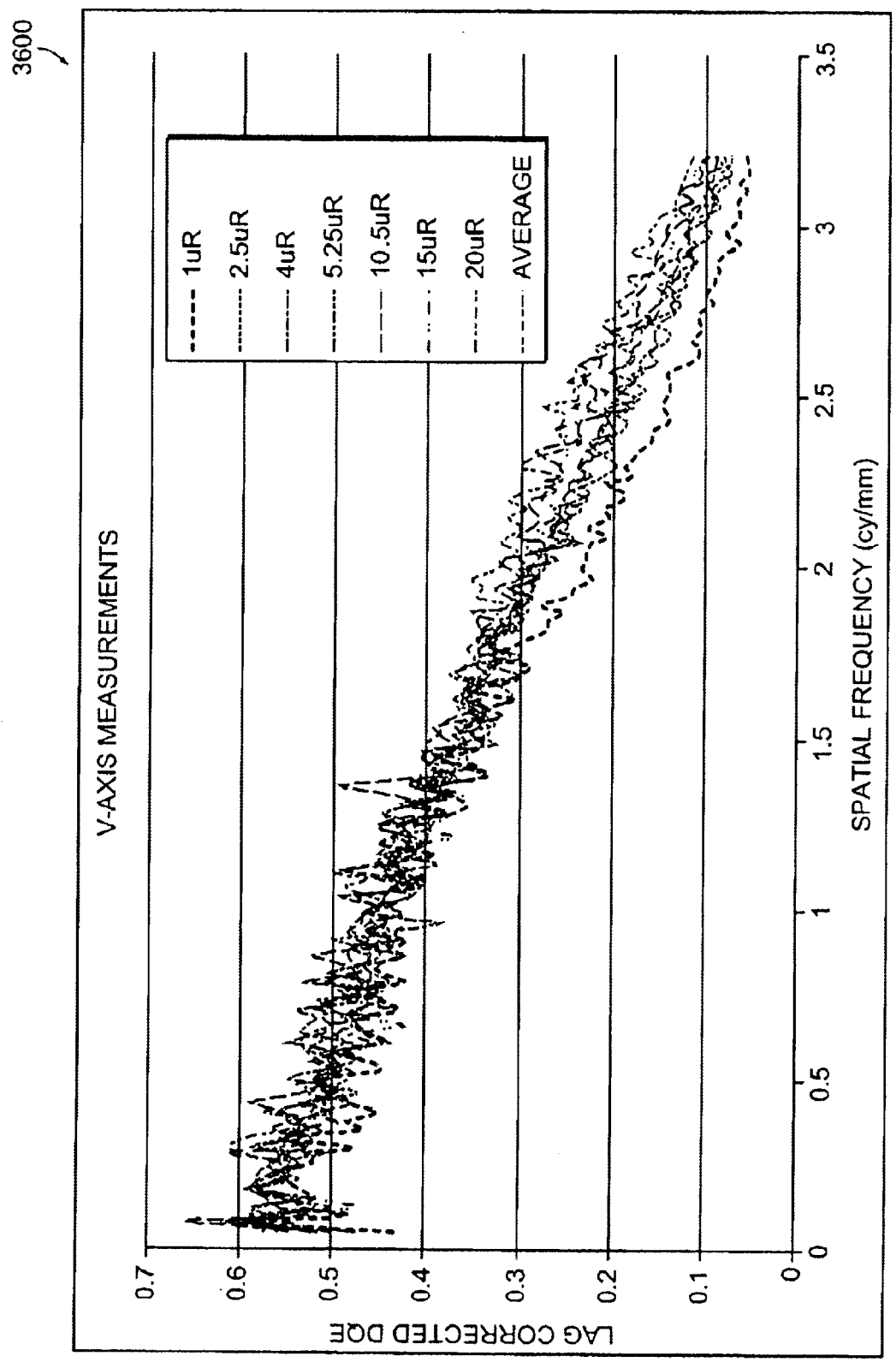
Figure 59:
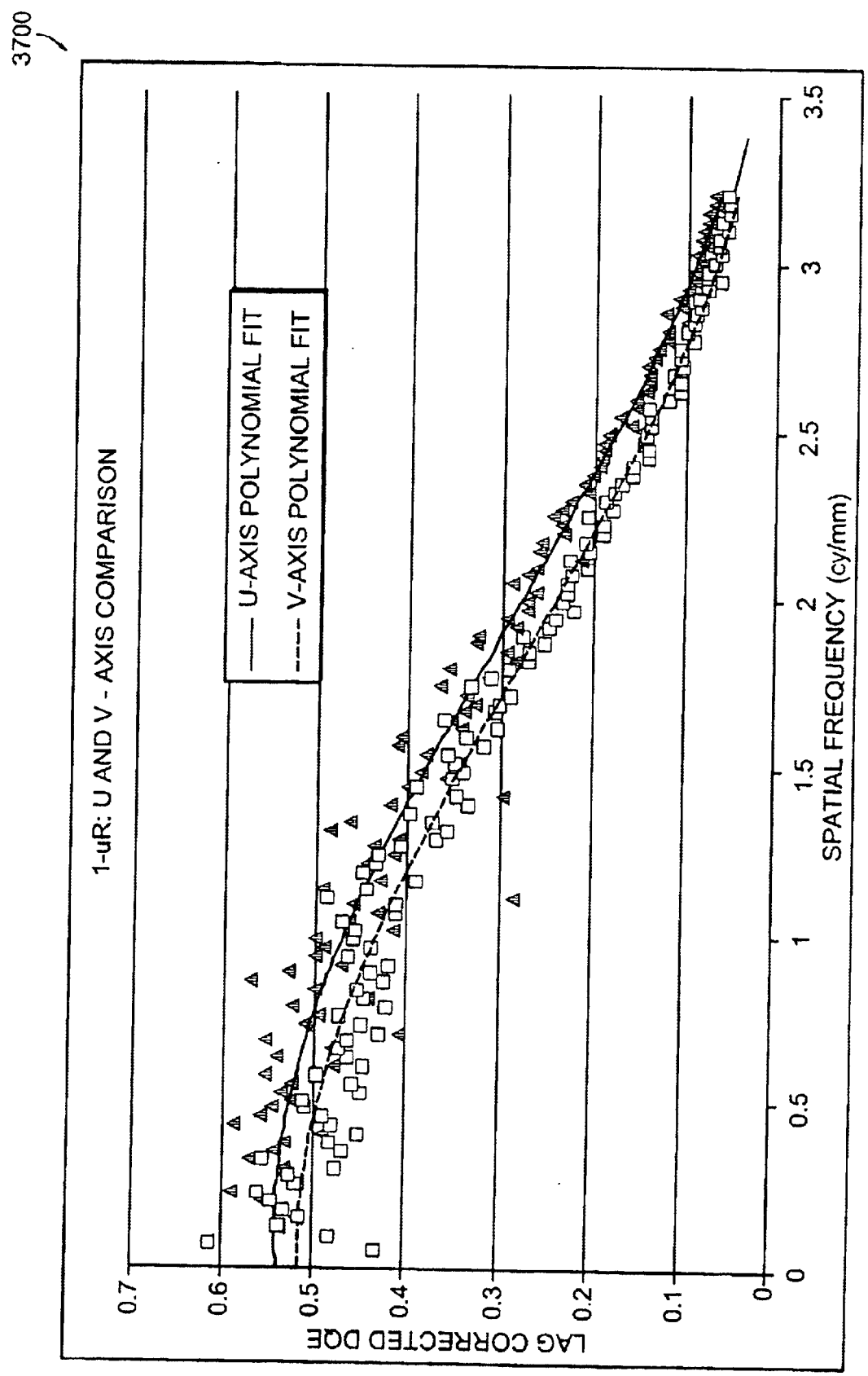
Figure 60:
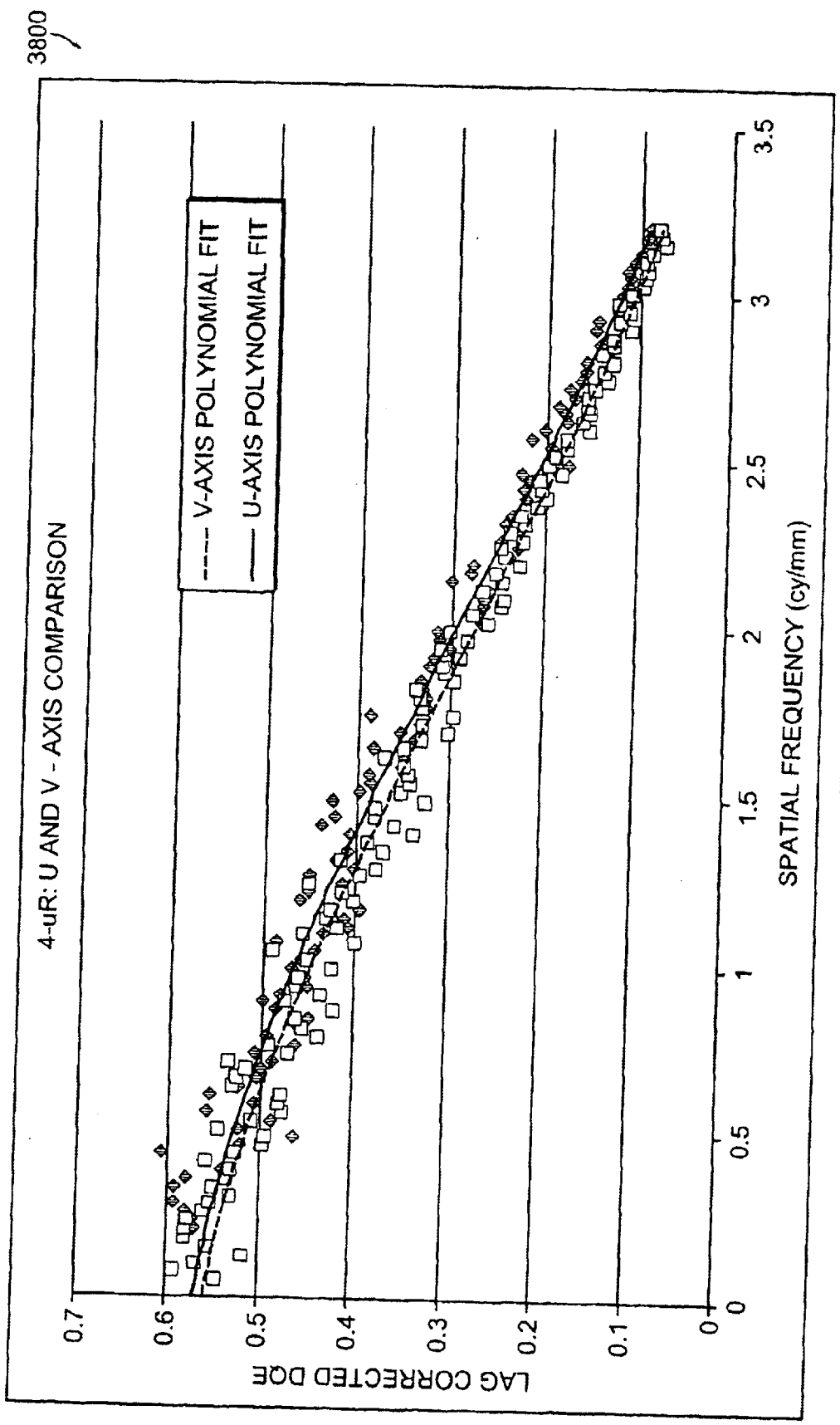

where B is the fit parameter and u is the spatial frequency in cycles/mm in accordance with a preferred embodiment of the present invention;

FIG. 31 graphically illustrates the fit parameter B, as a function of scintillator thickness in accordance with a preferred embodiment of the present invention;

FIGS. 32A–32D graphically illustrate the calculated exposure dependence of the detective quantum efficiency (DQE(0)) for the three pixel pitch modes of operation for each thickness of CsI:Tl scintillator in accordance with a preferred embodiment of the present invention;

FIG. 33 graphically illustrates the calculated detective quantum efficiency (DQE(0)) as a function of scintillator thickness at various exposure levels, for the imager operating at the 156-$\mu$m pixel pitch mode in accordance with a preferred embodiment of the present invention;

FIGS. 34A and 34B graphically illustrate the calculated detective quantum efficiency (DQE(0)) as a function of scintillator thickness for the three pixel pitch modes of operation at exposure levels of 0.1 and 1-$\mu$R in accordance with a preferred embodiment of the present invention;

FIGS. 35A–35D graphically illustrate the effect of additive noise on detective quantum efficiency (DQE(0)) using calculations performed at a nominal fluoroscopic exposure level of 2-μR in accordance with a preferred embodiment of the present invention;

FIGS. 36A–36D graphically illustrate the effect of charge trapping on the performance of the imaging system in accordance with a preferred embodiment of the present invention, wherein simulations were performed using a 2 μR exposure and certain additive noise levels;

FIGS. 37A and 37B graphically illustrate the detective quantum efficiency (DQE(f)) computed using the presampling signal and the presampling noise power spectrum (NPS) at a nominal fluoroscopic exposure level of 2-μR with additive noise for the 78 and 156-μm pixel pitch modes in accordance with a preferred embodiment of the present invention;

FIGS. 38A and 38B graphically illustrate the effect of aliasing on a frequency-dependent noise power spectrum (NPS), wherein the presampling NPS and the aliased NPS were computed using a 450-μm CsI:T1 scintillator at an exposure of 2-μR and additive noise for the 78 and 156-μm pixel pitch modes in accordance with a preferred embodiment of the present invention;

FIGS. 39 and 40 graphically illustrate detective quantum efficiency (DQE$^a$(f)) computed using the presampling signal and the aliased noise power spectrum (NPS) at a nominal fluoroscopic exposure level of 2-μR with additive noise for the 78 and 156-μm pixel pitch modes in accordance with a preferred embodiment of the present invention;

FIGS. 41A–41D illustrate two-dimensional noise power spectrum (NPS(u, v)) at various frame rates with no x-ray exposure to the detector (dark) in accordance with a preferred embodiment of the present invention;

FIGS. 42A–42D illustrate a three-dimensional perspective of the dark noise power spectrum at various frame rates in accordance with a preferred embodiment of the present invention;

FIG. 43 is a graphical illustration of the one-dimensional dark noise power spectrum at a frame rate of 6.865 frame/second in accordance with a preferred embodiment of the present invention;

FIG. 44 is a graphical illustration of the one-dimensional dark noise power spectrum at a frame rate of 13.73 frames/second in accordance with a preferred embodiment of the present invention;

FIG. 45 is a graphical illustration of the one-dimensional dark noise power spectrum at a frame rate of 18.307 frames/second in accordance with a preferred embodiment of the present invention;

FIG. 46 is a graphical illustration of the one-dimensional dark noise power spectrum at a frame rate of 27.46 frames/second in accordance with a preferred embodiment of the present invention;

FIG. 47 is a graphical illustration of the estimates of the one-dimensional dark noise power spectrum for all four frame rates in accordance with preferred embodiments of the present invention;

FIG. 48 is a graphical illustration of the time domain analysis of electronic noise for a plurality of frame rates in accordance with a preferred embodiment of the present invention;

FIG. 49 is a graphical illustration of the dark current at various discrete time points in accordance with a preferred embodiment of the present invention;

FIG. 50 is a graphical illustration of the read noise at different frame rates in accordance with a preferred embodiment of the present invention;

FIG. 51 graphically illustrates the presampling Modulation Transfer Function (MTF) measured along two orthogonal directions at 70 kVp in accordance with a preferred embodiment of the present invention;

FIG. 52 graphically illustrates the comparison of experimental measurements with the theoretically predicted Modulation Transfer Function (MTF) based on prior measurements with a similar scintillator and a laboratory small-area, low-noise CCD, in accordance with a preferred embodiment of the present invention;

FIG. 53 illustrates a two-dimensional normalized noise power spectrum measured at 8 μR indicating good isotropy in accordance with a preferred embodiment of the present invention;

FIG. 54 graphically illustrates a one-dimensional normalized noise power spectrum (NPS) determined along u, v-axes and by radial averaging of the 2-D normalized NPS in accordance with a preferred embodiment of the present invention;

FIG. 55 graphically illustrates the noise equivalent quanta (NEQ) measured at 8 μR in accordance with a preferred embodiment of the present invention;

FIG. 56 graphically illustrates the detective quantum efficiency measured at 8 μR in accordance with a preferred embodiment of the present invention;

FIG. 57 graphically illustrates the U-axis measurements of lag corrected detective quantum efficiency as a function of spatial frequency in accordance with a preferred embodiment of the present invention;

FIG. 58 graphically illustrates the V-axis measurements of lag corrected detective quantum efficiency as a function of spatial frequency in accordance with a preferred embodiment of the present invention;

FIG. 59 graphically illustrates a comparison of a 1 μR lag corrected detective quantum efficiency as a function of spatial frequency for the U and V axes in accordance with a preferred embodiment of the present invention; and FIG. 60 graphically illustrates a comparison of 4 μR lag corrected detective quantum efficiency as a function of spatial frequency for the U and V axes in accordance with a preferred embodiment of the present invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Systems for quantitative radiographic imaging are described in U.S. Pat. No. 5,864,146 issued on Jan. 26, 1999 to Karellas and in WO 97/42877 published on Nov. 20, 1997 also by Karellas, both of which being incorporated herein by reference in their entirety.

Figure 1A:
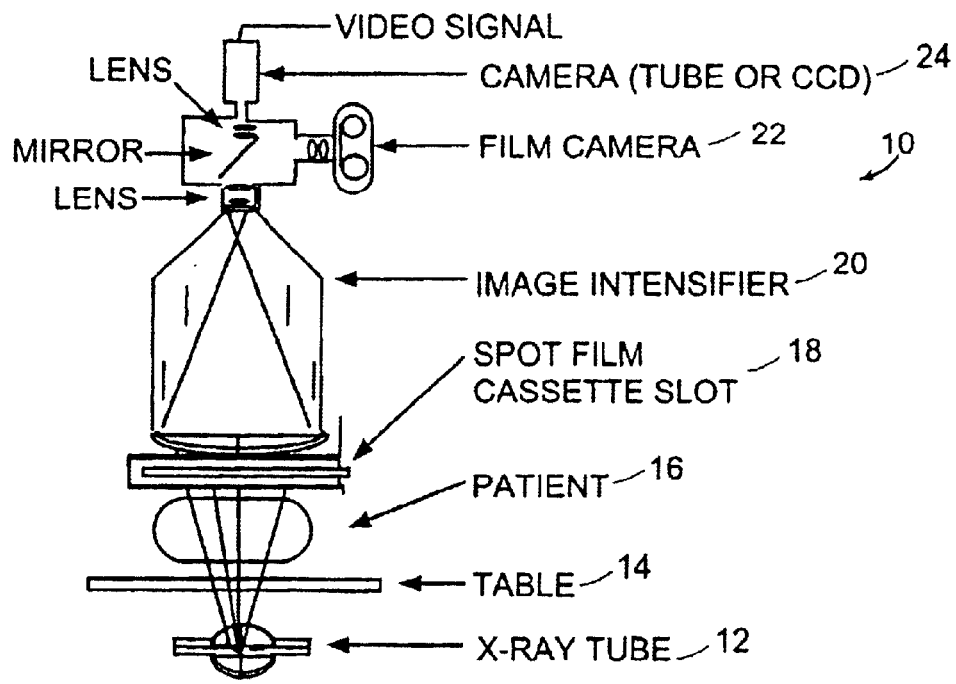
FIGS. 1A and 1B are schematic diagrams of prior art image intensifier based fluoroscopy systems illustrating the combination of image intensifier, spot film cassette device, film camera and video camera.
Figure 1B:
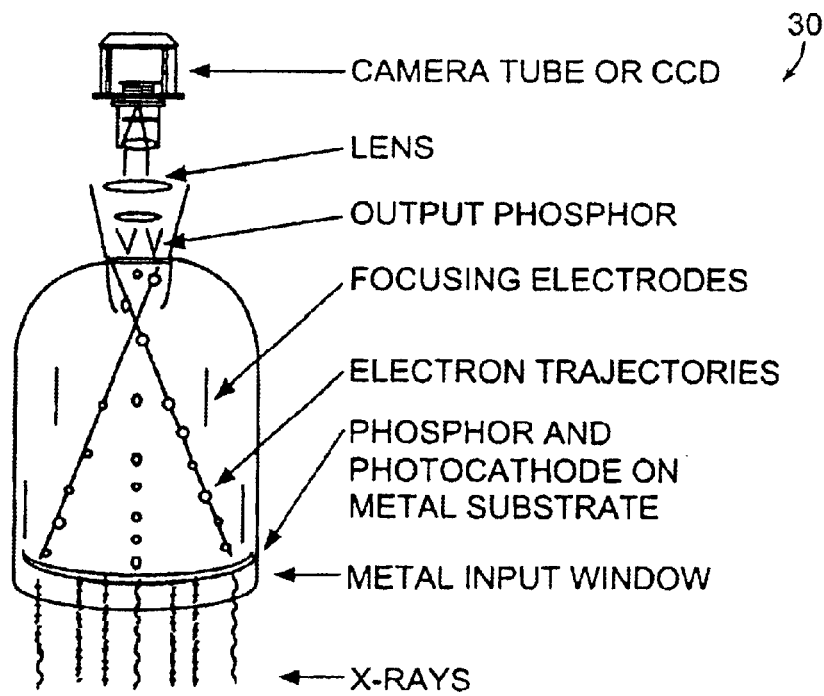

FIGS. 1A and 1B illustrate prior art fluoroscopic imaging devices for interventional radiology and cardiovascular applications which have traditionally used image intensifiers 20 coupled to either charge-coupled devices (CCDs) 24 or pick-up tubes. Conventionally, x-ray image intensifiers are used in conjunction with television cameras 24 for fluoroscopy. The x-ray image intensifier 20 detects the x-ray image and converts it to a small, bright image of visible light. Tropically, this visible image is then transferred by lenses to a television camera for final display on a monitor. FIG. 1B illustrates the details of the detection and amplification process.

While such devices provide image quality sufficient for most clinical applications, there are several limitations to this technology, which impedes further improvement. Some of these limitations include loss of resolution in the fringes of the image intensifier, veiling glare and associated contrast loss, distortion, size, and degradation with time.

Figure 2A:
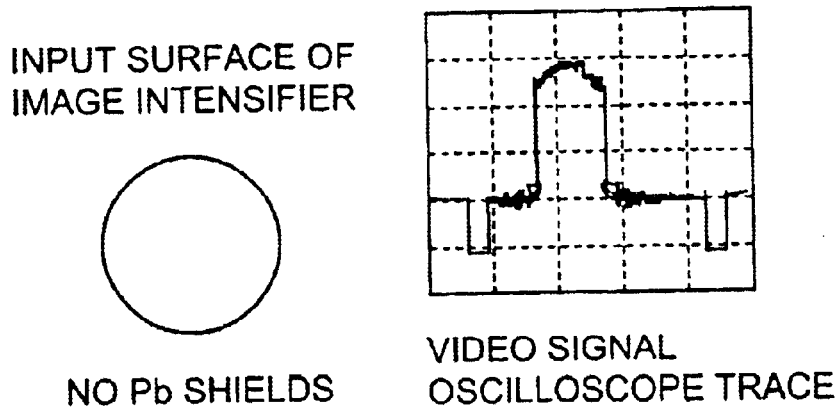
FIGS. 2A and 2B are schematic representations of the contrast loss in image intensified systems of the prior art.
Figure 2B:
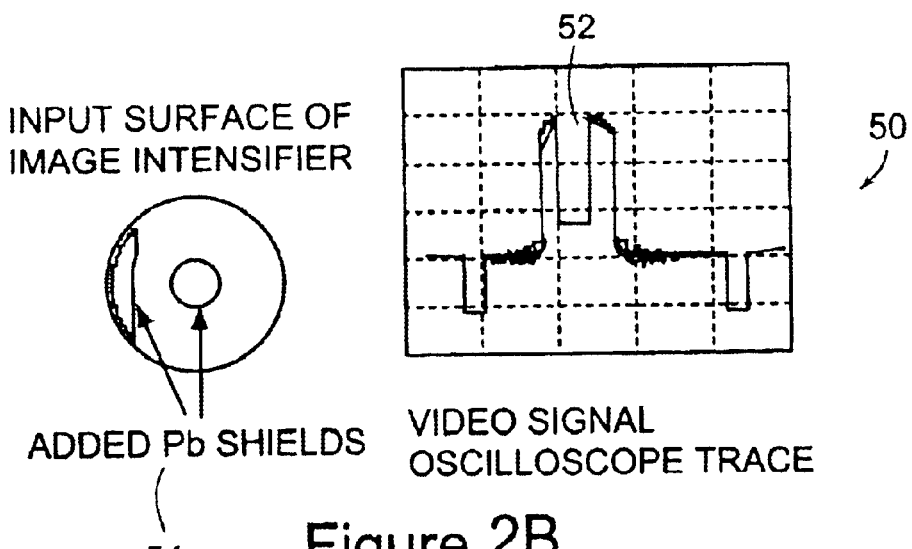

FIGS. 2A and 2B schematically illustrates the contrast loss in image intensified systems of the prior art. The image 40 of the uniform field shows pronounced drop-off in intensity away from the geometric center of the image intensifier input. FIG. 2B illustrates the effects of blocking a part of the edge and appropriately 10% of the area with a central lead disc. The oscilloscope signal 52 behind the lead shield 54 rises above the baseline and contributes to loss of contrast.

Figure 3A:
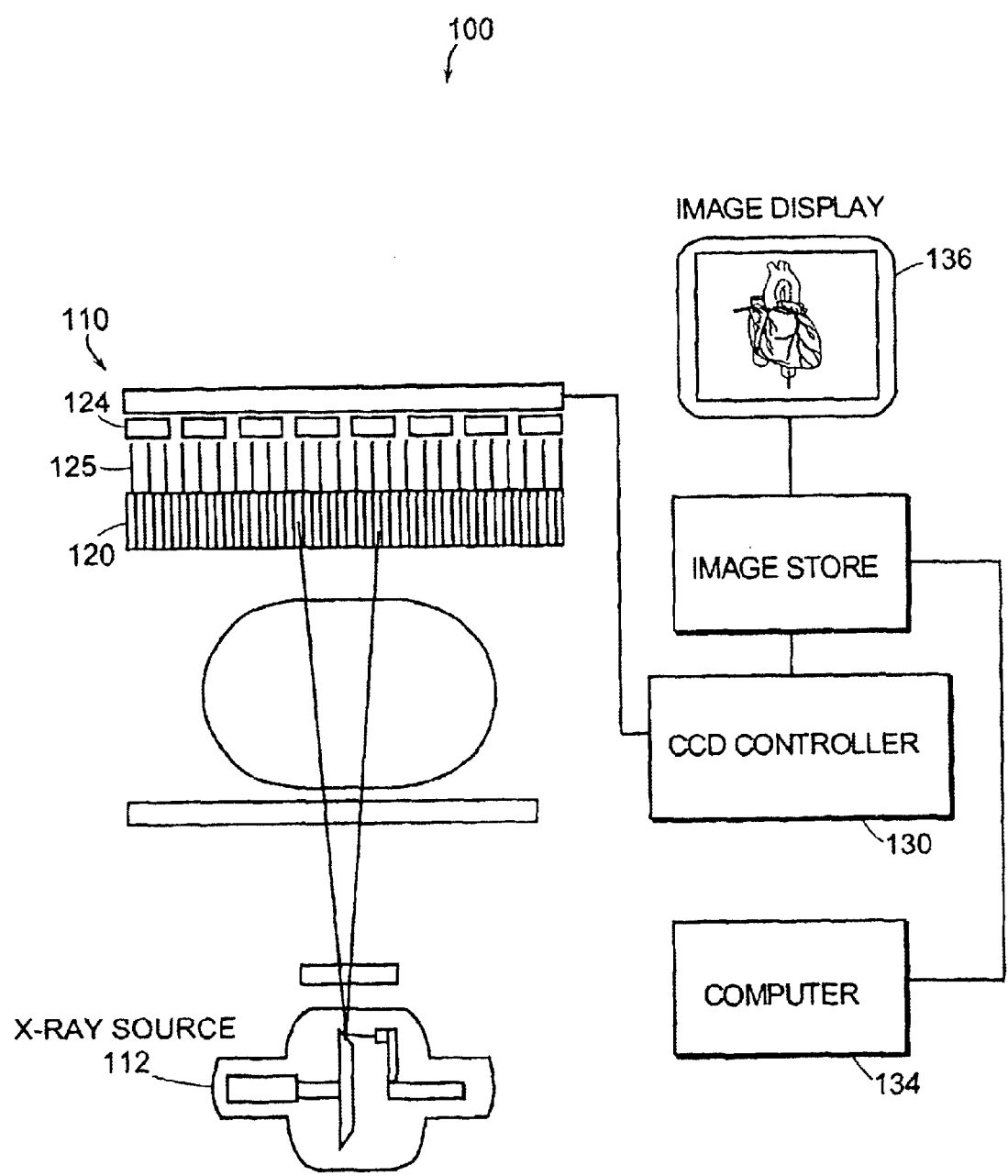
FIG. 3A is a schematic view of the fluoroscopic imaging system in accordance with a preferred embodiment of the present invention.

In FIG. 3A a preferred embodiment of the invention for performing x-ray fluoroscopic imaging uses a detector 110 and a x-ray tube 112. The detector 110 comprises a scintillating plate 120 which is optically coupled to a two-dimensional charge-coupled device 124 (CCD). The CCD is a two dimensional array of detectors integrated into a single compact electronic chip. The optical coupling between the scintillating plate 120 and the CCD 124 is accomplished by a fiberoptic coupler or plate 125. Such a plate 125 provides constrained propagation of light through the respective fiber channels thus minimizing and preferably eliminating undesired light spreading that can be deleterious to the spatial resolution of the imager.

Figure 3B:
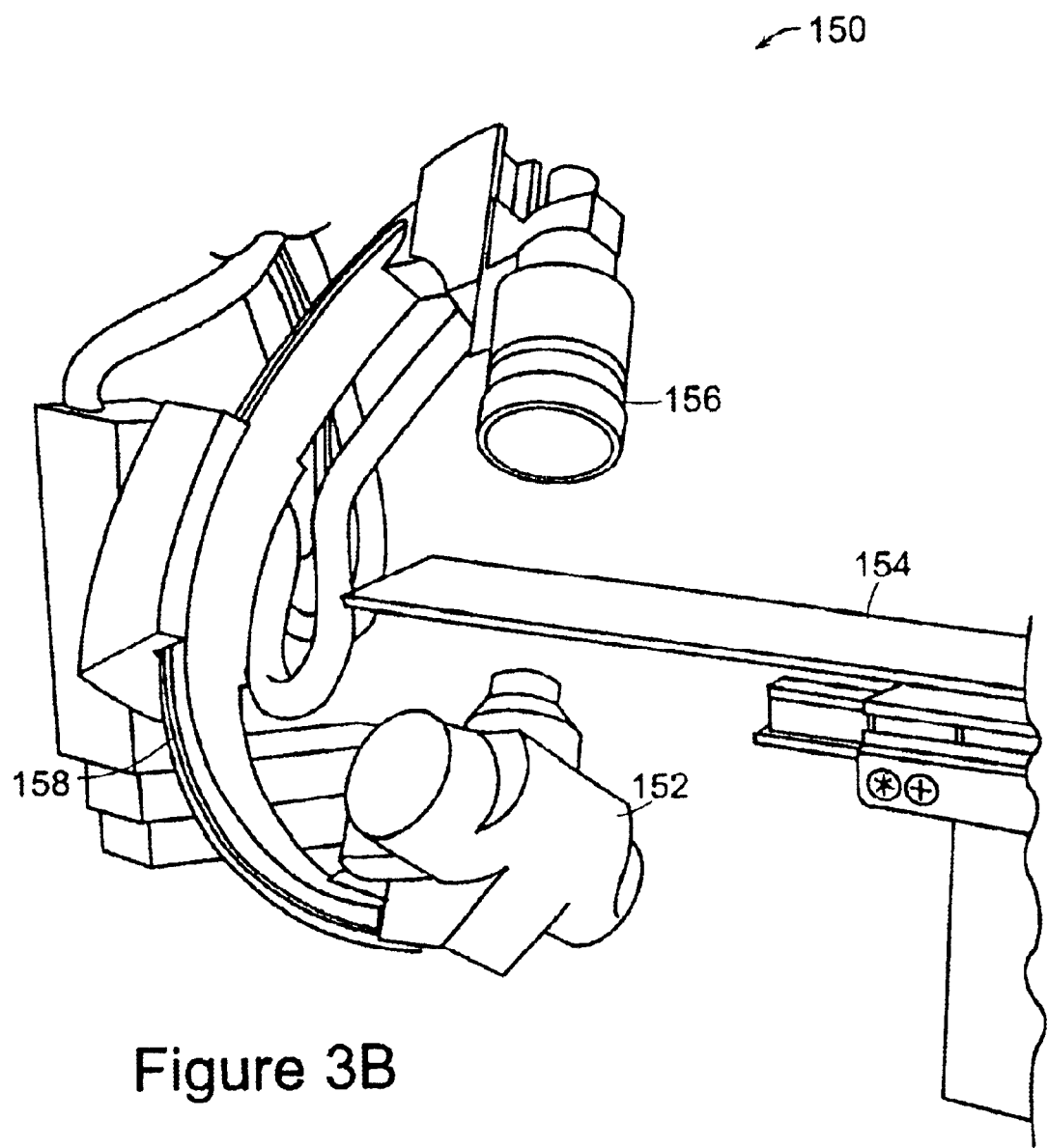
FIG. 3B illustrates an oblique position of the radiographic projection system in accordance with a preferred embodiment of the present invention.

FIG. 3B illustrates an oblique x-ray fluoroscopic imaging system 150 in accordance with a preferred embodiment of the present invention. It should be noted that the figure demonstrates the ability of oblique positioning with the digital imaging detector 156 to be in accordance with preferred embodiments of the present invention. The x-ray tube 152 is positioned below the table 154 with the detector 156 positioned above the table. A C-arm 158 configuration of the imaging system allows the oblique positioning of the projection system in accordance with the preferred embodiment. The C-arm 158 aligns the source and the detector assembly. It further rotates the source and detector about the patient on the table to provide multi-directional viewing of the human body.

Figure 4A:
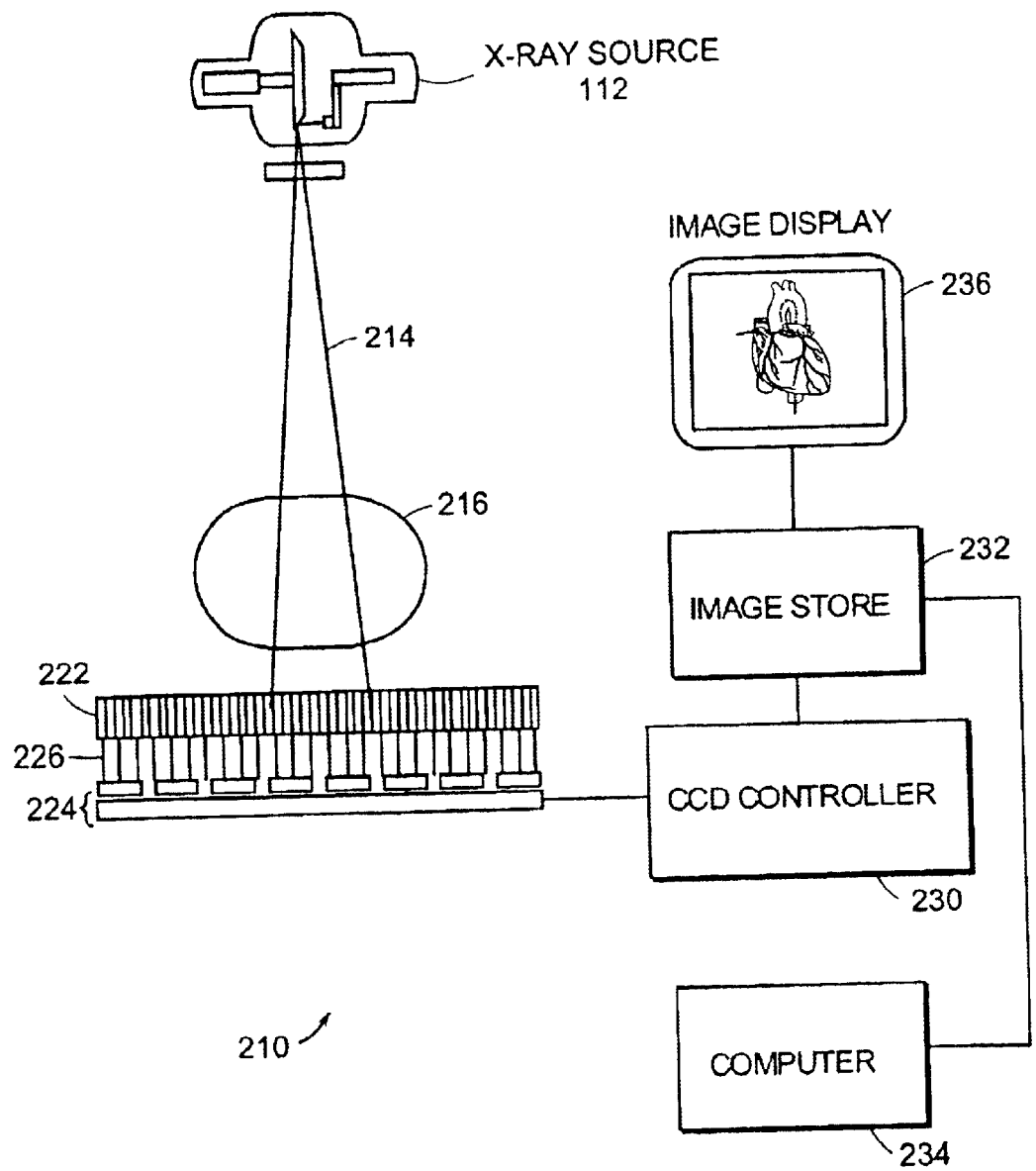
FIG. 4A illustrates in schematic view an x-ray fluoroscopic imaging apparatus to focus image data from a scintillator into a CCD sensor in accordance with a preferred embodiment of the present invention.
Figure 4B:
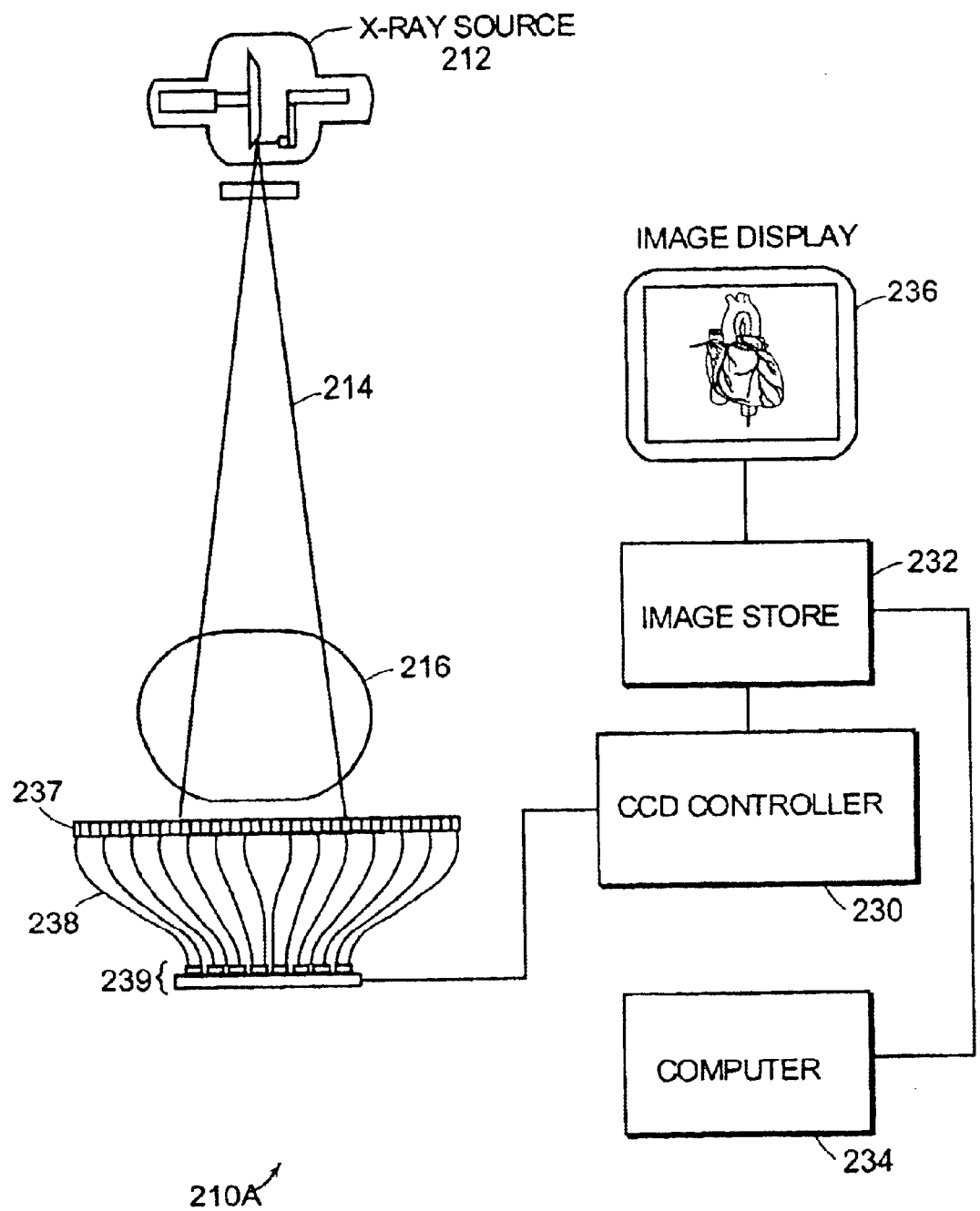
FIG. 4B illustrates in schematic view an x-ray fluoroscopic imaging apparatus in accordance with another preferred embodiment of the present invention.

Referring to FIGS. 4A and 4B, x-ray fluoroscopic apparatus 210, 210A have an x-ray tube 212 which deliver a beam of x-rays 214 towards the body of a subject 216 being examined. Note in comparison to FIG. 3A the source can be positioned above the patient and the detector below the table 220.

When the subject 216 is irradiated with the x-ray energy, a percentage of the x-rays reaching the subject 216 is absorbed by the subject's body, the amount of absorption depending on the tissue upon which the x-rays are incident. Since x-rays generally travel in a straight line, the x-ray energy exiting the subject's body on the side of the body away from the source 212 is a spatial representation of absorption in the subjects body, and therefore of relative tissue and skeletal densities.

To receive the x-rays passing through the subject's body, a scintillation screen 222, 237 provided on the side of the patient away from the x-ray source 212. The scintillation screen 222, 237 is a fluorescent material sensitive to x-rays, and when it receives x-ray energy it re-radiates visible light. The spatial intensity patterns of the radiation emitted from the scintillation screen is proportional to the spatial intensity pattern of the x-ray radiation received by the screen 222, 237. Thus the scintillation screen 222, 237 provides an image in the visible spectrum, or alternating in the ultraviolet or near infrared, which is regionally proportional to the x-ray image reaching the scintillation screen 222, 237.

The CCD sensor 224, 239 is an array of photosensitive pixels using closely spaced TAOS diodes which convert photons to electrons and thereby generate a discrete electronic representation of a received optical image. A fiberoptic plate 226, 238 focuses the visible light emitted from the scintillation screen 222, 237 onto the surface of the CCD sensor 224, 239. The fiberoptic plate may be straight or tapering as illustrated in FIG. 4B. In order to prevent ambient light from reaching the CCD sensor, a shade surrounding the region between the scintillation screen 222 and the sensor 224 may be provided in the form of a photographic bellows or hood. The bellows may serve to reduce the optical noise level of the image signal reaching the CCD sensor 224. The antiscatter grid is not shown in most of the schematics for simplicity.

Although the scintillation screen 222, 237 absorbs most of the x-rays incident upon it, some may still be transmitted through the screen 222, 237 and interfere with the optical image signal of the scintillation screen 222, 237. The direct interaction of x-rays with a CCD sensor produces very bright pixels resulting in a "snow" effect in an optical image detected by the sensor. In addition, prolonged direct x-ray irradiation of a CCD sensor can increase its dark current. For these reasons, an x-ray absorbing fiberoptic plate may be positioned between the scintillation screen 222, 237 and the CCD sensor 224, 239. An anti-scatter grid may optionally be used between the patient and the scintillation screen for preventing scattered x-rays from reaching the screen.

During a typical examination, the subject 216 is placed between the x-ray source 212 and the scintillation screen 222, 237. The x-rays are then activated from a pulsed or a continuous x-ray source. As x-rays are differentially transmitted and absorbed through the body of the subject 216, they interact with the scintillation screen 222, 237. Upon interaction, the screen 222, 237 emits light in the visible part of the electromagnetic spectrum. In the present embodiment, the scintillation screen is a thallium activated Cesium Iodide (CsI:Tl) material.

The light emitted from the scintillator and is transported to the CCD sensor via the fiberoptic plate 226, 238. Upon interaction with the CCD sensor 224, 239, light energy is converted into electrons which are stored in each pixel of the CCD sensor 224, 239. A single CCD sensor 224, 239 of the present embodiment consists of 2048×2048 pixels, but such sensors come in a number of different sizes. The pixel matrix can vary in the range from 256×256 pixels to 4096×4096 pixels. Preferred embodiments include 1024×1024 pixels for certain applications to improve geometric fill factors such as required for cardiac and vascular applications. The CCD sensor "integrates" the image signal from the scintillation screen in that it senses the optical image and stores charge during the entire x-ray exposure interval. After termination of the x-ray exposure, the discrete representation in the CCD 224, 239 is read out by controller 230. The controller 230 reads the image representation from the CCD sensor 224, 239 pixel by pixel and organizes it into a digital array. The digital array, representing spatial position and x-ray intensity, is then output to a memory or image store 232. From the image store 232, the image can be accessed by a data processor 234 for performing image processing techniques. A cathode ray tube (CRT) 236 or other type of electronic image display is also provided to allow the image to be displayed before or after processing by the data processor 234.

Unlike other conventional detection schemes, such as film screen radiography, CCD-based imaging provides a linear quantitative relationship between the transmitted x-ray intensity and the charge generated in each pixel of the CCD.

A preferred embodiment of the present invention is concerned with an area detector synchronous with a x-ray source that scans the region to be examined in a linear fashion. Alternatively the patient support table may be moved in relation to the x-ray source and detector to study vascular blood flow. This preferred embodiment uses multi-resolution modes or regions as discussed hereinafter.

Figure 5A:
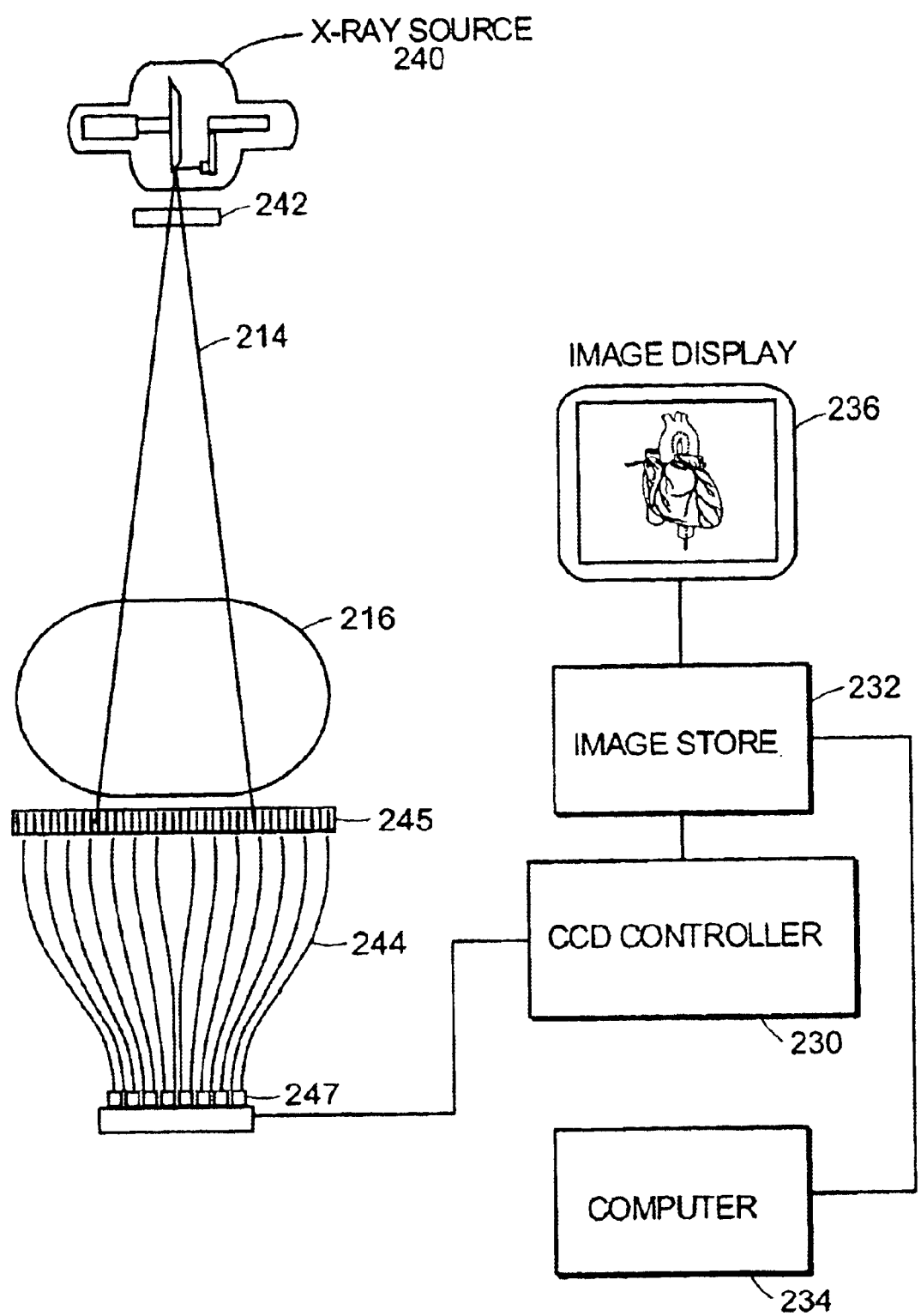
FIG. 5A illustrates in schematic view another preferred embodiment of the fluoroscopic imaging system in accordance with the present invention.

FIG. 5A shows an alternative embodiment to that of FIGS. 4A and 4B. In this embodiment, an x-ray filter 242 is placed between the x-ray source 240 and between the subject 216. The x-ray source 240 can be either tube-based or any other solid-state x-ray source. In the present embodiment, the filter 242 is copper or a K-edge filter. The filter 242 is implemented as an electromagnetic shutter which may be opened and closed in the line of the x-ray beam.

The fiber optic plate 244 is a focusing device consisting of a large array of optical fibers packed tightly together, and leading from the scintillating screen 245 to the CCD, sensor 247. Near the CCD sensor 247, many of the fibers can be fused together, thus combining the signals present on individual fibers. The effect is a compression of the image from the input of the reducer 244 at the scintillation screen 245 to the reducer output at the CCD sensor 247. In this manner, the reducer 244 effectively focuses light from the scintillating screen 245 onto the CCD sensor 247 without the necessity of a lens for the focusing region.

Figure 5B:
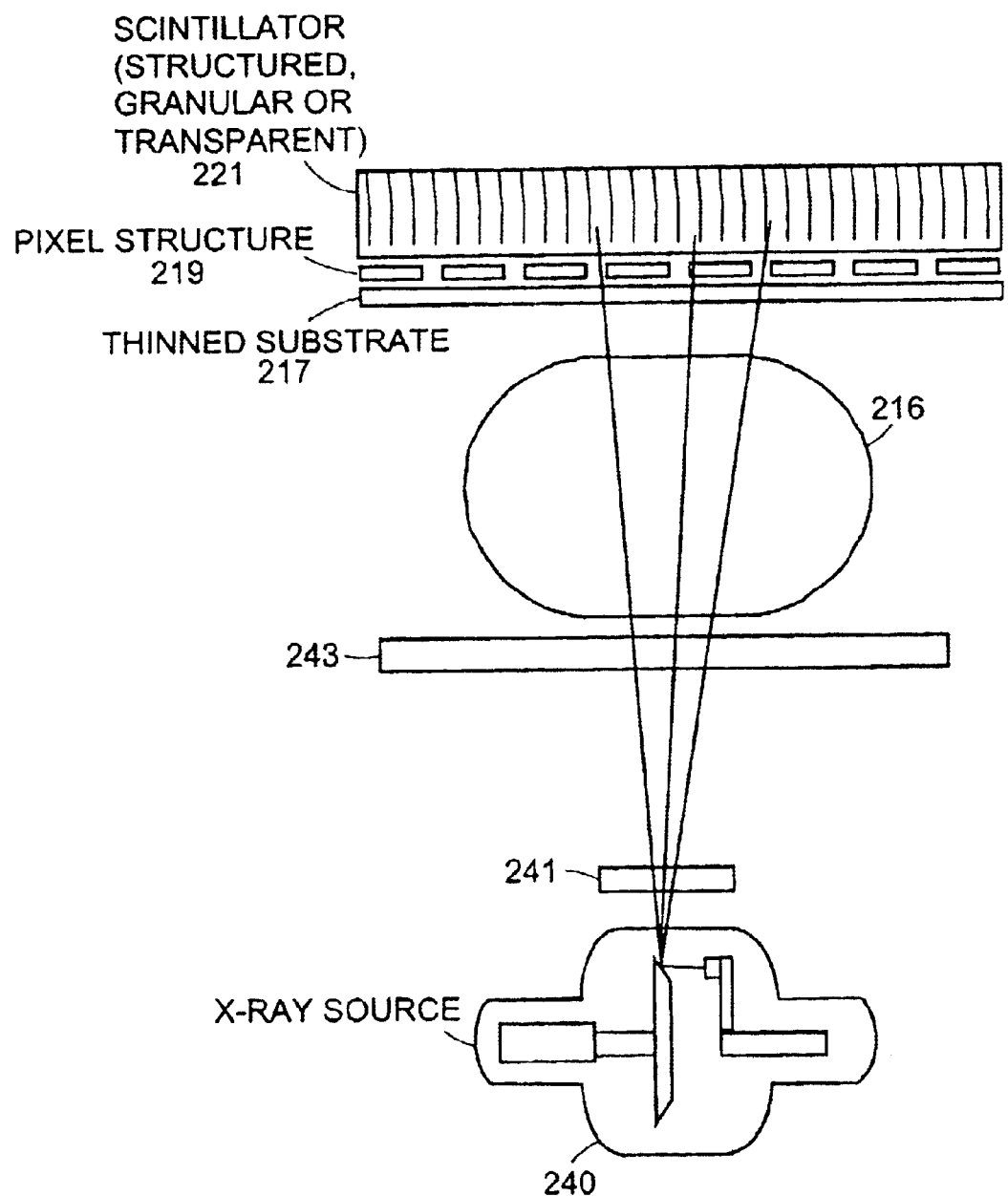
FIG. 5B is a schematic view of another preferred embodiment of the fluoroscopic imaging system in accordance with the present invention wherein the detector is radiated from the back.

FIG. 5B is another preferred embodiment of the x-ray fluoroscopic imaging apparatus of the present invention. An x-ray filter 241 is placed between the x-ray source 240 and the subject 216 positioned on a patient support 243. The filter 241 is an aluminum, copper or a combination of aluminum and copper filter. In this embodiment the x-ray radiation passing through the body of the subject are incident on a thinned substrate 217. The thinned substrate is a glass substrate of approximately 1 mm to 1 mm thickness or in an alternative embodiment is a non-glass substrate including polymers or non-absorbing composites. The substrate 217 may be made ultra by subjecting the substrate to mechanical, electrical and/or optical processes. In a preferred embodiment the glass substrate has a seed of amorphous x-ray transparent carbon fiber disposed on top of the glass or beryllium seeds to provide structural integrity and rigidity to the substrate 217. A pixellated structure 219 of an imaging detector is disposed on the substrate. A scintillator 221 which may be structured, granular or transparent is provided after the detector with the pixellated structure. This preferred embodiment enables the interaction of the x-rays and the scintillator to occur at the pixel structure to preserve the spatial resolution as the spread of light is minimized. Thus the detector is radiated by back illumination due to the positioning of the scintillator 221 relative to the pixel structure 219.

Figures 6, 7:
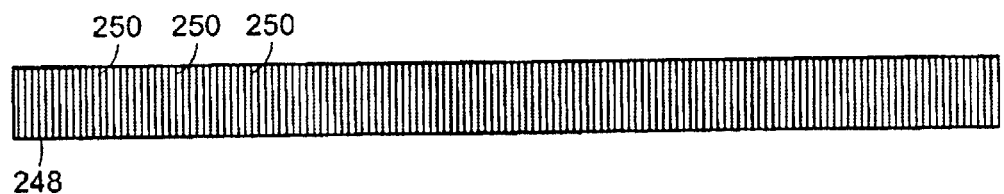
FIG. 6 illustrates another preferred embodiment for the scintillation screen employing a fiber optic plate in accordance with the present invention.
FIG. 7 is an illustration of the pixel array of a binnable CCD sensor in accordance with a preferred embodiment of the present invention.

FIG. 6 shows an alternative to the scintillation screen 222, 245 of FIGS. 4 and 5. The plate 248 is a fiber optic faceplate consisting of scintillating fibers 250 running though the plate. The fiber optic plate is optically interfaced to the CCD in essentially the same way as the scintillation screen 222 of FIG. 4, but the fiber optic plate 248 allows for greater quantum efficiency due to increased x-ray stopping capability.

FIG. 7 is a representation of the pixel array of a preferred embodiment of the CCD sensor 241. The array shown in FIG. 7 is only 10×10 for illustrative purposes, and the actual array can be of different dimensions. Each pixel in the array is an individual photosensitive element which contributes to the overall image detected by the array. A feature of the CCD sensor of the present embodiment is a capability of the pixels of the sensor 241 to be "binned" together. The binning of the pixel array refers to the ability of the sensor electronics to combine groups of pixels together to form "super pixels" which are then identified as single picture elements.

Charge is binned by combining charge packets contained in two or more adjacent potential wells into a single potential well during charge readout. Serial and parallel binning can be combined to perform two-dimensional binning from any rectangular group of wells or detector elements.

The dark lines in the binnable array of FIG. 7 illustrate where individual pixels might be grouped together. For example, the four upper left-hand corner pixels 250 can be binned together through control of the CCD sensor 241 to form a super pixel. The super pixel is then identified by the CCD electronics as a single pixel, the light intensity reaching each pixel 250 being averaged across the surface of the entire super pixel. In this manner, the dimension of the array can be electronically controlled. As can be seen in FIG. 7, if groups of four pixels are binned together across the 10×10 array, the overall array dimension becomes 5×5. Although the binning of the CCD sensor 241 reduces the resolution of the pixel array, the relative percentage of noise is also reduced, thus providing an improved signal to noise ratio (SNR). The pixel binning technique can be used to increase the signal to noise ratio and to decrease the radiation dose.

Figure 8:
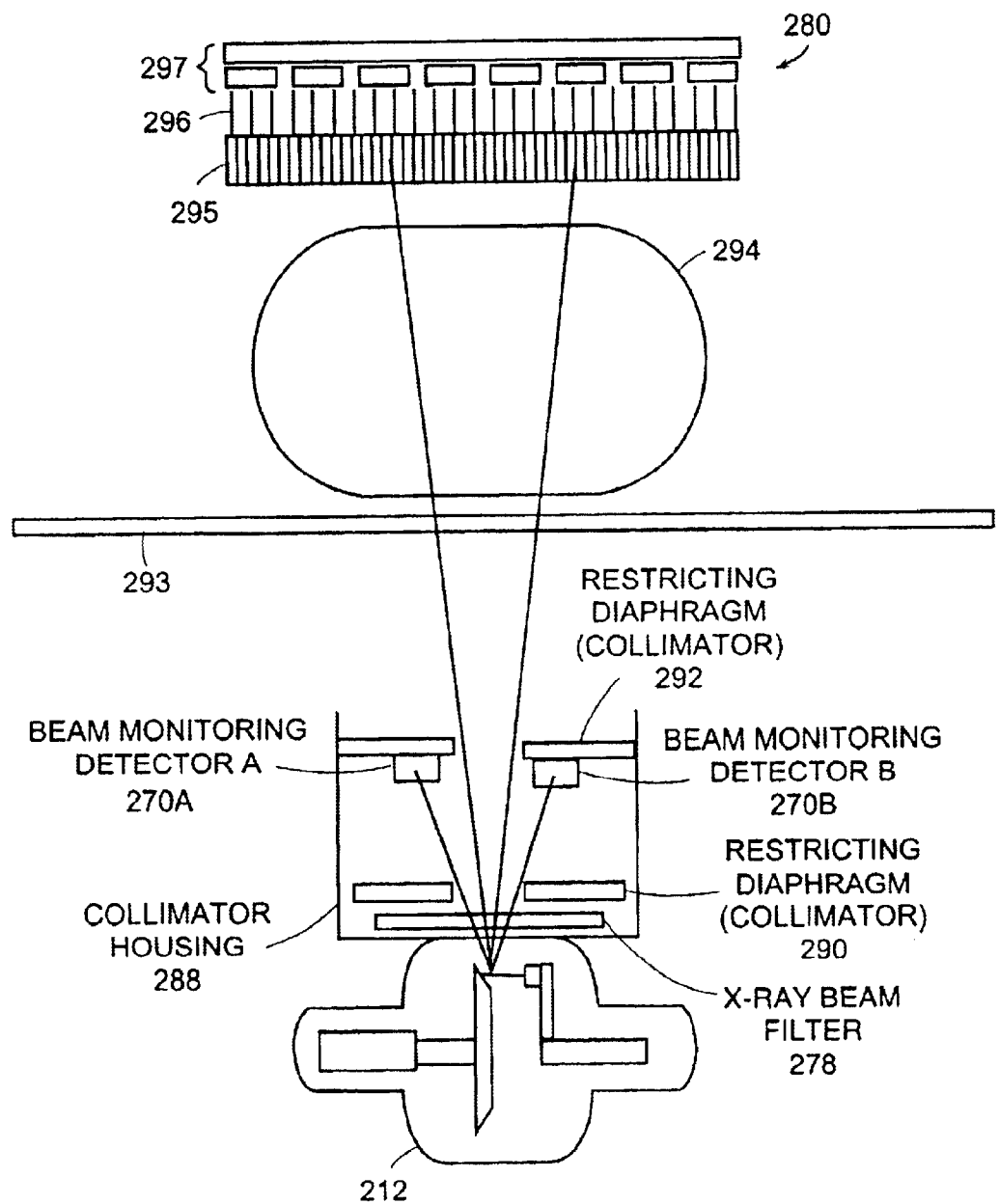
FIG. 8 is a schematic view illustrating the sensor control system in accordance with a preferred embodiment of the present invention.

An internal instrument stability control system can be incorporated to provide a means of automatic compensation for any instabilities in the x-ray tube potential and current. The stability control device is not essential for the operation of any of the described techniques but it provides better reliability and precision in x-ray fluoroscopic imaging. A schematic representation of the preferred embodiment of the stability control device is shown in FIG. 8. The output of x-ray tube 212 is monitored by a pair of x-ray sensors 270A, 270B placed on the jaws of the beam restricting diaphragm 292 of the collimator housing 288 such that the sensors do not interfere with the x-ray beam incident on the patient 294. These sensors can be silicon diodes, cadmium zinc telluride radiation sensors or any other solid-state x-ray sensor. Alternatively, a pair of compact photomultiplier coupled to scintillator or photodiode coupled to scintillator can be used. Either one or both of these sensors can be based on the same technology. Either one or both of these sensors can be of the charge integrating type to provide exposure information, or, of the photon counting type to provide energy information. Both sensors are operated continuously during the entire acquisition period. The time varying signal from each of the sensors is digitized and stored in the computer memory. These signals can be used to monitor and regulate the x-ray beam incident on the patient by controlling the x-ray source, but also can be used to provide quantifiable information about the anatomy being imaged. Based on the beam monitoring measurement of the x-ray beam incident on the patient 294 and image recorded by the detector 280, it is feasible to quantify the output to input ratio, which provides valuable information about the anatomy. In addition, the x-ray beam incident on each of these x-ray sensors 270A, 270B may be filtered by different type or thickness of filtration, such as x-ray beam filter 278 in order to derive energy information of the x-ray beam incident on the patient. For applications requiring quantitative information about the tissue or bone, these filters can be an amount of polymethyl methacrylate to simulate soft tissue or a hydroxyapatite-epoxy mixture to simulate bone. These beam monitoring sensors can be used in conjunction with the preferred embodiments of the image detectors such as amorphous silicon with scintillator, complementary metal oxide semiconductor (CMOS) with scintillator, amorphous selenium without scintillator and other direct conversion materials such as cadmium zinc telluride, lead iodide and mercuric iodide without scintillator described herein.

A preferred embodiment of the present system is based on a large-area interline CCD device for fast frame applications such as fluoroscopy. An interline transfer imager, also referenced herein as an interchannel device, and an interpixel channel imager, is constructed by placing several large area interline CCDs adjacent to each other. In a preferred embodiment, light shielded charge transport registers or interpixel channels are located near sensitive pixels. These interpixel channels can be oriented either vertically or horizontally. The integration of charge takes place in the pixels, which can be photodiodes or metal oxide semiconductor (MOS) capacitors. In a particular embodiment, at the end of the integration time, the charge packets are shifted from the pixels into a interpixel channel alongside them. These interpixel channels may be shielded from light and act as a temporary memory for the information coming from the pixels. The charge packets from the pixels may be transported through the interpixel channel to the horizontal-output or serial registers. The serial information in the horizontal output register is transferred to the output and consequently converted into an electrical voltage or current. The sequence of parallel to series conversion and the readout is repeated until all the charge packets are read out.

The interline-transfer imager can integrate a new image during the storage of the previous image in its memory element such as, for example, the interpixel channels.

In an alternate embodiment, the interline-transfer device may be integrated with a frame-transfer imager and thus be a frame-interline transfer CCD. It has the light sensitive area of the interline-transfer device (photodiodes and vertical shift registers), combined with the storage area of the frame-transfer device. In another embodiment, the CCD is a MOS addressable imager which is a matrix of photodiodes each of which is provided with a MOS-transistor acting as a switch.

Figure 9A:
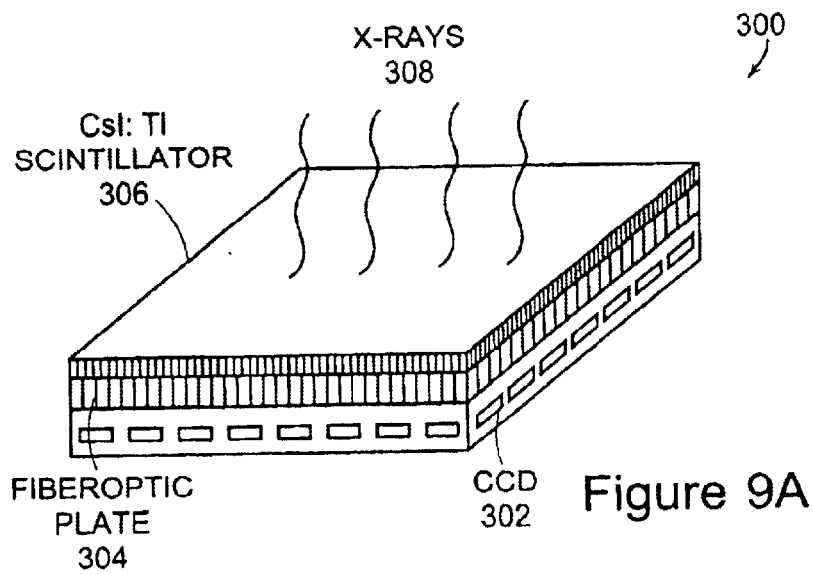
FIG. 9A is a schematic diagram of a preferred embodiment of a CCD imager in accordance with the system of the present invention.

In a preferred embodiment, four, three-side buttable interline CCDs can be tiled to form a large area, for example, a 16 cm×16 cm imager. A single module 300 is illustrated in FIG. 9A. A particular embodiment CCD consists of 1024× 1024 pixels, with pixel size of about 80 $\mu$m×80 $\mu$m. The selection of these pixel dimensions and pixel matrix are arbitrary. Similar imagers of any desired size can be constructed using the underlying concepts described herein. The pixel sizes may vary from approximately 10 to 400 $\mu$m in size. A preferred embodiment to perform fluoroscopy with an interline CCD device 302 uses a pulsed x-ray tube and synchronizes the frame rate with the pulsing of the x-ray tube. However, when x-ray pulsing cannot be attained due to equipment limitations, the system in accordance with the present invention can perform adequately with another preferred embodiment having a continuous (non-pulsed) x-ray beam due to its interline mode of operation.

Figure 9B:
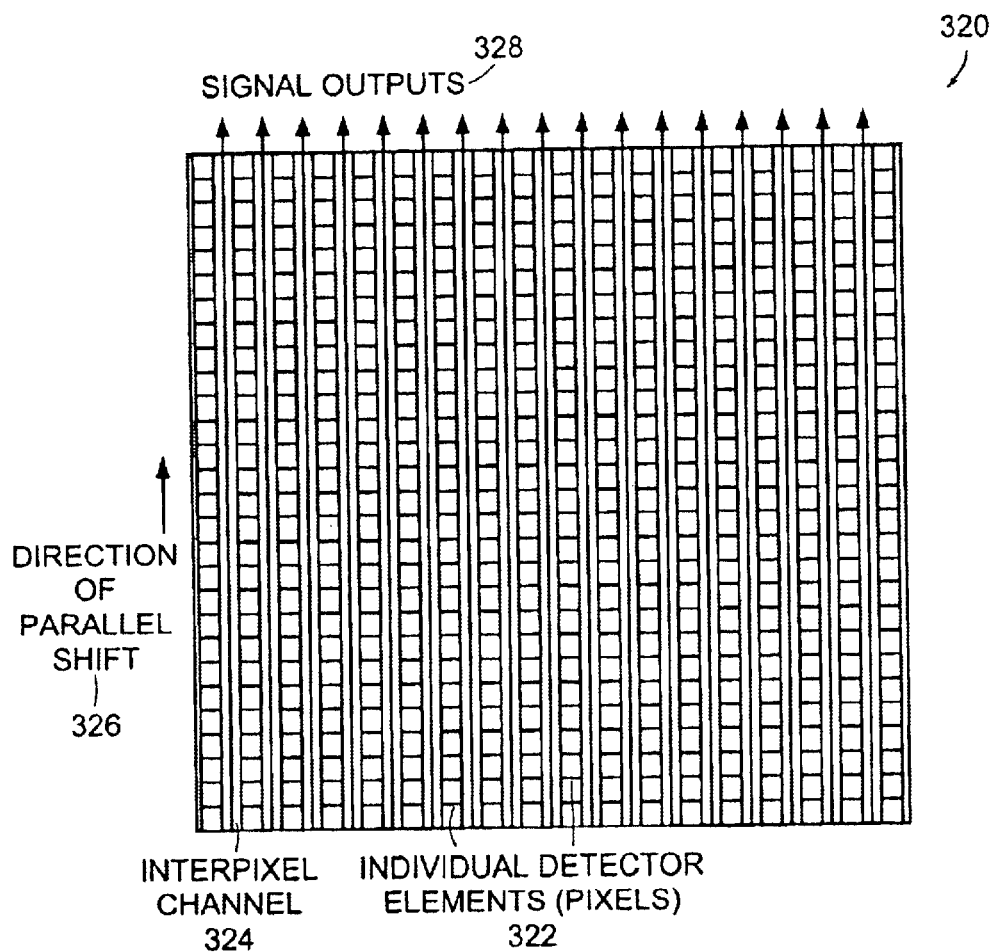
FIG. 9B is a schematic diagram of a charge readout process of a preferred embodiment of a CCD imager showing the interpixel channels of the interline CCD in accordance with the present invention.

The charge readout process for a single CCD in accordance with a preferred embodiment is illustrated in FIG. 9B. The time duration for transfer from the photosite 322 (active area of the pixel) to the data line (interpixel channel 324) can be extremely short, for example, in the order of approximately a few microseconds ($\mu$s) and therefore, any smearing due to the continuous x-ray beam is minimized. During this short period, the photosites in the imager do not integrate the charges and there is no shifting of charges along the vertical direction. This period is referred to as the vertical blanking time. Once the charges are transferred to the interline or interpixel channel, it takes a short time, for example, approximately 15 $\mu$s to transfer one row of 1024 pixels on to the horizontal register.

In a preferred embodiment, the interline channel can be made insensitive to light, therefore, image smearing during the readout is avoided. The readout process can occur in the background without interfering with the image acquisition since the CCD reads out its charge through the interline channel, from a given frame, while the subsequent frame is being acquired in the photosites (pixels). Vertical binning is achieved by transferring two or more rows of data on to the horizontal register at the same instant. Following this, all the pixels in each of a row are transferred to the summing well and on-chip amplifiers of the output port within a short duration for example, approximately 10 $\mu$s, such that the horizontal register is cleared of all the pixels prior to transfer of the next row of pixels to the horizontal register. Horizontal binning is achieved by transferring two or more pixels at the same instant to the summing well of the output port from the horizontal register. Thus a preferred embodiment of the system is capable of reading out a complete frame of, for example, 1024×1024 pixels in 15.4 ms (5 $\mu$s+1024×15 $\mu$s), which corresponds to a frame rate of 65 frames/sec. Higher frame rates can be achieved by increasing the number of output ports and also by reducing the transfer duration by increasing the clock rate in alternate preferred embodiments. An important advantage of this readout method is that the x-ray source can be operated in the continuous mode without affecting the readout process as the interline channel and the horizontal register can be made insensitive to light. The system derives its speed from the interline architecture. Hence, the imager in accordance with a preferred embodiment is capable of operating in both continuous and pulsed fluoroscopic modes and can be switched instantaneously to the radiographic or digital cine acquisition mode.

Figure 9C:
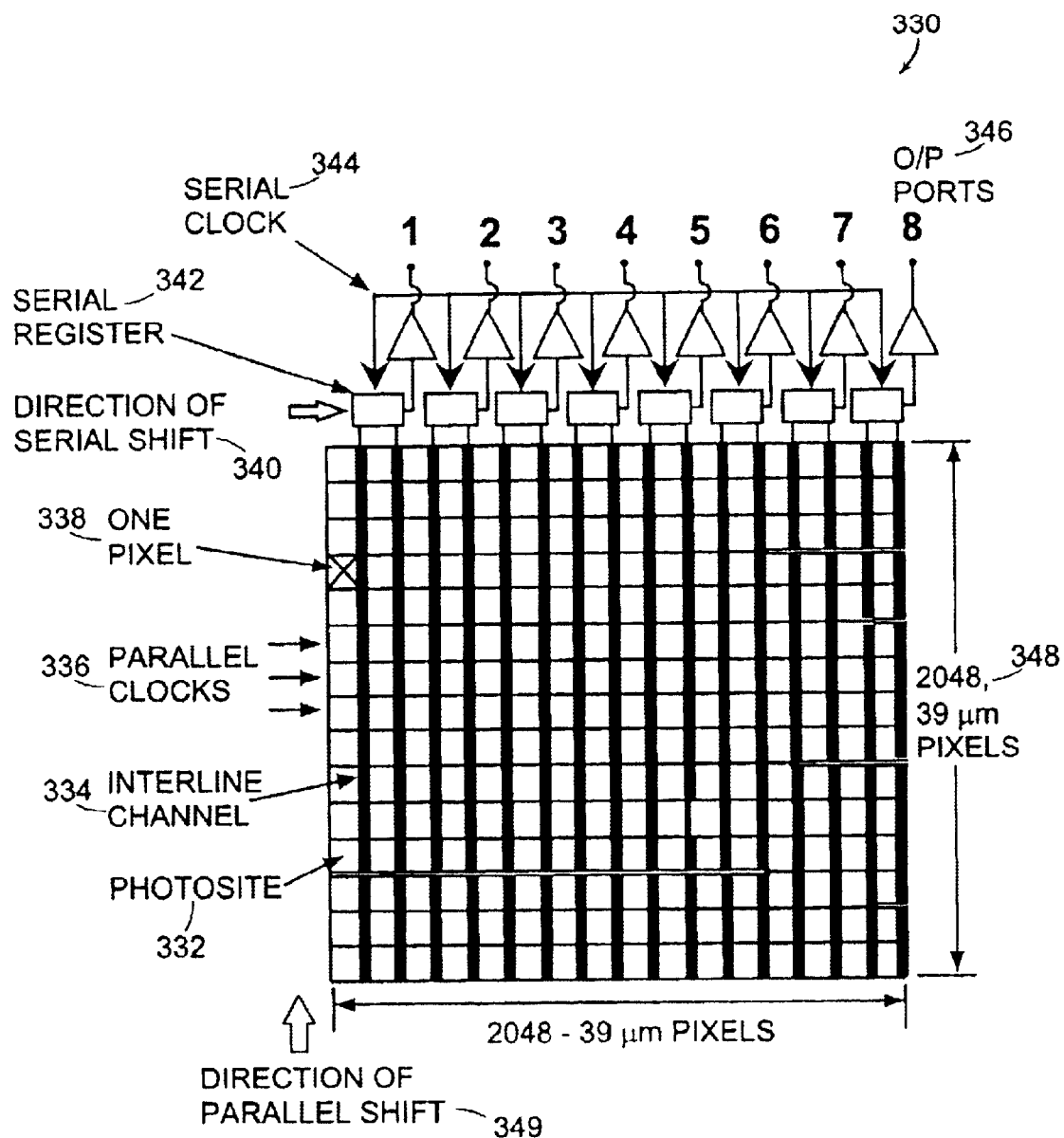
FIG. 9C is a diagram illustrating the architecture of each 8×8-cm CCD module showing the eight-readout ports in accordance with a preferred embodiment of the system of the present invention.

In a preferred embodiment, each CCD module has eight output ports as shown in FIG. 9C. During the 5-$\mu$s period when the charges are transferred from the photosites 332 to the interline channel 334, there is no shifting of charges along the direction of parallel shift 349. As described hereinbefore, this period is referred to as the vertical blanking time. Once the charges are transferred to the interline channel, it takes approximately 15-$\mu$s to transfer one row of 2048 pixels of 39×39-$\mu$m to the serial registers 342. Vertical binning is achieved by transferring two rows at the same instant. The clock rate of the serial register is 25 MHz, which corresponds to 40-ns for transferring one charge packet (vertically binned pixel) to the summing well of the output port 346. Horizontal binning is achieved by transferring two vertically binned pixels to the summing well at the same instant. Since the readout in a preferred embodiment uses eight (8) ports, the entire contents of the serial register are transferred in $$5.12\text{-}\mu s\left(=\frac{2048\text{ pixels/row}}{2(\text{binning})\times 8\text{ ports}\times 25\text{ MHz}}\right).$$

Hence, the contents of a single frame from a single CCD module are transferred in 20.61-ms (=5 $\mu$s+[(15 $\mu$s+5.12 $\mu$s)×1024 vertically binned rows]). Thus a preferred embodiment of the present invention system is capable of achieving frame rates of up to 30 fps, even in the 78-µm mode. In cardiovascular applications, pixel sizes of 78×78-µm or larger may be used instead of the 39×39-µm addressed before to improve the geometric pixel fill factor.

The most important characteristic of this readout scheme is that the x-ray source can be operated in the continuous mode without affecting the readout process as the interline channel and the horizontal register are opaque to light. In pulsed fluoroscopy, the CCD readout can be synchronized with the x-ray pulse to further reduce motion blur. Pulse width of commercially available x-ray generators range typically between 1 to 13-ms, depending upon the manufacturer. Then the preferred embodiment of the present system is operated at 30 fps, the time taken per frame is 33.33-ms. During this period, the x-ray source is active for at most approximately 13-ms. Hence, after the termination of the x-ray pulse, the charges on the photosites are transferred to the data line in 5-µs, and the imager integrates charges for the next frame immediately after this period. An additional delay of 2-ms between the control pulse for switching off the pulsed x-ray source and the start of charge transfer from the active area of the pixel has been provided for preferred embodiments which are not equipped with grid-controlled tubes to allow sufficient time for discharge due to capacitance of any high-tension cables.

Figure 9D:
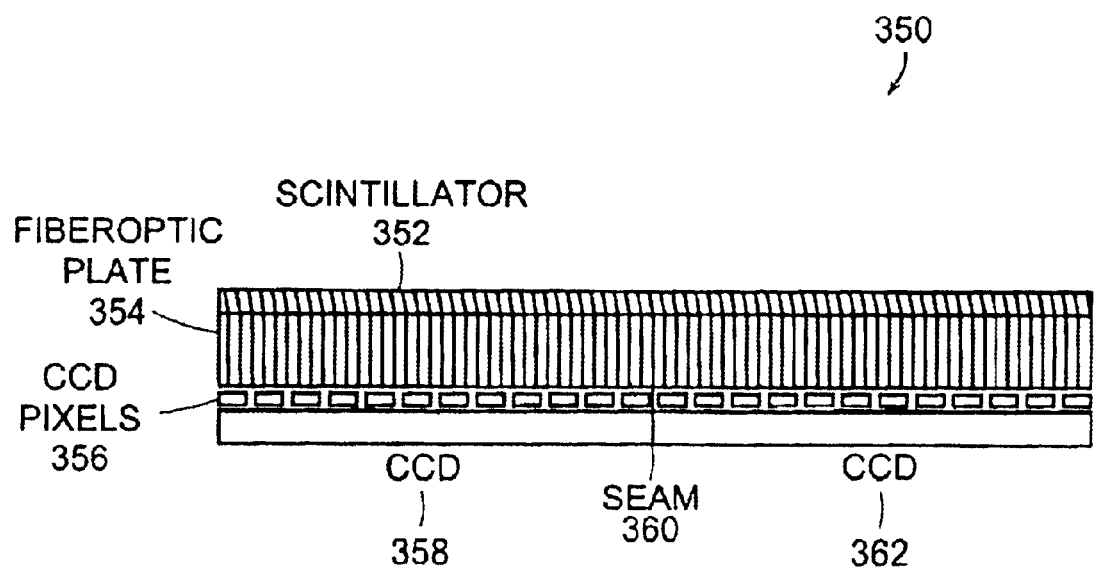
FIG. 9D is a schematic diagram illustrating the cross-section of a preferred embodiment multi-modular CCD array coupled to a scintillator through a fiberoptic faceplate in accordance with the present invention.

A schematic diagram showing the cross-sectional view of a multi-modular CCD array 350 is shown in FIG. 9D. A scintillator 352 is coupled to the CCD 358, 362 through a straight fiber-optic plate 354. The straight fiber ensures constrained propagation of light through the respective fiber channels thus, minimizing undesired light spreading that may be deleterious to the spatial resolution of the imager. A single fiberoptic faceplate can be used to cover all the CCD modules.

Figure 9E:
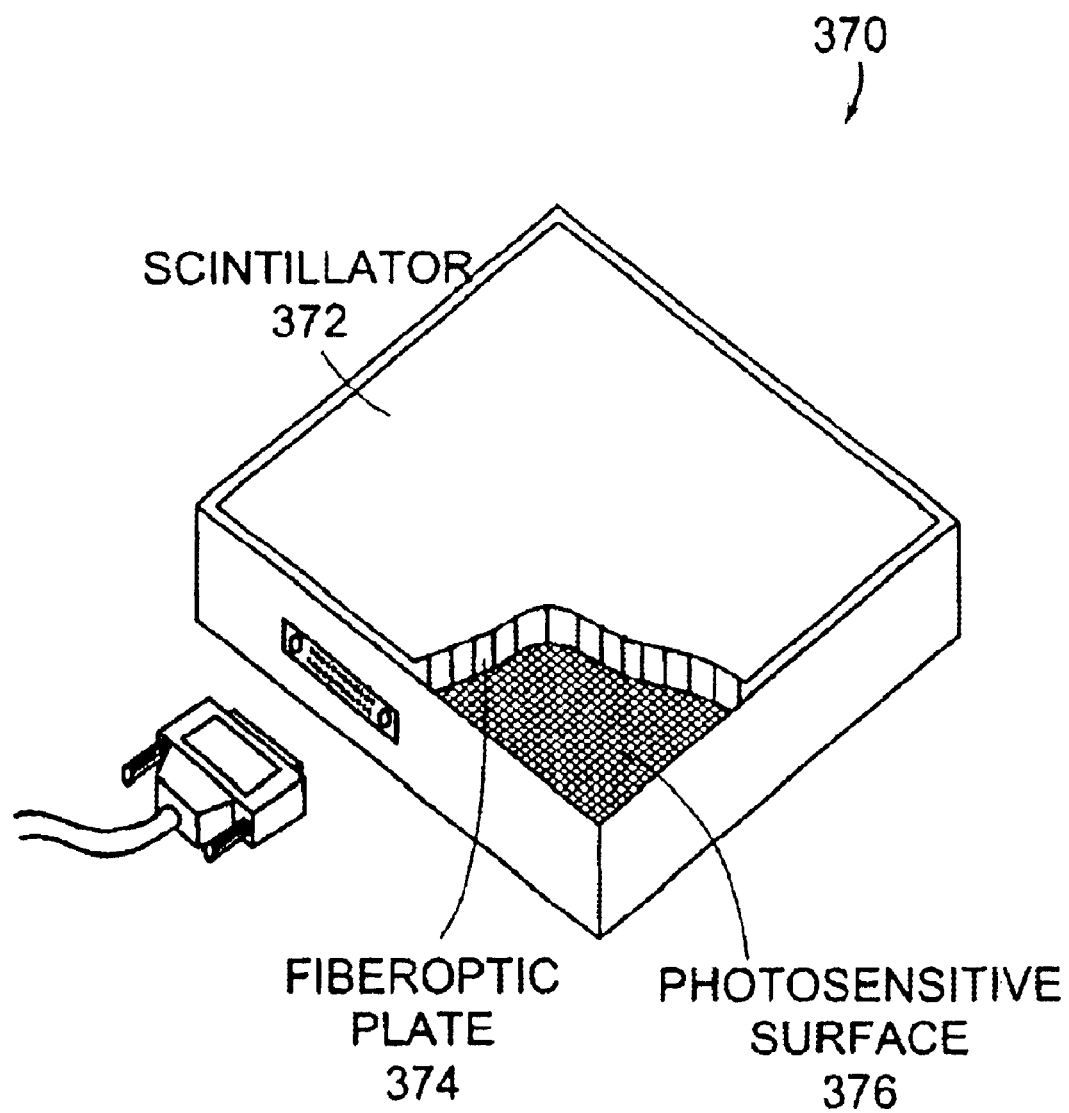
FIG. 9E is a diagram illustrating a preferred embodiment multi-modular CCD array coupled to a scintillator in accordance with the present invention.
Figure 9F:
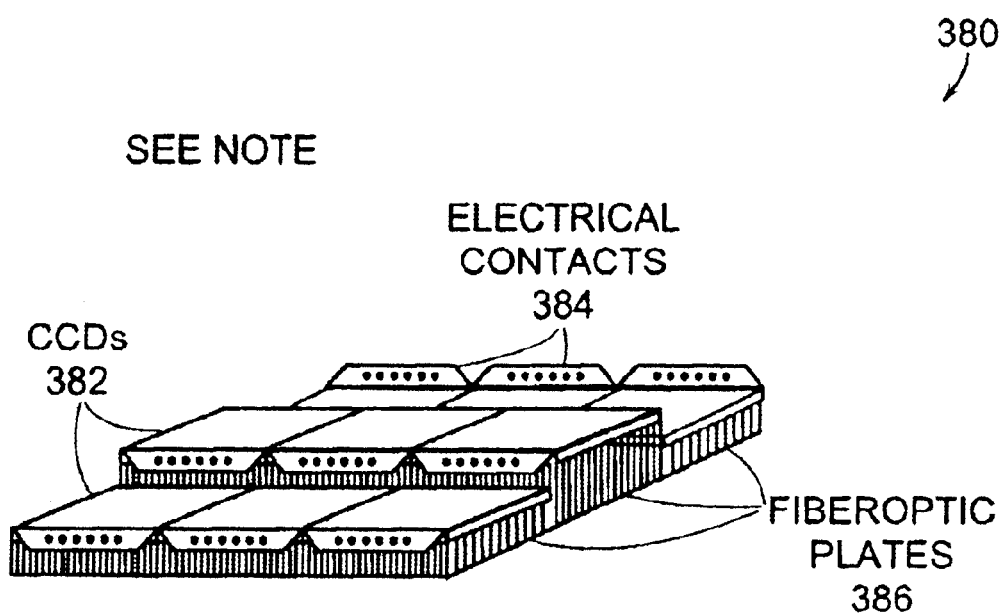
FIG. 9F illustrates a preferred embodiment of packaging or tiling multiple three-side interfacing (buttable) CCDs such that access to the readout pins of the central module can be achieved in accordance with the present invention.
Figure 9G:
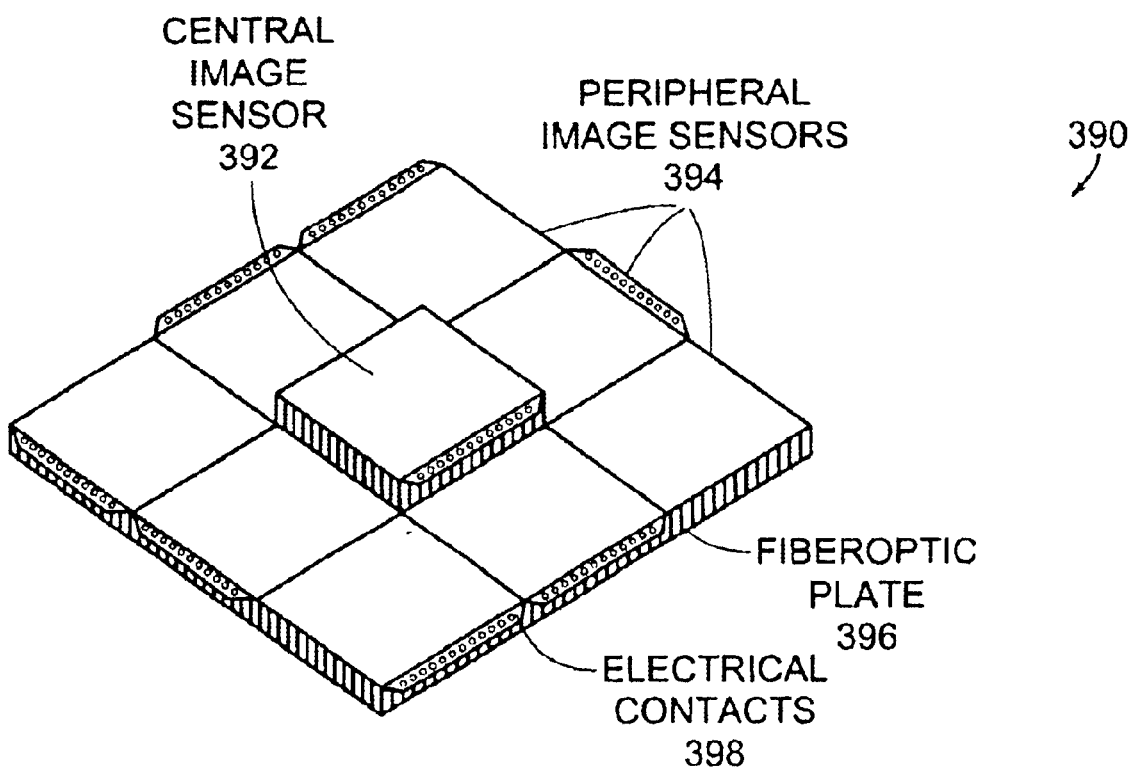
FIG. 9G illustrates another preferred embodiment of tiling of multiple three-sided buttable CCDs, wherein the central CCD is elevated to allow access to the readout pins in accordance with the present invention.

A tiled perspective of a complete imager 370 with multiple CCD modules is shown in FIG. 9E. In a preferred embodiment, the CCDs offer a convenient means of constructing large area flat-panel imagers. If a larger number of three-side buttable CCDs are to be tiled, a "stepped" approach can be used as illustrated in FIG. 9F, which enables signal routing from the headers of the centrally located CCD modules. Alternately, the central CCD 392 is elevated as shown in FIG. 9G. These approaches to tile three-side buttable or interfacing CCDs facilitate the fabrication of large-area imaging arrays. The fiber-optic faceplate 396 that rests on the CCD surface may also be stepped, while the top surface in contact with the scintillator can remain flat. Since, the CCDs are thin devices, magnification effects due to the stepped architecture can be neglected or corrected through magnification compensation algorithms or sequence of instructions if required. In another preferred embodiment, four-side buttable CCDs may be used wherein the geometry is simpler and tiling as shown in FIGS. 9D and 9F can be easily achieved.

Figure 10A:
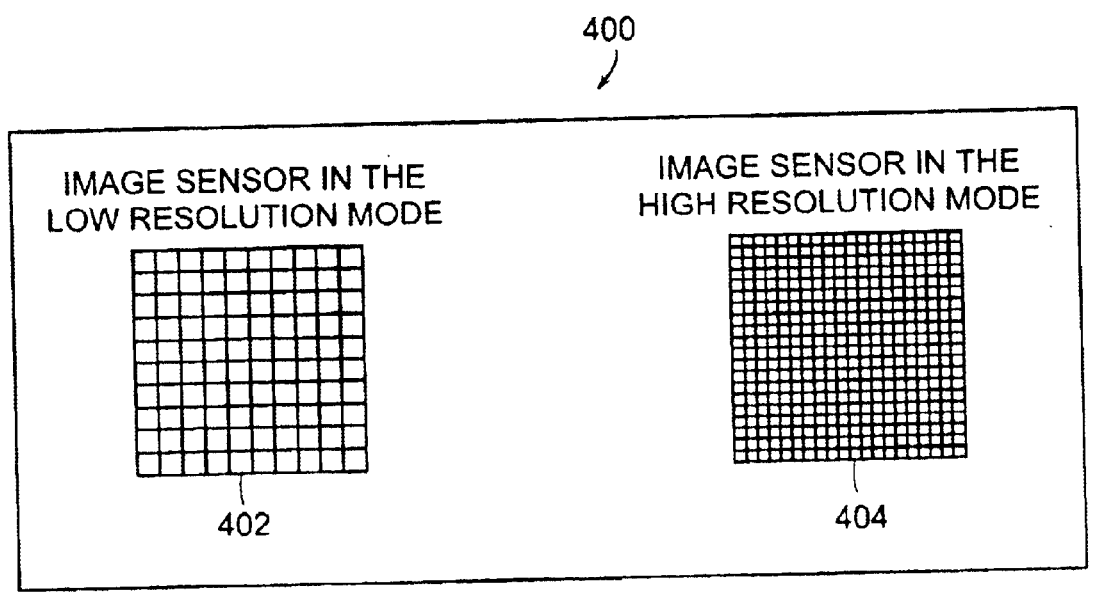
FIG. 10A illustrates the low resolution and high resolution modes in accordance with preferred embodiments of the present invention.

Although some coronary angiography and other procedures such as ventriculography can be performed with lower spatial resolution, therapeutic procedures such as percutaneous transluminal coronary angioplasty (PTCA) and stent deployment require high resolution and excellent contrast. Physicians use increasingly thinner guidewires, as small as 250 microns, which are frequently difficult to image clearly in large patients, and are engaging more in performing therapeutic procedures in smaller arteries. Therefore, the capability of high spatial resolution, with better contrast, is critical in these procedures. Recognizing this need, preferred embodiments of the present invention are designed to deliver the highest spatial resolution achieved with a fluoroscopic flat panel detector. The resolution capabilities of the present invention imager can be varied through a process called "pixel binning" wherein adjacent pixels are grouped together for low resolution applications. An illustration of the high 404 and low-resolution modes 402 of operation is shown in FIG. 10A.

Figure 10B:
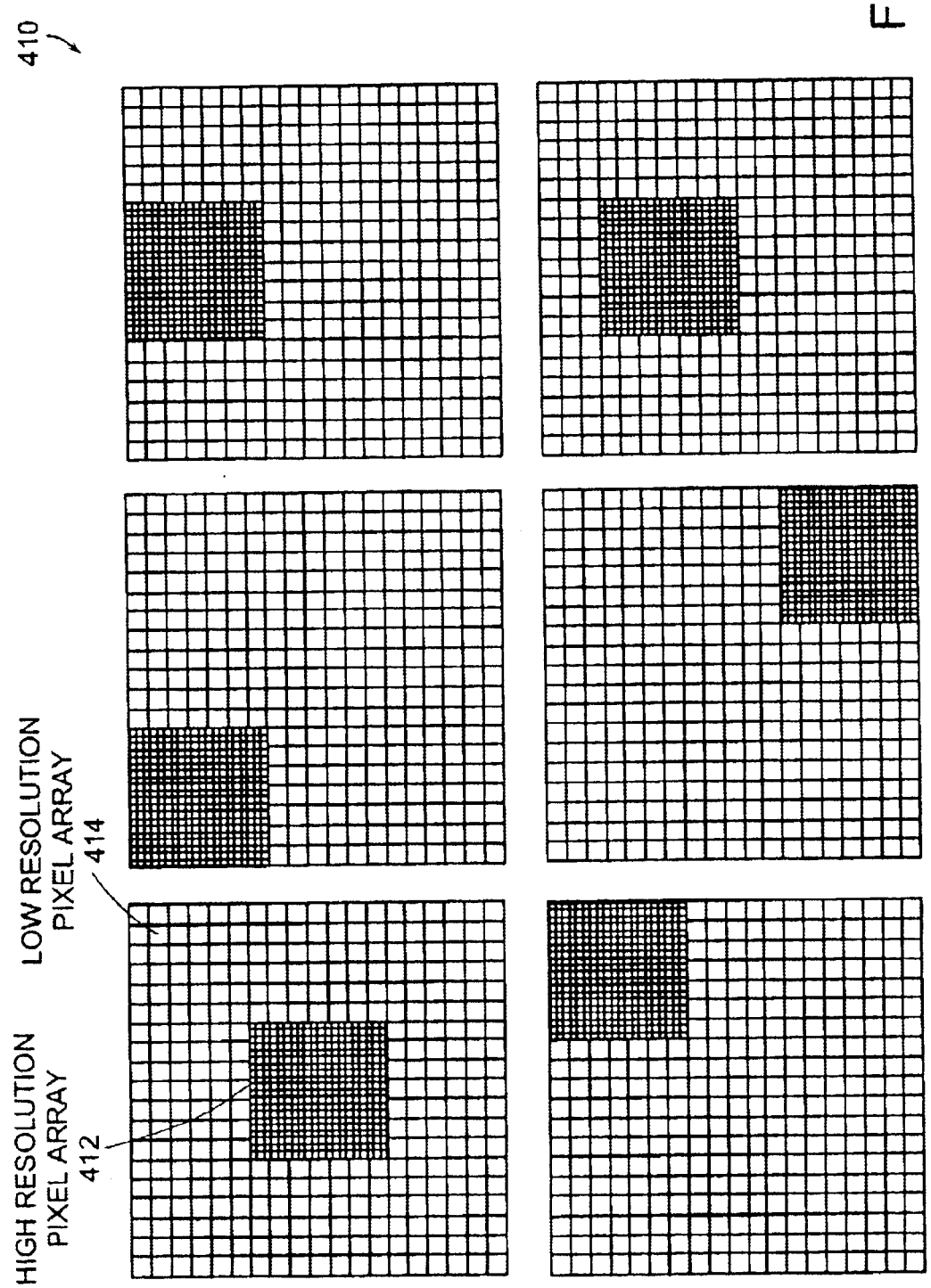
FIG. 10B illustrates the dynamic binning capabilities of the preferred embodiment of the present invention system.

Preferred embodiments of the present invention provide dynamic variable spatial resolution. Fixed spatial resolution is likely to be of limited use in cardiac imaging. In current practice, during the initial phase of a cardiac procedure, the low resolution mode is acceptable and is performed at a lower radiation dose, while when engaging in rotoablation or angioplasty, the high resolution mode is often essential in most cases. Current flat panel technology has yet to demonstrate capability or potential of dual or triple mode resolution. As an example, for preferred embodiments of the present invention system with a base pixel size of 80 µm, the resolution can be varied in multiples of the base pixel size, such as 80 microns (6.2 cycles/mm), 160 microns (3.1 cycles/mm), 240 microns (2.1 cycles/mm) and 320 microns (1.5 cycles/mm). This is accomplished by pixel binning (grouping of pixels) prior to readout at the hardware level. Further, the resolution of the imager can be varied dynamically amongst different regions 412, 414 as dictated by the diagnostic task as illustrated in FIG. 10B.

Figure 10C:
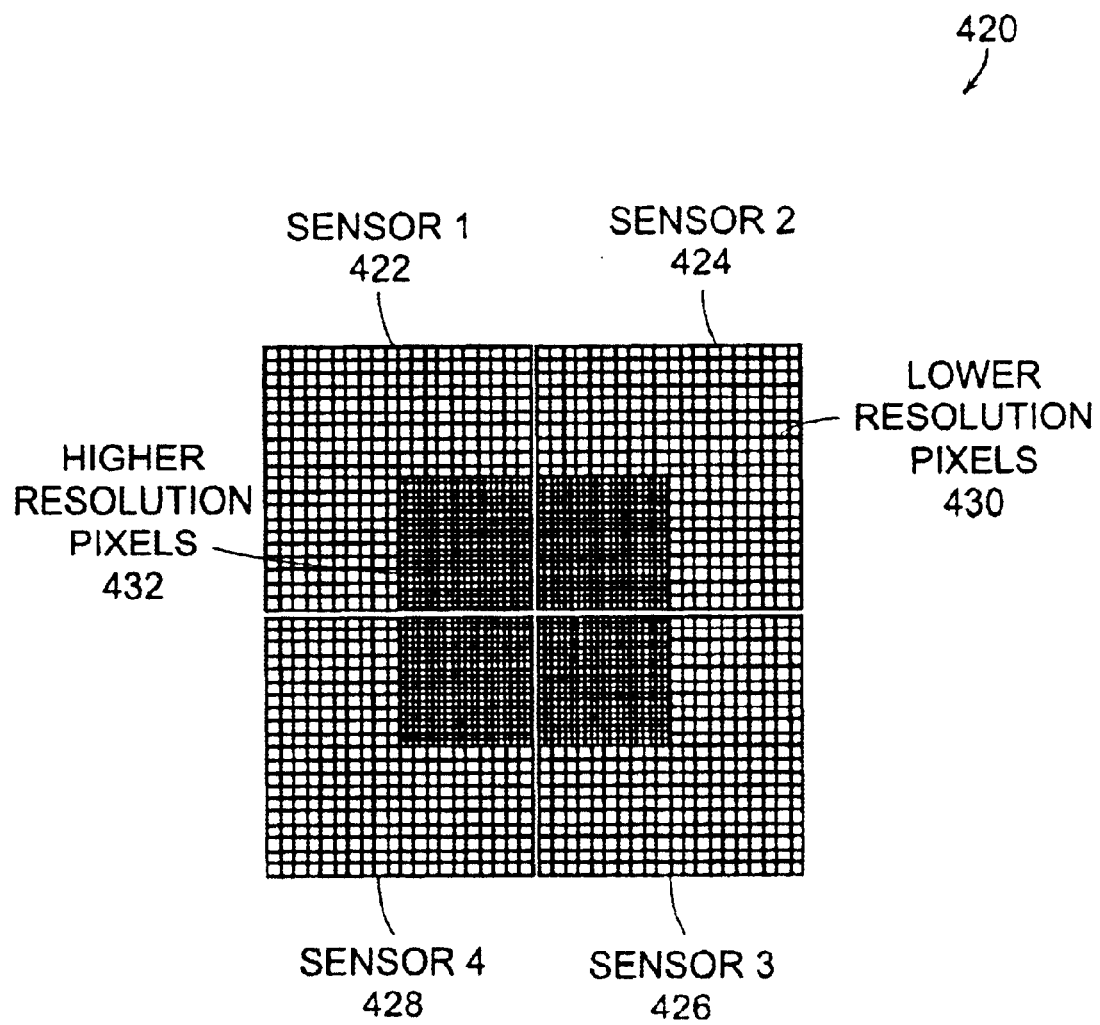
FIG. 10C is a schematic diagram of the formation of a central higher resolution area with four image sensors in accordance with a preferred embodiment of the present invention.

The schematic in FIG. 10C shows a fluoroscopic or radiographic panel that consists of four image sensors 422, 424, 426, 428. Each sensor, for example, sensor 1 422 can be read out in two segments, one segment is the lower quarter which can be read out in the high resolution mode 432 while the other three quarters can be read out in the lower resolution mode 430. This multiple resolution mode can be facilitated by employing a separate readout for each quadrant of an individual sensor. Further, preferred embodiments may provide interpolation techniques for the CCD seams at different resolution. It should be noted that in preferred embodiments, more than one region of the imager can be operated at a high resolution mode. For example, the upper right and lower left quadrants may be operated at the high resolution mode, while the rest of the imager is operated at the low resolution mode. This allows viewing of blood vessels, which may traverse along the diagonal of the imager at a high resolution.

Figure 10D:
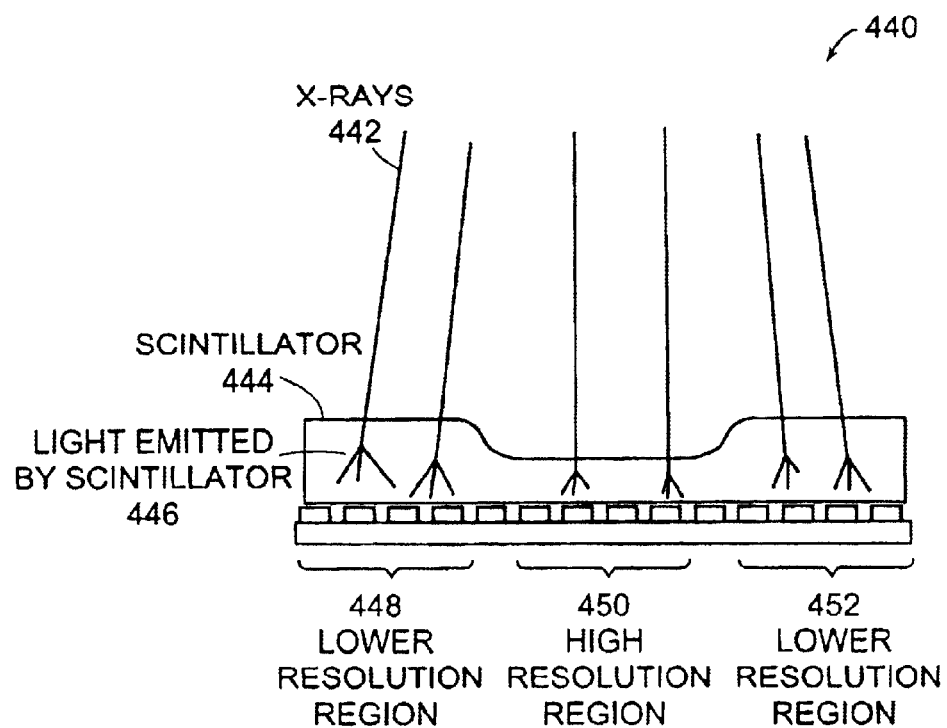
FIGS. 10D and 10E are schematic diagrams of preferred embodiments of multi-thickness scintillators for variable spatial resolution in accordance with the present invention.
Figure 10E:
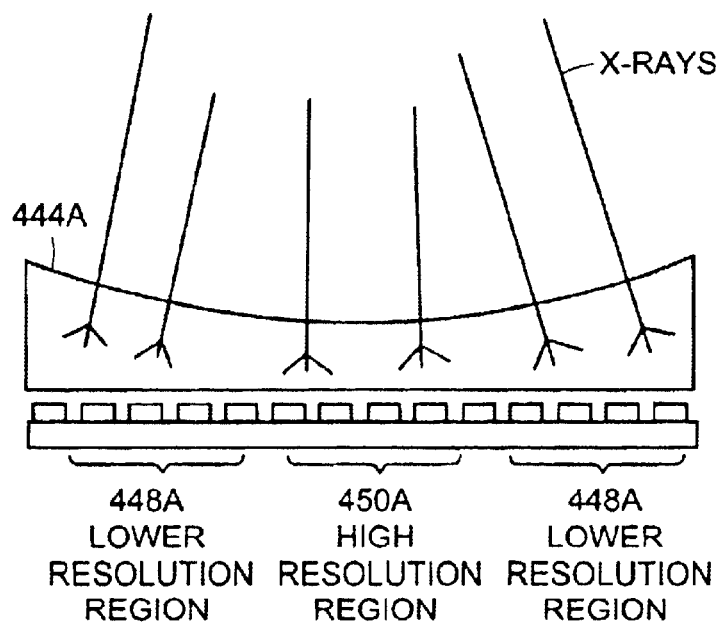

The schematic in FIGS. 10D and 10E illustrate preferred embodiments of the scintillators 444, 444A that are designed to be thinner in the central section 450, 450A and thicker in the periphery 448, 448A, 452, 452A. This enables higher spatial resolution in the central section while maintaining a high signal-to-noise ratio in the non-central region. The scintillator can be deposited as a gradually thinned layer as illustrated in FIG. 10E. A scintillator may include different scintillator materials and thus may have different wavelength or different absorption or decay characteristics. These preferred embodiments of the scintillators can be used with any indirect type detection technologies which use a scintillator such as, but not limited to, amorphous silicon, CCDs or CMOS.

Figure 10F:
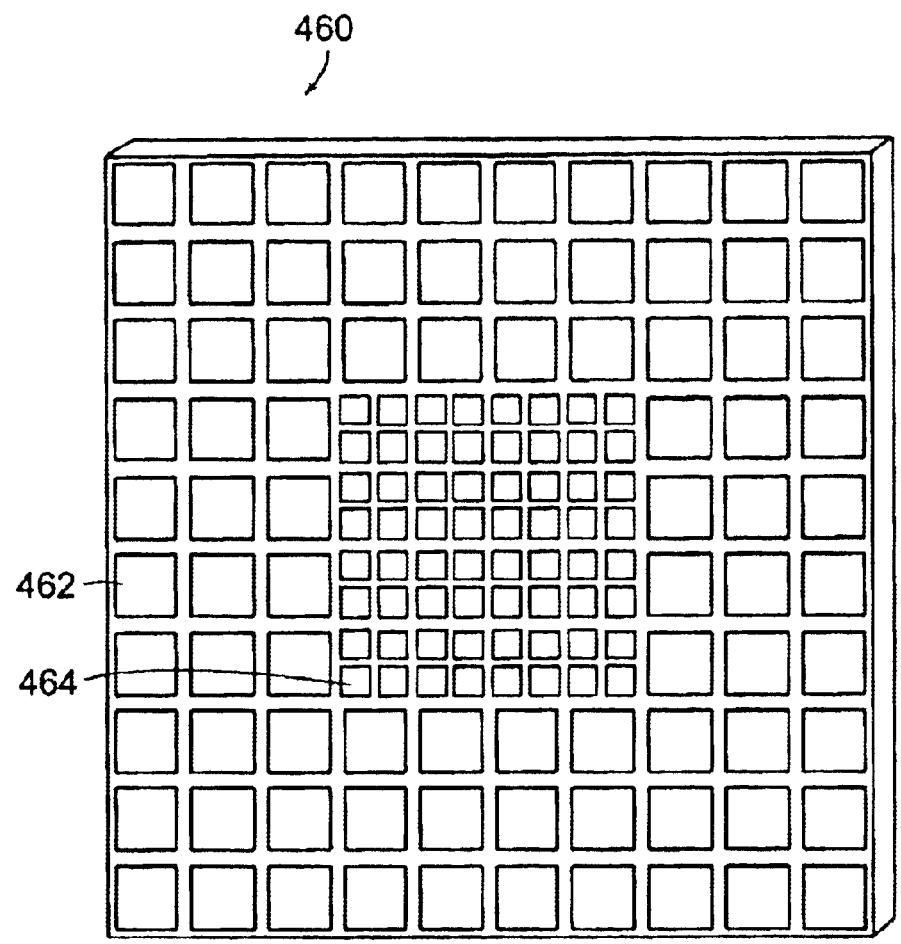
FIGS. 10F, 10G and 10H illustrate alternate embodiments of a multi-resolution image detector in accordance with the present invention.

FIG. 10F illustrates an alternate embodiment of a multi-resolution imaging detector 460 in accordance with the present invention. A flat panel imaging detector has a segment of the panel consisting of relatively large pixels 462, such as pixels of a square shape, and a segment of the panel consisting of smaller pixels 464. The spatial resolution of the central area is higher than the periphery. Alternatively, the entire sensor can be made of a single pixel size, but the periphery of the sensor is binned to provide a lower resolution of the periphery compared to the center area. The two sections, central and peripheral, may be controlled independently in a particular embodiment of the present invention. In a preferred embodiment, the fluoroscopic rate of the central section may be 30 frames per second while that of the periphery may be at 15, 7.5, 3, 1, 0.5 or 0.1 frames per second or even be displayed as a static image.

The flat panel imager may be of the indirect detection type such as, for example, but not limited to, an amorphous silicon detector with a scintillator, or of the direct detection type, using amorphous selenium or other direct detection material.

Figure 10G:
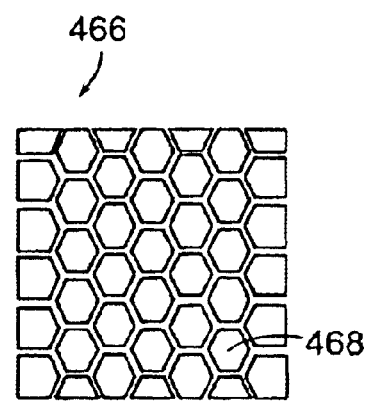

FIG. 10G illustrates an alternate preferred embodiment of a multi-resolution imaging detector 466 in accordance with the present invention. In this embodiment the pixels are hexagonal 468 with the corresponding hexagonal packing. In a preferred embodiment, the central regions can be a CCD coupled to a scintillator and the peripheral regions can be other types of detectors such as an amorphous silicon (a:Si) with a scintillator, CMOS with scintillator, amorphous selenium without a scintillator and other direct conversion materials such as cadmium zinc telluride, lead iodide and mercuric iodide without scintillator.

Figure 10H:
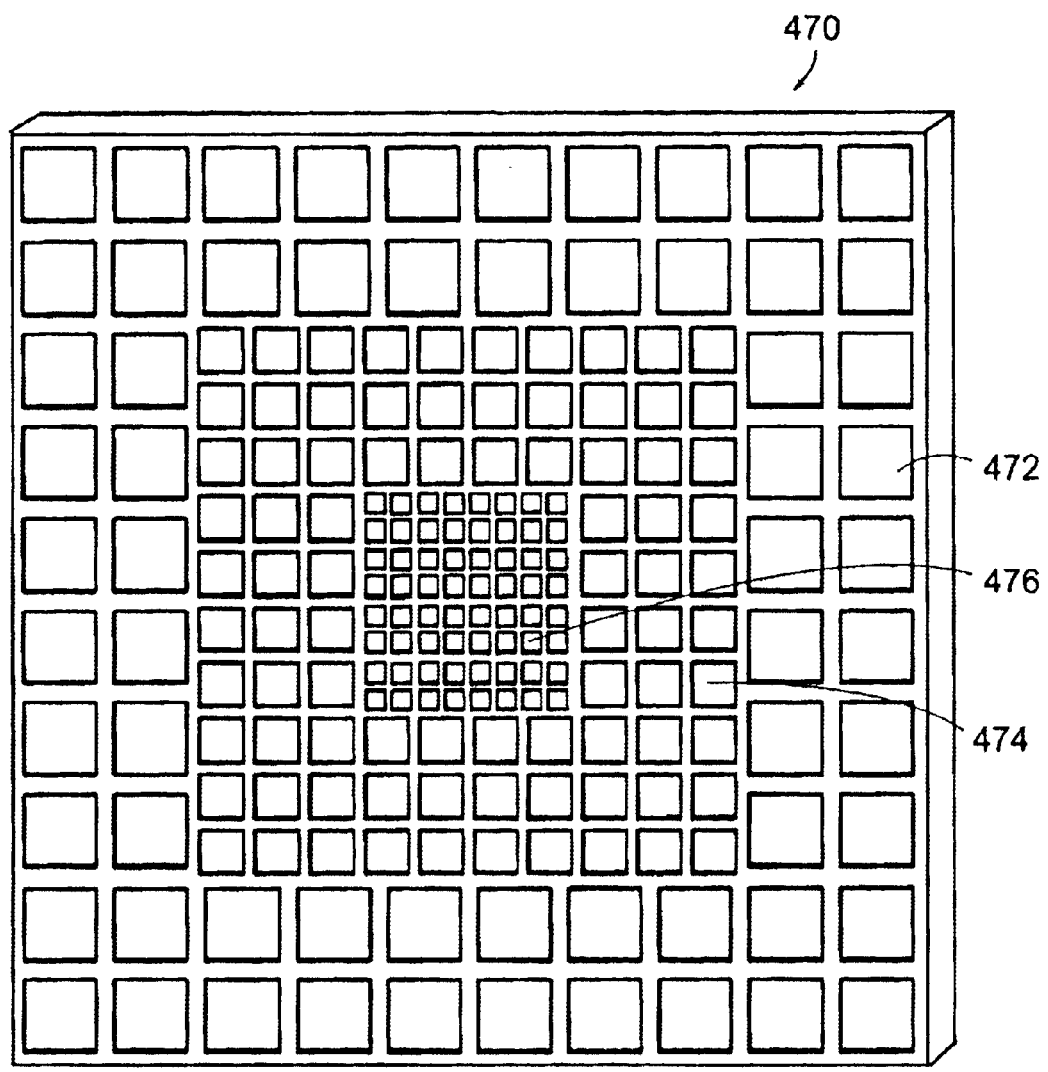

FIG. 10H illustrates yet another alternate embodiment of a multi-resolution imaging detector 470 in accordance with the present invention. The flat panel has three spatial resolution modes and associated pixels 472, 474, 476 that vary with size. In some applications the pixel size of the smallest pixels 476 range between 10 to 50 $\mu$m. In particular for cardiac applications the range of pixels 476 may be between 100 to 180 $\mu$m. The mid-size pixels 474 range from between 150–200 $\mu$m but for some applications they range from 150–250 $\mu$m. The largest pixels 472 in terms of size range from 150–400 $\mu$m. For cardiovascular applications they may preferably range from 200–300 $\mu$m. The largest pixels in terms of size range form 150–400 $\mu$m. For cardiovascular applications they may preferably range from 250–400 $\mu$m. Higher resolution fields may be reduced to a lower resolution by combining adjacent pixels through the process of pixel binning, discussed hereinbefore. Further, the central region can be operating at any desired rate independent of the surrounding regions. For example, the central region can be operating at 30 fps while the surrounding regions can be operating at 30, 15, 7.5, 3.5 fps or even as a static image.

Figure 11:
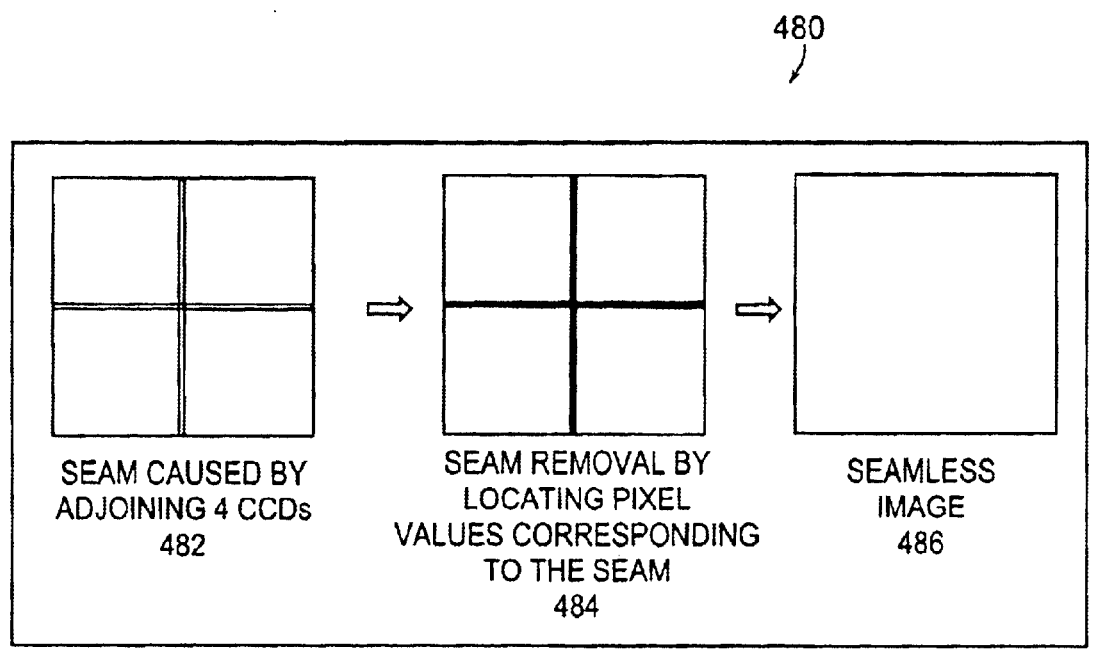
FIG. 11 illustrates the seam correction in a preferred embodiment of the present invention.

It is well known that seam artifacts occur when tiling CCDs and various embodiments of the present invention rectify this problem. In a particular embodiment, the frames are corrected for seam artifacts as soon as they are acquired. This is analogous to "pseudo real-time" because there may be a small lag between acquisition and correction. As soon as each frame is acquired, the region of the seam is identified by the algorithm or sequence of instructions by looking for pixel values corresponding to the seam and correcting it while the rest of the image is joined to form a "seamless" image 486 as illustrated in FIG. 11.

In another preferred embodiment, a hardware approach is used to correct seam artifacts. The data acquired from each of the four CCDs or four quadrants illustrated in FIG. 11 can be fused or combined by a frame grabber memory or suitable area and then combined without the seam.

Preferred embodiments of the present invention address automated ejection fraction, stenosis evaluation, catheter, guidewire positioning and imaging for the deployment of intravascular stents. One of the primary objectives of a diagnostic cardiac angiographic procedure is to determine not only the presence and location of a stenosis, but also to ascertain the degree to which such a stenotic lesion impedes blood flow. Estimation of ejection fraction during left-ventricular analysis is also an important element of a diagnostic cardiac procedure. Current approaches to estimate the degree of stenosis require the operator or physician to mark and draw lines using a mouse or a track-ball along the obstructed region of the vessel and to draw lines pertaining to the estimated periphery of the vessel. The computer then calculates the degree of stenosis based on the area, which is subject to an elevated degree of uncertainty due to the need for operator input. Similar techniques are also used for ejection fraction estimation. Since the preferred embodiments of the present system provide high resolution and contrast than that afforded by prior art imaging systems, estimation of degree of stenosis and ejection fraction can be determined by automated means. Specifically, the contrast provided by the injected media can be tracked along the vessel with high spatial resolution and any restriction in the flow can be used to automatically evaluate the degree of stenosis.

Preferred embodiments of the present invention also address rotational and three-dimensional angiography. Current cardiac diagnostic procedures involve imaging of the coronary arteries at multiple angulations or views. Typically three to seven views (depending on the procedure and physician's requirement) of the left and right coronary artery are acquired during a diagnostic exam. Due to the ability of a preferred embodiment of the present invention system to provide high resolution and contrast at reduced radiation dose, it is feasible to acquire more number of views than that afforded by prior art technology for an equivalent cumulative radiation dose to the patient. Such multiple acquisitions combined with robust reconstruction techniques provide for three-dimensional imaging of the anatomy with resolution and contrast. As a comparison, three-dimensional images acquired with Computerized Tomography (CT) scanners demonstrate resolution in the order 0.1–0.3 cycles/mm, which is an order of magnitude lower than that achieved by the preferred embodiments of the present invention.

Further, preferred embodiments of the present invention provide for guidewire tracking, real-time feedback and virtual surgery. Due to the higher resolution and contrast that is achieved by the preferred embodiments of the present invention system for the same radiation dose as with conventional prior art fluoroscopic systems, it is possible to track small guide wires with precision and provide real-time feedback to the operator regarding its position. In addition to tracking of guide wires, the preferred embodiments are able to track the contrast media and appropriately advance the patient positioning table or move the imaging system to provide continuous tracking of the contrast media without the need for manual tracking by the operator, if desired. This is beneficial for peripheral vascular procedures, where prior art technology is based on either manual tracking of the contrast media by the operator, or by a predetermined speed of movement of the table in a particular direction, which might not correlate to the rate and direction of movement of the contrast media. Due to the accurate tracking and automation capabilities, preferred embodiments are a valuable tool for virtual surgery.

The preferred embodiment as described hereinbefore includes four, three-side buttable, 8×8-cm large area inter-lined CCDs, coupled to a structured CsI:Tl scintillator by a straight (non-tapering) fiberoptic plate. The four CCDs are tiled in a seamless fashion, with the readout pins oriented away from the seam, to achieve a field of view (FOV) of 16×16-cm. Each CCD can have a 2048×2048 pixel matrix with a fundamental pixel pitch of 39-$\mu$m. The CCDs are capable of being operated in 3 different pixel pitch modes of 78, 156 and 234-μm, resulting in Nyquist limits of 6.4, 3.2 and 2.1 cycle/mm, respectively. The variable pixel pitch is achieved by grouping or binning 2×2, 4×4 and 6×6 adjacent pixels, respectively. This preferred embodiment having a CCD with an interline architecture hereinafter referred to as the interlined CCD facilitates frame rates of up to 30 frames per second (fps) even at the highest resolution mode of 78-μm. In addition, the x-ray source can be continuously on, as the time taken for transfer from the active area of the pixel (photosite) to the data line (interline or interpixel channel) is extremely short (5-μs) and does not contribute to smearing. This allows the use of these embodiments with cost efficient fluoroscopic devices, which do not employ a pulsed fluoroscopic source, such as some mobile C-arms. The interline channel is opaque to light resulting in degradation of the fill factor. The width of the interline channel is approximately 11-μm and traverses the length of the pixel, resulting in an active area of 28×39-μm for each fundamental pixel. This results in a fill factor of approximately 72%. The charge readout process for a single CCD module operating in the 2×2-binned (78-μm) mode is described with respect to FIG. 9C. Each CCD module has eight (8) output ports as discussed previously in FIG. 9C.

Figure 12:
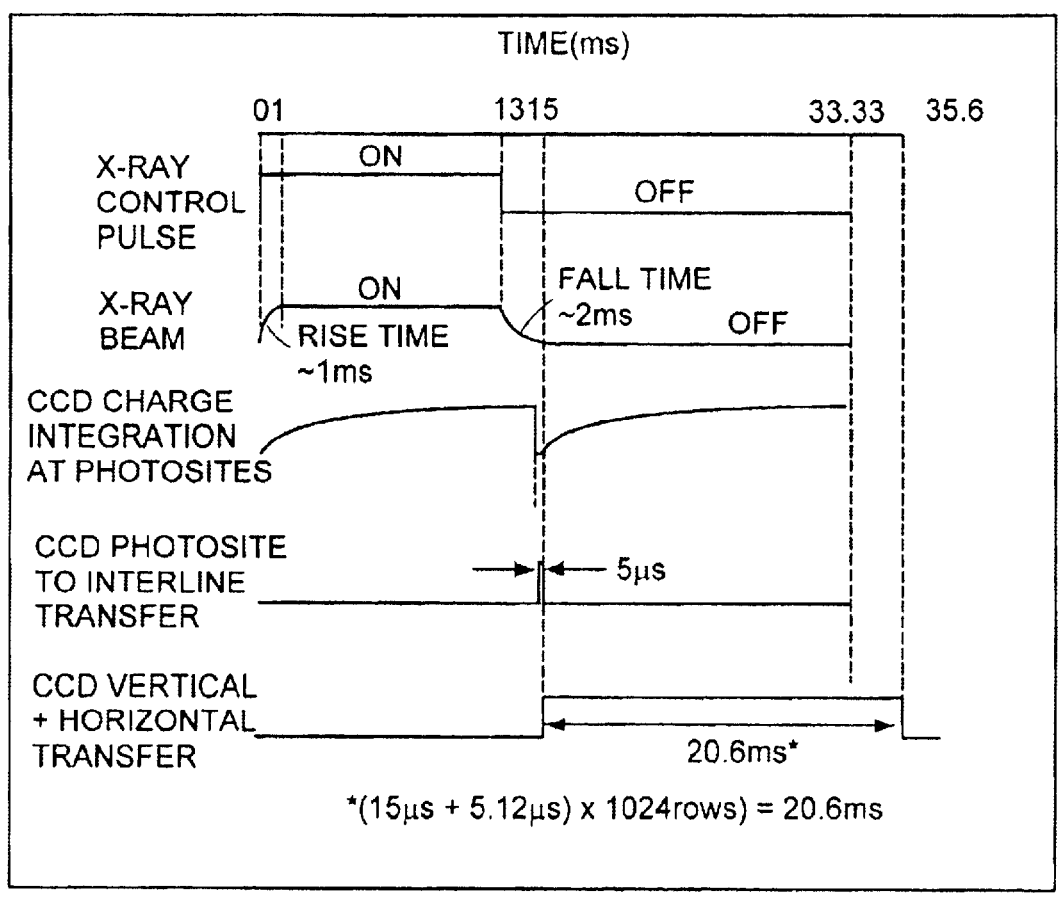
FIG. 12 is an example of a timing diagram for a single CCD module in accordance with a preferred embodiment of the system of the present invention.
Figure 13:
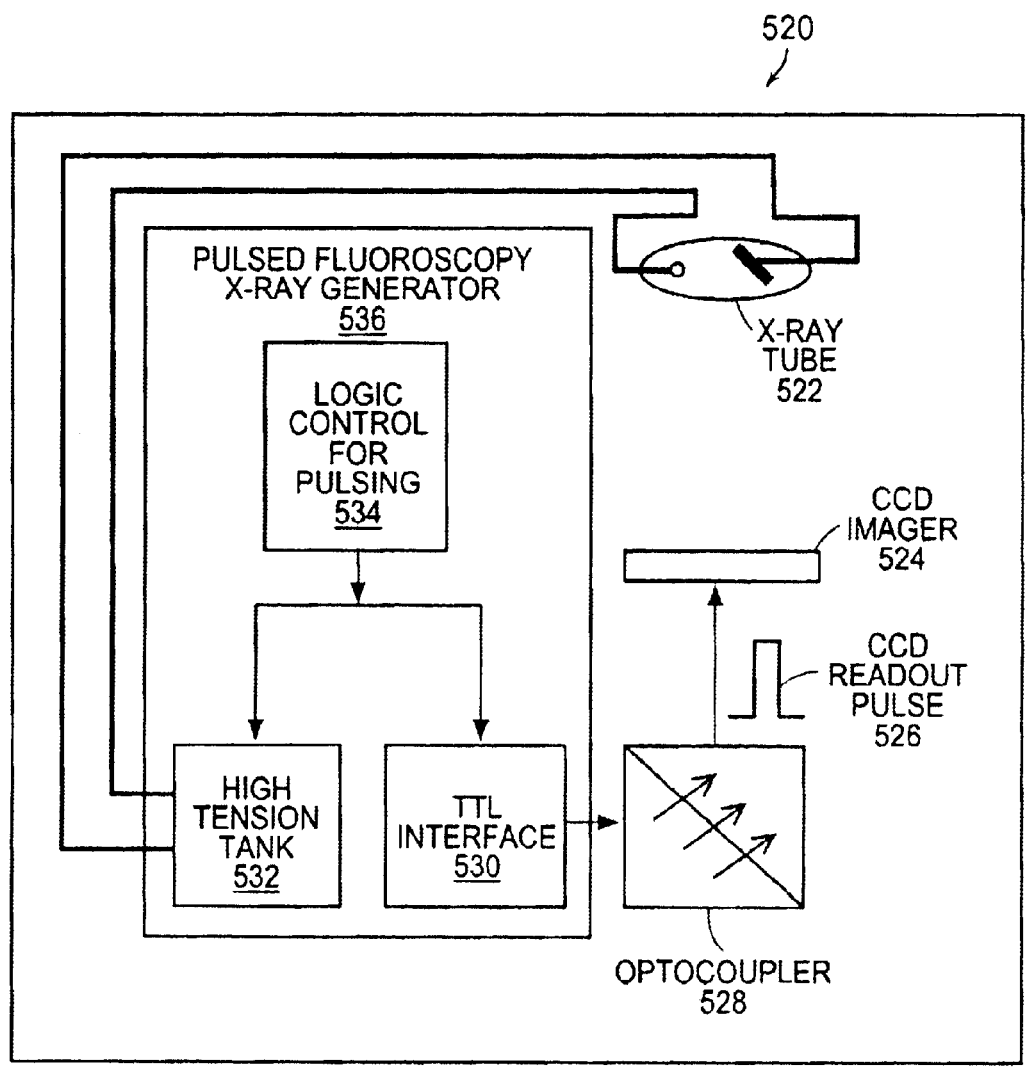
FIG. 13 is a schematic diagram illustrating the interface scheme for synchronizing the CCD-readout with a pulsed fluoroscopic source in accordance with a preferred embodiment of the system of the present invention.

FIG. 12 is a timing diagram 500 for a single CCD module in accordance with a preferred embodiment of the present invention. In addition, FIG. 13 illustrates the interface diagram 520 for synchronizing the CCD readout with a pulsed fluoroscopic source 536.

The high, tension tank 532 includes a bank of capacitors and a transformer to generate the high voltage for the x-ray tube 522. After the termination of the x-ray pulse, the charges on the photosites are transferred to the data line in 5-μs, and the imager integrates charges for the next frame immediately after this period. An additional delay of 2-ms between the control pulse for switching off the pulsed x-ray source and the start of charge transfer from the active area of the pixel is provided for preferred embodiments which are not equipped with grid-controlled tubes to allow sufficient time for discharge due to capacitance of any high-tension cables.

Figure 14:
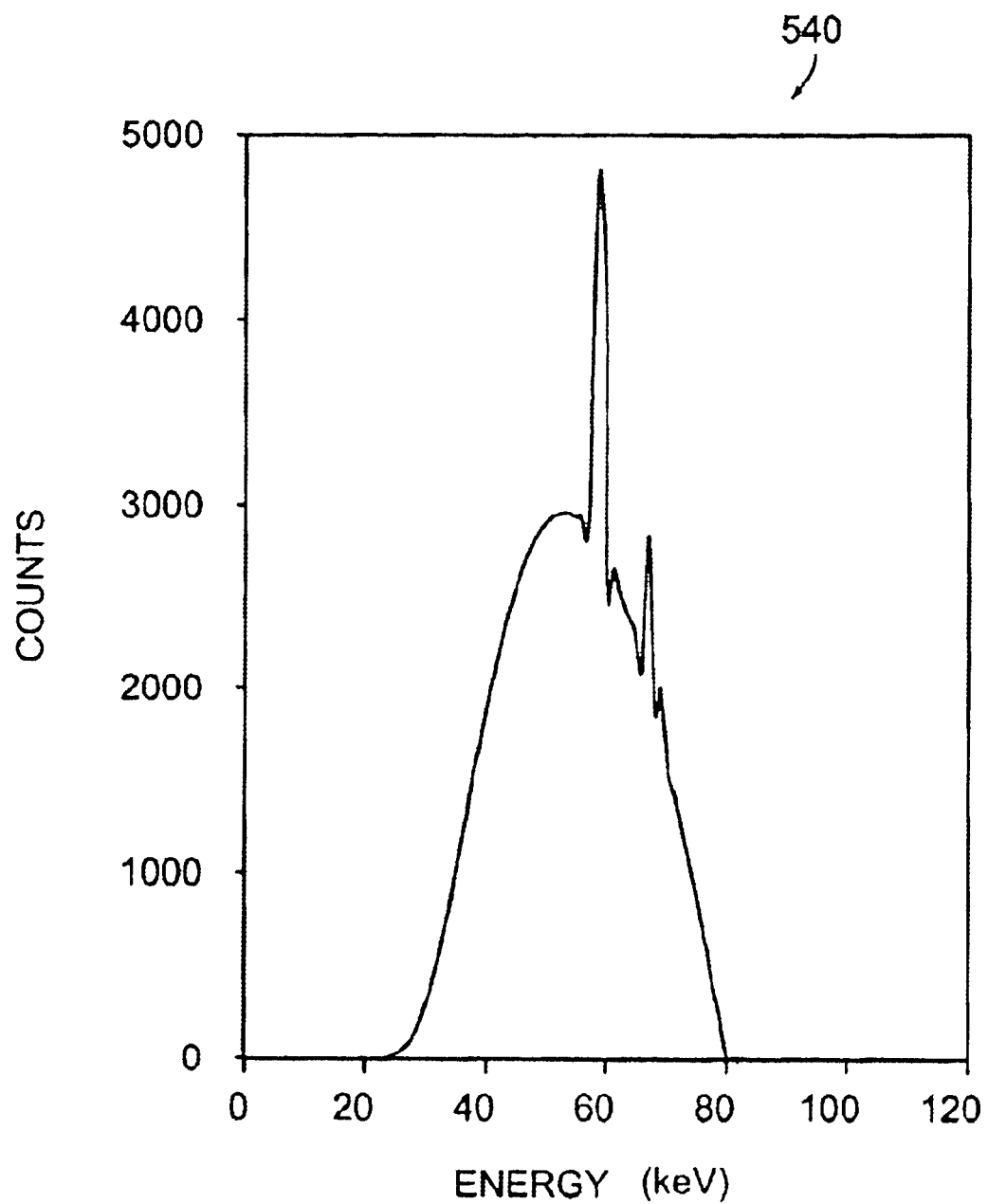
FIG. 14 graphically illustrates the 80-kVp spectrum beam-hardened with 20-cm of tissue (HVL: 6.75-mm Al), used for analysis of a preferred embodiment of the system of the present invention.

In a preferred embodiment, the scintillator is a cesium iodide (CsI:Tl) scintillator, as they have the capability to maintain high spatial resolution due to their structured columnar arrangement. Such scintillators have been successfully used with flat panel systems using amorphous silicon for mammography, radiography and fluoroscopy. Scintillators have also been used with CCD-based imaging devices, for mammography. In addition, the spectral emission of CsI:Tl scintillators is in the wavelength range of 400 to 700-nm, which matches well with the peak absorption range of the silicon photosites. The scintillator design parameters include quantum efficiency and scintillation yield. The fiberoptic design parameters include optical coupling efficiency and optimization of the fiberoptic length. The system parameters addressed in preferred embodiments include CCD read noise, sensitivity, dynamic range, and spatial resolution characteristics. Techniques for seamless tiling of the CCDs and extending the field of view for larger coverage are also addressed in preferred embodiments In a preferred embodiment, a polyenergetic 80-kVp x-ray beam filtered by 2-mm aluminum (Al) and transmitting through 20-cm of tissue from a 17° tungsten (W) target is used for the analysis of the parameters. This x-ray spectrum is plotted and illustrated in FIG. 14 and is referred to as q(E) hereinafter. The first half-value layer of this beam is 6.75-mm Al. The photon fluence per 1-μR of exposure $\left(\frac{q}{X}\right)$ for this beam calculated from the definition of Roentgen is $2.64 \times 10^2$ photons/(mm²·μR) where X represents exposure in units of μR. The incident spectrum q(E) can be represented as a normalized spectrum $q_{norm}(E)$ as is expressed by:

$$q_{norm}(E) = \frac{q(E)}{\int q(E)dE} \quad (1)$$

In another preferred embodiment, a monoenergetic x-ray beam with an energy of 60-keV is used for factors that do not have a direct impact on the performance of preferred embodiments the system such as the optimization of fiberoptic plate thickness, to provide adequate shielding to the CCD from direct x-ray photon interaction.

The quantum efficiency (η) calculations for various scintillator thicknesses, ranging from between approximately 300 to 525-μm thick, are performed as per equation 2 using energy-dependent attenuation coefficient values. A packing density of 90% is assumed for these calculations based on reported values for cesium iodide converters used in image intensifiers. For the 300, 375, 450 and 525 μm thick CsI:Tl scintillators the resultant surface density ($\rho_s$) were 122, 152, 183 and 213 mg/cm², respectively.

$$\eta(E, \rho_s) = 1 - e^{-\mu m(E)\rho_s} \quad (2)$$

where, $\eta(E, \rho_s)$ is the quantum efficiency, $\mu m(E)$ is the energy-dependent mass attenuation coefficient and $\eta_s$ is the surface density of the scintillator. The quantum efficiency for each thickness of the scintillator, for the 80-kVp x-ray spectrum is obtained as:

$$\eta(80\ kVp, \eta_s) = \int \eta(E, \rho_s) \cdot q_{norm}(E) \cdot dE \quad (3)$$

Holl measured the scintillation yield of CsI:Tl scintillators to be 52,000 optical quanta per absorbed 1 MeV x-ray photon. Recently, scintillation yield of up to 64,000 optical quanta per absorbed 1 MeV x-ray photon has been reported by researchers at the Lawrence Berkeley Laboratories. Hence, a mean value between the two measurements of 58,000 optical quanta per absorbed 1 MeV x-ray photon (58 optical quanta per absorbed 1-keV x-ray photon) corresponding to conversion energy of 17.24 eV is used in a preferred embodiment. The number of visible photons emitted $\{Y_s(E)\}$ per absorbed x-ray photon for various x-ray photon energies is calculated as:

$$Y_s(E) = 58 \times E \times \eta_{esc} \text{ for } E < E_k \text{ and} \quad (4a)$$

$$Y_s(E) = 58 \times E \times \eta_{esc} \times \left(1 - \frac{E_k \cdot K_f}{E}\right) \quad \text{for } E \geq E_k \quad (4b)$$

where, E indicates the energy of the incident x-ray photon expressed in keV, $E_k$ indicates the K-edge of the CsI:Tl scintillator (approximated to 34 keV), $K_f$ is the K-fluorescent x-rays escape fraction and $\eta_{esc}$ is the escape probability for the generated optical quanta to be emitted in the direction of the CCD. Rowlands and Taylor measured the K-fluorescent escape fraction for cesium iodide screens used in image intensifiers and found it to be constant above the K-edge. A mathematical model was developed by Dance and Day, which also reported similar findings. Lubinsky has developed an analytical model for the depth dependent escape probability of generated optical quanta. The depth dependent escape probability ($\eta_{esc}$) is modeled with the assumption that the scintillator substrate has no reflective coating. For the 80-kVp x-ray spectrum specified earlier, the absolute scintillation yield per mm$^2$ (Y) as a function of incident exposure, is calculated as per equation 5 for each scintillator thickness.

$$Y = X \cdot \left(\frac{q}{X}\right) \cdot \int Y_s(E) \cdot \eta(E, \rho_s) \cdot q_{norm}(E) \cdot dE \quad (5)$$

where, X is exposure in $\mu$R, $$\frac{q}{X}$$

is photon fluence in units of photons/(mm$^2\cdot\mu$R), $q_{norm}$(E) is normalized incident 80-kVp x-ray spectrum, and $\eta$(E,$\rho_s$) is the energy-dependent quantum efficiency of the scintillator.

The optical coupling efficiency of fiberoptic coupled CCD-based systems has been addressed in preferred embodiments of the present invention. Hejazi and Trauernicht have provided an analysis of the optical coupling efficiency of lens-coupled and fiber optically coupled CCD-based systems. Preferred embodiments also address the effect of taper on fiber optically coupled systems. A straight fiberoptic plate (non-tapering, 1:1 fiber) provides better optical coupling between the scintillator and the CCD with minimal loss of spatial resolution. The optical coupling efficiency (TIFO) of the fiber optics, which is the fraction of light captured and transmitted by a fiber pressed against a Lambertian source can be given as $$\eta_{FO} = n^2 \cdot \sin^2\theta_1 \cdot e^{-u \cdot l} \cdot (1-L_R) \cdot F_c \quad (6)$$

where, $\eta_{FO}$ is the optical coupling efficiency of the fiberoptic plate, n is the refractive index of the material before the fiber entrance, $\theta_1$ is the entrance angle such that the total internal reflection condition at the core-cladding interface is satisfied, u is the absorption coefficient of the fiber, l is the length of the fiber, $L_R$ is the loss at the surface due to Fresnel reflection and $F_C$ is the fill factor of the fiber core. The terms n·sin $\theta_1$ and $e^{-u \cdot l}$ are often referred to as the numerical aperture of the fiberoptic and the fiber core transmission efficiency, respectively. In a preferred embodiment, the fiber core transmission efficiency is approximately 0.8. Losses associated with Fresnel reflections ($L_R$) can be decreased by coating or using an optical coupling medium with matching index of refraction. The fiber optic coupling efficiency is calculated with the assumption that losses associated with the Fresnel reflection contributed to 10% loss of light ($L_R$=0.1). In order to satisfy the total internal reflection condition at the core-cladding interface, the entrance angle $\theta_1$, is such that, $$\sin\theta_1 < \frac{\sqrt{n_2^2 - n_3^2}}{n} \quad (7)$$

where, $n_2$ is the index of refraction of the core, $n_3$ is the index of refraction of the cladding and n is the refractive index of the material before the fiber entrance. For the fiberoptic plate in accordance with a preferred embodiment of the system such as Type 47A, as supplied by Schott Fiberoptics, MA, the fibers have a circular cross-section and the diameter of the clad and core are 12-$\mu$m and 10-$\mu$m, respectively. Also, the refractive index of the core and clad are 1.8 and 1.5, respectively.

Preferred embodiments of the present invention address the optimization of fiberoptic lengths. In addition to optically coupling the scintillator with the CCD, the fiberoptics also perform an important role of protecting the CCD from direct x-ray photon hits. Exposure to high-energy radiation over long duration might damage and degrade detector sensitivity. Hence, it is important to optimize the fiberoptic length to provide adequate shielding to the CCD. Measurements of the x-ray linear attenuation coefficient of various commercially available fiberoptic plates are considered. These fiberoptic plates are doped with non-scintillating high-atomic number (Z) material to efficiently attenuate the incident x-ray beam. Based on these attenuation measurements, Type 47A such as supplied by Schott Fiberoptics, MA is used for optimization of the fiberoptic length in a preferred embodiment. In addition, this type of fiberoptic plate is selected as the optical characteristics of this plate are found to be suitable for mammographic applications and has been successfully used with a CCD-based system developed for spot compression views and stereotactic localization. For simplicity, a monoenergetic x-ray beam with an energy of 60-keV is used for optimization. Also, the scintillator thickness is assumed to be 450-$\mu$m. The number of x-ray photons incident on the entire CCD as a function of time for various fiberoptic plate thickness is calculated based on an exposure rate of 2-$\mu$R/frame, 30 fps, 30 minutes of fluoroscopic usage each hour, 10 hours of usage per day and 300 days of usage per year.

The sensitivity ($\Gamma$) of a preferred embodiment of the system in units of electrons/$\mu$R can be theoretically computed as:

$$\Gamma = A_{pix} \cdot F_f \cdot \eta_{FO} \cdot \eta_{CCD} \cdot \frac{q}{X} \cdot \int Y_s(E) \cdot \eta(E, \rho_s) \cdot q_{norm}(E) \cdot dE \quad (8)$$

where, $A_{pix}$ is the area of a pixel in mm$^2$, $F_f$ is the pixel fill factor, $\eta_{FO}$ is the fiber optic coupling efficiency, $\eta_{CCD}$ is the CCD quantum efficiency average over the wavelength of emission from the scintillator, $$\frac{q}{X}$$

is the photon fluence in units of photons/(mm$^2\cdot\mu$R), $Y_s$(E) is the amount of optical quanta emitted per absorbed x-ray photon in the direction of the CCD, $\eta$(E,$\rho_s$) is the quantum efficiency of the scintillator and $q_{norm}$(E) is the normalized 80-kVp x-ray spectrum. The scintillator substrate is assumed to have no reflective coating and the quantum efficiency of the CCD is assumed to be 0.4.

The total noise ($\sigma_T$) associated with a CCD-based system for uniform illumination with visible radiation can been stated as:

$$\sigma_T = \sqrt{\sigma_{CCD}^2 + \sigma_{ADC}^2 + \sigma_S^2 + \sigma_e^2} \quad (9)$$

where, $\sigma_{CCD}$ is the CCD noise, $\sigma_{ADC}$ is the quantization noise, $\sigma_S$ is the shot noise of the generated electrons, and $\sigma_e$ is all other electronic noise. The CCD noise ($\sigma_{CCD}$) can been stated as:

$$\sigma_{CCD} = \sqrt{\sigma_r^2 + (t \cdot q_d \cdot A_{CCD})} \quad (10)$$

where, $\sigma_r$, is the readout noise, $q_d$ is the dark charge per unit time t per unit area and $A_{CCD}$ is the pixel area of the CCD. The dark current is approximately 10 pA/cm$^2$, resulting in 625,000 electrons/sec per mm$^2$. For a preferred embodiment of the present invention system operating at a frame rate of 30 fps, the integration time per frame is 33.3 ms.

The quantization noise ($\sigma_{ADC}$) is computed by taking into account the full-well capacity of the horizontal (serial) register and the number of quantization steps of the analog-to-digital converter (ADC), resulting in a maximum quantization noise of approximately 18 electrons.

Figure 15:
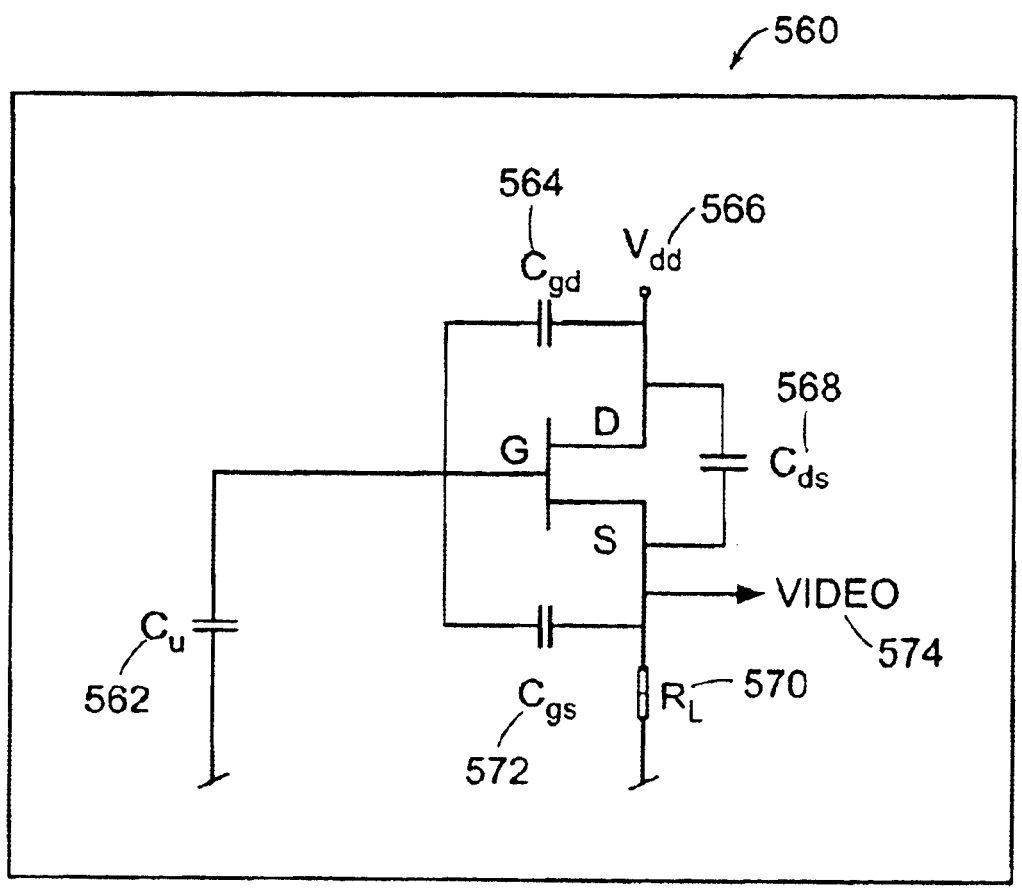
FIG. 15 is a simplified model of the output on-chip amplifier (MOSFET), used for determining the read noise of the CCD in accordance with a preferred embodiment of the system of the present invention.

Low noise CCD detectors have known to exhibit much lower read noise than amorphous silicon (a:Si) based flat panel detectors. Increased noise observed with a:Si based detectors are primarily due to the thin-film transistor (TFT) readout. The read noise characteristics of the preferred embodiment CCD-based imager are modeled. Read noise is a composite of white noise and 1/f noise. The read noise floor of the CCD is limited by the noise of the on-chip output amplifier. Reduction of white noise is possible by constraining the bandwidth (BW) of the CCD, but the time between the samples may be spaced sufficiently to accommodate a slowly changing signal. Read noise varies with the square root of the bandwidth, while the time between samples varies inversely with bandwidth. Theoretically, read noise of the CCD can be reduced unlimitedly if white noise were the only component present. There are however practical limits to this approach as the sampling rate of the output amplifier contributes to the overall read noise of the system. In fact at very high sampling rates, noise increases as the square root of the sampling time. A simplified output on-chip amplifier (MOSFET) modeled by Janesick is illustrated in FIG. 15 and it illustrates the effect of clamp-to-sample time (time at which the first sample is taken where the reference level is clamped to ground potential). The output read noise ($\sigma_r$) is given by $$\sigma_r = 10^{-12} \cdot \frac{\sqrt{2 \cdot k \cdot T}}{q_c \cdot \sqrt{g_m \cdot t}} \cdot (C_u + C_{gs}) \tag{11}$$

where, $\sigma_r$ is the read noise in electrons rms, $g_m$ is the transconductance of the MOSFET expressed in Siemens (S), k is the Boltzman's constant ($1.38 \times 10^{-23}$ W.s/K), $C_u$ is the output capacitance in pF, $C_{gs}$ is the gate-to-source capacitance in pF, $q_c$ is the electron charge ($1.6 \times 10^{-19}$), T is the temperature expressed in Kelvin (K), t is the clamp-to-sample time. A transconductance ($g_m$) of $300 \times 10^{-6}$ S and clamp-to-sample time of 0.04-$\mu$s were assumed. The channel width (W=120-$\mu$m) and length (L=10-$\mu$m) are used to compute the gate-to-source capacitance ($C_{gs}$) and output capacitance ($C_u$) defined by the model as:

$$C_{gs}(pF) \approx W \cdot (2.24 \times 10^{-4} \cdot L + 5.91 \times 10^{-4}) \tag{12}$$

$$C_u(pF) \approx 0.018 + 5.91 \times 10^{-4} \cdot W \tag{13}$$

The shot noise, assumed to be Poisson distributed, is the result of statistical fluctuations in the measured signal. Hence, the shot noise ($\sigma_s$) can be stated as:

$$\sigma_s = \sqrt{Signal} \tag{14}$$

$\sigma_e$ is a combination of several noise sources such as, trapping-state noise, reset noise and charge-transfer noise. Trapping-state noise is due to the uncertainty in the quantity of charge, due to trapping and slow release of charge either by surface or bulk states. Buried-channel operation prevents such noise from the surface states and material control during fabrication can reduce the bulk trapping-state density to negligible levels. Reset noise is due to the uncertainty in voltage to which the output node is reset after a charge packet is read. This noise can be removed very effectively using correlated double sampling methods. The charge-transfer noise is due to the finite inefficiency in the charge transfer process. The high charge transfer efficiency that is routinely being achieved by modern CCDs makes this source of noise relatively unimportant. Hence for this analysis, $\sigma_e$ has been assumed to be negligible.

Preferred embodiments of the present invention address dynamic range. Yaffe and Rowlands, have provided an alternate definition of the dynamic range, which they refer to as 'effective dynamic range' ($DR_{eff}$) and is defined as:

$$DR_{eff} = \frac{k_2 \cdot X_{max}}{k_1 \cdot X_{noise}} \tag{15}$$

where, $k_1$ is the factor by which minimum signal must exceed the noise for reliable detection, $X_{max}$ is the x-ray fluence providing the maximum signal that the detector can accommodate and $X_{noise}$ is the fluence that provides a signal equivalent to $\sigma_T$. The constant $k_2$ is the factor by which the signal-to-noise ratio (SNR) improves due to integration over multiple pixels. For simplicity and as the most conservative case, $k_2$ has been assumed as unity. The CCD in a preferred embodiment is designed to have a summing well capacity and hence saturation limit of $1 \times 10^6$ electrons. Assuming $k_1$ to be 5 based on the work of Rose, the system of a preferred embodiment is capable of providing signal response in the range of $5 \times \sigma_T$ to $1 \times 10^6$ elections. The corresponding exposure levels (X) can be calculated from the sensitivity ($\Gamma$) of the system as $$X = \frac{Signal}{\Gamma} \tag{16}$$

Preferred embodiments of the present invention address spatial resolution characteristics. The columnar arrangement of CsI:T1 scintillators restrict spatial spreading and hence, improves spatial resolution characteristics. Characteristics of these scintillators at mammographic energies have been reported. In order to study the impact of thickness of the scintillator on the spatial resolution characteristics, presampling modulation transfer function (MTF) measurements are performed for four different thickness of CsI:T1. A 1×1-inch, back-illuminated CCD operating at a pixel pitch of 96-$\mu$m is used. The thickness of the scintillator ranges between 300 to 525-$\mu$m, in steps of 75-$\mu$m. The presampling MTF is measured using the slanted-slit technique. The experimental procedure for these measurements has been described hereinbelow. Specifically, an image of a 10-mm long, 10-$\mu$m wide (±1-$\mu$m) slit is acquired. An 80-kVp x-ray beam with a half-value layer (HVL) of 6.8-mm Al is used for these measurements. The image is corrected for minor variations in slit width. The finely sampled line spread function (LSF) is obtained based on the angulation of the slit. The Fourier transform of the finely sampled LSF is performed and then deconvolved for the finite dimension of the slit to obtain the presampling MTF. The scintillator MTF can be determined by dividing the measured pre-sampling MTF by the sinc of the pixel aperture.

Seamless tiling of the CCDs can be achieved using techniques, which are currently used for defect correction in CCDs. Specifically, by treating the seams as defective columns, corrections can be performed based on linear interpolation from surrounding pixels. Since the seam of the proposed tiled system is expected to be approximately 40-μm, which corresponds well with the fundamental pixel size, it is easy to correct for this seam. An artificial column is created at the location of the seam by providing the mean values of the adjacent columns. In order to verify the effectiveness of such a method, two 6×6-cm CCDs operating at a pixel pitch of 30-μm were tiled. The seam between the two CCDs is approximately 30-μm.

The preferred embodiment of the system provides an extended FOV of 16×16-cm at the image plane. For applications requiring a larger FOV, additional CCDs can be tiled. As each of the CCD-modules are three-side buttable, extending the FOV in either of the two directions can be easily accomplished by tiling additional modules. For example, a 16×24-cm imager can be achieved by tiling 2×3 modules. However, extending the FOV in both directions requires considerable adaptation, as the readout pins of the central module cannot be easily accessed as shown in FIG. 9F. In order to overcome this issue, the height of the fiberoptic plate for the inaccessible CCD(s) have been increased to provide sufficient clearance, such that the readout pins are accessible. This staggered fiberoptic arrangement can be achieved in several ways.

Figure 16:
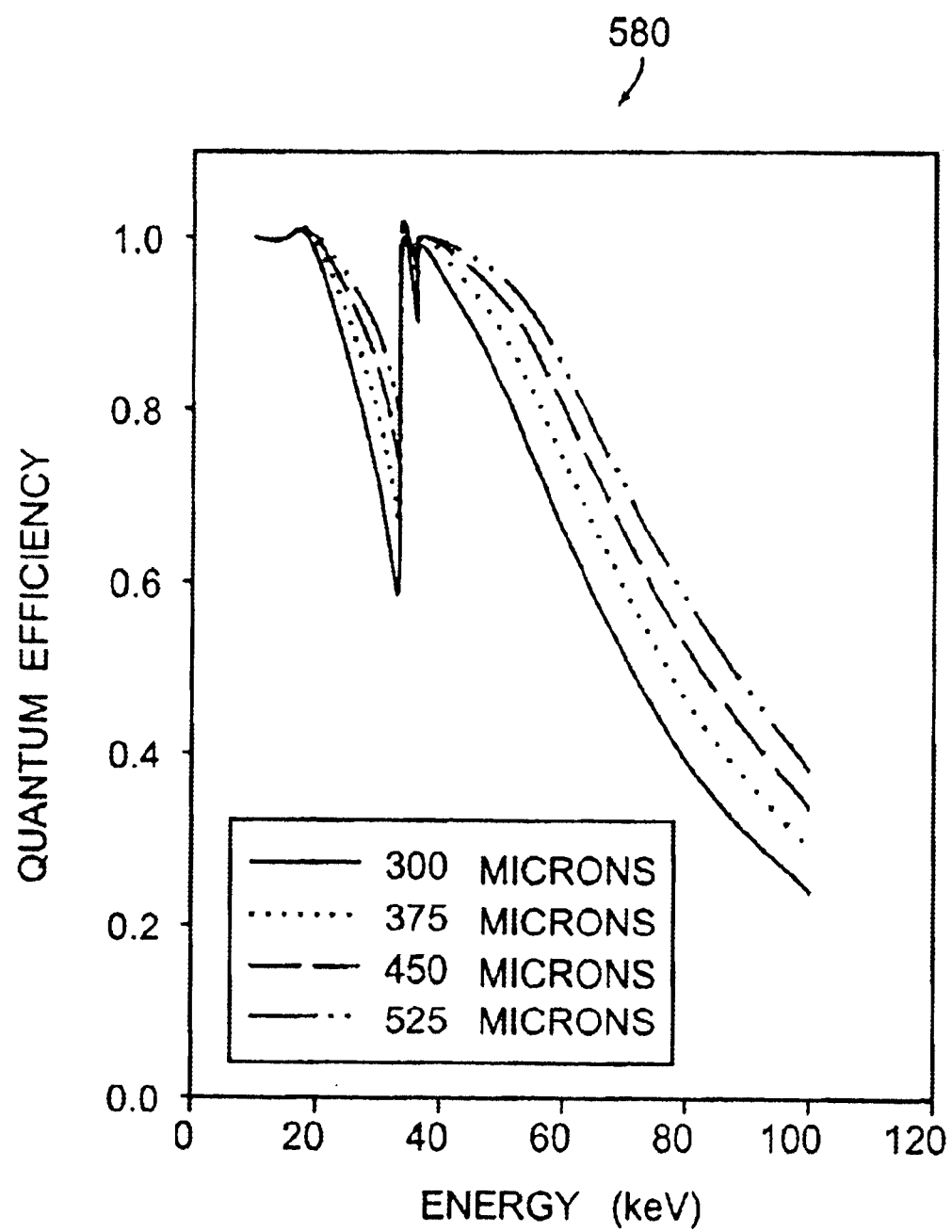
FIG. 16 graphically illustrates the quantum efficiency computed for various thickness of the cesium iodide (CsI) scintillator in accordance with a preferred embodiment of the system of the present invention.

The quantum efficiency of the scintillator as a function of incident photon energy is computed for various thicknesses as per equation 2 and is shown in FIG. 16. For the 80-kVp x-ray spectrum, the quantum efficiency of various thicknesses of the scintillator is computed as per equation 3 and is tabulated in Table 1.

TABLE 1

| Scintillator Thickness (μm) | Quantum Efficiency |
|---|---|
| 300 | 0.701 |
| 375 | 0.768 |
| 450 | 0.818 |
| 525 | 0.856 |

Figure 17:
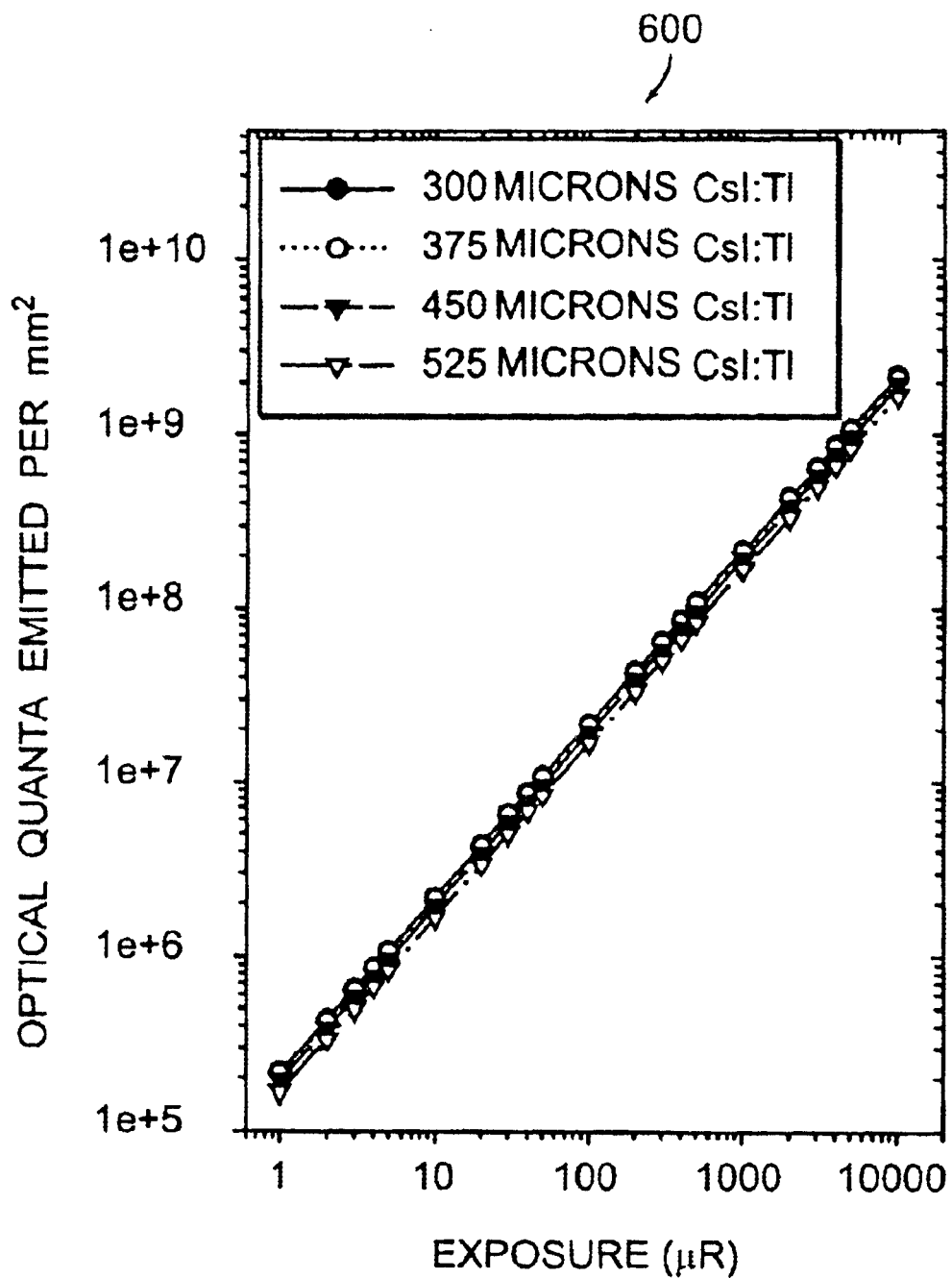
FIG. 17 graphically illustrates the number of optical quanta emitted per unit area computed for the four thicknesses of CsI:Tl scintillator as a function of incident exposure for the 80-kVp spectrum shown in FIG. 14 in accordance with a preferred embodiment of the system of the present invention.

The number of optical quanta emitted per unit area by the scintillator as a function of the energy of incident exposure for the 80-kVp spectrum is calculated as per equation 5. FIG. 17 shows the plot of the number of optical quanta emitted per unit area as a function of incident exposure for the four thicknesses of CsI:Tl scintillators. While increasing the thickness of the CsI:Tl scintillator improves the quantum efficiency, the light output decreases due to self-attenuation of the generated optical quanta.

Figure 18:
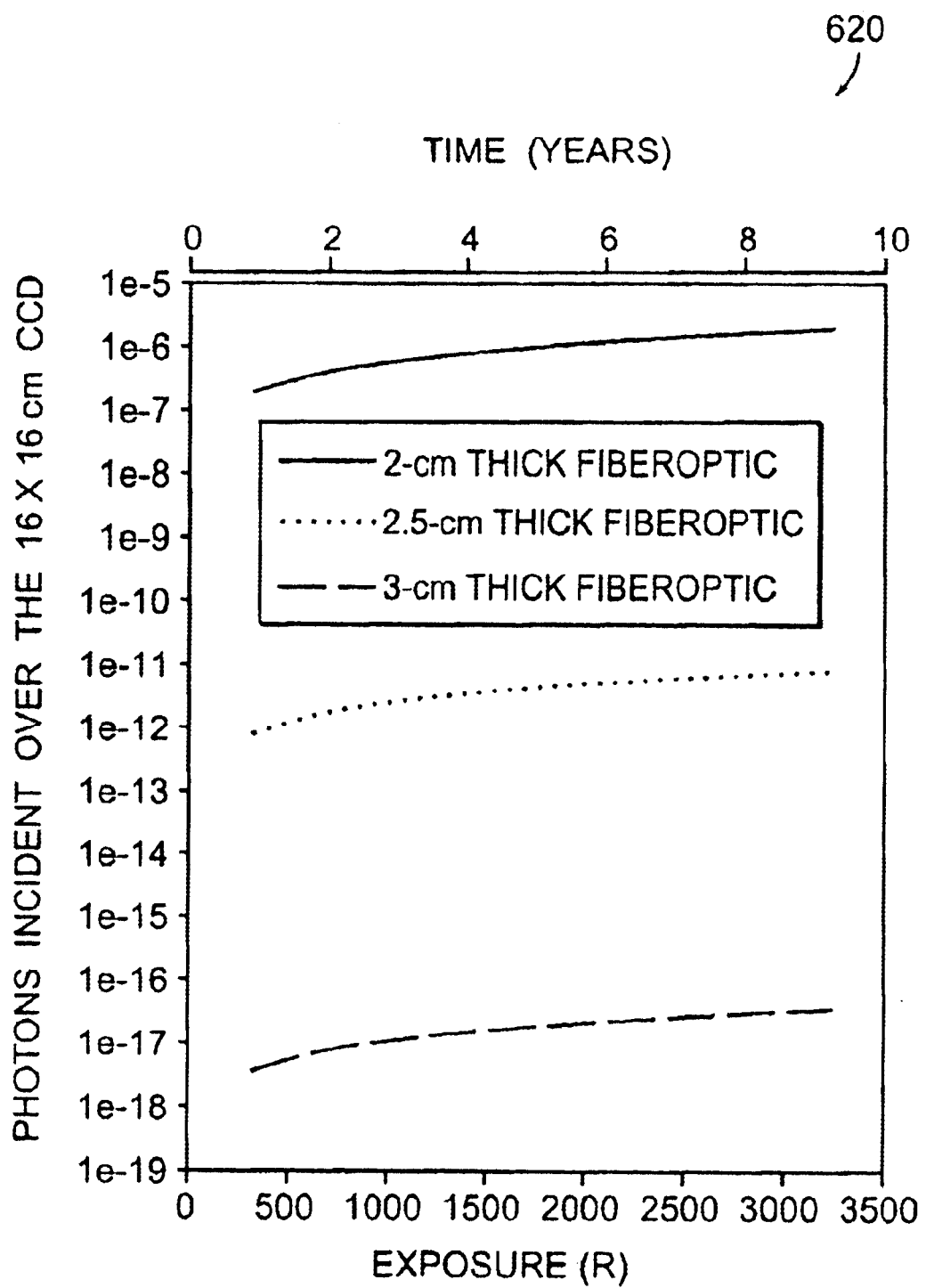
FIG. 18 graphically illustrates the number of x-ray photons incident on the entire CCD calculated for various fiberoptic plate (type 47A) thickness calculated as a function of time in accordance with a preferred embodiment of the present invention.
Figure 19A:
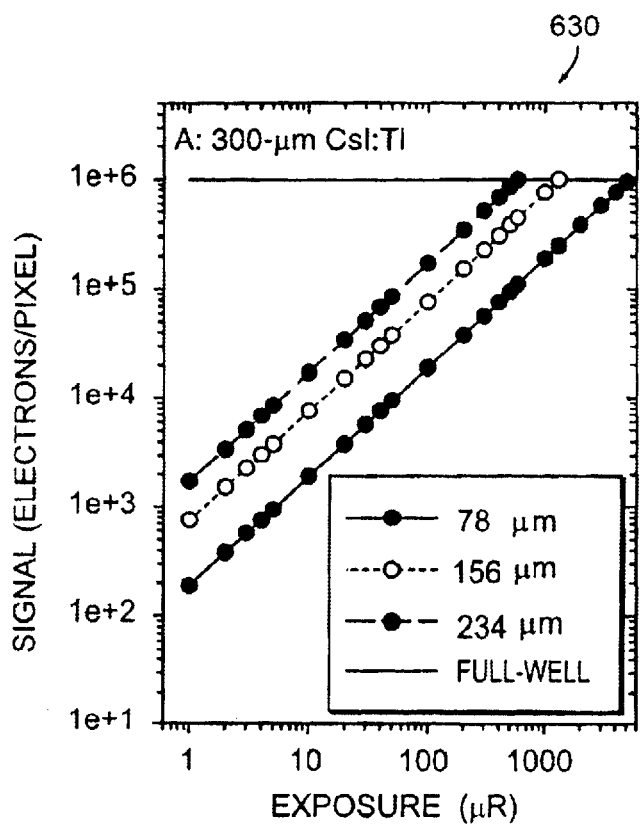
FIGS. 19A–19D graphically illustrates the calculated signal per pixel as a function of incident exposure for the 80-kVp spectrum in accordance with preferred embodiments of the system of the present invention wherein the thickness of the scintillator varies as 300 $\mu$m, 375 $\mu$m, 450 $\mu$m and 525 $\mu$m CsI:Tl and the full-well capacity of the output summing well of the CCD is $1\times10^6$ electrons.
Figure 19B:
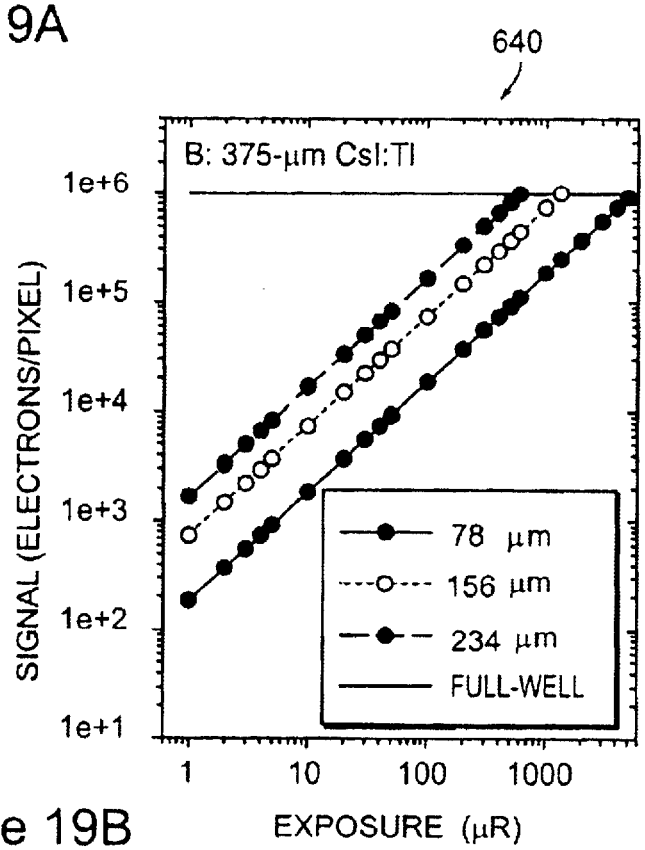
Figure 19C:
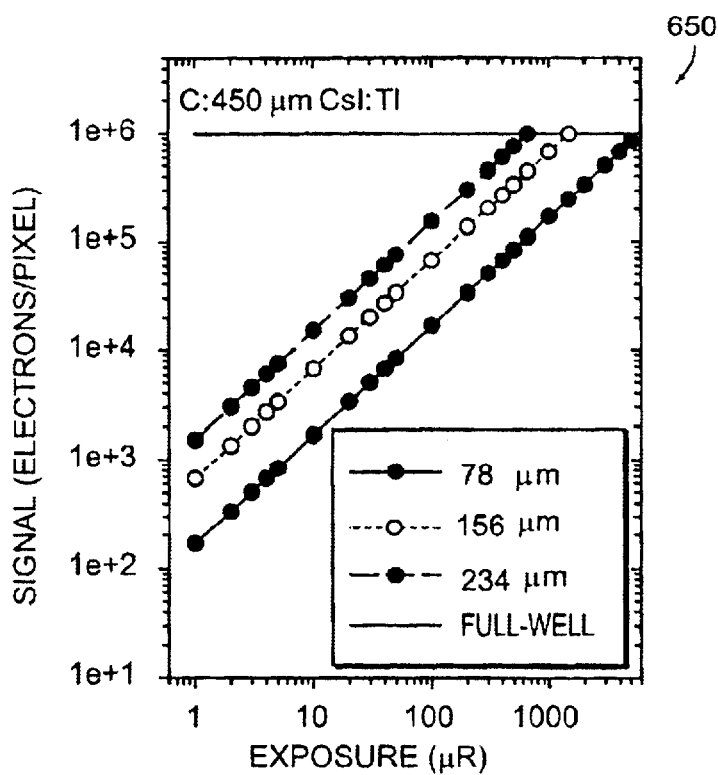
Figure 19D:
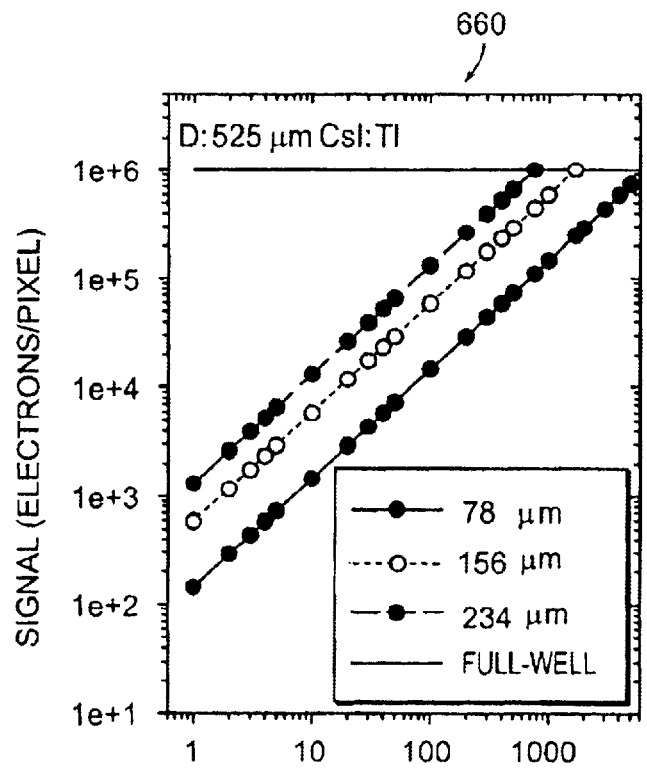
Figure 20A:
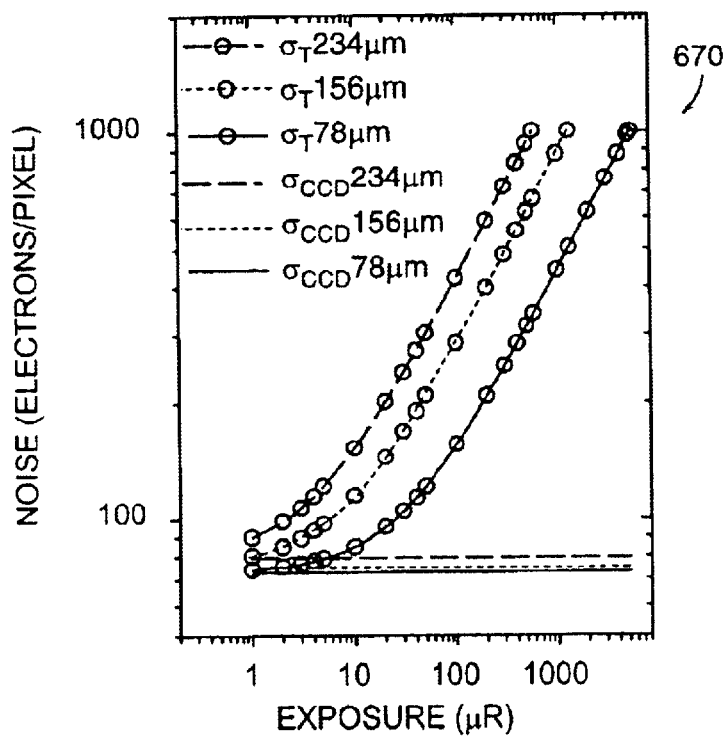
FIGS. 20A–20D graphically illustrates the estimated CCD noise and the total noise (inclusive of the shot noise) for the pixel sizes as a function of incident exposure in accordance with a preferred embodiment of the system of the present invention, wherein the calculations were performed with a dark current of 10 pA/cm$^2$ and a frame rate of 30 fps.
Figure 20B:
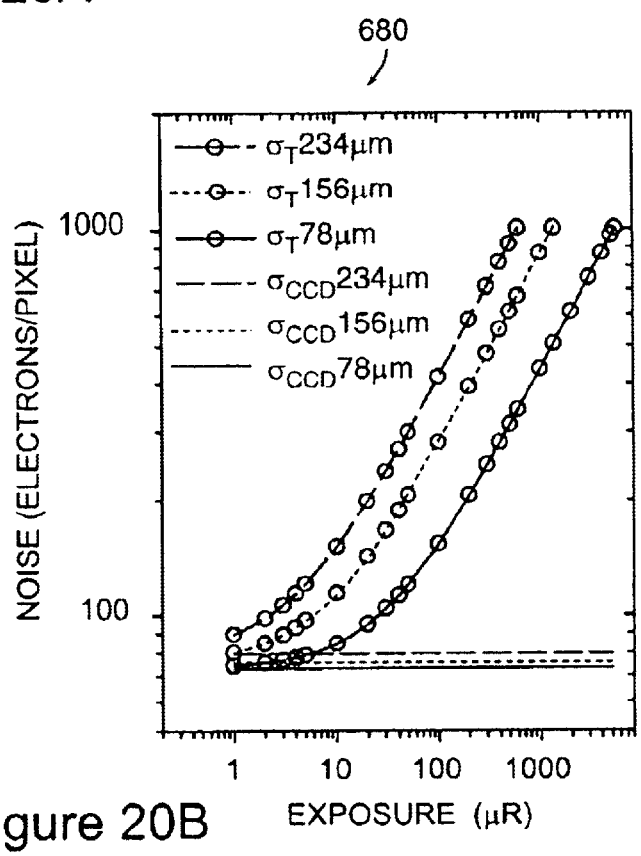
Figure 20C:
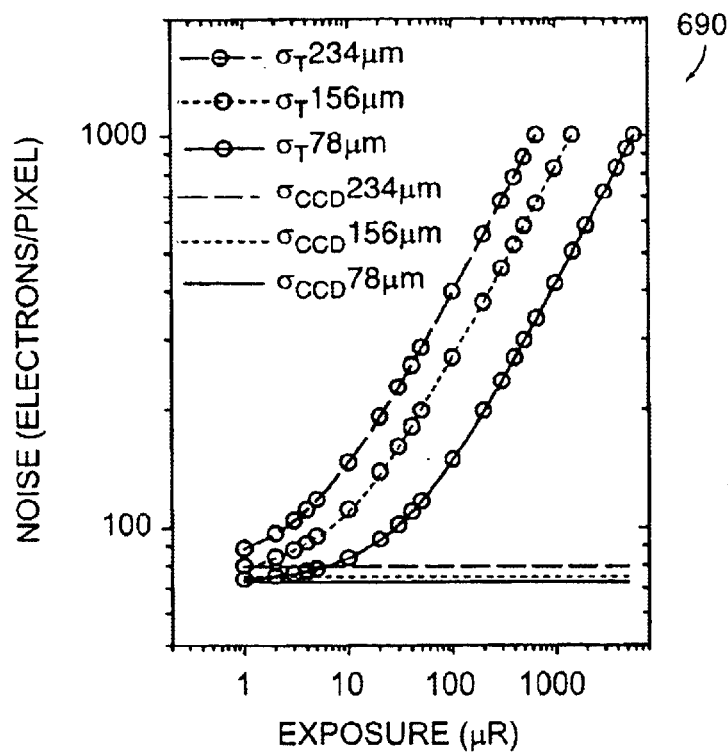
Figure 20D:
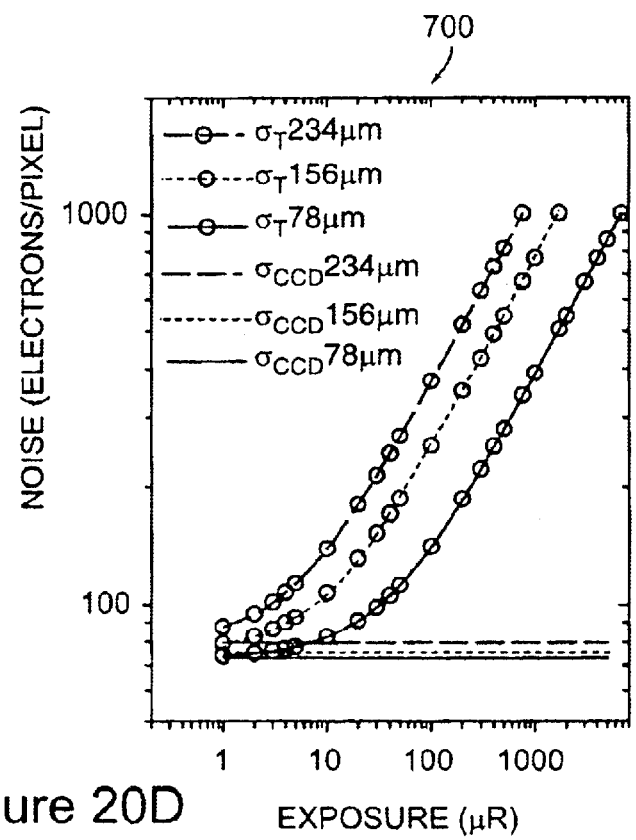

Based on the diameter of the fiber core and clad, the fill factor of the fiber core ($F_c$) was calculated to be 0.69. Also, the numerical aperture was calculated as 0.994. Hence, the fiberoptic coupling efficiency ($\eta_{FO}$) computed as per equation 6, with the assumption that the fiber core transmission efficiency is 0.8, was found to be 0.55. While the optical characteristics of the fiberoptic plate are important in ensuring good optical coupling, the thickness of the fiberoptic plate is optimized based on their attenuation characteristics. The number of x-ray photons incident on the entire CCD for various fiberoptic plate (Type 47A) thicknesses is calculated as a function of time and is shown in FIG. 18. This calculation was based on an exposure rate of 2-μR/frame, 30 fps, 30 minutes of fluoroscopic usage each hour, 10 hours of usage per day and 300 days of usage per year. Hence, a fiberoptic plate thickness of 2.5-cm (approximately 1-inch) provides reasonably adequate protection to the CCD from direct x-ray photon interactions. In another preferred embodiment, a thin depletion layer CCD that does not absorb x-rays may be used which eliminates the use of a fiberoptic plate.

The signal (electrons) per unit area for the four thickness of CsI:Tl scintillator are illustrated in FIGS. 19A–19D and calculated as a function of the incident exposure for the 80-kVp spectrum. The theoretically calculated sensitivity as per equation 8 of the CCD-based system for the four scintillator thicknesses and the three pixel pitch modes are calculated and tabulated in Table 2. The FIGS. 19A–19D and Table 2 show decreased signal intensity and sensitivity, respectively, with increasing scintillator thickness due to self-attenuation of the generated optical quanta. The variation in the thickness of scintillators is illustrated with a thickness range of 300–525 μm. A thinner scintillator reduces reabsorption of the optical quanta however at the cost of decreased x-ray absorption efficiency. For a preferred cardiovascular application the scintillator thickness ranges between 300–600 μm.

TABLE 2

| Scintillator Thickness (μm) | Pixel Pitch (μm) | Sensitivity [(electrons/pixel)/μR] |
|---|---|---|
| 300 | 78 | 191 |
|  | 156 | 762 |
|  | 234 | 1715 |
| 375 | 78 | 185 |
|  | 156 | 740 |
|  | 234 | 1664 |
| 450 | 78 | 169 |
|  | 156 | 677 |
|  | 234 | 1524 |
| 525 | 78 | 146 |
|  | 156 | 586 |
|  | 234 | 1318 |

Figure 21A:
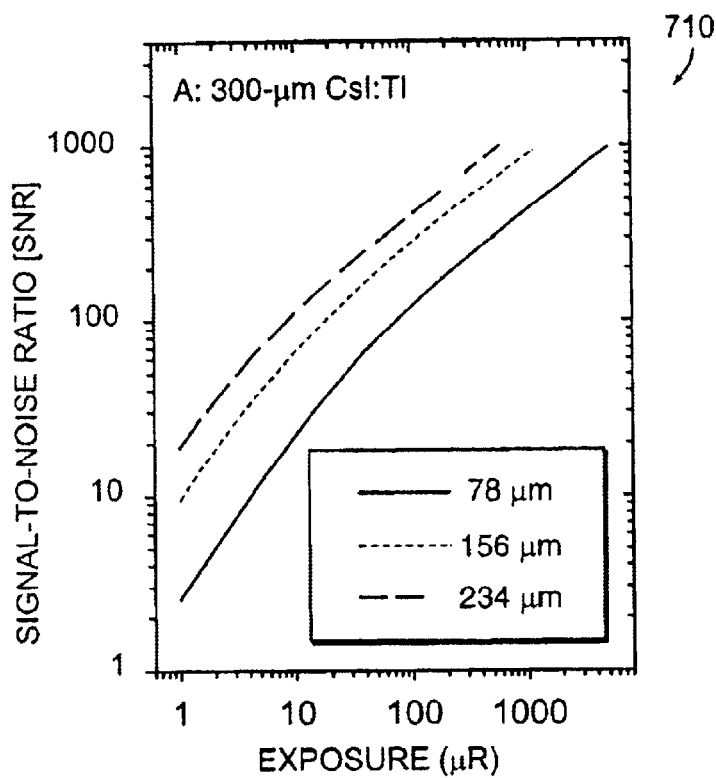
FIGS. 21A–21D graphically illustrate the calculated Signal-to-Noise Ratio (SNR) as a function of incident exposure for the 80-kVp spectrum, wherein the total noise, inclusive of the shot noise was used for computing the SNR.
Figure 21B:
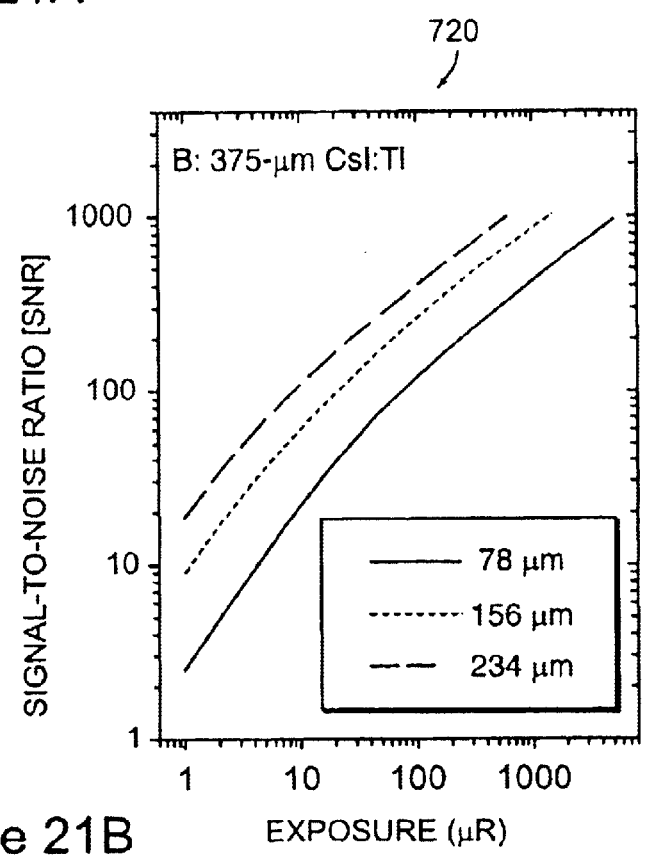
Figure 21C:
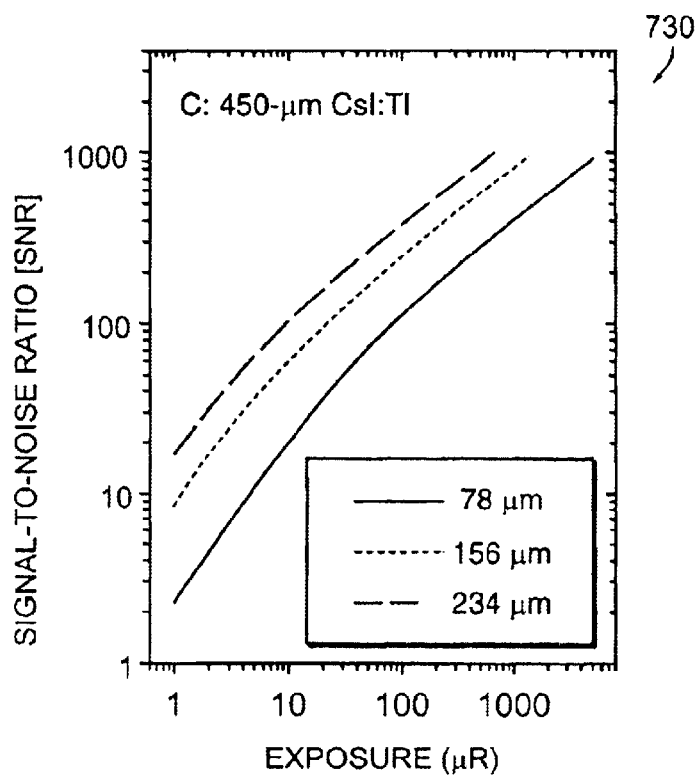
Figure 21D:
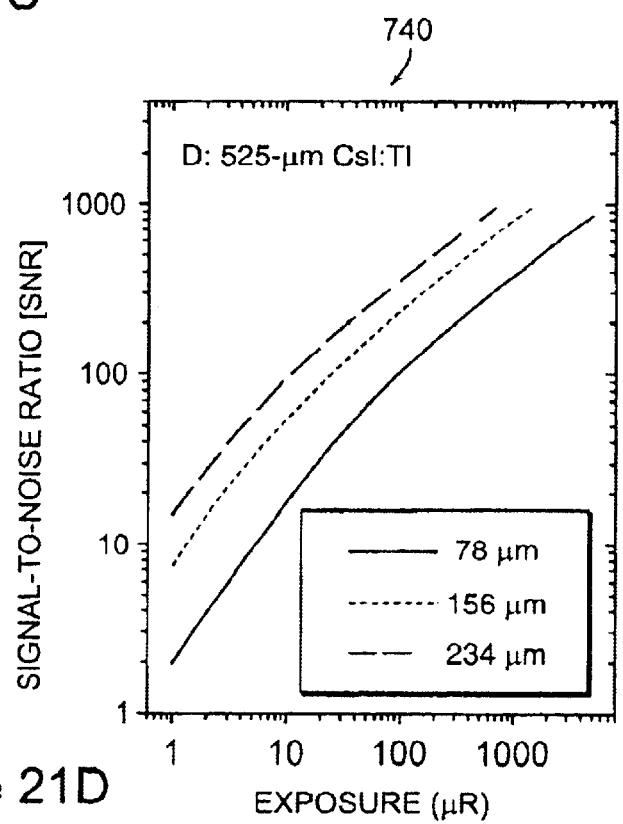

The CCD noise and the total noise are calculated as per equations 9–14, for the 3-pixel pitch modes of 78, 156 and 234-μm, as a function of the incident exposure. Plots of these noise sources for an imager operating at 30 fps are shown in FIGS. 20A–20D. The total noise increases with increasing exposure due to the increase in shot noise. The signal-to-noise ratio is calculated from the signal shown in FIGS. 19A–19D and the total noise inclusive of shot noise is shown in FIGS. 20A–20D. The SNR computed for the 3-pixel pitch modes of 78, 156 and 234 μm as a function of incident exposure for the four thicknesses of CsI:Tl scintillator is shown in FIGS. 21A–21C. The dynamic range of the preferred embodiment is calculated based on equations 15 and 16. The results of this calculation for the four thicknesses of CsI:Tl scintillator and the three pixel pitch modes are shown in Table 3.

TABLE 3

| Scintillator Thickness (μm) | Pixel Pitch (μm) | Exposure [(μR)] Minimum | Exposure [(μR)] Maximum | Dynamic Range |
|---|---|---|---|---|
| 300 | 78 | 1.95 | 5248.7 | 2698.2 |
|  | 156 | 0.53 | 1312.2 | 2491.2 |
|  | 234 | 0.26 | 583.2 | 2231.8 |
| 375 | 78 | 2.00 | 5408.5 | 2699.6 |
|  | 156 | 0.54 | 1352.1 | 2495.5 |
|  | 234 | 0.27 | 600.9 | 2238.9 |
| 450 | 78 | 2.19 | 5905.9 | 2703.4 |
|  | 156 | 0.59 | 1476.5 | 2507.7 |
|  | 234 | 0.29 | 656.2 | 2258.8 |
| 525 | 78 | 2.52 | 6830.9 | 2709.1 |
|  | 156 | 0.68 | 1707.7 | 2526.0 |
|  | 234 | 0.33 | 759.0 | 2289.1 |

Figure 22:
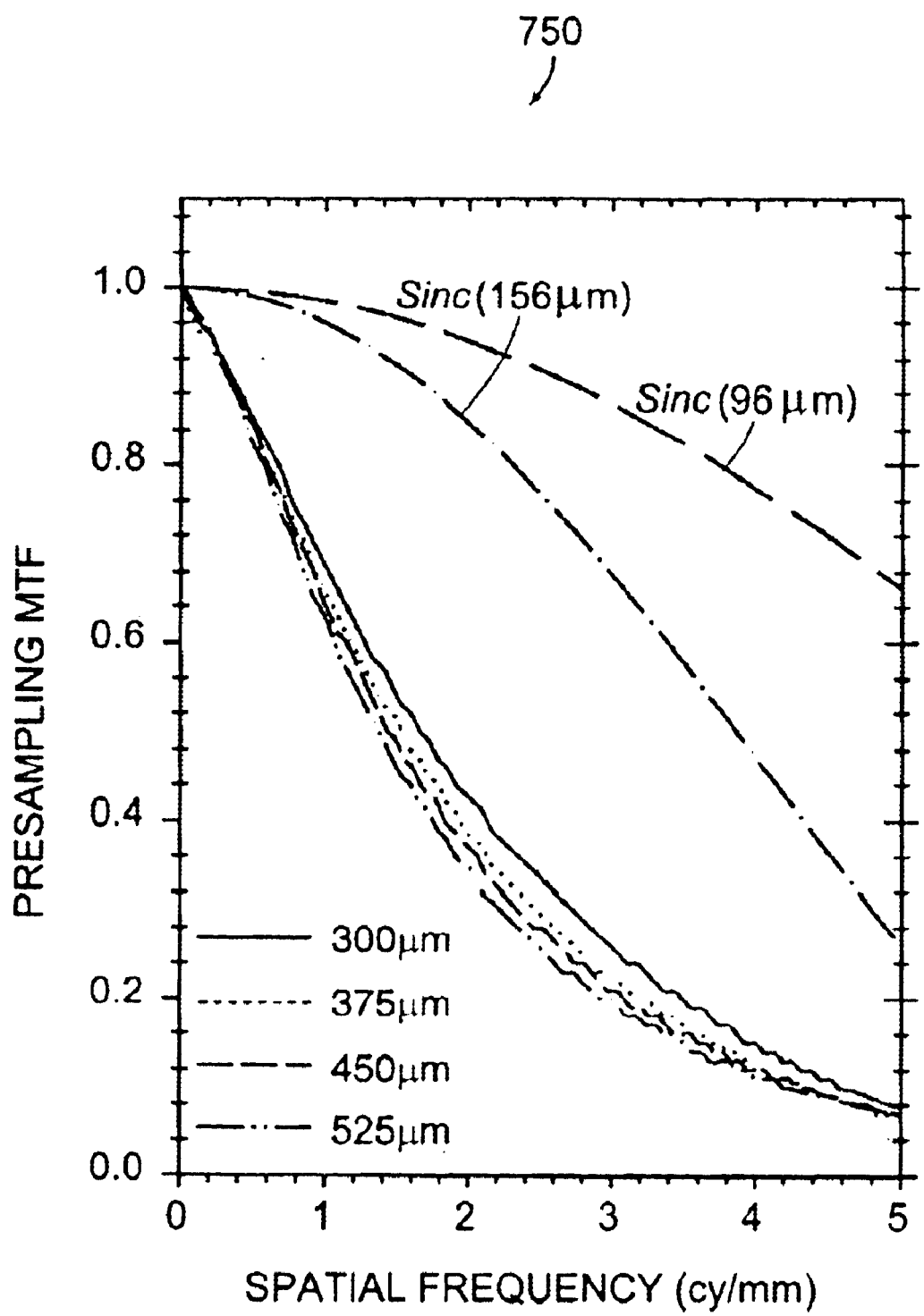
FIG. 22 graphically illustrates the measured presampling modulation transfer function (MTF) for different thicknesses of CsI scintillator using a 1×1-inch laboratory, CCD operating at a pixel pitch of 96-$\mu$m in accordance with a preferred embodiment of the system of the present invention.

The spatial resolution characteristics of various thickness of CsI was quantified through the presampling MTF, using a 1k×1k back-illuminated CCD operating at a pixel pitch of 96-μm. The presampling MTF for these scintillator thicknesses are shown in FIG. 22. An 80-kVp x-ray beam is used for these measurements. Plots of the sinc of the pixel pitch (96 μm) of the laboratory CCD and one of the pixel pitch modes (156-μm) of a preferred embodiment are also included in the FIG. 22. The pre-sampling MTF of the preferred embodiment can be determined by dividing the measured pre-sampling MTF by the sinc of the pixel pitch mode of a laboratory CCD and then multiplying by the sinc of the selected pixel pitch mode of a preferred embodiment. The scintillator thickness of 450 μm is preferred and represents a compromise between radiation dose and resolution wherein a lower dose is preferred.

Figure 23A:
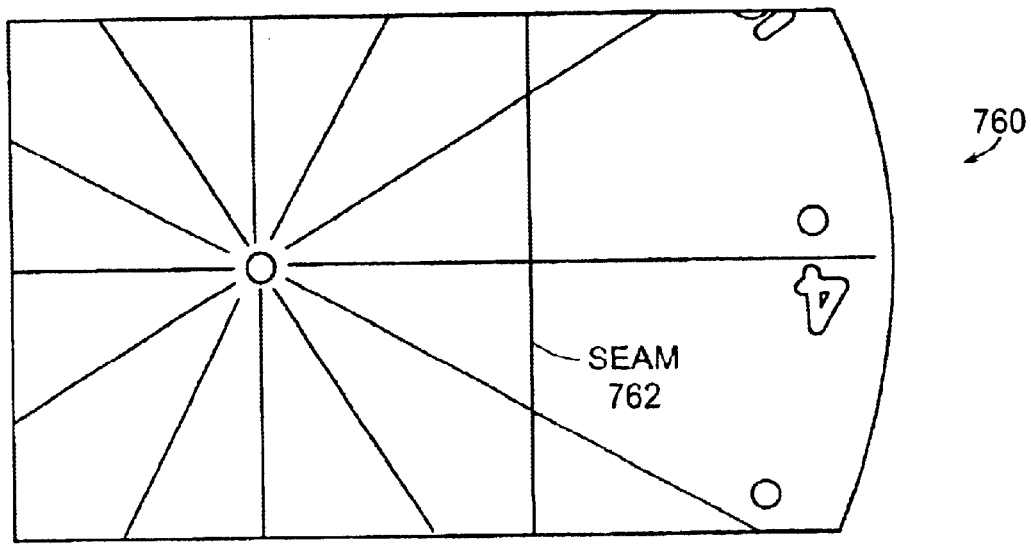
FIG. 23A illustrates an acquired image of a spoke wheel phantom, using two-tiled CCDs developed for mammographic applications, prior to implementing any correction algorithms to suppress seam artifacts in accordance with a preferred embodiment of the present invention.
Figure 23B:
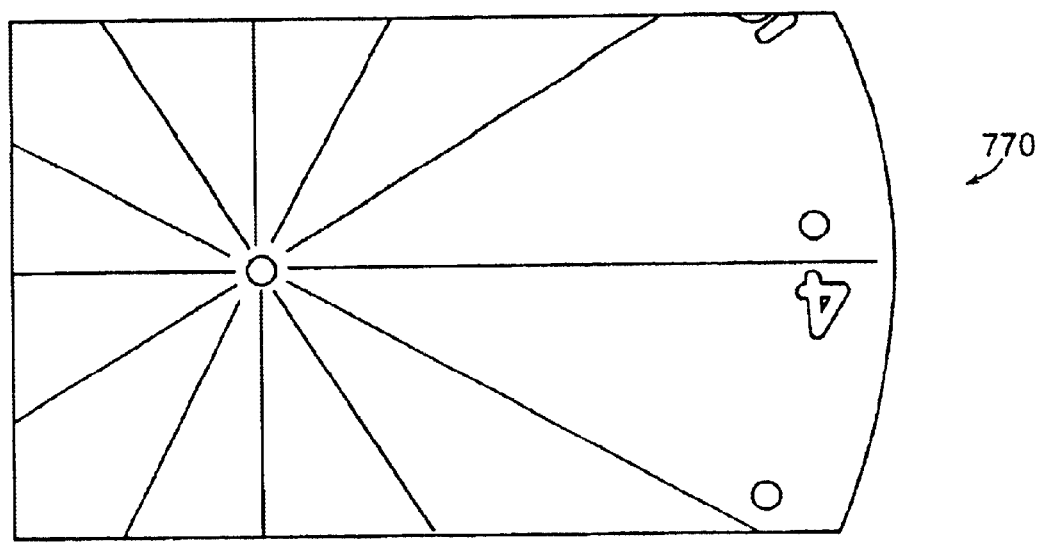
FIG. 23B illustrates the corrected image after implementation of a correction algorithm, which shows the suppression of a seam artifact in accordance with a preferred embodiment of the present invention.

In order to study the effectiveness of correction algorithm developed for the seam-less tiling method described hereinbefore, two 6×6-cm CCDs, employing a MinR-2000™ scintillator supplied by Eastman Kodak Company, Rochester, N.Y. developed mammographic applications were tiled. An image of a spoke-wheel phantom was acquired and the image prior to implementing the correction algorithm is illustrated in FIG. 23A. The correction algorithm for seam-less tiling was implemented and the corrected image is illustrated in FIG. 23B.

Figure 24:
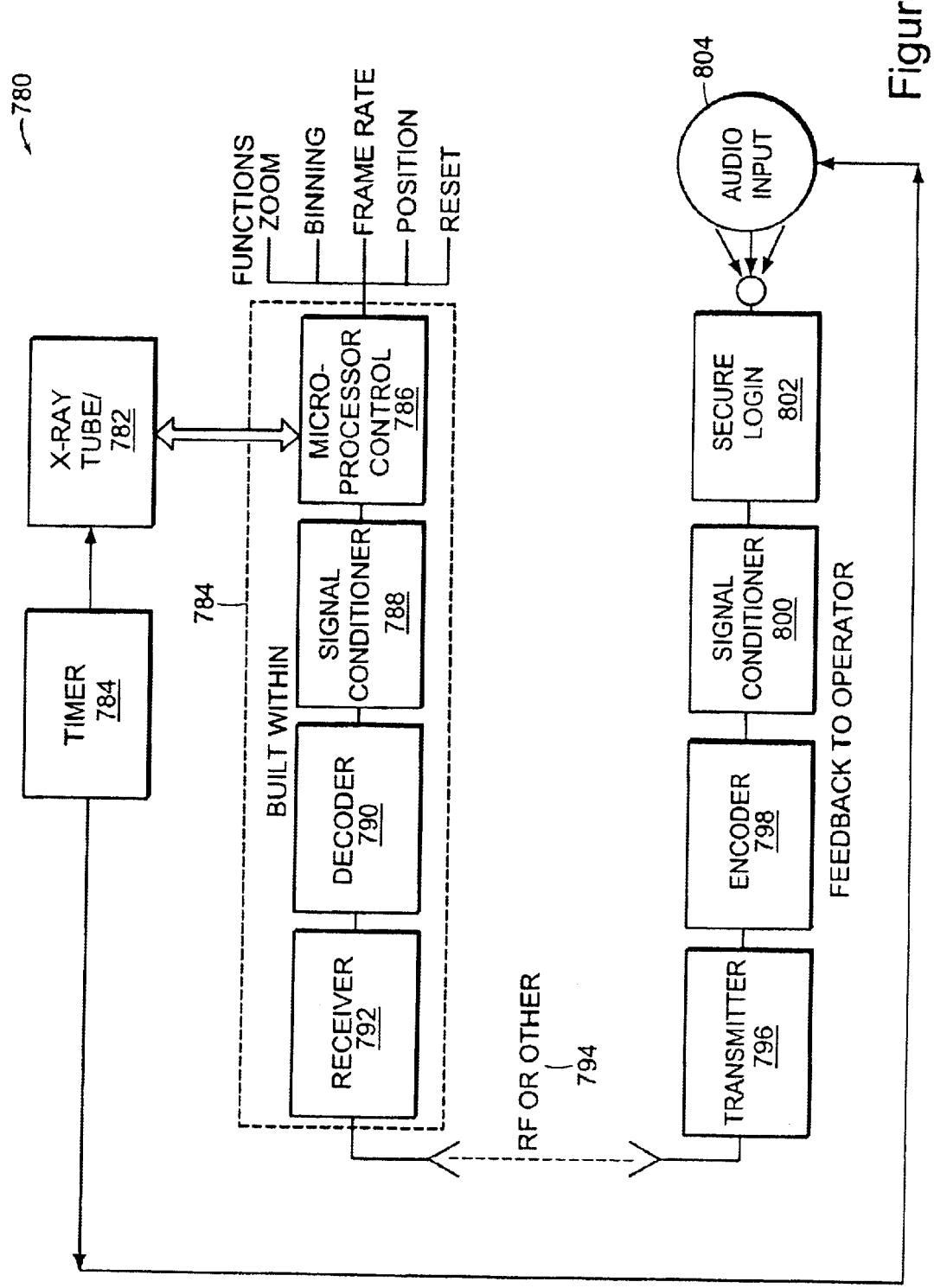
FIG. 24 is a schematic illustration of a preferred embodiment of a system using voice control in accordance with the present invention.

Preferred embodiments of the present invention uses a "voice activated" mechanism to control various operational features of the imager such as, but not limited to, binning, frame rate, zoom, positioning, and reset. This feature provides the unique ability to use one's voice to control the imager thereby obviating the need for manually (using hand) setting different controls during a medical procedure. A preferred embodiment using the voice activated system is described in FIG. 24. A "voice matching" device allows an authorized user to log 802 into the system. The "input signal" (voice command) is then conditioned to remove noise 800, encoded 798 and transmitted 796 using radiofrequency (RF) or other means to a receiver linked or placed within the camera system/CCD imager unit. The received signal is then decoded 790, conditioned 788, and processed. The "voice command" is then executed by the CCD imager. A timing mechanism 784 is provided which turns off the x-ray source after a predetermined time in case the operator fails to do so. This acts as a safety mechanism that prevents unwanted x-ray exposure to the patient.

Figure 25A:
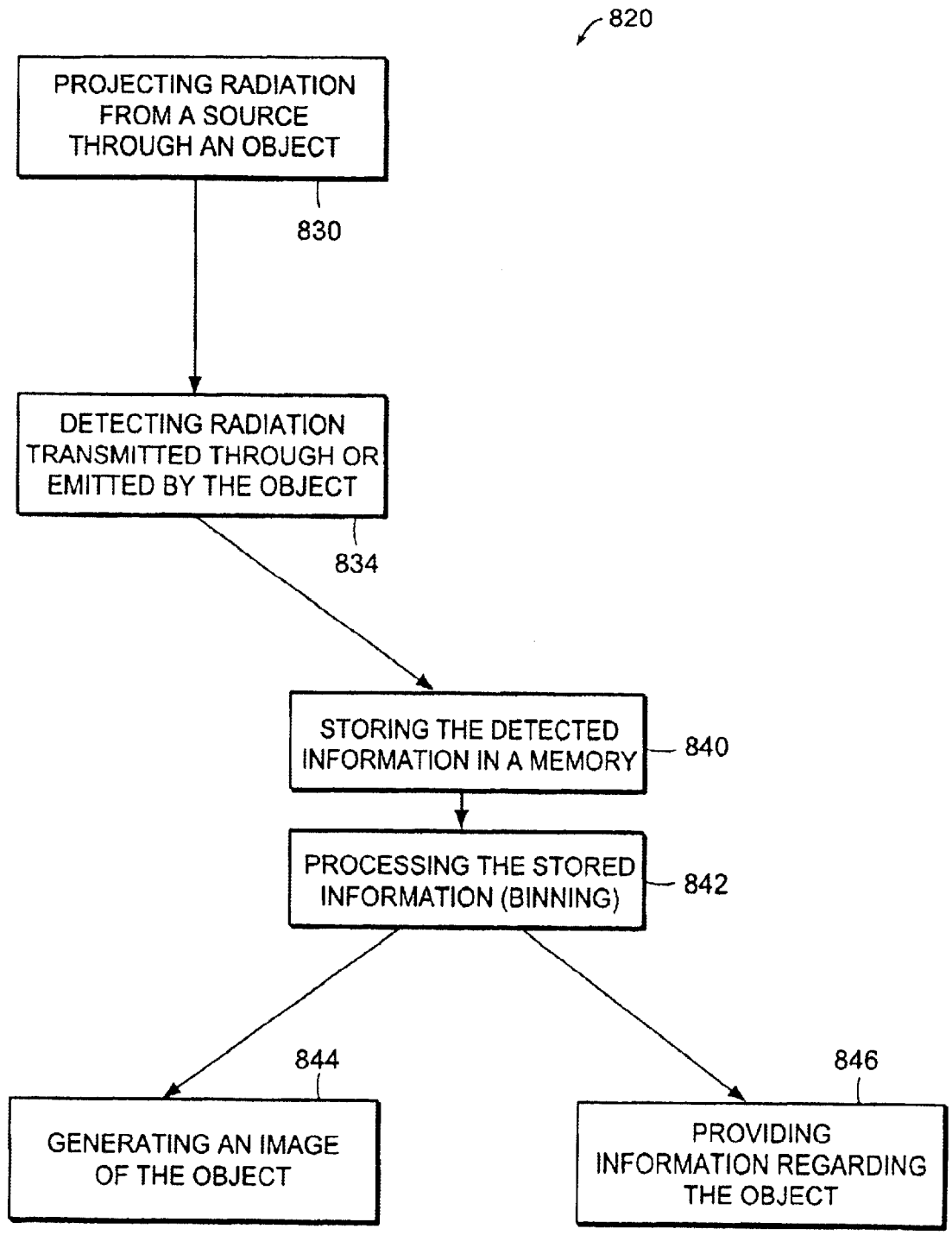
FIGS. 25A and 25B illustrate process flow sequences that are used in performing the imaging methods in accordance with preferred embodiments of the present invention.

FIG. 25A illustrates in schematic form a method that can be used in performing fluoroscopic imaging in accordance with the various embodiments of the present invention. Note that one can use either a stationary source and detector to project radiation 830, or a scanning source and detector assembly to scan the object being examined. Alternatively, the patient support table can be moved or translated relative to the x-ray source detector assembly to scan the object being examined such as tracking the movement of contrast media through blood vessels. Both stationary and scanning embodiments utilize a CCD detector that transfers the detected information to a memory 840. The information can be binned or processed 842 to accomplish various tasks. This processing can include the application of software modules to correct for non-uniformities in the source or collection components.

After each set of data is produced in both the stationary and scanning embodiments, the conditions for operation can be modified to produce an image at a different energy level, to rotate the source and detector assembly relative to the object under study to produce three dimensional images or two dimensional images at different angles.

Figure 25B:
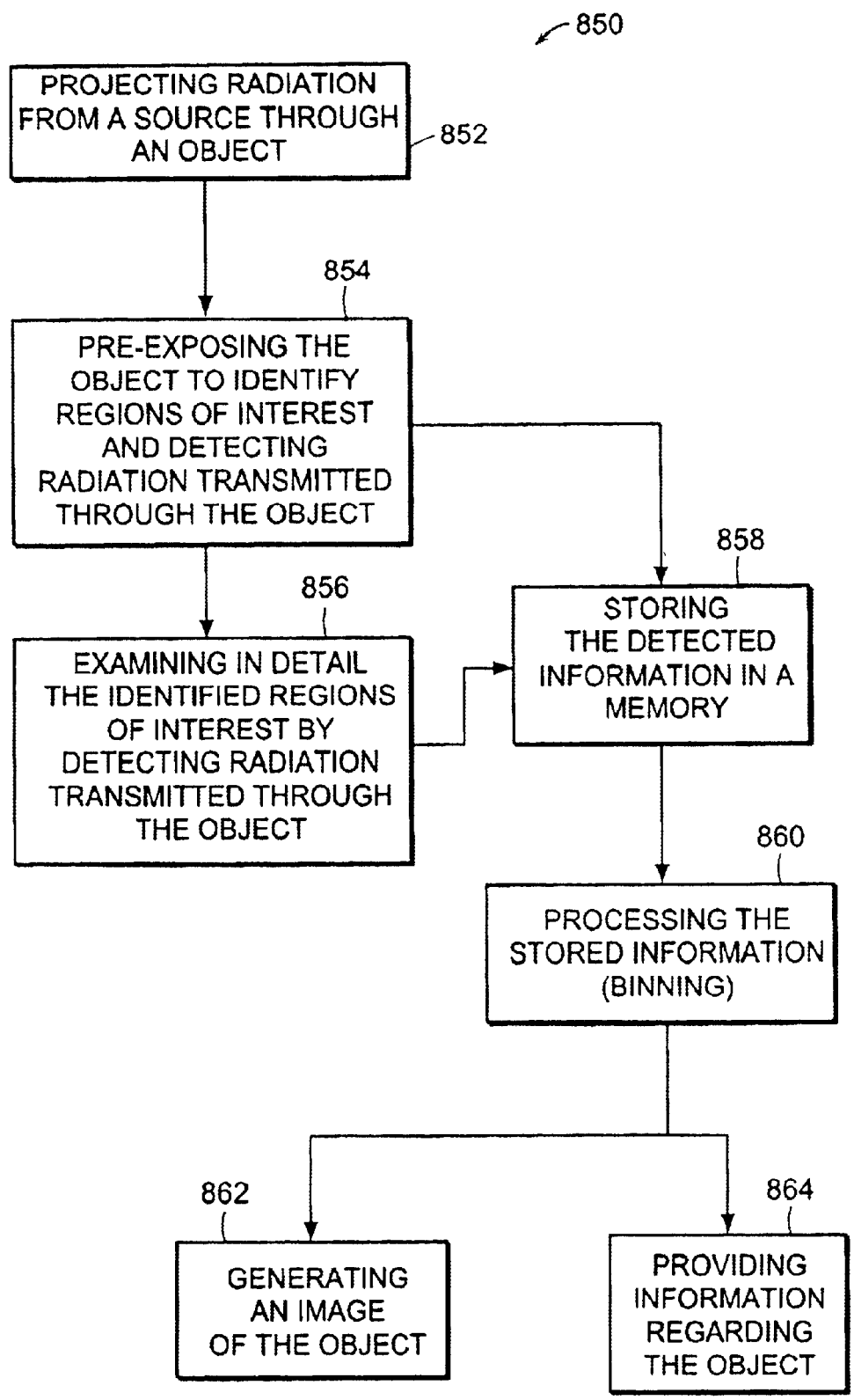

FIG. 25B illustrates a flow chart of a method used in performing fluoroscopic imaging 850 in accordance with a preferred embodiment of the present invention. The method 850 begins with the step 852 of projecting radiation from a source through an object. Pre-exposing 854 of the object is then performed to identify regions of interest. The pre-exposing may be made with the detector in the pixel binned mode to enable a very fast identification of regions of interest. This step includes detecting radiation transmitted through the object. The method then includes the step 856 of examining in detail the identified regions of interest by detecting radiation transmitted through the object. The method then includes the step 858 of storing the detected information in a memory. The step 860 then includes processing the stored information such as, for example, by binning the pixellated information. The method then includes the step 862 of generating an image of the object and/or the step 864 of providing information regarding the object.

Figure 26A:
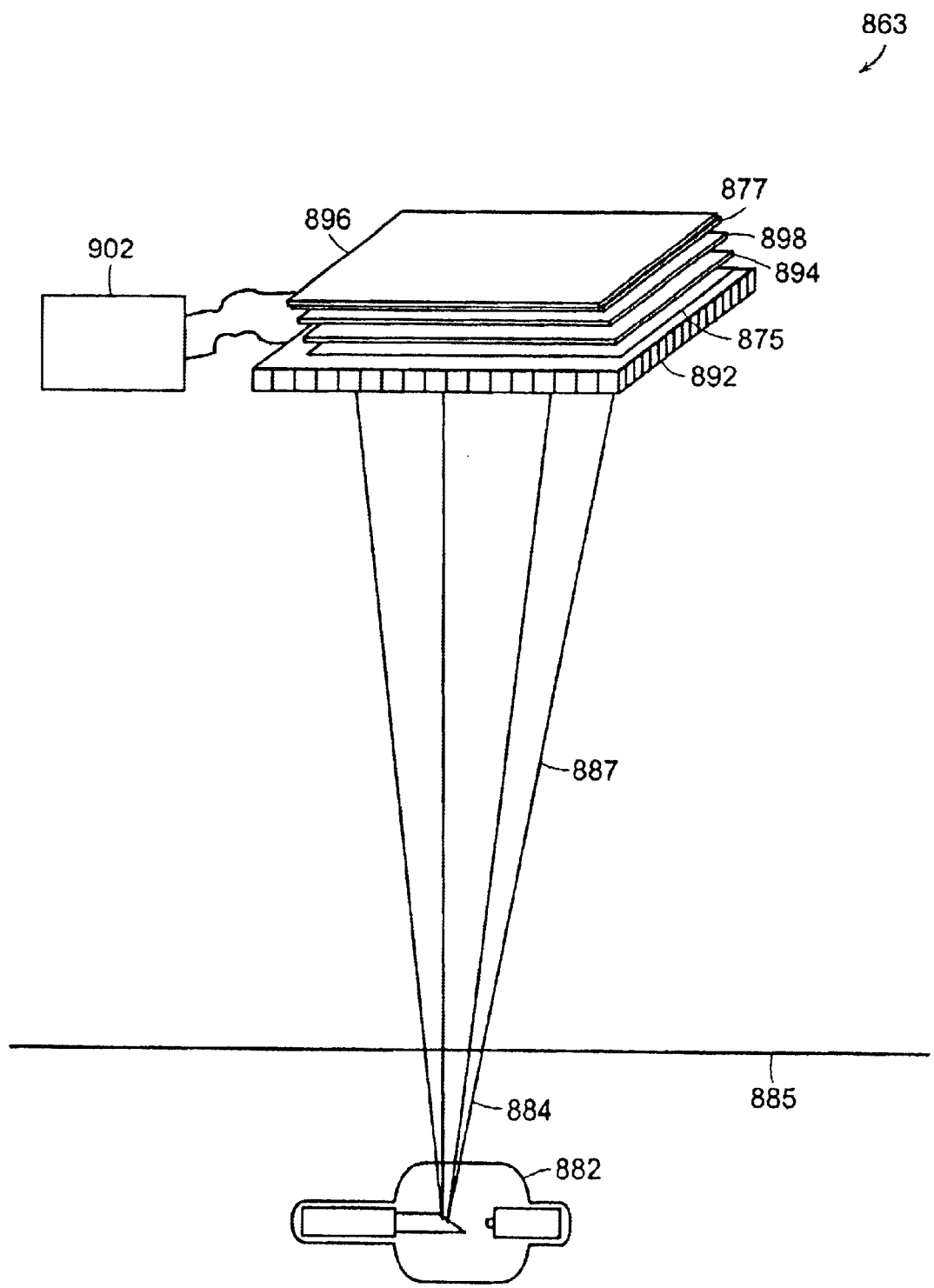
FIG. 26A illustrates a schematic diagram of an alternative preferred embodiment to the x-ray fluoroscopic imaging apparatus having dual amorphous silicon or any other type such as, but not limited to, amorphous selenium, cadmium zinc telluride, CCD or complementary metal oxide semiconductor (CMOS) image sensors in accordance with the present invention.

FIG. 26A is a schematic diagram of another embodiment of an x-ray fluoroscopic apparatus 863 in accordance with the present invention. In this embodiment, scintillator plates 875 and 877 are used to convert the x-ray energy into optical energy. Once again the x-ray tube 882 directs x-rays 884 through the patient table 885 and the patient. The x-rays 887 emanating from the patient first strike an anti-scatter grid 892 which prevents scattered x-rays from reaching the detectors. The x-rays then strike a first amorphous silicon or other indirect type image sensors such as CCDs or CMOS 894 which detects low-energy x-rays and generates the data which indicates the low energy x-ray pattern. The low energy sensor 894 can be thinner than the high energy sensor 896 to reduce the filtering requirements of the system. Also scintillator 875 can be thinner than scintillator 877 to improve collection efficiency of the system. High energy x-rays pass through the first sensor 894 and then through a copper, tungsten, gadolinium or aluminum x-ray filter 898 which filters out low energy x-rays. The substrate of the first (low energy) detector consists typically of a 1-mm thick glass, which also acts as a x-ray filter. The high-energy x-rays then strike the second amorphous silicon image sensor 896 which generates the data for the high energy x-ray pattern. The low-energy x-ray pattern data and the high energy x-ray pattern data are read out of the amorphous silicon image sensors 894 and 896, respectively, by a detector controller 902. Alternately, either or both of these detectors could be of the direct detection type which do not use a scintillator such as, but not limited to, amorphous selenium, cadmium zinc telluride, lead iodide or mercuric iodide.

Figure 26B:
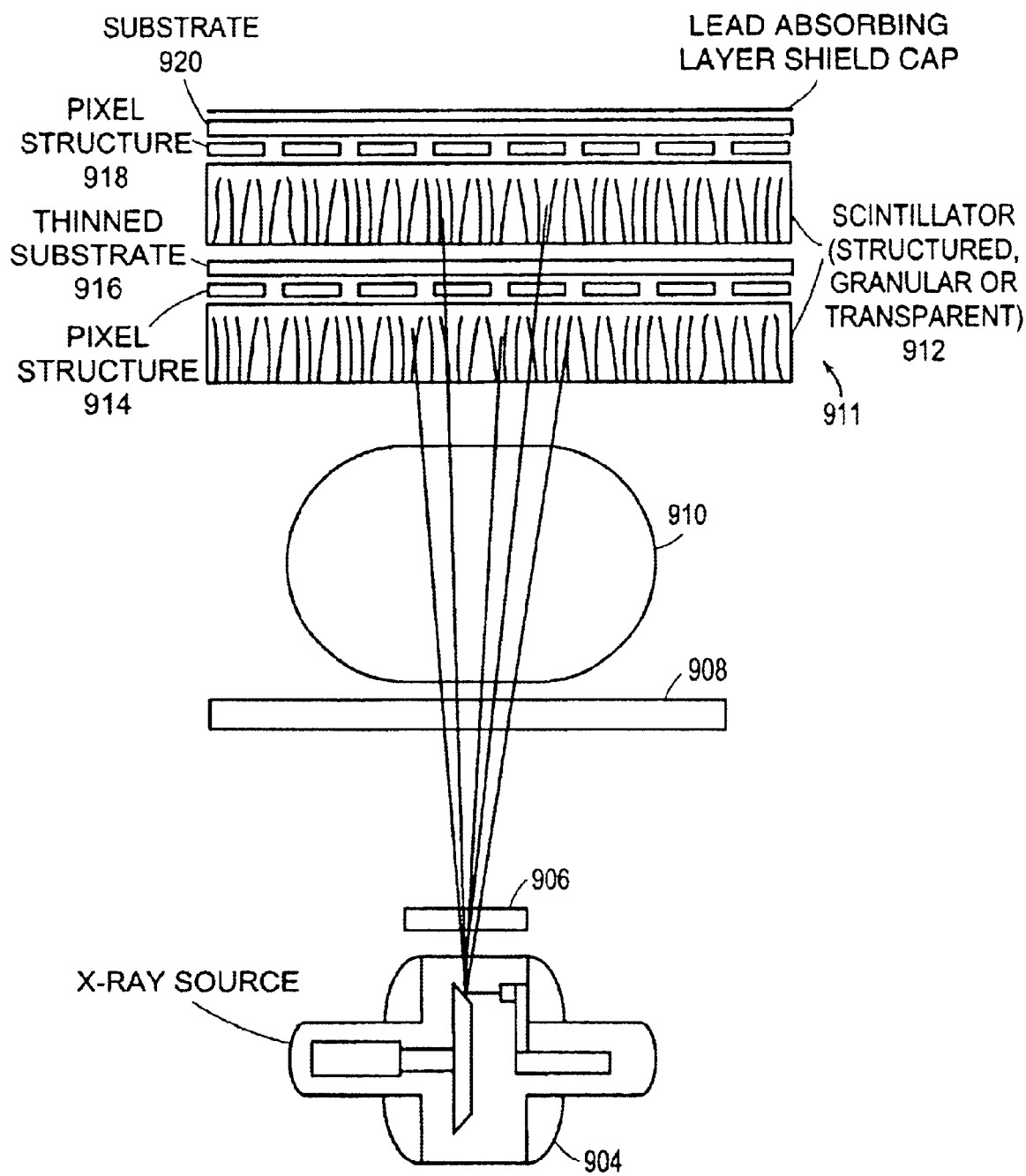
FIG. 26B is a schematic diagram of another preferred embodiment of the x-ray fluoroscopic imaging apparatus having dual detectors in accordance with the present invention.

FIG. 26B is an alternate preferred embodiment of the x-ray fluoroscopic imaging apparatus according to the present invention. The x-ray source 904 directs x-rays through a filter 906, through the patient support structure such as a table 908 and the patient 910. The stacked imaging detector configuration 911 includes two scintillators 912, and two image sensors having a thinned substrate 916, 920 and a pixellated structure 914, 918. The image sensors may be an amorphous silicon or other indirect type image sensors such as CCDs or CMOS. The dual image sensor configuration detects the x-rays that may penetrate the first scintillator and image sensor 914, 916. In an alternate embodiment a stacked imaging detector configuration includes amorphous selenium image sensors or other direct type image sensors described hereinbefore.

Figure 26C:
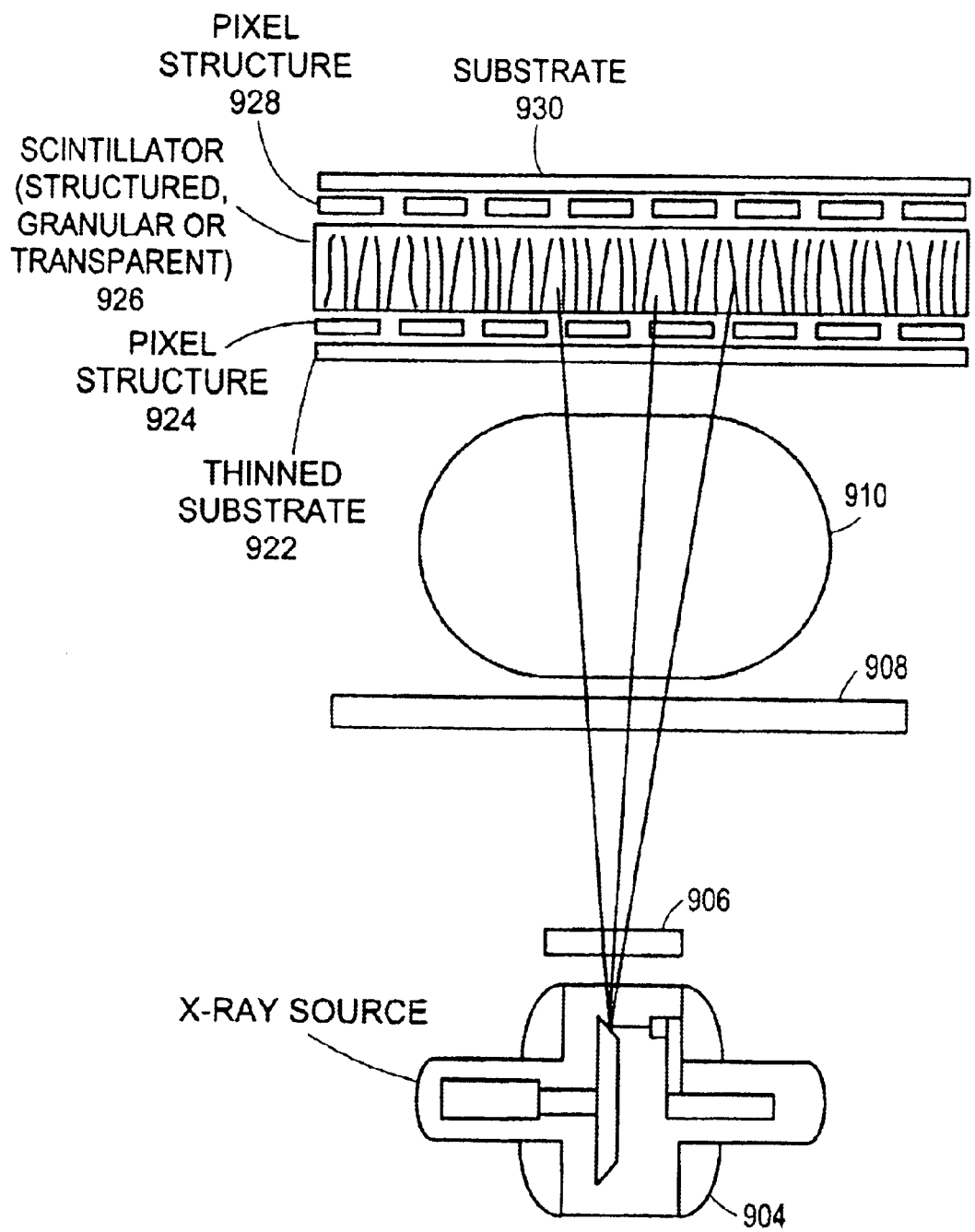
FIG. 26C is a schematic diagram of an alternative preferred embodiment of the x-ray fluoroscopic imaging apparatus having dual detectors in accordance with the present invention.

FIG. 26C schematically illustrates yet another preferred embodiment of a multi-image sensor configuration. The x-rays that pass through the patient 910 are detected by the image detector stack configuration which includes two image sensors and sharing a common scintillator. The scintillator 926 is disposed between two detectors. Each detector includes a thinned substrate 922, 930 having a pixel structure 924, 928 disposed thereon. The two detectors may be operated at the same frame rates or at different frame rates. This preferred embodiment, due to the increased thickness of the detectors provides an increased DQE.

Figure 26D:
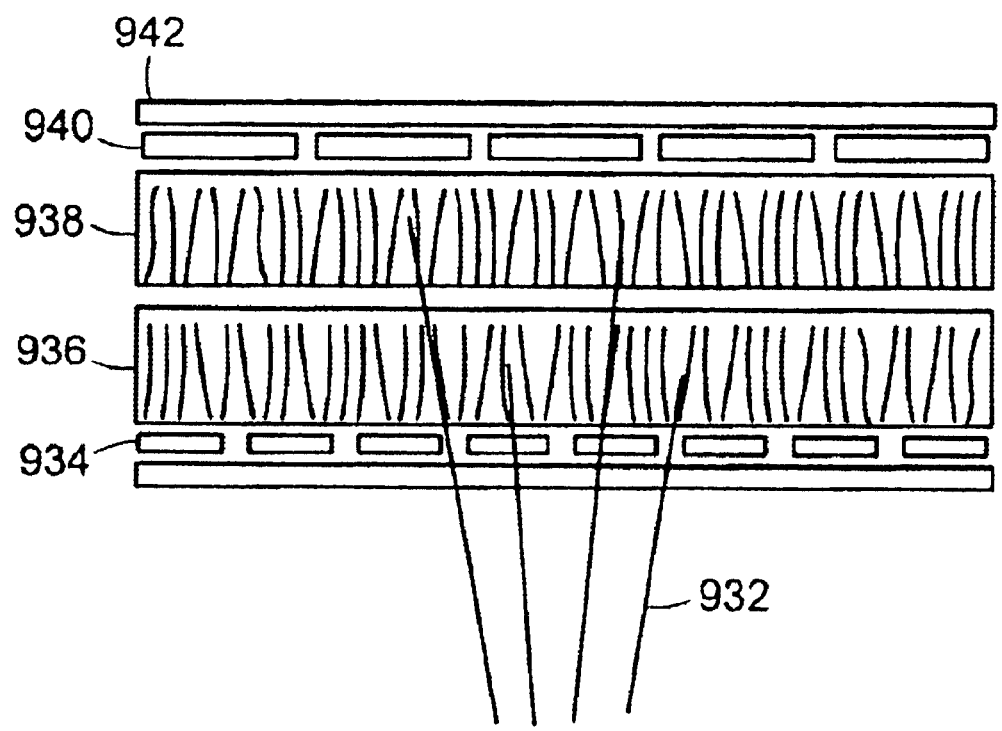
FIG. 26D is a schematic diagram of another preferred embodiment of a multi-resolution imaging detector in accordance with the present invention.

FIG. 26D is another preferred embodiment of the x-ray fluoroscopic imaging apparatus of the present invention. The stacked detector configuration provides for multi-resolution detection as the two detectors have varying sizes of the pixellated structure 934 and 940. The dual detector configuration can provide for automatic exposure control as one detector can be used to monitor the signal and provide feedback to the radiation control system. In the alternative, as discussed hereinabove, the dual detector configuration can produce an image.

Figure 26E:
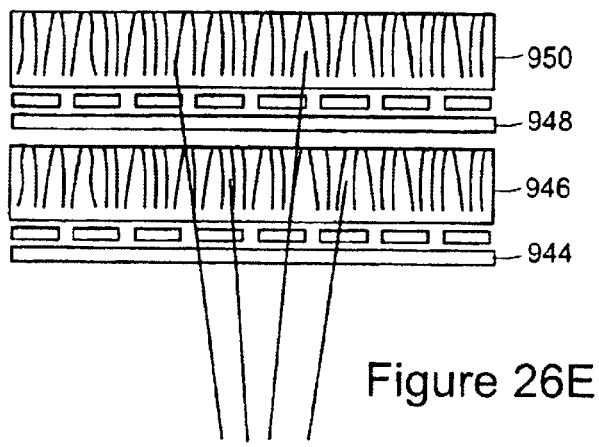
FIGS. 26E, 26F, and 26G are schematic diagrams of alternate preferred embodiments of imaging detectors in accordance with the present invention.
Figure 26F:
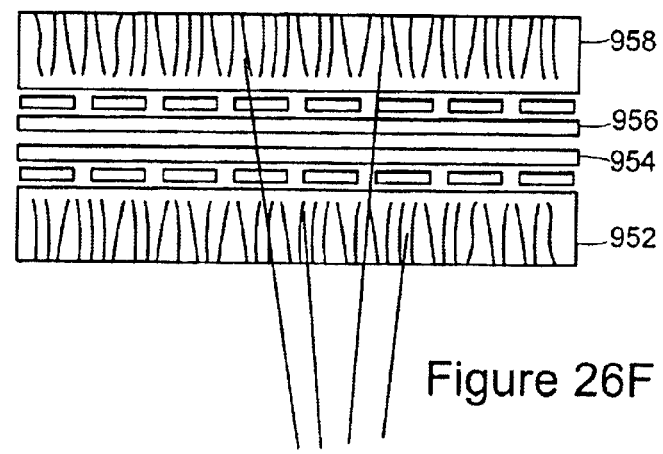
Figure 26G:
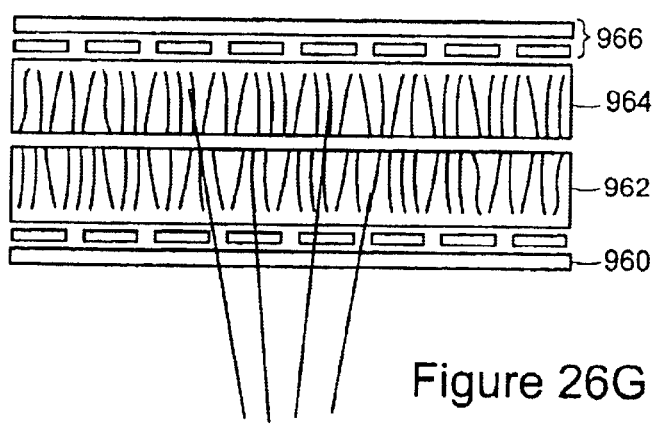

FIGS. 26E, 26F and 26G illustrate schematically alternative preferred embodiments of multi-detector imaging units of the present invention. The positioning of the scintillators relative to the substrate and pixellated structure of the image sensor vary with the multiple scintillators 962, 964 being disposed between two detectors 960, 966 as illustrated in FIG. 26G to the two detectors 954, 956 being disposed between the two scintillators 952, 958 as illustrated in FIG. 26F. Though a single pixel structure is used for simplicity and illustration, multi-pixel structures may also be used in preferred embodiments of the present invention.

Figure 27:
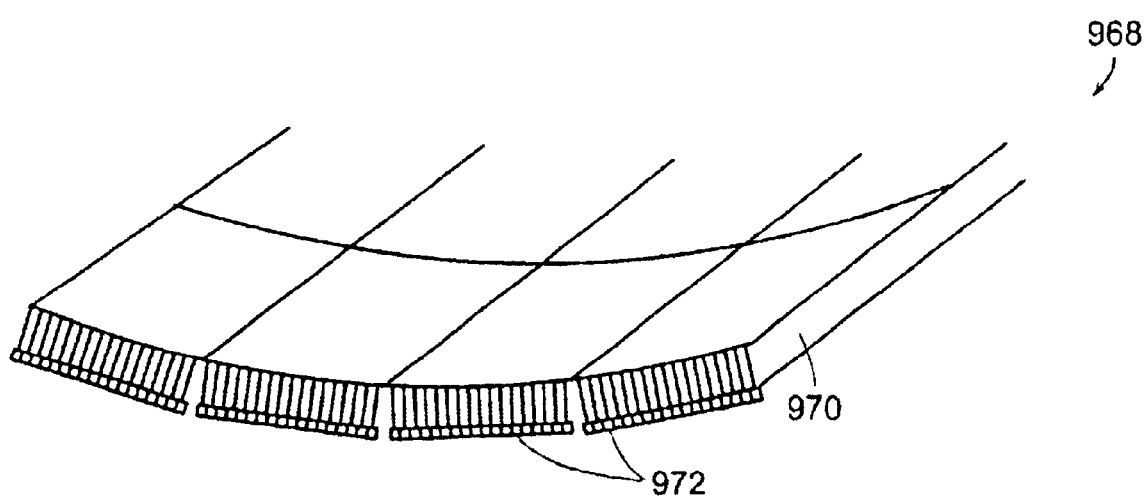
FIG. 27 illustrates another preferred embodiment in which the imaging elements in each linear array are positioned at a different angle relative to the patient and the x-ray source in accordance with the present invention.

FIG. 27 illustrates a preferred embodiment of the imaging elements in accordance with the present invention. The detector module 968 can include a plurality of sets of CCDs. The images that result from this embodiment can be joined and are substantially seamless with less than a 5–10 micron difference between the region of the body and the joined images of the region.

The sensing surface does not have to be on a plane. The CCDs 972 can be arranged on a curving or non-planar surface. This is a preferred embodiment because it provides for the use of straight (non-tapering) fiber-optic couplers or plates 970 which dramatically reduces the cost and contributes to better image quality. Note that the CCDs can be cooled or non-cooled and can be operated in a pixel binned or non-binned mode. Additionally, an anti-scatter grid can be used between the tissue and the detectors. Each element 972 in the array is generally equidistant from the x-ray source in order to reduce distortion across the entire field of view of the array. This arced linear array can be used for many different applications as described elsewhere herein.

This approach is preferable as current manufacturers can readily make CCDs which are buttable on two sides. It remains difficult and expensive to make CCDs buttable on three or four sides. In the illustrated embodiment there are only six joints required between the CCDs.

Cascaded linear systems based modeling techniques have been used to predict imaging performance of systems developed for x-ray imaging. Such models have been used to investigate key objective parameters of image quality such as the Wiener spectrum or noise power spectrum (NPS), noise equivalent quanta (NEQ) and detective quantum efficiency (DQE).

The imaging chain is represented as a serial cascade of amplifying and scattering mechanisms. In order to apply such a model to describe the image formation process, the preferred embodiments of the system have to be linear and shift invariant. Since, CCD-based imaging systems demonstrate a linear dependence with incident exposure over much of their dynamic range, the assumption of linearity can be supported. This assumption breaks down at high exposure levels such that the CCD saturates as well as at very low exposure levels where the electronic noise is a dominant factor. The assumption of shift-invariance is valid only up to the point that the image is sampled; hence much of the discussion is restricted to the presampling signal and noise. Further, the assumption that the system is spatially and temporally stationary has to be made to facilitate representation of image noise in terms of the Wiener spectrum (NPS). While such an assumption is not truly valid in the spatial domain, as pixel and scintillator nonuniformities exist, the process of background subtraction and flat-field correction does allow for such an assumption at lease in the widest sense. For fluoroscopic applications, image lag caused by trapping and slow release of signal to subsequent frames also limits the validity of such an assumption in the temporal domain. Hence, the description of image noise in terms of the spatio-temporal NPS, which incorporates the image lag is needed. Cunningham et al have shown experimentally and theoretically that the spatial component of the spatio-temporal DQE of a system operating in the fluoroscopic mode is the same as the conventional DQE of the same system operating in the radiographic mode under quantum-noise limited conditions. The model in accordance with, the preferred embodiment makes use of this finding so that a single frame of the fluoroscopic mode is considered as essentially a radiographic mode of operation with an exposure level corresponding to that typically used in fluoroscopy. It has also been assumed that the system is ergodic and hence stationary.

The preferred embodiment analyzes key parameters of output image quality of a high-resolution CCD-based imager designed for fluoroscopy. As described hereinbefore, the preferred embodiment uses four 8×8-cm three-side buttable CCDs tiled to achieve a field of view (FOV) of 16×16-cm at the image plane. Larger FOVs can be achieved by tiling more CCDs in a similar manner. The system employs a CsI:T1 scintillator coupled to the CCDs by straight (non-tapering) fiberoptics and can be operated in 78, 156 or 234-$\mu$m pixel pitch modes.

The preferred embodiment system is considered a serial cascade of discrete stages, which can be represented by one of the following processes: quantum gain, stochastic blurring or deterministic blurring. A quantum gain stage affects the mean number of image quanta and the blurring stage affects the spatial distribution of image quanta. The signal and noise transfer characteristics from the input to the output of each process is distinct. For any given stage i, the image quanta distribution of the output signal is represented as $q_i(x, y)$ in the spatial coordinates of (x,y), and the output Wiener spectrum (NPS) is represented as $W_i(u,v)$ in its orthogonal spatial frequency coordinates of (u,v). Based on the work of Rabbani, Shaw and Van Metter, for a quantum gain stage 'i' where the input signal is represented as $q_{i-1}$ and the output signal is represented as $q_i$ the signal transfer from the input to the output can be stated as:

$$q_i = q_{i-1} \cdot \overline{g_i} \quad (17)$$

where, $\overline{g_i}$ is the average quantum gain of that stage. The NPS transfer from the input to the output is expressed as:

$$W_i(u,v) = W_{i-1}(u,v) \cdot \overline{g_i}^2 + \overline{q_{i-1}} \cdot \sigma_{g_i}^2 + W_{add\ i}(u,v) \quad (18)$$

where, $\overline{q_{i-1}}$ represents the average input signal, $\sigma_{g_i}^2$ represents the variance in the quantum gain of that stage and $W_{add\ i}(u, v)$ represents any additive noise imparted by that stage.

Quantum gain stages can be classified into stages where there is a loss in image quanta such as attenuation of the incident radiation by the scintillator, self-absorption of the scintillations within the scintillator medium and fiberoptic coupling, and quantum amplification stages such as generation of optical quanta in the scintillator. Further, some gain stages can be described by a known probability distribution such as Poisson, binomial or deterministic, where the relationship between the average gain $\overline{g_i}$ and the gain-variance $\sigma_{g_1}^2$ can be expressed analytically. The gain variance can also be expressed in terms of the Poisson excess, $\epsilon_{g_1}$, or in terms of the Swank factor I for Poisson distribution, as shown below:

$$\varepsilon_{g_i} = \frac{\sigma_{g_i}^2}{\overline{g_i}} - 1 \quad (19)$$

$$I = \frac{1}{1 + \frac{\sigma_{g_i}^2}{\overline{g_i}^2}} \quad (20)$$

For a stochastic blurring stage i, such as the redistribution of image quanta in a scintillator, with a normalized point spread function (PSF) represented as $p_i(x, y)$ and the corresponding modulation transfer function (MTF) represented as $T_i(u,v)$, the signal transfer can be written as:

$$q_i(x,y) = q_{i-1}(x,y) **_s p_i(x,y) \quad (21)$$

where, $**_s$ represents the stochastic convolution operator. The noise transfer for the stochastic blurring stage can be expressed as:

$$W_i(u,v) = [W_{i-1}(u,v) - \overline{q_{i-1}}] T_i^2(u,v) + \overline{q_{i-1}} \quad (22)$$

The above equation indicates that for a stochastic blurring stage, the uncorrelated component, $\overline{q_{i-1}}$, is unaffected, and the correlated component, $[W_{i-1}(u,v) - \overline{q_{i-1}}]$ is modulated by the square of the MTF, $T_i^2(u,v)$. For a deterministic blurring state i, such as integration over the pixel aperture, with a MTF represented as $T_i(u,v)$, the signal transfer is written as:

$$q_i(u,v) = q_{i-1}(u,v) \cdot T_i(u,v) \quad (23)$$

The noise transfer for a deterministic blurring stage is expressed as:

$$W_i(u,v) = W_{i-1}(u,v) \cdot T_i^2(u,v) \quad (24)$$

The system is modeled by dividing the imaging chain into the following elementary stages: incident image quanta; attenuation of x-rays by the CsI:T1 scintillator; generation and emission of optical quanta by the CsI:T1 scintillator; stochastic blurring by the CsI:T1 scintillator; coupling of the optical quanta by straight (non-tapering) fiberoptics; absorption of optical quanta by the CCD; deterministic blurring by the pixel presampling MTF and effect of pixel fill factor; and additive noise.

The model in accordance with a preferred embodiment of the present invention encompasses elementary stages up to the aliasing stage, thus providing the presampling signal and the presampling NPS. While, most of the objective parameters of image quality can be addressed adequately by the presampling signal and the presampling NPS, in reality, DQE measurements performed on digital imaging systems are based on the presampling signal (MTF) and the aliased NPS. The effects of noise aliasing is of particular importance to a preferred embodiment imager as the system can be operated in any of the three pixel pitch modes and hence, their impact on the aliased NPS are addressed. Modeling of system performance is performed for the three pixel pitch modes of 78, 156 and 234-um and for four CsI:T1 scintillator thicknesses of 300, 375, 450 and 525-$\mu$m.

The system is modeled using a polyenergetic 80-kVp x-ray beam filtered by 2-mm aluminum (Al) and transmitting through 20-cm of tissue from a 17° tungsten (W) target, with a first half-value layer (HVL) of 6.75-mm of Al. It is convenient to represent the incident spectrum $q_0(E)$, as a normalized spectrum $q_{norm}(E)$ and expressed as:

$$q_{norm}(E) = \frac{q_0(E)}{\int q_0(E) \cdot dE} \quad (25)$$

Figure 28:
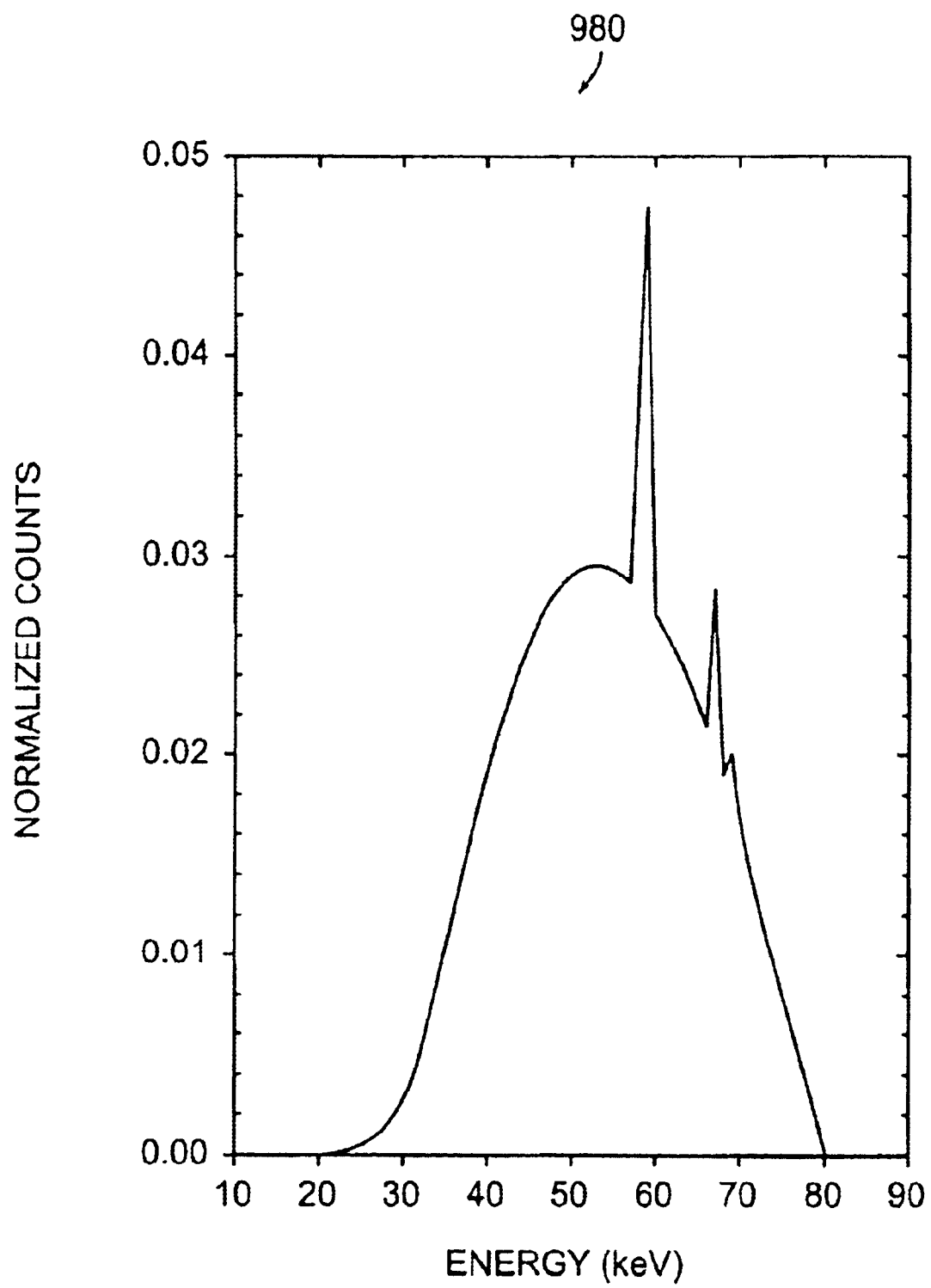
FIG. 28 illustrates a normalized spectrum of the spectrum illustrated in FIG. 14 in accordance with the present invention.

A plot of this normalized spectrum is shown in FIG. 28. The photon fluence per $\mu$R of exposure $$\left(\frac{\overline{q_0}}{X}\right)$$

for this beam was calculated based on the definition of Roentgen provided by Johns and Cunningham and the technique described by Siewerdsen et al.

In the first stage the x-rays are attenuated by the scintillator. The quantum efficiency $g_1(E)$ were calculated for various scintillator thicknesses, ranging from 300 to 525-$\mu$m thick in steps of 75-$\mu$m, as per equation 26, using energy-dependent mass attenuation coefficient values.

$$g_1(E) = \eta(E, \rho_s) = 1 - e^{-\mu_m(E) \cdot \rho_s} \quad (26)$$

where, $\mu_m(E)$ is the energy-dependent mass attenuation coefficient and $\rho_s$ is the surface density of the scintillator. A packing density of 90% is assumed for these calculations based on reported values for cesium iodide converters used in image intensifiers. For the 300, 375, 450 and 525-$\mu$m thick CsI:T1 scintillators the resultant surface density ($\rho_s$) are 122, 152, 183 and 213 mg/cm$^2$ respectively. The average quantum gain $\overline{g_1}$ for each thickness of the scintillator, for the 80-kVp x-ray spectrum is obtained as:

$$\overline{g_1} = \frac{\int_{E=0}^{80} g_1(E) \cdot q_{norm}(E) \cdot dE}{\int_{E=0}^{80} g_1(E) \cdot q_{norm}(E) \cdot dE} \quad (27)$$

By considering the x-ray attenuation stage as a binomial process, the signal and the NPS after simplification at the output of stage one are written as shown in equations 28 and 29, respectively.

$$\overline{q_1} = \overline{q_0} \cdot \overline{g_1} \quad (28)$$

$$W_1(u,v) = \overline{q_0} \cdot \overline{g_1} \quad (29)$$

In the second state the scintillator generates and emits optical quanta. This stage is considered as a quantum gain stage with an average gain $\overline{g_2}$, and is comprised of two sub-stages: a quantum gain stage with an average gain $\overline{g_{2+di\,g}}$, describing the generation of optical quanta per x-ray interaction, and a quantum gain (loss) stage with an average gain $\overline{g_{2+di\,e}}$, describing the probability (escape probability) of the generated optical quanta exiting the surface of the scintillator in contact with the fiberoptic coupling. Hence, the average quantum gain of this stage can be written as:

$$\overline{g_2} = \overline{g_{2+di\,g}} \cdot \overline{g_{2+di\,e}} \quad (30)$$

Figure 29:
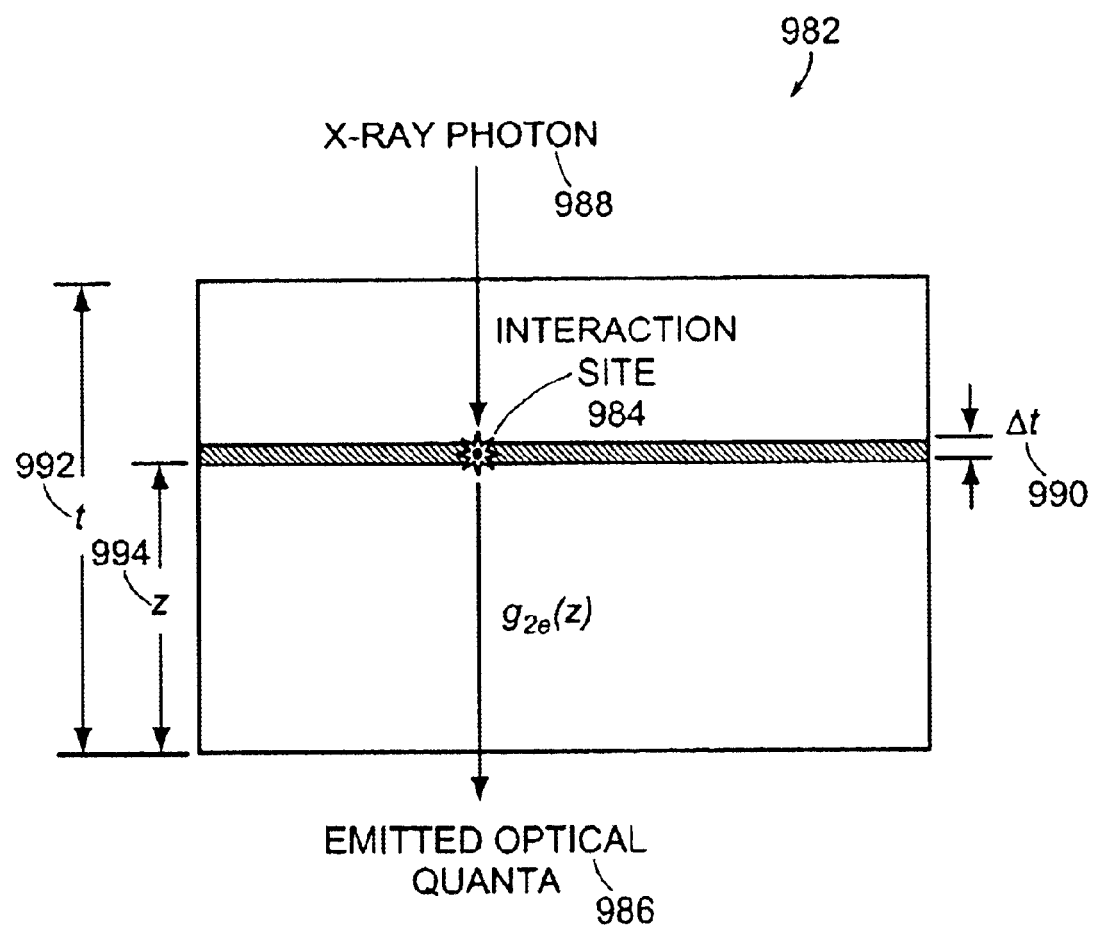
FIG. 29 illustrates the model for computing the number of optical quanta emitted per x-ray interaction in accordance with a preferred embodiment of the present invention.

CsI:T1 scintillators have been measured to yield 52,000 optical quanta per absorbed 1-MeV x-ray and more recently, yield of up to 64,000 optical quanta per absorbed 1-MeV x-ray photon has been reported. Hence, a mean value of 58,000 optical quanta per absorbed 1-MeV x-ray photon (58 optical quanta per absorbed 1-keV x-ray photon), corresponding to conversion energy of 17.24 eV, is used. It is assumed that for x-ray photon energies below the K-edge of the CsI:T1 scintillator (approximated to 34-keV) all of the absorbed energy results in the generation of the optical quanta, and that for x-ray photon energies above the K-edge a fraction of the energy is lost as K-fluorescence. The K-escape fraction above the K-edge is obtained by the average of the measured values reported by Rowlands and Taylor. The number of optical quanta generated $\lfloor g_{2_g}(E) \rfloor$ per absorbed x-ray photon for various x-ray photon energies is calculated as:

$$g_{2_g}(E) = 58 \times E \text{ for } E < E_K \tag{31A}$$

$$g_{2_g}(E) = 58 \times E \times \left(1 - \frac{E_K \cdot K_f}{E}\right) \text{ for } E \geq E_K \tag{31B}$$

where, E indicates the energy of the incident x-ray photon expressed in keV, $E_k$ indicates the K-edge of the CsI:T1 scintillator (approximated to 34 keV) and $K_f$ is the K-fluorescent x-rays escape fraction. After generation of the optical quanta a fraction of the generated optical quanta is reabsorbed (self-attenuated) within the scintillator medium. This is a depth-dependent process indicating as the path length increases the probability that the optical quanta would be reabsorbed within the scintillator medium increases and can be described as a binomial process. The escape probability that the generated optical quanta would exit the scintillator surface in contact with the fiberoptic is denoted as $g_{2_e}$. The depth-dependent escape probability $g_{2_e}(z)$, where z represents the depth of travel before the optical quanta escapes from the scintillator surface in contact with the fiberoptic have been modeled analytically by Lubinsky and estimated by Monte Carlo simulation techniques. A similar model is used with the assumption that the scintillator substrate has no reflective coating. The optical quanta emitted from the scintillator is modeled by considering the scintillator to be composed of fractional layers of thickness $\Delta t$, as shown in FIG. 29. For a scintillator of thickness t, and an x-ray photon interaction occurring at a distance z from the surface of the scintillator in contact with the fiberoptic, within a fractional layer of thickness $\Delta t$, the number of optical quanta emitted per incident x-ray photon with energy E is computed as:

$$g_1(E) \cdot g_2(E) = \sum_{z=0}^{t} [e^{-\mu_{lin}(E) \cdot (t-z)}][1 - e^{-\mu_{lin}(E) \cdot (\Delta t)}] \cdot g_{2_g}(E) \cdot g_{2_e}(z) \tag{32}$$

where, $\mu_{lin}(E)$ is the energy-dependent linear attenuation coefficient of CsI:T1. The terms $[e^{-\mu_{lin}(E) \cdot (t-z)}]$ and $[1-e^{-\mu_{lin}(E) \cdot (t-z)}]$ indicate the fraction of incident x-ray photons transmitted through a layer of thickness t−z and the fraction of x-ray photons attenuated within a scintillator layer of thickness $\Delta t$, respectively.

The average quantum gain $\overline{g_2}$ for the x-ray spectrum specified as $q_{norm}(E)$ is computed as:

$$\overline{g_2} = \frac{\int_{E=0}^{80} g_1(E) \cdot g_2(E) \cdot q_{norm} \cdot dE}{\int_{E=0}^{80} g_1(E) \cdot q_{norm} \cdot dE} \tag{33}$$

The variance in the quantum gain ($\sigma_{g_2}^2$) was computed from the Swank factor (I) and expressed in terms of the Poisson excess ($\epsilon_{g_2}$). The Swank factor for the specified spectrum is determined by averaging the moments of the monoenergetic absorbed energy distributions over the specified spectrum. The Poisson excess ($\epsilon_{g_2}$) is computed from the Swank factor (I) as:

$$\varepsilon_{g_2} = \overline{g_2} \cdot \left(\frac{1}{I} - 1\right) - 1 \tag{34}$$

The signal and NPS at the output of stage two can be written as:

$$\overline{q_2} = \overline{q_0} \cdot \overline{g_1} \cdot \overline{g_2} \tag{35}$$

$$W_2(u,v) = \overline{q_0} \cdot \overline{g_1} \cdot \overline{g_2} \cdot (\overline{g_2} + 1 + \epsilon_{g_2}) \tag{36}$$

Stage three addresses any stochastic blurring by the CsI:T1 scintillator. The scintillator blur represented as $T_3(u, v)$ is determined from the measured presampling MTF ($MTF_{pre}$) for each of the four CsI:T1 scintillators (300, 375, 450 and 525-$\mu$m thick) using a 1×1-inch back-illuminated laboratory CCD coupled to the scintillator by a straight fiberoptic coupler. The laboratory CCD system used has pixel dimensions of 24×24-$\mu$m and is operated in the 4×4 binning mode to provide a pixel pitch of 96×96-$\mu$m. Measurements are performed using a 10-$\mu$m wide slit oriented at a light angle (<4°) to the pixel matrix as per the technique described by Fujita et al. From the acquired slit image, the finely sampled line spread function (LSF) is determined; Fourier transformed; and deconvolved of the finite dimension of the slit. The resultant presampling MTF ($MTF_{pre}$) describes the MTF of a preferred embodiment of the system inclusive of the pixel presampling MTF. While the pixel presampling MTF can be represented as a sinc function for imagers with physical separation between neighboring pixels such as amorphous silicon photodiodes, such an assumption for the CCD imager which has no physical separation between pixels is verified in accordance with a preferred embodiment of the present invention. Hence, measurements are repeated with the CCD operating in a 24×24-$\mu$m pixel pitch mode. The scintillator blur along the u-axis represented as $T_3(u)$ is calculated as:

$$T_3(u) = MTF_{pre}(u) \cdot \frac{\pi \cdot a_{pix} \cdot u}{\sin(\pi \cdot a_{pix} \cdot u)} \tag{37}$$

Figure 30:
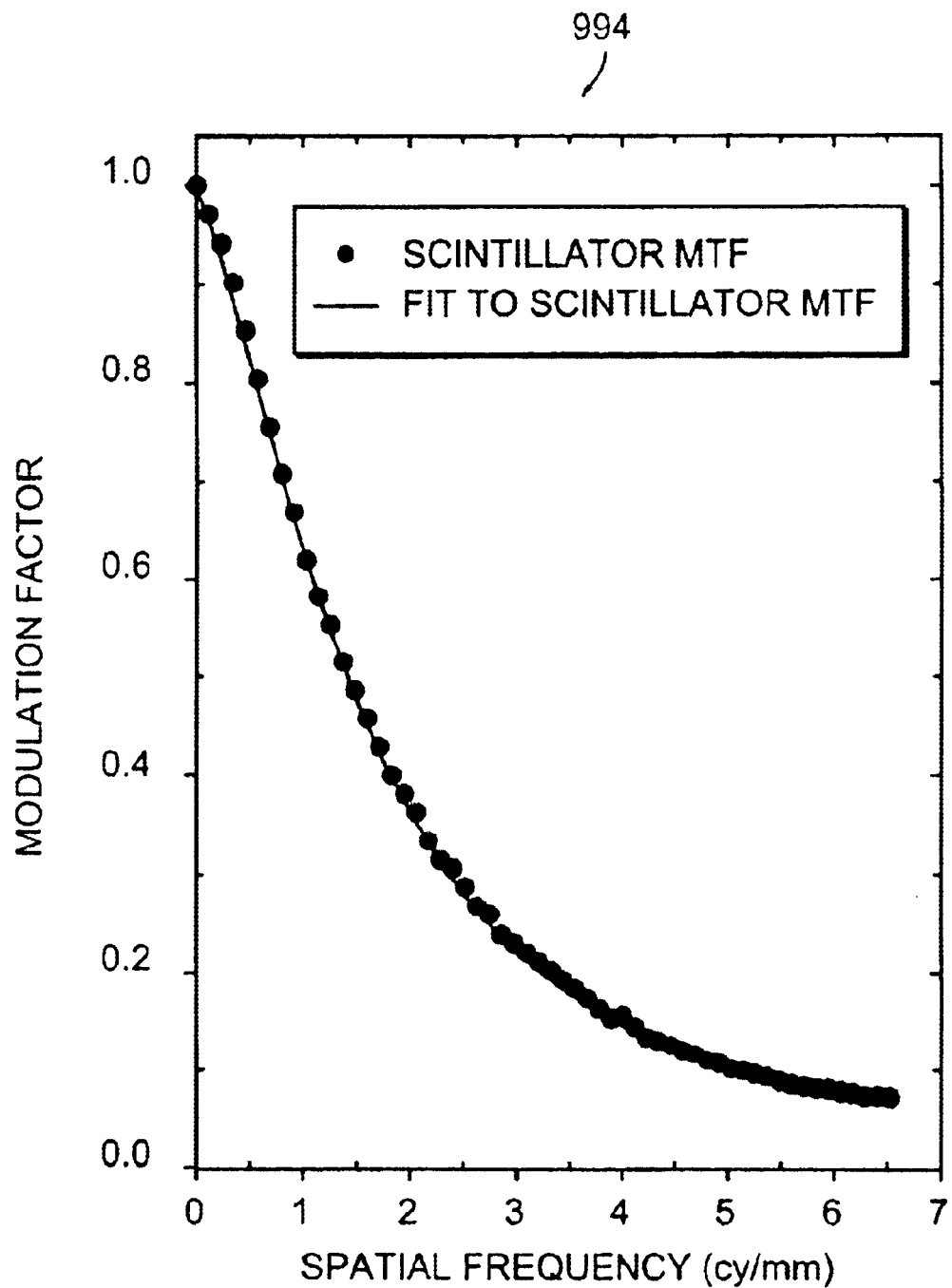
FIG. 30 graphically demonstrates the goodness of fit (modulation factor as a function of spatial frequency) to describe the scintillator blur, for a 525-$\mu$m thick CsI:Tl scintillator, where the straight line indicates a fit of the form $$\frac{1}{1 + B \cdot (u + u^2)},$$

Since, $T_3(u)$ determined using the 24×24-$\mu$m and 96×96-$\mu$m pixel pitch images are identical, the assumption that the pixel presampling MTF can be represented as a sinc function is thus validated. The measurement can also be repeated along the v-axis and the scintillator blur $T_3(v)$ is found to be identical to $T_3(u)$ for each scintillator. Hence, the assumption of isotropy is made for a preferred embodiment of the present invention. Siewerdsen et al have approximated the scintillator MTF[$T_3(u,v)$] for Lanex screen by a Lorentzian fit. However for the CsI:T1 scintillators, the measured $T_3(u)$ is best described by the fit:

$$T_3(u) = \frac{1}{1 + B \cdot (u + u^2)} \quad (38)$$

where, B is the fit parameter. As an example, the measured $T_3(u)$ for the 525-μm thick CsI:T1 scintillator and the fit to measured data using the equation of the form shown in equation 38 are plotted in FIG. 30. It should be noted that the fit parameter B is smaller than the attempted Lorentzian fit parameter which did not yield a satisfactory fit. Further, the fit parameter B is also plotted as a function of scintillator thickness (t, expressed in microns) to describe the scintillator blur for any intermediate thickness of the CsI:T1 scintillator and is shown in FIG. 31. The fit parameter, B, is well described within the thickness range studied, by the equation:

$$B = a \cdot \ln(t) + c \quad (39)$$

where, a is approximately 0.1451 and c is approximately −0.6186.

Thus, the signal and NPS at the output of stage three can be written as:

$$q_3(u,v) = \overline{q_0} \cdot \overline{g_1} \cdot \overline{g_2} \cdot T_3(u,v) \quad (40)$$

$$W_3(u,v) = \overline{q_0} \cdot \overline{g_1} \cdot \overline{g_2} \cdot [1 + T_3^2(u,v) \cdot (\overline{g_2} + \epsilon_{g_2})] \quad (41)$$

Stage four addresses the coupling of optical quanta by the fiberoptics coupler. In accordance with a preferred embodiment, Hejazi and Trauemicht have provided an analysis of the impact of lens and fiberoptic-coupling on the performance of CCD-based systems. The study also addresses the effect of taper on fiberoptic-coupled systems as described hereinbefore. A straight fiberoptic plate (non-tapering) is known to provide better optical coupling between the scintillator and the CCD with minimal loss of spatial resolution. The average quantum gain of this stage $\overline{g_4}$, which is the fraction of light capture and transmitted by a fiber pressed against a Lambertian source, can be given as, $$\overline{g_4} = [n \cdot \sin \theta_1]^2 \cdot e^{-u \cdot l} \cdot (1 - L_R) \cdot F_C \quad (42)$$

where, the terms $n \cdot \sin \theta_1$ and $e^{-u \cdot l}$ are the numerical aperture and the fiber core transmission efficiency, respectively. $L_R$ and $F_c$ denote the loss at the surface due to Fresnel reflection, and the fill factor of the fiber core, respectively. The fiber core transmission efficiency is approximately 0.8. Losses associated with Fresnel reflection can be decreased by coating or using an optical coupling medium with matching index of refraction. The fiberoptic coupling efficiency has been calculated with the assumption that losses associated with Fresnel reflection contributed to a 10% loss of light ($L_R = 0.1$). For the fiberoptic plate used in a preferred embodiment Type 47A, supplied by Schott Fiberoptics, MA, the numerical aperture is approximately 1 and the fill factor of the fiber core is approximately 0.7, resulting in an average quantum gain ($\overline{g_4}$) of 0.5.

The signal and the NPS at the output of stage four is written as:

$$q_4(u,v) = \overline{q_0} \cdot \overline{g_1} \cdot \overline{g_2} \cdot \overline{g_4} \cdot T_3(u,v) \quad (43)$$

$$W_4(u,v) = \overline{q_0} \cdot \overline{g_1} \cdot \overline{g_2} \cdot \overline{g_4} \cdot [1 + \overline{g_4} \cdot T_3^2(u,v) \cdot (\overline{g_2} + \epsilon_{g_2})] \quad (44)$$

In accordance with a preferred embodiment, stage five addresses the absorption of optical quanta by the CCD. This stage is considered as a quantum gain stage following a binomial process. The average quantum gain ($\overline{g_5}$) of the CCD is computed by weighting the wavelength-dependent quantum efficiency of the CCD [$\eta_{CCD}(\lambda)$] over the emission spectrum [$E(\lambda)$] of the CsI:T1 scintillator as shown below:

$$\overline{g_5} = \frac{\int_{\lambda = \lambda_{min}}^{\lambda_{max}} E(\lambda) \cdot \eta_{CCD}(\lambda) \cdot d\lambda}{\int_{\lambda = \lambda_{min}}^{\lambda_{max}} E(\lambda) \cdot d\lambda} \quad (45)$$

Hence, this signal and NPS at the output of stage five is written as:

$$q_5(u,v) = \overline{q_0} \cdot \overline{g_1} \cdot \overline{g_2} \cdot \overline{g_4} \cdot \overline{g_5} \cdot T_3(u,v) \quad (46)$$

$$W_5(u,v) = \overline{q_0} \cdot \overline{g_1} \cdot \overline{g_2} \cdot \overline{g_4} \cdot \overline{g_5} \cdot [1 + \overline{g_4} \cdot \overline{g_5} \cdot T_3^2(u,v) \cdot (\overline{g_2} + \epsilon_{g_2})] \quad (47)$$

The next stage, stage six in accordance with a preferred embodiment, addresses the deterministic blurring by the pixel presampling MTF and the effect of pixel fill factor The pixel presampling MTF is represented at $T_6(u,v)$ and expressed as:

$$T_6(u, v) = \left| \frac{\sin(\pi \cdot a_x \cdot u) \cdot \sin(\pi \cdot a_y \cdot v)}{(\pi \cdot a_x \cdot u)(\pi \cdot a_y \cdot v)} \right| \quad (48)$$

where, $a_x$ and $a_y$ represent the dimensions of the pixel that is sensitive to light (active dimension) in the x and y directions, respectively. The fill factor of the pixel ($F_f$), which is the ratio of the area of the pixel sensitive to light (active area) to the area of the pixel pitch is written as:

$$F_f = \frac{a_x \cdot a_y}{a_{pix,x} \cdot a_{pix,y}} \quad (49)$$

For a preferred embodiment of the CCD architecture, the active dimension along the x and y directions are not identical, as the interline channel is opaque to light. Hence, the pixel presampling MTF along the u and v axes are represented as:

$$T_6(u) = \left| \frac{\sin(\pi \cdot a_x \cdot u)}{(\pi \cdot a_x \cdot u)} \right| \quad (50A)$$

$$T_6(v) = \left| \frac{\sin(\pi \cdot a_y \cdot v)}{(\pi \cdot a_y \cdot v)} \right| \quad (50B)$$

However, the pixel pitch along both the x and y directions are identical ($a_{pix,x} = a_{pix,y} = a_{pix}$) and hence the fill factor is written as:

$$F_f = \frac{a_x \cdot a_y}{a_{pix}^2} \quad (51)$$

Thus the extension of the model from symmetric pixel geometry to an asymmetric pixel geometry is straight forward. The signal and NPS at the output of stage six is written as:

$$q_6(u,v) = \overline{q_0} \cdot \overline{g_1} \cdot \overline{g_2} \cdot \overline{g_4} \cdot \overline{g_5} \cdot a_{pix}^2 \cdot F_f \cdot T_3(u,v) \cdot T_6(u,v) \quad (52)$$

$$W_6(u,v) = \overline{q_0} \cdot \overline{g_1} \cdot \overline{g_2} \cdot \overline{g_4} \cdot \overline{g_5} \cdot a_{pix}^4 \cdot F_f^2 \cdot T_6^2(u,v) \cdot [1 + \overline{g_4} \cdot \overline{g_5} \cdot T_3^2(u,v) \cdot (\overline{g_2} + \epsilon_{g_2})] \quad (53)$$

The signal and NPS represented in the equations 52 and 53 are the pre-sampling signal and the presampling NPS.

However, DQE measurements reported in literature for digital imaging (sampled) systems are based on the presampling MTF and the aliased NPS. The aliased NPS represented as $W_6^a(u,v)$ is expressed as:

$$W_6^a(u,v) = W_6(u,v) ** III(u,v) \tag{54}$$

where, $III(u,v)$ is the Fourier transform of a rectangular array of δ-functions representing the pixel matrix with a spacing of $a_{pix}$. While most of the analysis addressed in a preferred embodiment is based on the presampling NPS; due to the varying pixel pitch (78, 156 and 234-μm) afforded by the preferred embodiment, the effect of aliasing is relevant.

Stage seven in accordance with a preferred embodiment addresses additive noise in the system. The total additive noise ($\sigma_{add}$) associated with a CCD-based system for uniform illumination with visible radiation can be written as:

$$\sigma_{add} = \sqrt{\sigma_{read}^2 + \sigma_{dark}^2 + \sigma_{ADC}^2 + \sigma_e^2} \tag{55}$$

where, $\sigma_{read}$ is the read noise, $\sigma_{dark}$ is the noise due to the dark current, $\sigma_{ADC}$ is the quantization noise due to the analog-to-digital converter (ADC), and $\sigma_e$ is electronic noise from all other sources such as reset noise, trapping-state noise and charge-transfer noise as described hereinbefore.

The read noise ($\sigma_{read}$) is modeled and described hereinbefore. The dark noise ($\sigma_{dark}$) due to dark charge generation can be stated as:

$$\sigma_{dark} = \sqrt{t \cdot q_d \cdot a_{pix}^2} \tag{56}$$

where, $q_d$ is the dark charge generated per unit time t per unit area and $a_{pix}^2$ is the pixel area of the CCD. The dark current is typically around 25 pA/cm². The integration time per frame is 33.3 ms at a frame rate of 30 fps, resulting in $\sigma_{dark}$ of 18, 36 and 53-electrons per pixel for 78, 156 and 234-μm pixel pitch, respectively.

Quantization noise ($\sigma_{ADC}$) arising due to the analog-to-digital converters (ADCs) depends on the ratio of the maximum charge capacity of the amplifier ($Q_{Amp,max}$) to the number of bits (n) used by the ADC as shown below:

$$\sigma_{ADC} = \frac{Q_{Amp,max}}{2^n \cdot \sqrt{12}} \tag{57}$$

The maximum ADC noise is observed when the $Q_{Amp,max}$ equals the maximum charge that can be accommodated in the serial (horizontal) register of the CCD, which is 1×10⁶ electrons. At this signal level, with a 14-bit ADC (n=14), the quantization noise ($\sigma_{ADC}$) is approximately 18 electrons.

$\sigma_e$ are is a combination of several noise sources such as, reset noise, charge-transfer noise, and trapping-state noise. Reset noise is due to the uncertainty in voltage to which the output node is reset after a charge packet is read. This noise can be removed very effectively using correlated double sampling techniques. The charge-transfer noise is due to the finite inefficiency in the charge transfer process. The high charge transfer efficiency that is routinely being achieved by modern CCDs makes this source of noise relatively unimportant. Trapping-state noise is due to the uncertainty in the quantity of charge, due to trapping and slow release of charge either by surface or bulk states. Buried-channel operation prevents such noise from the surface states and material control during fabrication can reduce the bulk trapping-state density to negligible levels. Hence for this analysis, $\sigma_e$ is assumed to be negligible.

The presampling signal and the presampling NPS at the output of stage seven is written as:

$$q_7(u,v) = \overline{q_0} \cdot \overline{g_1} \cdot \overline{g_2} \cdot \overline{g_4} \cdot \overline{g_5} \cdot a_{pix}^2 \cdot F_f$$

$$T_3(u,v) \cdot T_6(u,v) \tag{58}$$

$$W_7(u,v) = \overline{q_0} \cdot \overline{g_1} \cdot \overline{g_2} \cdot \overline{g_4} \cdot \overline{g_5} \cdot a_{pix}^4 \cdot F_f^2 \cdot T_6^2(u,v) \cdot$$

$$[1 + \overline{g_4} \cdot \overline{g_5} \cdot T_3^2(u,v) \cdot (\overline{g_2} + \varepsilon_{g_2})] + W_{add}(u,v) \tag{59}$$

where, the pixel variance ($\sigma_{add}^2$) is related to the additive noise power [$W_{add}(u,v)$] by:

$$\sigma_{add}^2 = \iint W_{add}(u,v) \cdot du \cdot dv \tag{60}$$

The detective quantum efficiency, which is defined as the ratio of the square of the output signal-to-noise ratio to the square of the input signal-to-noise ratio can be calculated from the above equations as:

$$DQE(u,v) = \frac{\overline{g_1} \cdot \overline{g_2} \cdot \overline{g_4} \cdot \overline{g_5} \cdot T_3^2(u,v)}{1 + \overline{g_4} \cdot \overline{g_5} \cdot T_3^2(u,v) \cdot (\overline{g_2} + \varepsilon_{g_2}) + \frac{W_{add}(u,v)}{\left(\frac{q_0}{X}\right) \cdot X \cdot \overline{g_1} \cdot \overline{g_2} \cdot \overline{g_4} \cdot \overline{g_5} \cdot a_{pix}^4 \cdot F_f^2 \cdot T_6^2(u,v)}} \tag{61}$$

As noted by Siewerdsen, may of the important signal and transfer properties can be adequately described by the zero-frequency DQE. Thus, the DQE(0) is written as:

$$DQE(0) = \frac{\overline{g_1} \cdot \overline{g_2} \cdot \overline{g_4} \cdot \overline{g_5}}{1 + \overline{g_4} \cdot \overline{g_5} \cdot (\overline{g_2} + \varepsilon_{g_2}) + \frac{\sigma_{add}^2}{\left(\frac{q_0}{X}\right) \cdot X \cdot \overline{g_1} \cdot \overline{g_2} \cdot \overline{g_4} \cdot \overline{g_5} \cdot a_{pix}^2 \cdot F_f}} \tag{62}$$

For fluoroscopic applications, in addition to the spatial characteristics, the temporal characteristics of the imager are addressed. Of particular importance is image lag, which is a result of a fraction of the generated electrons from a particular frame being trapped and released into subsequent frames. Based on the deterministic model of Matsunaga et al and under conditions of signal equilibrium, Siewerdesn et al have derived the pixel variance after readout from the n$^{th}$ frame ($\sigma_{R_{(n)}}^2$) as a function of the fraction of trapped charge (electrons) [$f_{trap}$] as:

$$\sigma_{R_{(n)}}^2 = \left(\frac{1 - f_{trap}}{1 + f_{trap}}\right) \cdot \left(\sigma_{G_{(n)}}^2 + \sigma_{N_{int(n)}}^2\right) + \sigma_{N_{ext(n)}}^2 \tag{63}$$

where, $\sigma_{G_{(n)}}^2$ is the variance in the number of electrons generated, $\sigma_{N_{int(n)}}^2$ is the additive noise generated within the active area of the pixel, and $\sigma_{N_{ext(n)}}^2$ is the additive noise generated external to the pixel, in the n$^{th}$ frame. Since, all the additive noise sources occur external to the active area of the pixel (i.e., $\sigma_{N_{int(n)}}^2 = 0$ and $\sigma_{Next_{(n)}}^2 = \sigma_{add}^2$), the pixel variance including the effects of charge trapping ($\sigma_{trap,n}^2$) is written as:

$$\sigma_{trap,n}^2 = \left(\frac{1-f_{trap}}{1+f_{trap}}\right) \cdot \frac{q_0}{X} \cdot X \cdot \overline{g_1} \cdot \overline{g_2} \cdot \quad (64)$$

$$\overline{g_4} \cdot \overline{g_5} \cdot a_{pix}^2 \cdot F_f \cdot [1 + \overline{g_4} \cdot \overline{g_5} \cdot s \cdot (\overline{g_2} + \varepsilon_{g_2})] + \sigma_{add}^2$$

where, s is the sharpness factor defined by:

$$s = a_{pix}^2 \cdot F_f \int\int T_3^2(u,v) \cdot T_6^2(u,v) \cdot du \cdot dv \quad (65)$$

In terms of the signal, under conditions of signal equilibrium, Siewerdsen et al have also derived the mean number of electrons readout in the $n^{th}$ frame $(\overline{R_n})$ to be equal to the mean number of electrons generated by x-ray photon interaction in the $(n+1)^{th}$ frame $(\overline{G_{n+1}})$. In a fluoroscopic sequence with uniform exposure over successive frames, $\overline{G_{n+1}} = \overline{q_7}$, where, $\overline{q_7}$ is the mean signal determined by equation 58. Hence, zero-frequency DQE including the effects of charge trapping $[DQE^{trap}(0)]$ can be derived to be:

$$DQE^{trap}(0) = \frac{\overline{g_1} \cdot \overline{g_2} \cdot \overline{g_4} \cdot \overline{g_5}}{\left(\frac{1-f_{trap}}{1+f_{trap}}\right)\left[1+\overline{g_4} \cdot \overline{g_5} \cdot (\overline{g_2}+\varepsilon_{g_2}) + \frac{\sigma_{add}^2}{\left(\frac{1-f_{trap}}{1+f_{trap}}\right) \cdot \left(\frac{q_0}{X}\right) \cdot X \cdot \overline{g_1} \cdot \overline{g_2} \cdot \overline{g_4} \cdot \overline{g_5} \cdot a_{pix}^2 \cdot F_f}\right]} \quad (66)$$

The photon fluence per $\mu R$ of exposure $$\left(\frac{q_0}{X}\right)$$

for the x-ray beam specified in FIG. 28 is determined to be $2.64 \times 10^2$ photons/(mm$^2 \cdot \mu R$), where X represents exposure in units of $\mu R$. The quantum efficiency and the number of optical quanta emitted per x-ray interaction for each scintillator is computed. A summary of gain and blur parameters used in the model is provided in Table 4.

TABLE 4

| Parameter | Description | Scintillator Thickness (microns) | | | |
|---|---|---|---|---|---|
| | | 300 | 375 | 450 | 525 |
| $\overline{g_1}$ | Scintillator quantum efficiency | 0.701 | 0.768 | 0.818 | 0.856 |
| $\overline{g_2}$ | Scintillator quantum gain | 1179 | 1044 | 898 | 742 |
| $\overline{g_4}$ | Fiberoptic coupling efficiency | | | 0.5 | |
| $\overline{g_5}$ | CCD quantum efficiency | | | 0.4 | |
| B | Scintillator blur parameter | 0.209 | 0.242 | 0.268 | 0.290 |

A list of various noise sources and the estimated values used for this analysis is summarized in Table 5.

TABLE 5

| Parameter | Description | Pixel pitch (microns) | | |
|---|---|---|---|---|
| | | 78 | 156 | 234 |
| $\sigma_{dark}$ | Dark noise | 18 | 36 | 53 |
| $\sigma_{read}$ | Read noise | | 50 | |

TABLE 5-continued

| Parameter | Description | Pixel pitch (microns) | | |
|---|---|---|---|---|
| | | 78 | 156 | 234 |
| $\sigma_{ADC}$ | ADC quantization noise | | 18 | |
| $\sigma_{add}$ | Total additive noise | 56 | 64 | 75 |

The zero-frequency DQE [DQE(0)] can provide vital information about the imager performance. In general, DQE (0) provides the upper limit of the frequency-dependent DQE and hence, studying the limitations of DQE(0) provides an understanding of the maximum performance that can be achieved by the imager. FIGS. 32A–32D shows the exposure dependence of DQE(0) would provide an understanding of the maximum performance that can be achieved by the imager. FIGS. 32A–32D show the exposure dependence of DQE(0) for the three pixel pitch modes of operation for each of the four scintillators. At typical fluoroscopic exposure levels of 1–2 $\mu R$ per frame, the DQE(0) performance is either comparable or improved, depending on the thickness of the scintillator, to state-of-the-art image intensifier-based technology, even when the imager is operated at the high-resolution mode of 78-$\mu m$. While increasing the scintillator thickness improves the DQE(0) at typical fluoroscopic and radiographic exposure levels; however at very low exposure levels, increasing the scintillator thickness results in degradation of the DQE(0). This is due to self-attenuation of optical quanta within the scintillator medium resulting in a decrease in the output signal, relative to the additive electronic noise, in spite of the improved quantum efficiency. This effect is observed clearly in FIG. 33, which is a plot of the DQE(0) as a function of scintillator thickness at various exposure levels, for the imager operating at the 156-$\mu m$ pixel pitch mode. The optimal range of the pixel size is 350–450 $\mu m$ for a preferred embodiment. This effect is more prominent for smaller pixel-pitch (higher resolution) modes of operation as seen in FIGS. 34A and 34B. It should be noted that this effect is observed only at very low exposure levels that are not typically used in current fluoroscopic clinical practice as observed by the comparison at exposure levels of 0.1 and 1-$\mu R$ in FIGS. 34A and 34B.

In a preferred embodiment, the impact of additive noise on DQE(0) is addressed. The DQE(0) shown in FIGS. 32–34 is calculated using nominal (estimated) values for the additive noise summarized in Table 5. However, at low frame rates, the dark noise ($\sigma_{dark}$) is higher due to the increased frame integration period (t), as per equation 56. Hence, the impact of additive noise is studied at a nominal fluoroscopic exposure of 2-$\mu R$ for the three pixel pitch modes of operation for each scintillator thickness. FIGS. 35A–35D show the results of these simulations. The plots indicate that as the additive noise increases, DQE(0) degrades faster with decreasing pixel pitch. It is also observed that while the DQE(0) improves with increasing scintillator thickness for additive noise less than approximately 25 electrons, the DQE(0) drop-off is higher with increasing scintillator thickness as the additive noise increases. This indicates that a thicker scintillator can be used to improve the DQE(0) performance, provided the additive noise is restricted to less than approximately 25 electrons.

Primary sources that contribute to image lag in pulsed fluoroscopic systems include the decay characteristics of the scintillator and charge traps within the CCD. Measurements of the CsI:T1 scintillator decay characteristics at room temperature by Valentine et al have found two primary decay time constants of 679±10 ns and 3.34±0.14 µs, which contribute to 63.7% and 36.1% of the emission. The design of a preferred embodiment system incorporates a delay of 2-ms after the termination of the x-ray pulse, which is sufficient to allow for almost complete integration of the emitted optical quanta within a particular frame. Hence, contribution to image lag from the scintillator is considered negligible. Scientific-grade CCDs are routinely used for fast-framing applications, typically by using frame-transfer architecture, due to their time characteristics. The preferred embodiment of the system uses the interline-transfer architecture and hence, the effect of charge trapping on the performance of the system is addressed. Simulations of $DQE^{trap}(0)$ are performed by varying the fraction of trapped charge ($f_{trap}$) in the range $0 < f^{trap} < 0.1$, using the $\sigma_{add}$ summarized in Table 5 for a nominal fluoroscopic exposure level of 2-µR. The results of these simulations performed for the three pixel pitch modes for each of the scintillator are shown in FIGS. 36A–36I). The results indicate that for increasing $f_{trap}$, the individual pixel variance reduces due to increased correlation between frames. This results in inflation of the DQE. These results further illustrate the need to measure the 'lag-free' DQE.

Besides the zero-frequency DQE [DQE(0)], the frequency-dependent DQE [DQE(f)] provides additional insight into the imaging performance of the preferred embodiments of the present invention system. Simulations of the frequency-dependent DQE [DQE(f)] are performed at a nominal fluoroscopic exposure level of 2-µR with the additive noise summarized in Table 5. These calculations are performed using the presampling signal and the presampling NPS and plotted up to Nyquist limit for the 78 and 156-µm pixel pitch modes of operation. Results of these simulations for the four thicknesses of CsI:T1 scintillator under consideration are shown in FIGS. 37A and 37B. While these simulations are also performed with the 234-µm pixel pitch mode, the results of these simulations are not plotted as similar trends are observed. The results shown in FIGS. 37A and 37B indicate that increasing the scintillator thickness improves the DQE at low frequencies and degrades the DQE at high frequencies. It is also observed that there is a slight improvement in the DQE with increasing pixel pitch at the exposure and noise levels used in these simulations, indicating that the additive electronic noise, relative to the signal, is sufficient to influence the DQE for the smaller pixel pitch modes. More importantly, these simulations indicate that it is feasible to achieve DQE performance superior to current image intensifier-based technology at nominal fluoroscopic exposure levels, with the added advantage of improved and uniform spatial resolution.

Measured DQE(f) reported in literature are based on the presampling signal (MTF) and the aliased NPS. Further, a preferred embodiment of the present invention system is capable of operation at the three pixel pitch modes of 78, 156 and 234-µm. Hence, it is pertinent to address the effect of aliasing on the DQE(f). The DQE(f) computed using the aliased NPS is denoted by $DQE^a(f)$ simulations of the $DQE^a(f)$ are performed using the aliased NPS at conditions identical to that used to yield the results in FIGS. 37A and 37B. As an example, the aliased NPS for the system using a 450-µm thick CsI:T1 scintillator operating at 78 and 156-µm pixel pitch modes is shown in FIGS. 38A and 38B. Results of the $DQE^a(f)$ simulations are shown in FIGS. 39 and 40. Aliasing results in a slight decrease in DQE at the zero frequency and a faster roll-off with increasing spatial frequency.

These results of the objective performance parameter DQE indicate that a CCD-based imaging system can provide DQE performance comparable to modern image intensifier-based systems, with the added advantage of improved spatial resolution. It is seen that at fluoroscopic exposure levels, DQE(0) in excess of 0.6 can be achieved even at a pixel pitch of 78-µm for a system coupled to a 300-µm thick CsI:T1 scintillator. It is also seen that for applications that do not require very high spatial resolution, using a thicker scintillator and operating at a larger pixel pitch mode, enables achieving DQE(0) performance in excess of 0.7, at fluoroscopic exposure levels. The preferred embodiment imager is aimed at producing the highest spatial resolution for fluoroscopic imaging, while preserving or improving on the DQE performance afforded by currently available imaging systems. Results from DQE(f) calculations at fluoroscopic exposure levels combined with the high spatial resolution indicate that the preferred embodiment imager is appropriate for cardiac and pediatric angiography.

In accordance with a preferred embodiment, the electronic noise present in a single module of the CCD imager is analyzed and quantified for the cardiac x-ray fluoroscopic imager. Frequency dependent noise analysis and time-domain noise analysis are performed. It should be noted that the two-dimensional and one-dimensional noise power spectrum is calculated for all frame rates, for example, the four frame rates (6.865, 13.73, 18.307 and 27.46 fps). Time domain noise analysis for all four frame rates is also calculated. The results indicate a maximum of approximately 60 electrons at 6.865 fps which drop down to a maximum of approximately 35 electrons at 27.46 fps.

One hundred full-frame images are acquired at each frame rate, five minutes after start-up, with no x-ray exposure to the imager. The average (AV100) and standard deviation (SD100) images from the 100 full-frame images are computed using a built-in script. Sixteen full-frame images, which do not exhibit any bad pixel, are selected from these 100 full-frame images. The average of these sixteen images (AV16) is computed. The computed average (AV16) is subtracted from each of the sixteen full-frame images and cropped to a 512×512 region-of-interest (ROI). The two-dimensional NPS(u,v) is computed as per equation 67 shown below:

$$NPS(u,v) = \frac{\langle |FT[ROI(x,y)]|^2 \rangle}{N_x \cdot N_y} \cdot \Delta_x \cdot \Delta_y \quad (67)$$

where, $\langle |FT[ROI(x,y)]|^2 \rangle$ indicates the ensemble average of the squares of the magnitude of the Fourier transform of the 512×512 ROIs, $\Delta_x$ and $\Delta_y$ represent the pixel pitch in the x and y-directions (which are both 0.156 mm) and $N_x$ and $N_y$ represent the number of pixels in the x and y-directions (which are both 512). The one-dimensional NPS(f) along the u-axis is estimated from the two-dimensional NPS(u,v), by taking a thin slice of eight lines of data on either side of the u-axis and averaging the data points of the same frequency (f), where f is computed as $f=\sqrt{u^2+v^2}$. The resultant NPS(f) has units of $DU^2 mm^2$, where DU represents digital units (digital numbers or digital counts). Similarly, the NPS(f) along the v-axis is also estimated. In addition, the NPS(f) is also computed by radial averaging of NPS(u,v) while excluding data points along NPS(u,0) and NPS(0,v). The rms variance computed from the sample images should be equal to the volume of the NPS(u,v) over the frequency range as shown in equation 68.

$$\text{rms Variance} = \int\int NPS(u,v).du.dv \tag{68}$$

Hence, rms variance is computed from the sixteen selected full-frame images and compared with the volume of NPS (u,v). The same procedure was repeated for all 4-frame rates.

In addition, the volume under the two-dimensional NPS, calculated by rotating the one-dimensional NPS(f) about the origin, estimated from each of three techniques (along u-axis, along v-axis and radial average), is also compared with the rms variance to check for the best one-dimensional estimate of the two-dimensional NPS.

Further, the one-dimensional NPS estimates are scaled by a factor of (16/15) to account for the loss of variance due to subtraction of the average image (AV16) from each of the sample images.

The two-dimensional NPS(u,v) for the four frame rates which correct for amplifier noise is shown in FIGS. 41A–41D. A three-dimensional perspective is shown in FIGS. 42A–42D. The plots indicate that there is no significant off-axis noise. The NPS at frame rates other than 6.865 fps indicate some distinct frequency peaks along the u-axis. The integral of the NPS(u,v) deviated by less than 0.2% of the rms variance at all four frame rates.

The one-dimensional NPS(f) for the four frame rates are shown respectively in FIGS. 43–46. Each figure contains the NPS(f) along the u-axis, along the v-axis and the NPS obtained by radial average. The volume under the two-dimensional NPS generated by rotating the one-dimensional NPS(f) about the origin is computed for all three techniques and at all four frame rates and compared to the rms variance for the corresponding frame rate. From this measurement, it is determined that the one-dimensional NPS(f) along the v-axis is the best representative for 6.865 and 13.73 fps and the one-dimensional NPS(f) determined by radial average is the best estimate for 18.307 and 27.46 fps. The best representative one-dimensional NPS(f) estimates for all four frame rates deviated by less than 2% of the rms variance at the respective frame rates.

The plot of the one-dimensional NPS(f) estimates are shown in FIG. 47. The plot indicates that the NPS increases with increasing frame integration period (decreasing frame rate) signifying that the electronic noise is dominated by the shot noise arising due to the dark current and not that due to read noise.

The time-domain noise analysis is performed by computing the mean from the standard deviation image from sixteen full-frame images (spatial mean of the temporal standard deviation image), at discrete time points for all frame rates. This mean provides the noise from all sources ($\sigma_T$) inclusive of read noise, shot noise arising from the dark current, quantization noise and other noise sources. The computed mean is scaled to electrons by using a conversion gain of 2.2 electrons/digital unit (DU). The preferred embodiment imager is operated to run at a continuous 30 fps between successive time point acquisitions.

The shot noise ($\sigma_{ds}$) arising from the dark current and the read noise component ($\sigma_R$) are determined in the following manner. It is assumed that the measured total noise, ($\sigma_T$) is comprised of two major sources, the shot noise from the dark current, $\sigma_{ds}$, and the read noise, $\sigma_R$, that is, the noise component from other sources are negligible. Hence, the total noise can be written as:

$$\sigma_T^2 = \sigma_{ds}^2 + \sigma_R^2 \tag{69}$$

In addition, it is assumed that the read noise, $\sigma_R$ is proportional to the square root of the pixel rate ($P_R$) and that the pixel rate is doubled when the frame rate is doubled as shown in equations 70 and 71.

$$\sigma_R \propto \sqrt{P_R} \Rightarrow \sigma_R^2 = k_1 \cdot P_R \tag{70}$$

$$P_{R,13.73FPS} = 2 \cdot P_{R,6.865FPS} \tag{71}$$

Based on equations 69, 70 and 71, the following two equations can be written to express the total noise at 6.865 and 13.73 FPS:

$$\sigma_{T,6.865\ FPS}^2 = \frac{q_D}{6.865} + k_1 \cdot P_{R,6.865\ FPS} \tag{72}$$

$$\sigma_{T,13.73\ FPS}^2 = \frac{q_D}{13.73} + 2k_1 \cdot P_{R,6.865\ FPS} \tag{73}$$

where, $q_D$ is the dark charge generation rate in electrons/pixel/second and $k_1$ is a proportionality constant. Solving for $q_D$ and $\sqrt{k_1 \cdot P_R}$ from equations 72 and 73 it can be determined:

$$q_D = \frac{13.73}{3}[2\sigma_{T,6.865\ FPS}^2 - \sigma_{T,13.73\ FPS}^2] \tag{74}$$

$$\sigma_{R,6.865\ FPS} = \sqrt{k_1 \cdot P_{R,6.865\ FPS}} = \sqrt{\frac{2\sigma_{T,13.73\ FPS}^2 - \sigma_{T,6.865\ FPS}^2}{3}} \tag{75}$$

The time-domain noise analysis is shown in FIG. 48. The plot indicates that the electronic noise stabilizes to approximately 60 electrons at 6.865 fps and approximately 35 electrons at 27.46 fps.

FIG. 49 is a plot of the dark current determined from equation 74 at various discrete time points. The plot indicates that the dark current stabilizes at approximately 15 pA/cm². FIG. 50 illustrates graphically the read noise determined from equation 75 at various discrete time points. The graph indicates that the read noise stabilizes at approximately 9, 13, 15 and 18 electrons at 6.865, 13.73, 18.31 and 27.46 frames/second.

The correlation between the space-domain and time-domain analyses is addressed in a preferred embodiment of the present invention. The standard deviation (in electrons) obtained by the spatial mean of the temporal standard deviation image is compared with the standard deviation (square-root of the variance) computed from the volume under the NPS(u,v) and the results are shown in Table 6.

TABLE 6

| | 6.865 FPS | 13.73 FPS | 18.307 FPS | 27.46 FPS |
|---|---|---|---|---|
| Std. Dev at t = 5 min from time-domain analysis | 51.132 | 38.544 | 35.341 | 31.962 |
| Volume under NPS (u,v) from space-domain analysis | 51.282 | 40.201 | 34.831 | 31.544 |
| % Deviation from time-domain analysis | 0.292% | 4.299% | −1.442% | −1.306% |

Further, additional results from the measurements of pre-sampling modulation transfer function (MTF), NPS, noise equivalent quanta (NEQ) and DQE are computed in preferred embodiments of the present invention. The measurement conditions included the following conditions particular to the generator settings, the beam quality and the imager settings. The generator settings included: peak applied tube voltage: 70 kVp; tube current: 200 mA; duration of exposure: 1.25 ms; nominal focal spot size: 0.6 mm; and source-to-imager distance: 115 cm. The beam quality settings included: half-value layer prior to added filtration: 3.1 mm of Al; added filtration: 4.1 cm of Al at 50 cm from focal spot; calculated photon fluence per unit exposure: 302 photons/mm$^2$/$\mu$R; and exposure incident on detector: 8 $\mu$R. Further, the imager settings included a frame rate of 7.5 fps. The frame rate of 7.5 fps is used as the electronic noise of the imager is found to be higher at 7.5 fps than other frame rates, thereby providing a conservative measure.

The presampling MTF measured along two orthogonal directions are shown in FIG. 51. FIG. 52 illustrates graphically a comparison with the theoretically predicted MTF based on prior measurements with a similar scintillator and a laboratory small-area low-noise CCD. FIG. 53 is the two-dimensional normalized NPS measured at 8 $\mu$R. The two-dimensional NPS indicates good isotropy. FIG. 54 is the plot of the one-dimensional normalized NPS determined along u, v-axes and by radial averaging the two-dimensional normalized NPS. FIG. 55 is the plot of the NEQ measured at 8 $\mu$R. FIG. 56 illustrates graphically the DQE measured at 8 $\mu$R.

FIG. 57 illustrates graphically the lag corrected DQE as a function of spatial frequency in cycles/mm for u-axis measurements for different radiation doses. The DQE does not drop appreciably at lower exposure levels. Similarly, FIG. 58 illustrates graphically the lag corrected DQE as a function of spatial frequency for v-axis measurements for different radiation doses. The performance of a single module operating at 156-$\mu$m pixel pitch in fluoroscopic (30 fps) and radiographic modes with a 7-mm half-value layer, 72-kVp x-ray beam is used in terms of the pre-sampling modulation transfer function (MTF), noise power spectrum (NPS), and detective quantum efficiency (DQE). The fluoroscopic image lag is measured and accounted for in the DQE estimate to provide 'lag-free' DQE.

The measured limiting spatial resolution at 10% pre-sampling MTF is 3.5 cycle/mm (Tyquist limit: 3.2 cycle/mm). In the pulsed fluoroscopic mode, the first-frame image lag was less than 1%. The 'lag-free' DQE(0) of approximately 0.52 is achieved even at a vary low fluoroscopic exposure rate of 1-$\mu$R/frame. Grid phantom measurements indicate no appreciable distortion.

The results demonstrate very high and uniform spatial resolution at 30 fps fluoroscopy, while preserving and potentially improving on the DQE performance. Results from DQE and image lag measurements at fluoroscopic exposure rates combined with the high spatial resolution observed from the MTF provide support for the use of this imager for cardiovascular and pediatric angiogrpahy.

FIG. 59 illustrates graphically a comparison of the u-axis and v-axis polynomial fit of the lag corrected DQE as a function of spatial frequency for a 1 $\mu$R radiation dose. Similarly, FIG. 60 illustrates graphically a comparison of the u-axis and v-axis polynomial fit of the lag corrected DQE as a function of spatial frequency for a 4 $\mu$R radiation dose.

The claims should not be read as limited to the described order or elements unless stated to that effect. Therefore, all embodiments that come within the scope and spirit of the following claims and equivalents thereto are claimed as the invention.

What is claimed:

1. An apparatus for examining cardiovascular tissue of a patient comprising:
    an x-ray radiation source emitting radiation which is directed through cardiovascular tissue;
    a scintillator receiving radiation transmitted through the tissue and generating an optical signal in response to the received radiation;
    a non-reducing optical coupler that receives the optical signal;
    a binning image sensor to receive the optical signal from the optical coupler at a plurality of pixels and generate an electronic representation of the tissue; and
    a controller that is electrically connected to the imagine sensor, the controller actuating readout of the electronic representation from the imaging sensor to provide an image frame including a first region having a first resolution and including a second region having a second resolution that is higher than the first resolution.

2. The apparatus of claim 1 further comprising a display for displaying an image of the cardiovascular tissue.

3. The apparatus of claim 1 further comprising a display for displaying an image of the soft tissue, and a data processor receiving the electronic representation of the soft tissue and processing the image of the soft tissue on the display.

4. The apparatus of claim 1 wherein the image sensor comprises a charge coupled device (CCD) that includes a plurality of interpixel channels.

5. The apparatus of claim 1 further wherein the CCD comprises a plurality of CCDs, each CCD having a plurality of surfaces which interface with an adjoining CCD.

6. The apparatus of claim 1 further comprising a processor programmed to correct a seam artifact.

7. The apparatus of claim 1 further comprising a frame holding the radiation source and the imaging sensor in fixed relation to each other.

8. The apparatus of claim 1 wherein the imaging sensor has a first plurality of pixels having a first size and a second plurality of pixels having a second size that is different from the first size.

9. The apparatus of claim 1 further comprising a processor that combines data stored by groups of adjacent pixels of the imaging sensor to generate the electronic representation of the cardiovascular tissue.

10. The apparatus of claim 1 further comprising an audio controller, such that the audio controller actuates a procedure.

11. The apparatus of claim 1 wherein the imaging sensor performs time delay integration to generate the electronic representation of the cardiovascular tissue.

12. The apparatus of claim 1 wherein the imaging sensor comprises an array of pixels at least as large as 2048×2048 pixels.

13. The apparatus of claim 1 further comprising a straight fiber optic coupler between the optical surface and the imaging sensor.

14. The apparatus of claim 1 wherein the scintillator has a variable thickness.

15. The apparatus of claim 1 wherein the controller bins rectangular groups of pixels during charge readout.

16. The apparatus of claim 1 wherein the sensor performs pixel binning.

17. An apparatus for determining of a cardiac diagnostic characteristic of a patient comprising:
    an x-ray radiation source emitting radiation which is directed through a patient;

a scintillator receiving x-ray radiation transmitted through the tissue and generating an optical signal correlated with the received radiation and directing the optical signal along a first optical path;

a plurality of abutting charge coupled devices (CCD) that are optically coupled to the scintillator to receive the optical signal at a plurality of pixels and generate an electronic representation of the soft tissue;

a fiber optic coupler positioned between the scintillator and the CCDs;

a controller that is electrically connected to the CCDs such that the controller bins charge from separate pixels to form an electronic representation of a region of interest of the patient to provide an image frame including a first region having a first resolution and including a second region having a second resolution that is higher than the first resolution.

18. The apparatus of claim 17 wherein the cardiac diagnostic characteristic includes one of ejection fraction, degree of stenosis or stent position.

19. A method of three-dimensional fluoroscopic imaging of cardiac tissue in a patient comprising:

providing an x-ray radiation source such that radiation emitted by the source is transmitted through a patients cardiac tissue onto a scintillator;

providing a plurality of abutting silicon circuit sensors, each sensor having a two dimensional array of pixel elements that detect light from the scintillator that is emitted in response to radiation from the x-ray source;

positioning the patient on a support surface;

directing x-ray radiation through the region of the patient's cardiac tissue onto the scintillator which emits a spatial intensity pattern of light that is detected by the sensors, the spatial intensity pattern being coupled to the sensors with an optical system;

binning charge from separate pixel elements of the sensors for readout with an electronic controller; and forming a three-dimensional image of the cardiac tissue from the binned representation.

20. The method of claim 19 wherein the step of providing a pixellated sensors comprises providing a plurality of binnable sensors.

21. The method of claim 19 further comprising providing data processor connected to the sensors, the data processor having a memory for storing a discrete electronic representation.

22. The method of claim 19 wherein each silicon circuit sensor has a plurality of interpixel channels.

23. The method of claim 19 further comprising providing a fiber optic coupler between the scintillator and the sensors.

24. The method of claim 19 further comprising forming the image in less than 60 seconds after directing the x-ray radiation through the patient.

25. The method of claim 19 further comprising simultaneously irradiating an entire region of the patient with x-ray tube that is stationary relative to the patient.

26. The method of claim 19 further comprising forming an image having a resolution of at least about 1 mm.

27. The method of claim 19 further comprising providing a sensor having a two dimensional array of MOS capacitors.

28. The method of claim 19 further comprising performing serial and parallel binning of pixels of each sensor.

29. The method of claim 19 further comprising binning pixels during charge readout of the sensors.

30. An apparatus for fluoroscopic examination of cardiovascular tissue of a patient comprising:

an x-ray radiation source emitting radiation which is directed through cardiovascular tissue;

a scintillator receiving radiation transmitted through the tissue and generating an optical signal in response to the received radiation;

a non-reducing optical coupler that receives the optical signal;

a binning amorphous silicon image sensor to receive the optical signal from the optical coupler at a plurality of pixels and generate an electronic representation of the tissue; and a controller that is electrically connected to the imaging sensor, the controller actuating readout of a multi-resolution mode electronic representation from the imaging sensor.

31. The apparatus of claim 30 further comprising a display for displaying an image of the cardiovascular tissue.

32. The apparatus of claim 30 further comprising a display for displaying an image of the soft tissue, and a data processor receiving the electronic representation of the soft tissue and processing the image of the soft tissue on the display.

33. The apparatus of claim 30 wherein the image sensor comprises a charge coupled device (COD) that includes a plurality of interpixel channels.

34. The apparatus of claim 30 further wherein the CCD comprises a plurality of CCDs, each CCD having a plurality of surfaces which interface with an adjoining CCD.

35. The apparatus of claim 30 further comprising a processor programmed to correct a seam artifact.

36. The apparatus of claim 30 further comprising a frame holding the radiation source and the imaging sensor in fixed relation to each other.

37. The apparatus of claim 30 wherein the imaging sensor has a first plurality of pixels having a first size and a second plurality of pixels having a second size that is different from the first size.

38. The apparatus of claim 30 further comprising a processor that combines data stored by groups of adjacent pixels of the imaging sensor to generate the electronic representation of the cardiovascular tissue.

39. The apparatus of claim 30 further comprising an audio controller, such that the audio controller actuates a procedure.

40. The apparatus of claim 30 wherein the imaging sensor performs time delay integration to generate the electronic representation of the cardiovascular tissue.

41. The apparatus of claim 30 wherein the imaging sensor comprises an array of pixels at least as large as 2048×2048 pixels.

42. The apparatus of claim 30 further comprising a straight fiber optic coupler between the optical surface and the imaging sensor.

43. The apparatus of claim 30 wherein the scintillator has a variable thickness.

44. The apparatus of claim 30 wherein the controller bins rectangular groups of pixels during charge readout.

45. The apparatus of claim 30 wherein the sensor performs pixel binning of image regions having different resolutions.

* * * * *